(12) United States Patent
Emmanuel et al.

(10) Patent No.: US 6,756,372 B2
(45) Date of Patent: Jun. 29, 2004

(54) COMPOUNDS USEFUL AS REVERSIBLE INHIBITORS OF CYSTEINE PROTEASES

(75) Inventors: Michel Jose Emmanuel, Danbury, CT (US); Weimin Liu, Shelton, CT (US); Denice Mary Spero, West Redding, CT (US); Sanxing Sun, Danbury, CT (US); David S. Thomson, Ridgefield, CT (US); Yancey David Ward, Sandy Hook, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 10/001,134

(22) Filed: Nov. 2, 2001

(65) Prior Publication Data

US 2002/0058809 A1 May 16, 2002

Related U.S. Application Data

(62) Division of application No. 09/655,351, filed on Sep. 8, 2000, now Pat. No. 6,420,364.
(60) Provisional application No. 60/153,738, filed on Sep. 13, 1999, and provisional application No. 60/222,900, filed on Aug. 3, 2000.

(51) Int. Cl.$^7$ .................. A61K 31/5355; C07D 413/12; A61P 9/10

(52) U.S. Cl. .................. 514/231.5; 544/58.4; 544/145; 544/149

(58) Field of Search .......................... 544/149, 60, 145; 514/231.5

(56) References Cited

U.S. PATENT DOCUMENTS

| | | |
|---|---|---|
| 4,734,425 A | 3/1988 | Nakane et al. |
| 4,749,715 A | 6/1988 | Hall |
| 4,797,202 A | 1/1989 | Klimpel et al. |
| 4,957,932 A | 9/1990 | Young et al. |
| 4,962,117 A | 10/1990 | Young et al. |
| 5,196,291 A | 3/1993 | Okada et al. |
| 5,218,123 A | 6/1993 | Horwell et al. |
| 5,250,732 A | 10/1993 | Kogan et al. |
| 5,328,803 A | 7/1994 | Fujikura et al. |
| 5,346,907 A | 9/1994 | Kerwin et al. |
| 5,461,176 A | 10/1995 | Sun et al. |
| 5,504,109 A | 4/1996 | Seitz et al. |
| 5,514,778 A | 5/1996 | Hammond et al. |
| 5,633,248 A | 5/1997 | Kato et al. |
| 5,691,368 A | 11/1997 | Peet et al. |
| 5,710,129 A | 1/1998 | Lynch et al. |
| 5,744,451 A | 4/1998 | Allen et al. |
| 5,756,528 A | 5/1998 | Anthony et al. |
| 5,847,135 A | 12/1998 | Bemis et al. |
| 5,872,122 A | 2/1999 | Bovy et al. |
| 5,976,858 A | 11/1999 | Palmer et al. |

FOREIGN PATENT DOCUMENTS

| | | |
|---|---|---|
| DE | 3827727 A1 | 2/1990 |
| DE | 4343528 A1 | 12/1993 |
| DE | 4225487 A1 | 2/1994 |
| DE | 4303145 A1 | 8/1994 |
| DE | 4321897 A1 | 1/1995 |
| DE | 19609955 A1 | 9/1997 |
| DE | 19653647 A1 | 6/1998 |
| EP | 0 115 472 | 8/1984 |
| EP | 0294668 A2 | 12/1988 |
| EP | 0308885 A1 | 3/1989 |
| EP | 0314060 A2 | 5/1989 |
| EP | 0318083 A2 | 5/1989 |

(List continued on next page.)

OTHER PUBLICATIONS

Bence Ashboth, et al; Mechanism of Action of Cysteine Proteinases: Oxyanion Binding Site Is Not Essential in the Hydrolysis of Specific Substrates, BioChemistry 1985, 24, 606–609.

(List continued on next page.)

*Primary Examiner*—Robert W. Ramsuer
*Assistant Examiner*—Ebenezer Sackey
(74) *Attorney, Agent, or Firm*—Robert P. Raymond; Anthony P. Bottino; Timothy X. Witkowski

(57) ABSTRACT

Disclosed are novel cathepsin S, K, F, L and B reversible inhibitory compounds of the formulas (I), (II), (Ia) and (Ib) further defined herein. The compounds are useful for treating autoimmune diseases. Also disclosed are processes for making such novel compounds.

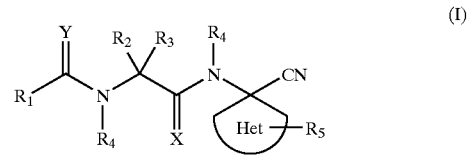

(I)

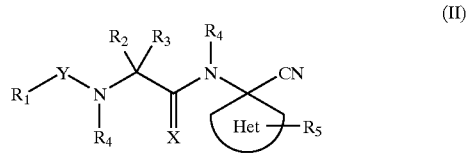

(II)

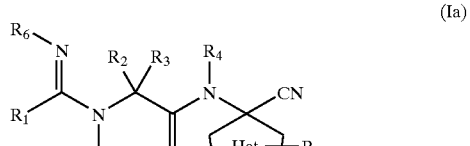

(Ia)

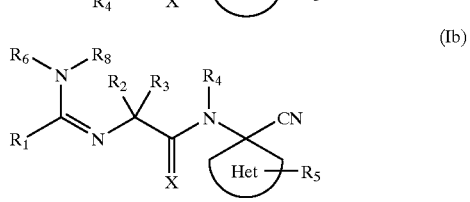

(Ib)

20 Claims, No Drawings

FOREIGN PATENT DOCUMENTS

| | | |
|---|---|---|
| EP | 0336356 A2 | 10/1989 |
| EP | 0374098 A2 | 6/1990 |
| EP | 0398072 A3 | 11/1990 |
| EP | 0483667 A2 | 5/1992 |
| EP | 0506008 A1 | 9/1992 |
| EP | 0529737 A1 | 3/1993 |
| EP | 0533244 A1 | 3/1993 |
| EP | 0542463 A1 | 5/1993 |
| EP | 0547699 A1 | 6/1993 |
| EP | 587110 A2 | 3/1994 |
| EP | 0 604 182 A2 | 6/1994 |
| EP | 0611756 A3 | 8/1994 |
| EP | 0611756 A2 | 8/1994 |
| EP | 0644198 A1 | 3/1995 |
| EP | 0649057 A2 | 4/1995 |
| EP | 0 652 229 A2 | 5/1995 |
| EP | 0672654 | 9/1995 |
| EP | 805147 A1 | 11/1997 |
| EP | 810206 A1 | 12/1997 |
| EP | 0 838 471 A1 | 4/1998 |
| EP | 844248 A2 | 5/1998 |
| EP | 844248 A3 | 5/1998 |
| EP | 846464 A2 | 6/1998 |
| EP | 846464 A3 | 6/1998 |
| EP | 897908 A1 | 2/1999 |
| FR | 2694006 A1 | 1/1994 |
| JP | 662788 | 8/1965 |
| JP | 68010619 | 5/1968 |
| JP | 6358346 A2 | 3/1988 |
| JP | 63301868 A2 | 12/1988 |
| JP | 3002872 A2 | 1/1991 |
| JP | 6003787 A2 | 1/1994 |
| JP | 6051451 A2 | 2/1994 |
| JP | 6145173 A2 | 5/1994 |
| JP | 6293772 A2 | 10/1994 |
| JP | 6340643 A2 | 12/1994 |
| JP | 7-101959 A2 | 4/1995 |
| JP | 7285931 A2 | 10/1995 |
| JP | 8248579 A2 | 9/1996 |
| JP | 11100373 A2 | 4/1999 |
| WO | WO 8808717 A2 | 11/1988 |
| WO | WO 89/10920 A1 | 11/1989 |
| WO | WO 90/13561 A1 | 11/1990 |
| WO | WO 91/19733 A1 | 12/1991 |
| WO | WO 92/01675 A2 | 2/1992 |
| WO | WO 92/14465 A1 | 9/1992 |
| WO | WO 92/17453 | 10/1992 |
| WO | WO 92/21361 A1 | 12/1992 |
| WO | WO 92/22570 A1 | 12/1992 |
| WO | WO 93/05444 A1 | 3/1993 |
| WO | WO 93/12075 A1 | 6/1993 |
| WO | WO 93/14069 A1 | 7/1993 |
| WO | WO 94/00435 A1 | 1/1994 |
| WO | WO 94/06757 A1 | 3/1994 |
| WO | WO 94/07841 A1 | 4/1994 |
| WO | WO 94/21657 A1 | 9/1994 |
| WO | WO 94/22911 A2 | 10/1994 |
| WO | WO 94/25432 A1 | 10/1994 |
| WO | WO 95/01344 A1 | 1/1995 |
| WO | WO 95/06029 A1 | 3/1995 |
| WO | WO 95/09838 | 4/1995 |
| WO | WO 95/12611 A1 | 5/1995 |
| WO | WO 95/15749 | 6/1995 |
| WO | WO 95/23222 A1 | 8/1995 |
| WO | WO 95/24382 A1 | 9/1995 |
| WO | WO 95/29899 A1 | 11/1995 |
| WO | WO 95/33728 A1 | 12/1995 |
| WO | WO 95/35308 A1 | 12/1995 |
| WO | WO 96/07638 A1 | 3/1996 |
| WO | WO 96/10559 A1 | 4/1996 |
| WO | WO 96/12499 A1 | 5/1996 |
| WO | WO 96/13502 A1 | 5/1996 |
| WO | WO 96/16940 A1 | 6/1996 |
| WO | WO 96/20725 A2 | 7/1996 |
| WO | WO 96/20949 A1 | 7/1996 |
| WO | WO 96/22970 A1 | 8/1996 |
| WO | WO 96/26194 A1 | 8/1996 |
| WO | WO 96/30353 A1 | 10/1996 |
| WO | WO 96/33168 A1 | 10/1996 |
| WO | WO 96/33170 A1 | 10/1996 |
| WO | WO 96/33211 A1 | 10/1996 |
| WO | WO 96/37499 A1 | 11/1996 |
| WO | WO 96/39137 A1 | 12/1996 |
| WO | WO 96/39384 A1 | 12/1996 |
| WO | WO 96/40647 | 12/1996 |
| WO | WO 96/40737 A1 | 12/1996 |
| WO | WO 96/40741 A1 | 12/1996 |
| WO | WO 96/40742 A1 | 12/1996 |
| WO | WO 96/40744 A1 | 12/1996 |
| WO | WO 96/40751 A1 | 12/1996 |
| WO | WO 96/40752 A1 | 12/1996 |
| WO | WO 96/40753 A1 | 12/1996 |
| WO | WO 97/01275 A1 | 1/1997 |
| WO | WO 97/10219 A1 | 3/1997 |
| WO | WO 97/19908 A1 | 6/1997 |
| WO | WO 97/22618 A1 | 6/1997 |
| WO | WO 97/22619 A3 | 6/1997 |
| WO | WO 97/22621 A2 | 6/1997 |
| WO | WO 97/22621 A3 | 6/1997 |
| WO | WO 97/24343 A1 | 7/1997 |
| WO | WO 97/26246 A1 | 7/1997 |
| WO | WO 97/27200 A1 | 7/1997 |
| WO | WO 97/27220 A2 | 7/1997 |
| WO | WO 97/31016 A2 | 8/1997 |
| WO | WO 97/31016 A3 | 8/1997 |
| WO | WO 97/45016 A1 | 12/1997 |
| WO | WO 97/46518 A1 | 12/1997 |
| WO | WO 98/04278 A2 | 2/1998 |
| WO | WO 98/04518 A1 | 2/1998 |
| WO | WO 98/14450 A1 | 4/1998 |
| WO | WO 98/17679 A1 | 4/1998 |
| WO | WO 98/21199 A2 | 5/1998 |
| WO | WO 98/21199 A3 | 5/1998 |
| WO | WO 98/22433 A1 | 5/1998 |
| WO | WO 98/25617 A1 | 6/1998 |
| WO | WO 98/26654 A2 | 6/1998 |
| WO | WO 98/26654 A3 | 6/1998 |
| WO | WO 98/28269 A1 | 7/1998 |
| WO | WO 98/38177 A1 | 9/1998 |
| WO | WO 98/47863 A1 | 10/1998 |
| WO | WO 98/52558 A1 | 11/1998 |
| WO | WO 98/52559 A1 | 11/1998 |
| WO | WO 98/52941 A1 | 11/1998 |
| WO | WO 98/57937 A1 | 12/1998 |
| WO | WO 98/57937 A3 | 12/1998 |
| WO | WO 98/57951 A1 | 12/1998 |
| WO | WO 99/23063 A1 | 5/1999 |
| WO | WO 99/24460 A2 | 5/1999 |
| WO | WO 99/32106 A1 | 7/1999 |
| WO | WO 99/32455 A1 | 7/1999 |
| WO | WO 99/56765 A1 | 11/1999 |
| WO | WO 00/51998 A1 | 8/2000 |
| WO | WO 00/55125 | 9/2000 |
| WO | WO 00/55126 | 9/2000 |
| WO | WO 01/19816 A1 * | 3/2001 |
| ZA | 950892 | 2/1995 |

OTHER PUBLICATIONS

Robert P. Hanzlik, et al; Reversible Covalent Binding of Peptide Nitriles to Papain; Biochimica et Biophysica Acta, 1035 (1990) 62–70 Elsevier.

Tzyy–Chyau Liang, et al; Inhibition of Papain by Nitriles: Mechanistic Studies Using NMR and Kinetic Measurements, Archives of Biochemistry and Biophysics vol. 252, No. 2, Feb. 1, pp. 626–634, 1987.

David J. Buttle, et al; Affinity Purification of the Novel Cysteine Proteinase Papaya Proteinase IV, and Papain from Papaya Latex, Biochem J. (1989) 261, 469–476.

Paul R. Carey, et al; Identity of acyl group conformation in the active sites of papain and cathepsin B by resonance Raman spectroscopy, J. Biol. Chem 1984, 259(23), 14357–14360—XP002129209 from Chem. Abstract 102:2545e.

Siming Liu, et al; The Contribution of intermolecular hydrogen bonding to the kinetic specificity of papain, Biochim. Biophys. Acta 1993, 1158(3), 264–72—XP–002129210 from Chem Abstract 120:292661a.

Eric Dufour, et al; Engineering Nitrile Hydratase Activity into a Cysteine Protease by a Single Mutation, Biochemistry 1995, 34, 16382–16388,—XP 002129204.

Joseph B. Moon, et al; Reversible Covalent Inhibition of Papain by a Peptide Nitrile, C NME Evidence for a Thiomidate Ester Adduct, J. Am. Chem. Soc. 1986, 108, 1350–1351.

Barbara J. Gour–Salin et al ; Inhibition of papain by peptide nitriles; conversion of the nitrile group into other functionalities via the papain:nitrile thioimidate ester adduct, Can J. Chem vol. 69—pp 1288–1297 1991.

Robert P. Hanzlik, et al; Chemical Abstract 113:187051j—Reversible covalent binding of peptide nitriles to papain, Biochim. Biophys. Acta 1990, 1035(1) 62–70,—XP 002129211.

David J. Buttle, et al; Chemical Abstract 111:129491a—Affinity Purification of the Novel Cysteine Proteinase Papaya Proteinase IV, and Papain from Papaya Latex, Biochem J. (1989) 261, 469–476—XP–002129212.

Tzyy–Chyau Liang, et al; Chemical Abstract 107:3097a—Inhibition of Papain by Nitriles: Mechanistic Studies Using NMR and Kinetic Measurements, Archives of Biochemistry and Biophysics vol. 252, No. 2, Feb. 1, pp. 626–634, 1987—XP 002129213.

Ming Tao; Inhibition by Peptidyl Heterocycles, Bioorganic & Medicinal Chemistry Letters, vol. 6 No. 24, pp. 3009–3012, 1996.

A.W. Edith Chan, Prediction of Relative Potency of Ketone Protease Inhibitors Using Molecular Orbital Theory; Bioorganic & Medicinal Chemistry, vol. 4 No. 10, pp 1673–1677, 1996.

* cited by examiner

US 6,756,372 B2

COMPOUNDS USEFUL AS REVERSIBLE INHIBITORS OF CYSTEINE PROTEASES

RELATED APPLICATION DATA

This is a divisional application of U.S. application Ser. No. 09/655,351 filed Sep. 8, 2000, now U.S. Pat. No. 6,420,364, which claims the benefit of Provisional application Ser. Nos. 60/153,738, filed Sep. 13, 1999, and 60/222,900, filed Aug. 3, 2000.

TECHNICAL FIELD OF THE INVENTION

This invention relates to peptidyl spiroheterocyclic, amidino and guanidino compounds. The compounds are reversible inhibitors of the cysteine protease cathepsin S, K, F, L and B and are therefore useful in the treatment of autoimmune and other related diseases. The invention also relates to processes for preparing such compounds and pharmaceutical compositions comprising them.

BACKGROUND OF THE INVENTION

Cathepsin S and cathepsin K are members of the papain family, within the papain superfamily of cysteine proteases. The papain family is the largest group of cysteine proteases and includes proteases such as cathepsins B, H, K, L, O and S. (A. J. Barrett et al., 1996, Perspectives in Drug Discovery and Design, 6, 1). The cysteine proteases have important roles in human biology and diseases including atherosclerosis, emphysema, osteoporosis, chronic inflammation and immune disorders (H. A. Chapman et al., 1997, Ann. Rev. Physiol., 59, 63). Cathepsin S plays a key role in regulating antigen presentation and immunity (H. A. Chapman, 1998, Current Opinion in Immunology, 10, 93; R. J. Riese et al., 1998, J. Clin. Invest., 101, 2351; R. J. Riese et al., 1996, Immunity, 4, 357). Cathepsin S deficient mice have impaired invariant chain degradation resulting in decreased antigen presentation and germinal center formation, and diminished susceptibility to collagen-induced arthritis indicating the therapeutic potential for a cathepsin S inhibitor (G. Shi et al., 1999, Immunity, 10, 197; T. Y. Nakagawa et al, 1999, Immunity, 10, 207)

The specificity of the immune response relies on processing of foreign protein and presentation of antigenic peptide at the cell surface. Antigenic peptide is presented bound to MHC Class II, a heterodimeric glycoprotein expressed in certain antigen presenting cells of hematopoietic lineage, such as B cells, macrophages and dendritic cells. Presentation of antigen to effector cells, such as T-cells, is a fundamental step in recognition of non-self and thus initiation of the immune response.

Recently MHC Class II heterodimers were shown to associate intracellularly with a third molecule designated invariant chain. Invariant chain facilitates Class II transport to the endosomal compartment and stabilizes the Class II protein prior to loading with antigen. Invariant chain interacts directly with Class II dimers in the antigen-binding groove and therefore must be proteolyzed and removed or antigen cannot be loaded or presented. Current research suggests that invariant chain is selectively proteolyzed by cathepsin S, which is compartmentalized with MHC Class II complexes within the cell. Cathepsin S degrades invariant chain to a small peptide, termed CLIP, which occupies the antigen-binding groove. CLIP is released from MHC Class II by the interaction of MHC Class II with HLA-DM, a MHC-like molecule thus freeing MHC Class II to associate with antigenic peptides. MHC Class II-antigen complexes are then transported to the cell surface for presentation to T-cells, and initiation of the immune response.

Cathepsin S, through proteolytic degradation of invariant chain to CLIP, provides a fundamental step in generation of an immune response. It follows that inhibition of antigen presentation via prevention of invariant chain degradation by cathepsin S could provide a mechanism for immunoregulation. Control of antigen-specific immune responses has long been desirable as a useful and safe therapy for autoimmune diseases. Such diseases include Crohn's disease and arthritis, as well as other T-cell-mediated immune responses (C. Janeway and P. Travers, 1996, Immunobiology, The Immune System in Health and Disease, Chapter 12). Furthermore, cathepsin S, which has broad pH specificity, has been implicated in a variety of other diseases involving extracellular proteolysis, such as Alzheimer's disease (U. Muller-Ladner et al., 1996, Perspectives in Drug Discovery and Design, 6, 87) and atherosclerosis (G. K. Sukhova et al., 1998, J. Clin. Invest., 102, 576).

A cathepsin S inhibitor has been found to block the rise in IgE titers and eosinophil infiltration in the lung in a mouse model of pulmonary hypersensitivity, suggesting that cathepsin S may be involved in asthma (R. J. Riese et al., J. Clin. Investigation,1998, 101, 2351).

Another cysteine protease, cathepsin F has been found in macrophages and is also involved in antigen processing. It has been postulated that cathepsin F in stimulated lung macrophages and possibly other antigen presenting cells could play a role in airway inflammation (G. -P. Shi et al., J. Exp. Med., 2000, 191, 1177).

Cathepsin K, another cysteine protease has been found to be highly expressed in osteoclasts and to degrade bone collagen and other bone matrix proteins. Inhibitors of cathepsin K have been shown to inhibit bone resorption in mice. Therefore, cathepsin K may play a role in osteoclastic bone resorption and cathepsin K inhibitors may be useful in the treatment of diseases involving bone resorption such as osteoporosis (F. Lazner et al., Human Molecular Genetics, 1999, 8, 1839).

Cysteine proteases are characterized by having a cysteine residue at the active site which serves as a nucleophile. The active site also contains a histidine residue. The imidazole ring on the histidine serves as a base to generate a thiolate anion on the active site cysteine, increasing its nucleophilicity. When a substrate is recognized by the protease, the amide bond to be cleaved is directed to the active site, where the thiolate attacks the carbonyl carbon forming an acyl-enzyme intermediate and cleaving the amide bond, liberating an amine. Subsequently, water cleaves the acyl-enzyme species regenerating the enzyme and liberating the other cleavage product of the substrate, a carboxylic acid.

Inhibitors of cysteine proteases contain a functionality that can react reversibly or irreversibly with the active site cysteine. Examples of reactive functionalities that have been described (D. Rasnick, 1996, Perspectives in Drug Discovery and Design, 6, 47) on cysteine protease inhibitors include peptidyl diazomethanes, epoxides, monofluoroalkanes and acyloxymethanes, which irreversibly alkylate the cysteine thiol. Other irreversible inhibitors include Michael acceptors such as peptidyl vinyl esters and other carboxylic acid derivatives (S. Liu et al., J. Med Chem., 1992, 35, 1067) and vinyl sulfones (J. T. Palmer et al., 1995, J. Med Chem., 38, 3193).

Reactive functionalities that form reversible complexes with the active site cysteine include peptidyl aldehydes (R.

P. Hanzlik et al., 1991, Biochim. Biophys. Acta., 1073, 33), which are non-selective, inhibiting both cysteine and serine proteases as well as other nucleophiles. Peptidyl nitrites (R. P. Hanzlik et al., 1990, Biochim. Biophys. Acta., 1035, 62) are less reactive than aldehydes and therefore more selective for the more nucleophilic cysteine proteases. Various reactive ketones have also been reported to be reversible inhibitors of cysteine proteases (D. Rasnick, 1996, ibid). In addition to reacting with the nucleophilic cysteine of the active site, reactive ketones may react with water, forming a hemiketal which may act as a transition state inhibitor.

Examples of cathepsin S inhibitors have been reported. J. L. Klaus et al. (WO 9640737) described reversible inhibitors of cysteine proteases including cathepsin S, containing an ethylene diamine. In U.S. Pat. No. 5,776,718 to Palmer et al. there is disclosed in it's broadest generic aspect a protease inhibitor comprising a targeting group linked through a two carbon atom chain to an electron withdrawing group (EWG). The compounds of the present application are structurally distinct and thus excluded from the U.S. Pat. No. 5,776,718 patent with particular embodiments possessing unexpectedly greater activity than the closest compounds of the prior art. Other examples of cathepsin S inhibitors have been reported by E. T. Altmann et al, (WO 9924460, 1999) which describes dipeptide nitriles asserted to have activity as inhibitors of Cathepsins B, K, L and S. The WO publication does not disclose any compounds possessing an imino or guanidino moiety and fails to provide any description, methods or examples for particular spiroheterocylic moieties at the P2 position.

Additional peptidyl nitrites have been reported as protease inhibitors. For example, both nitriles and ketoheterocycles are described by B. A. Rowe et al. (U.S. Pat. No. 5,714,471) as protease inhibitors useful in the treatment of neurodegenerative diseases. Peptidyl nitrites are reported by B. Malcolm et al. (WO 9222570) as inhibitors of picomavirus protease. B. J. Gour-Salin (Can. J. Chem., 1991, 69, 1288) and T. C. Liang (Arch. Biochim. Biophys., 1987, 252, 626) described peptidyl nitrites as inhibitors of papain.

A reversible inhibitor presents a more attractive therapy than irreversible inhibitors. Even compounds with high specificity for a particular protease can bind non-target enzymes. An irreversible compound could therefore permanently inactivate a non-target enzyme, increasing the likelihood of toxicity. Furthermore, any toxic effects resulting from inactivation of the target enzyme would be mitigated by reversible inhibitors, and could be easily remedied by modified or lower dosing. Finally, covalent modification of an enzyme by an irreversible inhibitor could potentially generate an antibody response by acting as a hapten.

In light of the above, there is a clear need for compounds which reversibly and selectively inhibit cysteine proteases cathepsin S, K, F, L and B for indications in which these proteases exacerbate disease.

BRIEF DESCRIPTION OF THE INVENTION

It is therefore an object of this invention to provide novel compounds according to the formulas (I), (II), (Ia) and (Ib) as described herein which reversibly inhibit the cysteine proteases cathepsin S, K, F, L and B. It is a further object of the invention to provide methods for treating diseases and pathological conditions exacerbated by these cysteine proteases such as, but not limited, to rheumatoid arthritis, multiple sclerosis, asthma and osteoporosis. It is yet a further object of the invention to provide novel processes for preparation of the above-mentioned novel compounds.

DETAILED DESCRIPTION OF THE INVENTION

A proposed mechanism of action of the cysteine protease inhibitors of this invention is that the inhibitors contain a functionality that can react (reversibly or irreversibly) with the active site cysteine. The reactive functionality is attached to a peptide or peptide mimic that can be recognized and accommodated by the region of the protease surrounding the active site. The nature of both the reactive functionality and the remaining portion of the inhibitor determine the degree of selectivity and potency toward a particular protease.

Given the similarity of the active sites in cysteine proteases, it may be anticipated that a given class of inhibitors might have activity against more that one cysteine protease. It may also be expected that due to structural differences between individual cysteine proteases, different compounds of the invention may have different inhibitory potencies against different cysteine proteases. Thus some of the compounds of the invention may also be expected to be most effective in treating diseases mediated by cysteine proteases that they inhibit most potently. The activity of particular compounds disclosed herein against cysteine proteases cathepsin S, K, F, L and B may be determined by the screens described in the section entitled "Assessment of Biological Properties."

In one broad generic aspect, the invention provides novel compounds of the formula (I):

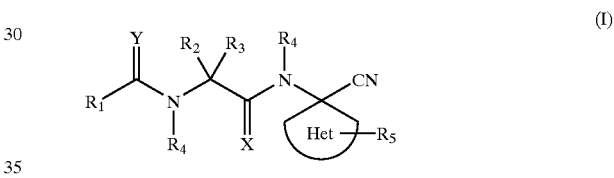

(I)

wherein:
Het is piperidinyl, pyrrolidinyl, tetrahydropyranyl, tetrahydrothiopyranyl, tetrahydrofuranyl, hexahydropyrimidinyl, hexahydropyridazinyl, piperazinyl, 1,4,5,6-tetrahydropyrimidin-2-ylamine, dihydro-oxazolyl, 1,2-thiazinanyl-1,1-dioxide, 1,2,6-thiadiazinanyl-1,1-dioxide, isothiazolidinyl-1,1-dioxide or imidazolidinyl-2,4-dione, each being optionally substituted with one or more $R_5$;
Y is O or S;
$R_1$ is C1–5 alkyl, C1–5 alkoxy, aryloxy, C3–7 cycloalkyl, phenyl, benzyl, naphthyl, tetrahydronaphthyl, C1–5alkylsulfonylC1–5alkyl, C3–7cycloalkylsulfonylC1–5alkyl, arylsulfonylC1–5alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl, quinoxalinyl, or amino; wherein $R_1$ is optionally substituted by one or more $R_a$;
$R_a$ is C1–5 alkyl, C3–7 cycloalkyl, phenyl, naphthyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, benzisoxazolyl, quinolinyl, isoquinolinyl, quinazolinyl, quinoxalinyl, C1–5 alkoxy, C1–5alkanoyl, C1–5alkanoyloxy, aryloxy, benzyloxy, C1–5 alkoxycarbonyl, aryloxycarbonyl, aroyloxy, carbamoyl wherein the nitrogen atom may be independently mono or di-substituted by C1–8 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–5 alkanoylamino, aroylamino, C1–5 alkylthio, arylthio wherein the sulfur atom may be oxidized to a sulfoxide or sulfone, ureido wherein either nitrogen atom may be independently substituted by alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, halogen, hydroxy, oxo, carboxy, cyano, nitro, amidino or guanidino, $R_a$ may be further optionally substituted by one or more $R_b$;

$R_b$ is C1–5 alkyl, C3–6 cycloalkyl, aryl, C1–5 alkoxy, aryloxy, benzyloxy, halogen, hydroxy, oxo, carboxy, cyano, nitro, amidino or guanidino;

$R_2$ is hydrogen or C1–3 alkyl;

$R_3$ is hydrogen, C1–5 alkyl, C2–5alkylene, C3–7 cycloalkyl, arylC1–3alkyl or aryl wherein $R_3$ is optionally substituted by one or more $R_c$;

$R_c$ is C1–5 alkyl, C3–7 cycloalkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, pyrazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, C1–5 alkoxy, aryloxy, C1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylalkyl, C1–5 alkoxy, aryloxy, arylC1–5alkoxy, aroyl, amino, halogen, hydroxy, oxo, carboxy, cyano, nitro, amidino or guanidino;

$R_4$ is hydrogen or C1–3 alkyl;

$R_5$ is C1–5 alkyl chain optionally interrupted by one or two O or S, phenyl, naphthyl, arylC1–3alkyl, furanyl, thienyl, pyrrolyl, imidazolyl, pyridinyl, pyrimidinyl, C1–5 alkanoyl, aroyl, C1–5 alkoxycarbonyl, aryloxycarbonyl, benzyloxycarbonyl, carbamoyl wherein the nitrogen atom may be independantly mono or disubstituted by C1–5 alkyl, aryl, pyrrolidinyl, piperidinyl, morpholinyl, piperazinyl, furanyl, thienyl, pyrrolyl, thiazolyl, imidazolyl, pyridinyl, benzimidazolyl or quinolinyl, or $R_5$ is C1–5 alkanoylamino, aroylamino, C1–5 alkylthio wherein the sulfur atom may be oxidised to a sulfoxide or sulfone, arylthio wherein the sulfur atom may be oxidised to a sulfoxide or sulfone, C1–5 alkylsulfonylamino, arylsulfonylamino, C1–5 alkylaminosulfonyl, arylaminosulfonyl, amino wherein the nitrogen atom may be independently mono or disubstituted by alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyridinylcarbonyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl or arylsulfonyl, or $R_5$ is halogen, hydroxy, oxo, carboxy, cyano, nitro, amidino or guanidino, $R_5$ may be further optionally substituted by one or more $R_e$;

$R_e$ is C1–5 alkyl, C3–6 cycloalkyl, aryl, pyrrolidinyl, piperidinyl, morpholinyl, thiomorpholinyl, piperazinyl, indolinyl, pyranyl, thiopyranyl, furanyl, thienyl pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl, quinoxalinyl, C1–5 alkoxy, aryloxy, aroyl, amino wherein the nitrogen atom may be independently mono or di-substituted by C1–5 alkyl, aryl, pyrrolidinyl, piperidinyl, morpholinyl, furanyl, thienyl, pyrrolyl or pyridinyl, halogen, hydroxy, oxo, carboxy, cyano, nitro, benzyloxy, arylC1–3alkoxycarbonyl, amidino or guanidino;

X is O or S and pharmaceutically acceptable derivatives thereof.

In another embodiment of the invention, there are provided novel compounds of the formula (I) as described immediately above, and wherein:

Het is piperidinyl, pyrrolidinyl, tetrahydropyranyl or tetrahydrothiopyranyl each ring being substituted with one or more $R_5$;

Y is O;

$R_1$ is C1–3 alkyl, C1–3alkoxy, C3–7 cycloalkyl, phenyl, benzyl, naphthyl, tetrahydronaphthyl, piperidinyl, morpholinyl, piperazinyl, furanyl, thienyl, pyridinyl, isoxazolyl, pyrazinyl, indolyl, quinolinyl, benzofuranyl, benzimidazolyl, benzoisoxazolyl or amino; wherein $R_1$ is optionally substituted by one or more $R_a$;

$R_a$ is C1–3 alkyl, phenyl, naphthyl, piperidinyl, indolinyl, morpholinyl, piperazinyl, furanyl, thienyl, benzimidazolyl, C1–3 alkoxy, C1–3 alkanoyl, phenoxy, naphthyloxy, benzyloxy, C1–3 alkoxycarbonyl, benzoyloxy, carbamoyl wherein the nitrogen atom may be independently mono or di-substituted by C1–5 alkyl, phenyl, piperidinyl, morpholinyl, piperazinyl, furanyl, thienyl or pyridinyl, or $R_a$ is C1–5 alkanoylamino, benzoylamino, C1–3 alkylsulfonyl, phenylsulfonyl, ureido wherein either nitrogen atom may be independently substituted by alkyl, phenyl, piperidinyl, morpholinyl, furanyl, thienyl or pyridinyl, C1–3 alkoxycarbonylamino, C1–5 alkylcarbamoyloxy, C1–5 alkylsulfonylamino, phenylsulfonylamino, C1–5 alkylaminosulfonyl, phenylaminosulfonyl, amino wherein the nitrogen atom may be independently mono or di-substituted by C1–5 alkyl, phenyl, piperidinyl, morpholinyl, piperazinyl, furanyl, thienyl or pyridinyl, halogen, hydroxy, oxo, carboxy, nitro or cyano, $R_a$ may be further optionally substituted by one or more $R_b$;

$R_b$ is halogen, hydroxy, benzyloxy, oxo or cyano;

$R_2$ is hydrogen;

$R_3$ is C1–5 alkyl or C2–5 alkylene, C4–6 cycloalkyl or benzyl wherein R3 is optionally substituted by one or more $R_c$;

$R_c$ is C1–4 alkyl, C5–6 cycloalkyl, phenyl, naphthyl, C1–4 alkoxy, phenoxy, benzoyl, benzyloxy, indolinyl, imidazolyl, C1–3alkylthio, C1–3alkylsulfonyl, halogen, hydroxy, oxo, carboxy, nitro or cyano, $R_c$ may be further optionally substituted by one or more $R_d$;

$R_d$ is methyl, phenyl, benzyl, benzyloxy, C1–3alkoxy, halogen, hydroxy, nitro or cyano;

$R_4$ is hydrogen;

$R_5$ is C1–4alkyl chain optionally interrupted by one O or S atom, phenyl, phenylC1–2alkyl, furanyl, pyrimidinyl, thienyl, C1–3 alkanoyl, benzoyl, C1–4 alkoxycarbonyl, carbamoyl wherein the nitrogen atom may be independently mono or disubstituted by C1–5 alkyl, phenyl, piperidinyl, morpholinyl, piperazinyl, furanyl, thienyl or pyridinyl, C1–3 alkylthio, phenylthio, C1–5 alkylaminosulfonyl, phenylaminosulfonyl, C1–5alkylamino wherein the nitrogen atom may be independently mono- or disubstituted by naphthylsulfonyl or pyridinylcarbonyl, halogen, hydroxy, carboxy, oxo or cyano, $R_5$ may be further optionally substituted by one or more $R_e$;

$R_e$ is C1–3 alkyl, C5–6 cycloalkyl, phenyl, naphthylmethyl, piperidinyl, morpholinyl, piperazinyl, imidazolyl, pyridinyl, pyrimidinyl, pyrazinyl, benzimidazolyl, quinolinyl, isoquinolinyl, C1–4 alkoxy, benzoyl, amino wherein the nitrogen atom may be independently mono or di-substituted by C1–5 alkyl, phenyl, piperidinyl, morpholinyl, furanyl, thienyl or pyridinyl, halogen, hydroxy, oxo or cyano; and X is O.

In yet another embodiment of the invention, there are provided novel compounds of the formula (I) as described immediately above, and wherein:

$R_1$ is methyl, ethyl, phenyl, piperidinyl, morpholinyl, piperazinyl, pyridinyl, furanyl, thienyl, benzyl, benzofuranyl, cyclohexyl, quinolinyl or amino; wherein $R_1$ is optionally substituted by one or more $R_a$;

$R_a$ is C1–3 alkyl, phenyl, piperidinyl, thienyl, C1–3 alkoxy, phenoxy, C1–3 alkanoyl, C1–3 alkoxycarbonyl, benzyloxy, C1–3 alkanoylamino, thiophenyl, benzimidazolyl, C1–3 alkylthio or chloro, $R_a$ may be further optionally substituted by one or more $R_b$;

$R_b$ is bromo, chloro, fluoro, iodo, hydroxy, oxo or cyano;

$R_3$ is methyl, ethyl, n-propyl, n-butyl, isobutyl, propene, butene, isobutene, C3–7 cycloalkyl or benzyl wherein $R_3$ is optionally substituted by one or more $R_c$;

$R_c$ is methyl, ethyl, n-propyl, isopropyl, n-butyl, isobutyl, tert-butyl, methoxy, ethoxy, methylthio, ethylthio, cyclohexyl, phenyl, naphthyl, imidazolyl, indolinyl, cyclohexyl, bromo, chloro, fluoro, iodo, hydroxy, oxo, carboxy, nitro, benzoyl, benzyloxy, N-benzylimidazolyl or cyano, $R_c$ may be further optionally substituted by one or more $R_d$;

$R_d$ is methyl, methoxy, ethoxy, chloro, fluoro, nitro or hydroxy;

$R_5$ is methyl, ethyl, n-propyl, isopropyl, n-butyl, isobutyl, tert-butyl, phenyl, methoxycarbonyl, ethoxycarbonyl, n-propoxycarbonyl, isopropoxycarbonyl, n-butoxycarbonyl, isobutyloxycarbonyl, tert-butoxycarbonyl and pyrimidinyl, $R_5$ may be further optionally substituted by one or more $R_e$;

$R_e$ is methyl, ethyl, n-propyl, isopropyl, phenyl, methoxy, ethoxy, n-propoxy, isopropoxy, n-butoxy, isobutoxy, tert-butoxycarbonyl, bromo, chloro, fluoro, iodo, hydroxy, oxo or cyano.

In yet still another embodiment of the invention, there are provided novel compounds of the formula (I) as described immediately above, and wherein:

Het is piperidinyl or pyrrolidinyl;

$R_1$ is N-acetylaminophenyl, chlorophenyl, methoxyphenyl, m-phenoxyphenyl, morpholinyl, pyrazinyl, pyridinyl, furanyl, chlorothienyl, thienyl or thienylmethyl;

$R_3$ is n-butyl, isobutyl, 2,2-dimethylpropyl, cyclohexylmethyl, p-methoxybenzyl or 2-naphthylmethyl; and wherein the configuration at the stereocenter defined by $R_2$ and $R_3$ when they are different and the carbon they are attached to is defined as L; and $R_5$ is methyl, propyl, isopropyl, ethoxycarbonyl, benzyloxycarbonyl, benzyl, phenethyl, N,N-dimethylaminoacetyl or pyrimidinyl.

In yet a further embodiment of the invention, there are provided novel compounds of the formula (I) as described immediately above, and wherein:

Het is piperidin-4-yl or pyrrolidinyl;

$R_1$ is morpholinyl or N-acetylaminophenyl;

$R_3$ is 2,2-dimethylpropyl or cyclohexylmethyl; and $R_5$ is methyl, propyl, isopropyl, ethoxycarbonyl, benzyloxycarbonyl, benzyl, phenethyl, N,N-dimethylaminoacetyl or pyrimidinyl.

In a second broad generic aspect of the invention, there are provided novel compounds of the formula (II):

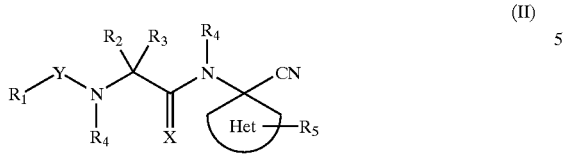

(II)

wherein:
Het is azepanyl, piperidinyl, pyrrolidinyl, azetidinyl, oxepanyl, tetrahydropyranyl, tetrahydrothiopyranyl, tetrahydrofuranyl, oxetanyl, azocanyl, oxocanyl, 1,3-diazocanyl, 1,4-diazocanyl, 1,5-diazocanyl, 1,3-dioxocanyl, 1,4-dioxocanyl, 1,5-dioxocanyl, 1,3-oxazocanyl, 1,4-oxazocanyl, 1,5-oxazocanyl, 1,3-diazepanyl, 1,4-diazepanyl, 1,3-dioxepanyl, 1,4-dioxepanyl, 1,3-oxazepanyl, 1,4-oxazepanyl, 1,2-thiazocanyl-1,1-dioxide, 1,2,8-thiadiazocanyl-1,1-dioxide, 1,2-thiazepanyl-1,1-dioxide, 1,2,7-thiadiazepanyl-1,1-dioxide, tetrahydrothiophenyl, hexahydropyrimidinyl, hexahydropyridazinyl, piperazinyl, 1,4,5,6-tetrahydropyrimidinyl, pyrazolidinyl, dihydrooxazolyl, dihydrothiazolyl, dihydroimidazolyl, isoxazolinyl, oxazolidinyl, 1,2-thiazinanyl-1,1-dioxide, 1,2,6-thiadiazinanyl-1,1-dioxide, isothiazolidinyl-1,1-dioxide, imidazolidinyl-2,4-dione, imidazolidinyl, morpholinyl, dioxanyl, tetrahydropyridinyl, thiomorpholinyl, thiazolidinyl, dihydropyranyl, dithianyl, decahydro-quinolinyl, decahydro-isoquinolinyl, 1,2,3,4-tetrahydro-quinolinyl, indolinyl, octahydro-quinolizinyl, dihydro-indolizinyl, octahydro-indolizinyl, octahydro-indolyl, decahydroquinazolinyl, decahydroquinoxalinyl, 1,2,3,4-tetrahydroquinazolinyl or 1,2,3,4-tetrahydroquinoxalinyl;
A C6–C10 bridged bicyclo wherein one or more carbon atoms are optionally replaced by a heteroatom chosen from N, O and S;
each being optionally substituted with one or more $R_5$;
Y is C(O), C(S) or S(O)$_2$;
$R_1$ is a bond, hydrogen, C1–10 alkyl, C1–10 alkoxy, aryloxy, C3–8 cycloalkyl, C3–8 cycloalkyloxy, aryl, benzyl, tetrahydronaphthyl, indenyl, indanyl, C1–10alkylsulfonylC1–10alkyl, C3–8cycloalkylsulfonylC1–10alkyl, arylsulfonylC1–10alkyl, heterocyclyl selected from pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzisoxazolyl, quinolinyl, tetrahydroquinolinyl, isoquinolinyl, tetrahydroisoquinolinyl, quinazolinyl, tetrahydroquinazolinyl, benzoxazolyl and quinoxalinyl, heterocyclyloxy wherein the heterocyclyl moiety is selected from those herein described in this paragraph, hydroxy or amino; wherein $R_1$ is optionally substituted by one or more $R_a$;
$R_a$ is a bond, C1–10 alkyl, C3–8 cycloalkyl, aryl, tetrahydronaphthyl, indenyl, indanyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, benzisoxazolyl, quinolinyl, isoquinolinyl, quinazolinyl, quinoxalinyl, C1–10 alkoxy, C1–10alkanoyl, C1–10alkanoyloxy, aryloxy, benzyloxy, C1–10 alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl,
or $R_a$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl,
or $R_a$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl,
or $R_a$ is halogen, hydroxy, oxo, carboxy, cyano, nitro, carboxamide, amidino or guanidino, $R_a$ may be further optionally substituted by one or more $R_b$; with the proviso that $R_1$ and $R_a$ simultaneously cannot be a bond;
$R_b$ is a C1–6 saturated or unsaturated branched or unbranched carbon chain optionally partially or fully halogenated wherein one or more carbon atoms are optionally replaced by O, N, S(O), S(O)$_2$ or S and wherein said chain is optionally independently substituted with 1–2 oxo groups, —NH$_2$, or one or more C1–4 alkyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl;
or $R_b$ is C3–6 cycloalkyl, aryl, aryloxy, benzyloxy, halogen, hydroxy, oxo, carboxy, cyano, nitro, mono-C1–5alkylamino, di-C1–5alkylamino, carboxamide, amidino or guanidino;
$R_2$ is hydrogen or C1–3 alkyl;
$R_3$ is a bond, hydrogen, C1–10 alkyl, C2–10alkylene, C3–8 cycloalkyl, arylC1–5alkyl or aryl wherein $R_3$ is optionally substituted by one or more $R_c$;
$R_c$ is C1–10 alkyl, C3–8 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, decahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, dihydrobenzofuranyl, octohydrobenzofuranyl, benzofuranyl, benzothienyl, benzimidazolyl, benzthiazolyl, tetrahydroquinolinyl, quinolinyl, tetrahydroisoquinolinyl, isoquinolinyl, quinazolinyl, quinoxalinyl, C1–10 alkoxy, aryloxy, C1–10 alkanoyl, aroyl, C1–10 alkoxycarbonyl, aryloxycarbonyl, C1–10 alkanoyloxy, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–5alkyl, C1–5 alkoxy, aryloxy, arylC1–5alkoxy, aroyl, amino, halogen, hydroxy, oxo, carboxy, cyano, nitro, amidino or guanidino;

$R_2$ and $R_3$ together with the carbon they are attached optionally form a nonaromatic 5–7 membered cycloalkyl or heterocyclic ring;

$R_4$ is hydrogen, hydroxy or C1–3 alkyl;

$R_5$ is a bond, hydrogen, carbonyl, C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C1–10 alkoxy, aryloxy, C3–8 cycloalkyl, aryl, benzyl, tetrahydronaphthyl, indenyl, indanyl, C3–7cycloalkylsulfonylC1–5alkyl, arylsulfonylC1–5alkyl, heterocyclyl selected from pyrrolidinyl, piperidinyl, morpholinyl, thiomorpholinyl, piperazinyl, indolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridizinyl, tetrazolyl, triazolyl, pyrazolyl, indolyl, benzofuranyl, benzothienyl, benzimidazolyl, benzthiazolyl, quinolinyl, tetrahydroquinolinyl, isoquinolinyl, tetrahydroisoquinolinyl, quinazolinyl, tetrahydroquinazolinyl, benzoxazolyl and quinoxalinyl, heterocyclyloxy wherein the heterocyclyl moiety is selected from those herein described in this paragraph, C1–10alkanoyl, aroyl, C1–10alkanoyloxy, benzyloxy, C1–10alkoxycarbonyl, arylC1–5alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is halogen, hydroxy, oxy, oxo, carboxy, cyano, nitro, carboxamide, amidino or guanidino, $R_5$ may be further optionally substituted by one or more $R_e$;

$R_e$ is C1–10 alkyl, C1–10alkoxyC1–10alkyl, C1–10alkylaminoC1–10alkyl, C1–10alkylthioC1–10 alkyl wherein the sulfur atom may be oxidized to a sulfoxide or sulfone, C1–10 alkoxy, C3–8 cycloalkyl, aryl, tetrahydronaphthyl, indenyl, indanyl, pyrrolidinyl, piperidinyl, morpholinyl, thiomorpholinyl, piperazinyl, indolinyl, thiopyranyl, tetrahydrothiopyranyl, pyranyl, tetrahydropyranyl, tetrahydrofuranyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, benzisoxazolyl, quinolinyl, isoquinolinyl, quinazolinyl, quinoxalinyl, C1–10alkanoyl, aroyl, C1–10alkanoyloxy, aryloxy, benzyloxy, C1–10 alkoxycarbonyl, arylC1–3alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–10 alkoxycarbonylamino, aryloxycarbonylamino, C1–10 alkycarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is halogen, hydroxy, oxo, carboxy, cyano, nitro, carboxamide, amidino or guanidino, $R_e$ may be further optionally substituted by one or more $R_f$;

$R_f$ is C1–5 alkyl, C3–6 cycloalkyl, tolylsulfonyl, C1–5 alkoxy, aryl, aryloxy, benzyloxy, halogen, hydroxy, oxo, carboxy, cyano, nitro, carboxamide, amidino or guanidino;

X is O or S and pharmaceutically acceptable derivatives thereof.

In another embodiment of the invention, there are provided novel compounds of the formula (II) as described immediately above, and wherein:

Het is piperidinyl, pyrrolidinyl, tetrahydropyranyl, tetrahydrothiopyranyl, azetidinyl, azepanyl, oxepanyl, tetrahydrofuranyl, oxetanyl, hexahydropyrimidinyl, hexahydropryidazinyl, piperazinyl, 1,4,5,6-tetrahydropyrimidinyl, octahydro-indolizinyl, octahydro-quinolizinyl, decahydro-quinolinyl, 1,2,3,4-tetrahydro-quinolinyl, dihydro-oxazolyl, 1,2-thiazinanyl-1,1-dioxide, 1,2,6-thiadiazinanyl-1,1-dioxide, isothiazolidinyl-1,1-dioxide, imidazolidinyl, pyrazolidinyl or a bridged bicyclo chosen from aza-bicyclo[3.2.1] octane, aza-bicyclo[2.2.1]heptane, aza-bicyclo[2.2.2] octane, aza-bicyclo[3.2.2]nonane, aza-bicyclo[2.1.1] hexane, aza-bicyclo[3.1.1]heptane, aza-bicyclo[3.3.2] decane and 2-oxa or 2-thia-5-aza-bicyclo[2.2.1]heptane; each ring being substituted with one or more $R_5$;

Y is C(O) or S(O)$_2$;

$R_1$ is a bond, hydrogen, C1–7 alkyl, C1–7 alkoxy, C3–7 cycloalkyl, aryloxy, phenyl, benzyl, naphthyl, tetrahydronaphthyl, C1–7alkylsulfonylC1–7alkyl, C3–7cycloalkylsulfonylC1–7alkyl, arylsulfonylC1–7alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, thiazolyl, imidazolyl, pyridinyl, isoxazolyl, pyrimidinyl, pyrazinyl, pyridazinyl, indolyl, quinolinyl, benzofuranyl, benzthienyl, benzimidazolyl, benzthiazolyl, benzoisoxazolyl, benzoxazolyl or amino; wherein $R_1$ is optionally substituted by one or more $R_a$;

$R_a$ is a bond C1–7 alkyl, C3–6 cycloalkyl, phenyl, naphthyl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl, quinoxalinyl, C1–7 alkoxy, C1–7alkanoyl, C1–7alkanoyloxy, aryloxy, benzyloxy, C1–7 alkoxycarbonyl, aryloxycarbonyl, aroyloxy, carbamoyl wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–7 alkanoylamino, aroylamino, C1–7 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–7 alkoxycarbonylamino, aryloxycarbonylamino, C1–7 alkylcarbamoyloxy, arylcarbamoyloxy, C1–7 alkylsulfonylamino, arylsulfonylamino, C1–7 alkylaminosulfonyl, arylaminosulfonyl, amino wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is halogen, hydroxy, oxo, carboxy, cyano, nitro, carboxamide, amidino or guanidino, $R_a$ may be further optionally substituted by one or more $R_b$;

$R_b$ is C1–5 alkyl, C3–6 cycloalkyl, aryl, C1–5 alkoxy, aryloxy, benzyloxy, halogen, hydroxy, oxo, carboxy, cyano, nitro, carboxamide, amidino or guanidino;

$R_2$ is hydrogen or methyl or ethyl;

$R_3$ is a bond, hydrogen, C1–5 alkyl, C2–5alkylene, C3–7 cycloalkyl, arylC1–3alkyl or aryl wherein $R_3$ is optionally substituted by one or more $R_c$;

$R_c$ is C1–5 alkyl, C3–7 cycloalkyl, aryl, indanyl, indenyl, bicyclo[2.2.1]heptanyl, bicyclo[2.2.2]octanyl, bicyclo [4.1.0]heptanyl, bicyclo[3.1.0]hexanyl, bicyclo[1.1.1] pentanyl, cubanyl, 1,2,3,4-tetrahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, C1–5 alkoxy, aryloxy, C1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–4 alkyl, C1–5 alkoxy, aryloxy, arylC1–5alkoxy, aroyl, halogen, hydroxy, oxo or cyano;

$R_4$ is hydrogen or methyl;

$R_5$ is a bond, hydrogen, carbonyl, C1–8 alkyl, C1–8alkoxyC1–8alkyl, C1–8alkylaminoC1–8alkyl, C1–8alkylthioC1–8alkyl wherein the sulfur atom may be oxidized to a sulfoxide or sulfone, C1–8 alkoxy, aryloxy, C3–7 cycloalkyl, aryl, benzyl, tetrahydronaphthyl, indanyl, heterocyclyl selected from pyrrolidinyl, piperidinyl, morpholinyl, thiomorpholinyl, piperazinyl, indolinyl, pyranyl, tetrahydropyranyl, thiopyranyl, tetrahydrothiopyranyl, furanyl, tetrahydrofuranyl, thienyl, oxazolyl, thiazolyl, imidazolyl, pyridinyl, pyrimidinyl, pyrazinyl, tetrazolyl, triazolyl, pyrazolyl, indolyl, benzofuranyl, benzothienyl, benzimidazolyl, benzthiazolyl, quinolinyl, isoquinolinyl, quinazolinyl, benzoxazolyl and quinoxalinyl, heterocyclyloxy wherein the heterocyclyl moiety is selected from those herein described in this paragraph, C1–7alkanoyl, aroyl, C1–7alkanoyloxy, benzyloxy, C1–7 alkoxycarbonyl, arylC1–4alkoxycarbonyl, aryloxycarbonyl, aroyloxy, carbamoyl wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is C1–7 alkanoylamino, aroylamino, C1–7 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is C1–7 alkoxycarbonylamino, aryloxycarbonylamino, C1–7 alkylcarbamoyloxy, arylcarbamoyloxy, C1–7 alkylsulfonylamino, arylsulfonylamino, C1–7 alkylaminosulfonyl, arylaminosulfonyl, amino wherein the nitrogen atom may be independently mono or di-substituted by C1–7 alkyl, aryl, pyrrolidinyl, piperidinyl, morpholinyl, thiomorpholinyl, piperazinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is halogen, hydroxy, oxy, oxo, carboxy, cyano, nitro or carboxamide, $R_5$ may be further optionally substituted by one or more $R_e$;

$R_e$ is C1–7 alkyl, C1–7alkoxyC1–7alkyl, C1–7alkylaminoC1–7alkyl, C1–7alkylthioC1–7alkyl wherein the sulfur atom may be oxidized to a sulfoxide or sulfone, C1–7 alkoxy, C3–7 cycloalkyl, aryl, tetrahydronaphthyl, indanyl, pyrrolidinyl, piperidinyl, morpholinyl, thiomorpholinyl, piperazinyl, thiopyranyl, tetrahydrothiopyranyl, tetrahydropyranyl, tetrahydrofuranyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl, quinoxalinyl, C1–5 alkanoyl, aroyl, C1–5alkanoyloxy, aryloxy, benzyloxy, C1–5 alkoxycarbonyl, aryloxycarbonyl, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is halogen, hydroxy, oxo, carboxy, cyano, nitro, carboxamide, amidino or guanidino, $R_e$ may be further optionally substituted by one or more $R_f$;

$R_f$ is methyl, ethyl, t-butyl, tolylsulfonyl, C1–3 alkoxy, cyclopropyl, cyclohexyl, phenyl, naphthyl, phenoxy, benzyloxy, fluoro, chloro, bromo, hydroxy, oxo, carboxy, cyano, nitro or carboxamide;

and

X is O.

In yet another embodiment of the invention, there are provided novel compounds of the formula (II) as described immediately above, and wherein:

wherein:

Het is piperidinyl, pyrrolidinyl, azetidinyl, azepanyl, oxepanyl, tetrahydropyranyl, tetrahydrothiopyranyl, tetrahydrofuranyl, oxetanyl, octahydro-indolizinyl, octahydro-quinolizinyl or aza-bicyclo[3.2.1]octanyl, each ring being optionally substituted with one or more $R_5$;

$R_1$ is a bond, C1–5 alkyl, C1–5 alkoxy, C3–6 cycloalkyl, aryloxy, phenyl, benzyl, naphthyl, C1–3alkylsulfonylC1–3alkyl, C3–6cycloalkylsulfonylC1–3alkyl, arylsulfonylC1–3alkyl, pyrrolidinyl, piperidinyl, morpholinyl, thiomorpholinyl, piperazinyl, furanyl, thienyl, oxazolyl, thiazolyl, imidazolyl, pyridinyl, isoxazolyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is a bond, C1–3 alkyl, cyclopropyl, cyclopentyl, cyclohexyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl, benzthiazolyl, benzoxazolyl, C1–3 alkoxy, C1–3alkanoyl, C1–3alkanoyloxy, aryloxy, benzyloxy, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl, piperazinyl, thienyl, oxazolyl, thiazolyl, imidazolyl, pyridinyl, pyrimidinyl, benzimidazolyl or benzthiazolyl, or $R_a$ is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or $R_a$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl, aryl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is C1–3 alkyl, C3–6 cycloalkyl, aryl, C1–3 alkoxy, aryloxy, benzyloxy, halogen, hydroxy, oxo, carboxy, cyano, nitro, carboxamide, amidino or guanidino;

$R_2$ is hydrogen or methyl;

$R_3$ is a bond, hydrogen, C1–5 alkyl, C2–5alkylene, C4–6 cycloalkyl or arylC1–2alkyl wherein $R_3$ is optionally substituted by one or more $R_c$;

$R_c$ is C1–4 alkyl, C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, pyrrolidinyl, piperidinyl, morpholinyl, thiomorpholinyl, indolinyl, fuiranyl, tetrahydrofuranyl, pyranyl, tetrahydropyranyl, thienyl, pyrrolyl, oxazolyl, thiazolyl, imidazolyl, pyrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, C1–4 alkoxy, phenoxy, naphthyloxy, C1–3 alkanoyl, benzoyl, C1–3 alkoxycarbonyl, phenoxycarbonyl, C1–3 alkanoyloxy, benzoyloxy, carbamoyl wherein the nitrogen atom may be independently mono or di-substituted by C1–5 alkyl or aryl, or $R_c$ is C1–3 alkanoylamino, benzoylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–5 alkyl or aryl, or $R_c$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–5 alkyl or aryl, or $R_c$ is halogen, hydroxy, oxo, carboxy, cyano, nitro, amidino or guanidino, $R_c$ may be further optionally substituted by one or more $R_d$;

$R_d$ is C1–3 alkyl, C3–6 cycloalkyl, phenyl, benzyl, C1–3 alkoxy, phenoxy, phenylC1–3alkoxy, benzoyl, halogen, hydroxy, oxo or cyano;

$R_4$ is hydrogen;

$R_5$ is a bond, hydrogen, carbonyl, C1–6 alkyl, C1–6alkoxyC1–6alkyl, C1–6alkylaminoC1–6alkyl, C1–6alkylthioC1–6alkyl wherein the sulfiur atom may be oxidized to a sulfoxide or sulfone, C1–6 alkoxy, phenoxy, naphthyloxy, C3–6 cycloalkyl, phenyl, naphthyl, benzyl, indanyl, heterocyclyl selected from pyrrolidinyl, piperidinyl, morpholinyl, thiomorpholinyl, piperazinyl, tetrahydropyranyl, tetrahydrothiopyranyl, furanyl, tetrahydrofuranyl, thienyl, oxazolyl, thiazolyl, imidazolyl, pyridinyl, pyrimidinyl, pyrazolyl, benzofuranyl, benzothienyl, benzimidazolyl, benzthiazolyl, quinolinyl, isoquinolinyl and benzoxazolyl, heterocyclyloxy wherein the heterocyclyl moiety is selected from those herein described in this paragraph, C1–3alkanoyl, benzoyl, naphthoyl, C1–4alkanoyloxy, benzyloxy, C1–4 alkoxycarbonyl, arylC1–2alkoxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–4 alkanoylamino, aroylamino, C1–4 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, phenyl, naphthyl, pyrrolidinyl, piperidinyl, morpholinyl, piperazinyl, oxazolyl, thiazolyl, imidazolyl, pyridinyl, pyrimidinyl, pyrazinyl, indolyl, benzofuranyl, benzothienyl, benzimidazolyl or benzthiazolyl, or $R_5$ is C1–4 alkoxycarbonylamino, phenoxycarbonylamino, C1–4 alkylcarbamoyloxy, phenylcarbamoyloxy, C1–4 alkylsulfonylamino, phenylsulfonylamino, C1–3 alkylaminosulfonyl, phenylaminosulfonyl, amino wherein the nitrogen atom may be independently mono or di-substituted by C1–4 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzthiazolyl, or $R_5$ is halogen, hydroxy, oxo, carboxy, cyano, nitro or carboxamide, $R_5$ may be further optionally substituted by one or more $R_e$;

$R_e$ is C1–4 alkyl, C1–4 alkoxy, C3–7 cycloalkyl, phenyl, naphthyl, indanyl, pyrrolidinyl, piperidinyl, morpholinyl, thiomorpholinyl, piperazinyl, tetrahydrothiopyranyl, tetrahydropyranyl, tetrahydrofuranyl, thienyl, oxazolyl, thiazolyl, imidazolyl, pyridinyl, pyrimidinyl, pyrazinyl, indolyl, benzimidazolyl, benzthiazolyl, benzoxazolyl, quinolinyl, isoquinolinyl, quinazolinyl, quinoxalinyl, C1–4 alkanoyl, aroyl, C1–4alkanoyloxy, phenoxy, naphthyloxy, benzyloxy, C1–4 alkoxycarbonyl, phenoxycarbonyl, benzoyloxy, carbamoyl wherein the nitrogen atom may be independently mono or di-substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl, or benzthiazolyl, or $R_e$ is C1–4 alkanoylamino, benzoylamino, C1–4 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzthiazolyl, or $R_e$ is C1–4 alkoxycarbonylamino, phenoxycarbonylamino, C1–4 alkylcarbamoyloxy, phenylcarbamoyloxy, C1–4 alkylsulfonylamino, phenylsulfonylamino, C1–4 alkylaminosulfonyl, phenylaminosulfonyl, amino wherein the nitrogen atom may be independently mono or di-substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzthiazolyl, or $R_e$ is halogen, hydroxy, oxo, carboxy, cyano, nitro or carboxamide, $R_e$ may be further optionally substituted by one or more $R_f$;

$R_f$ is methyl, ethyl, t-butyl, tolylsulfonyl, methoxy, cyclopropyl, phenyl, phenoxy, benzyloxy, fluoro, chloro, bromo, hydroxy, oxo, carboxy or carboxamide.

In yet still another embodiment of the invention, there are provided novel compounds of the formula (II) as described immediately above, and wherein:

Het is piperidinyl, pyrrolidinyl, azetidinyl, azepanyl, oxepanyl, tetrahydropyranyl, oxetanyl or tetrahydrothiopyranyl each ring being optionally substituted with one or more $R_5$;

$R_1$ is a bond, C1–5 alkyl, C1–5 alkoxy, C3–6 cycloalkyl, aryloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is a bond, C1–3 alkyl, cyclopropyl, cyclohexyl, phenyl, pyrrolidinyl, piperidinyl, morpholinyl, thiomorpholinyl, piperazinyl, thienyl, imidazolyl, C1–3 alkoxy, C1–3alkanoyl, C1–3alkanoyloxy, aryloxy, benzyloxy, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl or piperazinyl, or $R_a$ is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or $R_a$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl, aryl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is methyl, ethyl, n-propyl, i-propyl, cyclopropyl, cyclopentyl, cyclohexyl, phenyl, methoxy, ethoxy, n-propoxy, i-propoxy, phenoxy, benzyloxy, fluoro, chloro, bromo, iodo, hydroxy, oxo, carboxy, cyano, nitro or carboxamide;

$R_2$ is hydrogen;

$R_3$ is a bond, C1–3 alkyl, C2–4alkylene, C5–6 cycloalkyl, benzyl or naphthylmethyl wherein $R_3$ is optionally substituted by one or more $R_c$;

$R_c$ is C1–3 alkyl, C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, furanyl, tetrahydropyranyl, thienyl, oxazolyl, thiazolyl, imidazolyl, pyrimidinyl, indolyl, benzofuranyl, benzothienyl, benzthiazolyl, C1–3 alkoxy, phenoxy, naphthyloxy, C1–2 alkanoyl, benzoyl, C1–2 alkoxycarbonyl, phenoxycarbonyl, C1–2alkanoyloxy, benzoyloxy, carbamoyl wherein the nitrogen atom may be independently mono or di-substituted by C1–3 alkyl or aryl, or $R_c$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl or aryl, or $R_c$ is C1–2 alkoxycarbonylamino, phenoxycarbonylamino, C1–2 alkylcarbamoyloxy, arylcarbamoyloxy, C1–2 alkylsulfonylamino, phenylsulfonylamino, C1–2alkylaminosulfonyl, phenylaminosulfonyl, amino wherein the nitrogen atom may be independently mono or di-substituted by C1–3 alkyl or phenyl, or $R_c$ is halogen, hydroxy, oxo, carboxy or cyano, $R_c$ may be further optionally substituted by one or more $R_d$;
 $R_d$ is methyl, cyclopropyl, cyclohexyl, phenyl, benzyl, methoxy, phenoxy, benzyloxy, benzoyl, fluoro, chloro, oxo or cyano;

$R_5$ is a bond, hydrogen, carbonyl, C1–5 alkyl, C1–5alkoxyC1–5alkyl, C1–5alkylaminoC1–5alkyl, C1–5alkylthioC1–5alkyl wherein the sulfur atom may be oxidized to a sulfoxide or sulfone, C1–5 alkoxy, phenoxy, C3–6 cycloalkyl, phenyl, naphthyl, benzyl, indanyl, heterocyclyl selected from pyrrolidinyl, piperidinyl, morpholinyl, thiomorpholinyl, piperazinyl, tetrahydropyranyl, oxazolyl, thiazolyl, imidazolyl, pyridinyl, pyrimidinyl, benzimidazolyl and benzthiazolyl, heterocyclyloxy wherein the heterocyclyl moiety is selected from those herein described in this paragraph, C1–3alkanoyl, benzoyl, naphthoyl, C1–3alkanoyloxy, benzyloxy, C1–3 alkoxycarbonyl, benzyloxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–3 alkanoylamino, aroylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzofuranyl, benzothienyl, benzimidazolyl or benzthiazolyl, or $R_5$ is C1–3 alkoxycarbonylamino, phenoxycarbonylamino, C1–3 alkylcarbamoyloxy, phenylcarbamoyloxy, C1–3 alkylsulfonylamino, phenylsulfonylamino, C1–3 alkylaminosulfonyl, phenylaminosulfonyl, amino wherein the nitrogen atom may be independently mono or di-substituted by C1–3 alkyl, phenyl, pyrrolidinyl, piperidinyl, morpholinyl, thiomorpholinyl, piperazinyl, oxazolyl, thiazolyl, imidazolyl, pyridinyl, pyrimidinyl, benzimidazolyl or benzthiazolyl, or $R_5$ is halogen, hydroxy, oxo, carboxy, cyano or carboxamide, $R_5$ may be further optionally substituted by one or more $R_e$;

$R_e$ is C1–3 alkyl, C1–3 alkoxy, C3–7 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzthiazolyl, benzoxazolyl, C1–3 alkanoyl, aroyl, C1–3alkanoyloxy, phenoxy, benzyloxy, C1–3 alkoxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is C1–3 alkanoylamino, benzoylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is C1–3 alkoxycarbonylamino, phenoxycarbonylamino, C1–3 alkylcarbamoyloxy, phenylcarbamoyloxy, C1–3 alkylsulfonylamino, phenylsulfonylamino, C1–3 alkylaminosulfonyl, phenylaminosulfonyl, amino wherein the nitrogen atom may be independently mono or di-substituted by C1–3 alkyl, phenyl, naphthyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is halogen, hydroxy, oxo, carboxy, cyano or carboxamide, $R_e$ may be further optionally substituted by one or more $R_f$; and
 $R_f$ is methyl, phenyl, tolylsulfonyl, methoxy, phenoxy, benzyloxy, fluoro, chloro, bromo, hydroxy, oxo, carboxy or carboxamide.

In yet still another embodiment of the invention, there are provided novel compounds of the formula (II) as described immediately above, and wherein:

Het is piperidinyl, pyrrolidinyl, azetidinyl, azepanyl or tetrahydropyranyl each ring being substituted with one or more $R_5$;

Y is C(O);

$R_1$ is a bond, methyl, ethyl, i-propyl, methoxy, ethoxy, cyclopropyl, cyclopentyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein $R_1$ is optionally substituted by one or more $R_a$;

$R_a$ is a bond, methyl, ethyl, cyclopropyl, phenyl, pyrrolidinyl, piperidinyl, morpholinyl, thiomorpholinyl, piperazinyl, thienyl, imidazolyl, methoxy, acetyl, acetoxy, phenoxy, benzyloxy, methoxycarbonyl, phenoxycarbonyl, benzoyloxy, carbamoyl wherein the nitrogen atom may be independently mono or di-substituted by methyl, ethyl or phenyl, or $R_a$ is acetylamino, benzoylamino, methylthio, phenylthio wherein the sulfur atom may be oxidized to a sulfoxide or sulfone, ureido wherein either nitrogen atom may be independently substituted by methyl, ethyl or phenyl, or $R_a$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl or phenyl, or $R_a$ is fluoro, chloro, bromo, iodo, hydroxy, oxo, carboxy, cyano, nitro or carboxamide, $R_a$ may be further optionally substituted by one or more $R_b$;

$R_b$ is methyl, cyclopropyl, phenyl, methoxy, phenoxy, benzyloxy, fluoro, chloro, hydroxy, oxo, carboxy or carboxamide;

$R_3$ is a bond, C1–3 alkyl, C2–4alkylene, C5–6 cycloalkyl, benzyl or naphthylmethyl wherein $R_3$ is optionally substituted by one or more $R_c$;

$R_c$ is methyl, ethyl, n-propyl, i-propyl, C5–6 cycloalkyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, thienyl, oxazolyl, thiazolyl, indolyl, benzofuranyl, benzothienyl, benzthiazolyl, methoxy, ethoxy, phenoxy, acetyl, benzoyl, methoxycarbonyl, phenoxycarbonyl, acetoxy, benzoyloxy, carbamoyl wherein the nitrogen atom may be independently mono or di-substituted by methyl, ethyl or aryl, or $R_c$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or aryl, or $R_c$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_c$ is fluoro, chloro or oxo, $R_c$ may be further optionally substituted by one or more $R_d$;

$R_d$ is methyl, cyclopropyl, phenyl, methoxy, fluoro, chloro or oxo;

$R_5$ is a bond, hydrogen, carbonyl, C1–4 alkyl, C1–4alkoxyC1–4alkyl, C1–4alkylaminoC1–4alkyl, C1–4alkylthioC1–4alkyl wherein the sulfur atom may be oxidized to a sulfoxide or sulfone, C1–4 alkoxy,phenoxy, cyclopropyl, cyclopentyl, cyclohexyl, phenyl, naphthyl, benzyl, indanyl, heterocyclyl selected from pyrrolidinyl, piperidinyl, morpholinyl, piperazinyl, tetrahydropyranyl, oxazolyl, thiazolyl, imidazolyl, pyridinyl, pyrimidinyl, benzimidazolyl and benzthiazolyl, heterocyclyloxy wherein the heterocyclyl moiety is selected from those herein described in this paragraph, C1–2alkanoyl, benzoyl, naphthoyl, C1–2alkanoyloxy, benzyloxy, C1–2 alkoxycarbonyl, benzyloxycarbonyl, phenoxycarbonyl, benzoyloxy, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_5$ is C1–2 alkoxycarbonylamino, phenoxycarbonylamino, C1–2 alkylcarbamoyloxy, phenylcarbamoyloxy, C1–2 alkylsulfonylamino, phenylsulfonylamino, C1–2 alkylaminosulfonyl, phenylaminosulfonyl, amino wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_5$ is fluoro, chloro, bromo, hydroxy, oxo, carboxy or carboxamide, $R_5$ may be further optionally substituted by one or more $R_e$;

$R_e$ is C1–3 alkyl, C1–2 alkoxy, C3–6 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzthiazolyl, benzoxazolyl, C1–2 alkanoyl, aroyl, C1–2alkanoyloxy, phenoxy, benzyloxy, C1–2 alkoxycarbonyl, phenoxycarbonyl, benzoyloxy, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is C1–2 alkoxycarbonylamino, phenoxycarbonylamino, C1–2 alkylcarbamoyloxy, phenylcarbamoyloxy, C1–2 alkylsulfonylamino, phenylsulfonylamino, C1–2 alkylaminosulfonyl, phenylaminosulfonyl, amino wherein the nitrogen atom may be independently mono or di-substituted by C1–2 alkyl, phenyl, naphthyl, pyrrolidinyl, piperidinyl, morpholinyl, piperazinyl, oxazolyl, thiazolyl, imidazolyl, pyridinyl or pyrimidinyl, or $R_e$ is fluoro, chloro, bromo, hydroxy, oxo, carboxy or carboxamide, $R_e$ may be further optionally substituted by one or more $R_f$; and $R_f$ is methyl, phenyl, tolylsulfonyl, methoxy, phenoxy, benzyloxy, fluoro, chloro, hydroxy, oxo, carboxy or carboxamide.

In yet a further embodiment of the invention, there are provided novel compounds of the formula (II) as described immediately above, and wherein:

Het is piperidin-4-yl, piperidin-3-yl, pyrrolidin-3-yl, azetidin-3-yl, azepan-3-yl, azepan-4-yl or tetrahydropyran-4-yl, each ring being optionally substituted with one or more $R_5$;

$R_1$ is a bond, methyl, ethyl, i-propyl, methoxy, cyclopropyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein $R_1$ is optionally substituted by one or more $R_a$;

$R_a$ is methyl, phenyl, thienyl, methoxy, acetyl, acetoxy, phenoxy, benzyloxy, methoxycarbonyl, benzoyloxy, carbamoyl wherein the nitrogen atom may be independently mono or di-substituted by methyl or phenyl, or $R_a$ is acetylamino, methylthio, phenylthio wherein the sulfur atom may be oxidized to a sulfoxide or sulfone, ureido wherein either nitrogen atom may be independently substituted by methyl or phenyl, or $R_a$ is methoxycarbonylamino, methylcarbamoyloxy, phenylcarbamoyloxy, methylsulfonylamino, phenylsulfonylamino, amino wherein the nitrogen atom may be independently mono or di-substituted by methyl or phenyl, or $R_a$ is fluoro, chloro, hydroxy, oxo, carboxy, cyano or carboxamide;

$R_3$ is a bond, methyl, ethyl, n-propyl, propenyl, butenyl, i-butenyl, cyclohexyl, benzyl or naphthylmethyl wherein $R_3$ is optionally substituted by one or more $R_c$;

$R_c$ is methyl, ethyl, n-propyl, i-propyl, cyclohexyl, cyclopentyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, methoxy, phenoxy, acetyl, benzoyl, methoxycarbonyl, phenoxycarbonyl, acetoxy, benzoyloxy, methylthio wherein the sulfur atom may be oxidized to a sulfoxide or sulfone, phenylthio wherein the sulfur atom may be oxidized to a sulfoxide or sulfone, fluoro, chloro or oxo;

$R_5$ is a bond, hydrogen, carbonyl, C1–4 alkyl, C1–2alkoxyC1–2alkyl, C1–2alkylaminoC1–2alkyl, C1–2alkylthioC1–2alkyl wherein the sulfur atom may be oxidized to a sulfoxide or sulfone, C1–2 alkoxy, phenoxy, cyclopropyl, cyclopentyl, cyclohexyl, phenyl, benzyl, heterocyclyl selected from pyrrolidinyl, piperidinyl, morpholinyl, tetrahydropyranyl, pyridinyl, and pyrimidinyl, heterocyclyloxy wherein the heterocyclyl moiety is selected from those herein described in this paragraph, acetyl, benzoyl, acetyloxy, benzyloxy, methoxycarbonyl, ethoxycarbonyl, benzyloxycarbonyl, benzoyloxy, carbamoyl wherein the nitrogen atom may be independently mono or di-substituted by methyl, ethyl or phenyl, or $R_5$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or phenyl, or $R_5$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_5$ is fluoro, chloro, hydroxy, oxo, carboxy or carboxamide, $R_5$ may be further optionally substituted by one or more $R_e$;

$R_e$ is methyl, methoxy, ethoxy, cyclopropyl, cyclopentyl, cyclohexyl, phenyl, naphthyl, indanyl, piperidinyl, morpholinyl, indolyl, thienyl, pyridinyl, acetyl, benzoyl, acetyloxy, phenoxy, benzyloxy, methoxycarbonyl, ethoxycarbonyl, carbamoyl wherein the nitrogen atom may be independently mono or di-substituted by methyl, ethyl or phenyl, or $R_e$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or phenyl, or $R_e$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_e$ is fluoro, chloro, hydroxy, oxo, carboxy or carboxamide, $R_e$ may be further optionally substituted by one or more $R_f$; and $R_f$ is methyl, phenyl, tolylsulfonyl, phenoxy, benzyloxy, fluoro, chloro or oxo.

In yet still a further embodiment of the invention, there are provided novel compounds of the formula (II) as described immediately above, and wherein:

Het is piperidin-4-yl, piperidin-3-yl, pyrrolidin-3-yl, azetidin-3-yl or tetrahydropyran-4-yl, each ring being substituted with one or more $R_5$;

$R_1$ is i-propyl, benzyloxy, cyclohexyl, phenyl, 4-(acetylamino)-phenyl, 4-(methanesulfonylamino)-phenyl, 4-methoxyphenyl, 3-phenoxyphenyl, 4-chlorophenyl, 4-fluorophenyl, 2-fluorophenyl, 2-fluoro-4-chlorophenyl, naphthyl, thienylmethyl, piperidinyl, morpholinyl, pyrrolidinyl, piperazinyl, furanyl, thienyl, 5-chlorothienyl, pyridin-4-yl, pyrazinyl, methylamino, ethylamino, dimethylamino or diethylamino;

$R_3$ is ethyl, n-propyl, propenyl, butenyl, i-butenyl, benzyl or naphthylmethyl wherein $R_3$ is optionally substituted by one or more $R_c$;

$R_c$ is methyl, cyclohexyl, cyclopentyl, indanyl, 1,2,3,4-tetrahydronaphthyl, methoxy, methylthio wherein the sulfur atom may be oxidized to a sulfoxide or sulfone, fluoro or chloro;

$R_5$ is a bond, carbonyl, methyl, ethyl, n-propyl, n-butyl, t-butyl, i-propyl, i-butyl, cyclopropyl, cyclopentyl, cyclohexyl, phenyl, benzyl, piperidinyl, tetrahydropyranyl, pyrimidinyl, acetyl, benzoyl, ethoxycarbonyl, benzyloxycarbonyl, methylsulfonylamino, phenylsulfonylamino, methylamino, dimethylamino, fluoro, oxo or carboxy, $R_5$ may be further optionally substituted by one or more $R_e$;

$R_e$ is methyl, cyclopropyl, cyclopentyl, cyclohexyl, phenyl, naphthyl, indanyl, thienyl, 5-methylthienyl, methoxy, phenoxy, benzyloxy, piperidinyl, pyridinyl, indolyl, 1-(tolyl-sulfonyl)-indolyl, carbamoyl wherein the nitrogen atom may be independently mono or di-substituted by methyl, phenyl or benzyl, or $R_e$ is hydroxy, fluoro, chloro, oxo, dimethylamino or trifluoromethyl;

In yet another embodiment of the invention, there are provided novel compounds of the formula (II) as described immediately above, and wherein:

Het is piperidin-4-yl, piperidin-3-yl, pyrrolidin-3-yl or azetidin-3-yl, each ring being substituted with one or more $R_5$;

$R_1$ is phenyl, 4-(acetylamino)-phenyl, 4-(methanesulfonylamino)-phenyl, 3-phenoxyphenyl, 4-chlorophenyl, 4-fluorophenyl, thienylmethyl, morpholinyl, pyrrolidinyl, piperidinyl, piperazinyl, 5-chlorothienyl, pyridin-4-yl or pyrazinyl;

$R_3$ is n-butyl, i-butyl, 2,2-dimethylpropyl, cyclohexylmethyl, propenyl, i-butenyl, 4-methoxybenzyl, 4-chlorobenzyl, 3,4-dichlorobenzyl, 3-chlorobenzyl, 2,4-dichlorobenzyl, 4-methylbenzyl, 3-methylbenzyl or naphth-2-ylmethyl; wherein the configuration at the stereocenter defined by $R_2$ and $R_3$ when they are different and the carbon they are attached to is defined as L; and $R_5$ is a bond, methyl, ethyl, n-propyl, n-butyl, n-pentyl, 2-pentyl, 3-pentyl, phenethyl, phenpropyl, 2,2-dimethylpropyl, t-butyl, i-propyl, i-butyl, cyclopropyl, cyclopentyl, cyclohexyl, cyclopropylmethyl, cyclopentylmethyl, cyclohexylmethyl, phenyl, benzyl, naphthylmethyl, indanylmethyl, pyridinylmethyl, indolylmethyl, thienylmethyl, 5-methylthienylmethyl, piperidinyl, piperidinylcarbonyl, pyridinylcarbonyl, tetrahydropyranyl, pyrimidinyl, acetyl, benzoyl, ethoxycarbonyl, benzyloxycarbonyl, t-butoxycarbonyl, methylcarbamoyl, phenylcarbamoyl, benzylcarbamoyl, methylsulfonylamino, phenylsulfonylamino, methylamino, dimethylamino, methylcyclohexyl, methylbenzyl, methoxybenzyl, phenoxybenzyl, benzyloxybenzyl, N-[(4-methylphenyl)-sulfonyl]- indolylmethyl, fluorobenzyl, difluorobenzyl, chlorobenzyl, N,N-dimethylaminoacetyl, trifluoromethylbenzyl, fluoro, oxo or carboxy.

Another embodiment of the invention provides for the following compounds of the formulas (I) and (II) above which have demonstrated potent inhibition of Cathepsin S in a cell based assay at concentrations of 15 uM or less.

Morpholine-4-carboxylic acid [1-(4-cyano-tetrahydro-pyran-4-ylcarbamoyl)-2-cyclohexyl-ethyl]-amide;
Morpholine-4-carboxylic acid [1-(4-cyano-1-methyl-piperidin-4-ylcarbamoyl)-2-cyclohexyl-ethyl]-amide;
4-Acetylamino-N-[1-(4-cyano-1-methyl-piperidin-4-ylcarbamoyl)-2-cyclohexyl-ethyl]-benzamide;
4-Acetylamino-N-[1-(4-cyano-1-methyl-piperidin-4-ylcarbamoyl)-3,3-dimethyl-butyl]-benzamide;
Morpholine-4-carboxylic acid [1-(4-cyano-1-methyl-piperidin-4-ylcarbamoyl)-3,3-dimethyl-butyl]-amide;
4-Cyano-4-{3-cyclohexyl-2-[(morpholine-4-carbonyl)-amino]-propionylamino}-piperidine-1-carboxylic acid t-butyl ester;
4-Cyano-4-{3-cyclohexyl-2-[(morpholine-4-carbonyl)-amino]-propionylamino}-piperidine-1-carboxylic acid ethyl ester;
Morpholine-4-carboxylic acid [1-(1-benzyl-4-cyano-piperidin-4-ylcarbamoyl)-2-cyclohexyl-ethyl]-amide;
Morpholine-4-carboxylic acid [1-(4-cyano-piperidin-4-ylcarbamoyl)-2-cyclohexyl-ethyl]-amide hydrochloride;
Morpholine-4-carboxylic acid {1-[4-cyano-1-(1-methyl-ethyl)-piperidin-4-ylcarbamoyl]-2-cyclohexyl-ethyl}-amide;
Morpholine-4-carboxylic acid [1-(4-cyano-1-phenethyl-piperidin-4-ylcarbamoyl)-2-cyclohexyl-ethyl]-amide;
Morpholine-4-carboxylic acid {1-[3-cyano-1-benzyl-pyrrolidin-3-ylcarbamoyl]-2-cyclohexyl-ethyl}-amide;
Morpholine-4-carboxylic acid [1-(4-cyano-1-propyl-piperidin-4-ylcarbamoyl)-2-cyclohexyl-ethyl]-amide;
4-Cyano-4-{3-cyclohexyl-2-[(morpholine-4-carbonyl)-amino]-propionylamino}-piperidine-1-carboxylic acid benzyl ester;
Morpholine-4-carboxylic acid [1-(4-cyano-1-isopropyl-piperidin-4-ylcarbamoyl)-3,3-dimethyl-butyl]-amide;
Morpholine-4-carboxylic acid [1-(1-phenethyl-4-cyano-piperidin-4-ylcarbamoyl)-3,3-dimethyl-butyl]-amide;
Morpholine-4-carboxylic acid [1-(1-n-propyl-4-cyano-piperidin-4-ylcarbamoyl)-3,3-dimethyl-butyl]-amide;
Morpholine-4-carboxylic acid [1-(1-benzyl-4-cyano-piperidin-4-ylcarbamoyl)-3,3-dimethyl-butyl]-amide;
Morpholine-4-carboxylic acid [1-(4-cyano-tetrahydro-thiopyran-4-ylcarbamoyl)-2-cyclohexyl-ethyl]-amide;
Morpholine-4-carboxylic acid {1-[4-cyano-1-(2-dimethylamino-acetyl)-piperidin-4-ylcarbamoyl]-2-cyclohexyl-ethyl}-amide;
4-Cyano-4-{3-cyclohexyl-2-[({4-acetylamino}-phenyl-1-carbonyl)-amino]-propionylamino}-piperidine-1-carboxylic acid ethyl ester;
Morpholine-4-carboxylic acid [1-(3-cyano-1-pyrimidin-2-yl-piperidin-3-ylcarbamoyl)-2-cyclohexyl-ethyl]-amide;
4-Cyano-4-{4,4-dimethyl-2-[(morpholine-4-carbonyl)-amino]-propionylamino}-piperidine-1-carboxylic acid benzyl ester;
4-Acetylamino-N-[1-(1-benzyl-4-cyano-piperidin-4-ylcarbamoyl)-2-cyclohexyl-ethyl]-benzamide;
4-Acetylamino-N-[1-(4-cyano-1-isopropyl-piperidin-4-ylcarbamoyl)-2-cyclohexyl-ethyl]-benzamide;
Morpholine-4-carboxylic acid [1-(1-benzyl-3-cyano-pyrrolidin-3-ylcarbamoyl)-2-cyclohexyl-ethyl]-amide;
4-Cyano-4-{3-cyclohexyl-2-[({4-acetylamino}-phenyl-1-carbonyl)-amino]-propionylamino}-piperidine-1-carboxylic acid benzyl ester;
N-[1-(4-cyano-1-methyl-piperidin-4-ylcarbamoyl)-2-cyclohexyl-ethyl]-benzamide;
Morpholine-4-carboxylic acid [1-(1-carbamimidoyl-4-cyano-piperidin-4-ylcarbamoyl)-2-cyclohexyl-ethyl]-amide p-toluenesulfonate;
4-Acetylamino-N-[1-(4-cyano-1-phenethyl-piperidin-4-ylcarbamoyl)-2-cyclohexyl-ethyl]-benzamide;
4-(Acetylamino-methyl)-N-[1-(4-cyano-1-methyl-piperidin-4-ylcarbamoyl)-2-cyclohexyl-ethyl]-benzamide;
4-Cyano-4-{4,4-dimethyl-2-[(morpholine-4-carbonyl)-amino]-pentanoylamino}-piperidine-1-carboxylic acid ethyl ester;
Morpholine-4-carboxylic acid [1-(1-acetyl-4-cyano-piperidin-4-ylcarbamoyl)-3,3-dimethyl-butyl]-amide;
Morpholine-4-carboxylic acid [1-(1-benzoyl-4-cyano-piperidin-4-ylcarbamoyl)-3,3-dimethyl-butyl]-amide;
3-Cyano-3-{3-cyclohexyl-2-[(morpholine-4-carbonyl)-amino]-propionylamino}-pyrrolidine-1-carboxylic acid benzyl ester;
N-[1-(4-cyano-1-methyl-piperidin-4-ylcarbamoyl)-2-cyclohexyl-ethyl]-isonicotinamide;
Pyrazine-2-carboxylic acid [1-(4-cyano-1-methyl-piperidin-4-ylcarbamoyl)-2-cyclohexyl-ethyl]-amide;
Morpholine-4-carboxylic acid [1-(1-acetyl-4-cyano-piperidin-4-ylcarbamoyl)-2-cyclohexyl-ethyl]-amide;
Morpholine-4-carboxylic acid [1-(1-benzoyl-4-cyano-piperidin-4-ylcarbamoyl)-2-cyclohexyl-ethyl]-amide;
Morpholine-4-carboxylic acid {1-[3-cyano-1-(2-chloro-benzyl)-pyrrolidin-3-ylcarbamoyl]-2-cyclohexyl-ethyl}-amide;
5-Chloro-thiophene-2-carboxylic acid [1-(4-cyano-1-methyl-piperidin-4-ylcarbamoyl)-2-cyclohexyl-ethyl]-amide;
4-Chloro-N-[1-(4-cyano-1-methyl-piperidin-4-ylcarbamoyl)-2-cyclohexyl-ethyl]-benzamide;
Morpholine-4-carboxylic acid [1-(4-cyano-1-phenylcarbamoyl-piperidin-4-ylcarbamoyl)-3,3-dimethyl-butyl]-amide;
Morpholine-4-carboxylic acid [1-(1-benzylcarbamoyl-4-cyano-piperidin-4-ylcarbamoyl)-3,3-dimethyl-butyl]-amide;
N-[1-(4-cyano-1-methyl-piperidin-4-ylcarbamoyl)-2-cyclohexyl-ethyl]-4-methanesulfonylamino-benzamide;
N-[1-(4-cyano-1-methyl-piperidin-4-ylcarbamoyl)-2-cyclohexyl-ethyl]-3-phenoxy-benzamide;
N-[1-(1-Benzyl-3-cyano-pyrrolidin-3-ylcarbamoyl)-2-cyclohexyl-ethyl-ethyl]-isonicotinamide;
Pyrazine-2-carboxylic acid [1-(1-benzyl-3-cyano-pyrrolidin-3-ylcarbamoyl)-2-cyclohexyl-ethyl]-amide;
N-(1-Benzyl-3-cyano-pyrrolidin-3-yl)-3-cyclohexyl-2-(2-thiophen-2-yl-acetylamino)propionamide;
5-Chloro-thiophene-2-carboxylic acid [1-(1-benzyl-3-cyano-pyrrolidin-3-ylcarbamoyl)-2-cyclohexyl-ethyl]-amide;
Morpholine-4-carboxylic acid {1-[3-cyano-1-(cyclohexyl-methyl)-pyrrolidin-3-ylcarbamoyl]-2-cyclohexyl-ethyl}-amide;
N-[1-(1-Benzyl-3-cyano-pyrrolidin-3-ylcarbamoyl)-2-cyclohexyl-ethyl]-3-phenoxy-benzamide;
Morpholine-4-carboxylic acid [1-(3-cyano-1-benzyl-pyrrolidin-3-ylcarbamoyl)-3,3-dimethyl-butyl]-amide;
N-[1-(1-Benzyl-3-cyano-pyrrolidin-3-ylcarbamoyl)-2-cyclohexyl-ethyl]-4-chloro-benzamide;
N-[1-(1-Benzyl-3-cyano-pyrrolidin-3-ylcarbamoyl)-3,3-dimethyl-butyl]-benzamide;
Pyrazine-2-carboxylic acid [1-(1-benzyl-3-cyano-pyrrolidin-3-ylcarbamoyl)-3,3-dimethyl-butyl]-amide;

Morpholine-4-carboxylic acid {1-[3-cyano-1-(1-methyl-ethyl)-pyrrolidin-3-ylcarbamoyl]-2-cyclohexyl-ethyl}-amide;
N-[1-(1-benzyl-3-cyano-pyrrolidin-3-ylcarbamoyl)-3,3-dimethyl-butyl]-4-methanesulfonylamino-benzamide;
Morpholine-4-carboxylic acid {1-[3-cyano-1-(3-benzyloxy-benzyl)-pyrrolidin-3-ylcarbamoyl]-2-cyclohexyl-ethyl}-amide;
N-[1-(1-Benzyl-3-cyano-pyrrolidin-3-ylcarbamoyl)-2-cyclohexyl-ethyl]-benzamide;
N-[1-(1-Benzyl-3-cyano-pyrrolidin-3-ylcarbamoyl)-2-cyclohexyl-ethyl]-4-methanesulfonylamino-benzamide;
Morpholine-4-carboxylic acid {1-[3-cyano-1-(2-benzyloxy-benzyl)-pyrrolidin-3-ylcarbamoyl]-2-cyclohexyl-ethyl}-amide;
N-[1-(4-cyano-1-methyl-piperidin-4-ylcarbamoyl)-3,3-dimethyl-butyl]-benzamide;
Morpholine-4-carboxylic acid {1-[3-cyano-1-(3,5-difluoro-benzyl)-pyrrolidin-3-ylcarbamoyl]-2-cyclohexyl-ethyl}-amide;
Morpholine-4-carboxylic acid {1-[3-cyano-1-(2,6-difluoro-benzyl)-pyrrolidin-3-ylcarbamoyl]-2-cyclohexyl-ethyl}-amide;
Morpholine-4-carboxylic acid {1-[3-cyano-1-(3-trifluoromethyl-benzyl)-pyrrolidin-3-ylcarbamoyl]-2-cyclohexyl-ethyl}-amide;
N-[1-(4-cyano-1-methyl-piperidin-4-ylcarbamoyl)-2-cyclohexyl-ethyl]-2-fluoro-benzamide;
4-Chloro-N-[1-(4-cyano-1-methyl-piperidin-4-ylcarbamoyl)-2-cyclohexyl-ethyl]-2-fluoro-benzamide;
N-[1-(4-cyano-1-methyl-piperidin-4-ylcarbamoyl)-2-cyclohexyl-ethyl]-4-methoxy-benzamide;
N-[1-(4-cyano-1-methyl-piperidin-4-ylcarbamoyl)-2-cyclohexyl-ethyl]-4-fluoro-benzamide;
N-[1-(4-cyano-1-methyl-piperidin-4-ylcarbamoyl)-3,3-dimethyl-butyl]-4-methanesulfonylamino-benzamide;
Morpholine-4-carboxylic acid {1-[3-cyano-1-(3-phenoxy-benzyl)-pyrrolidin-3-ylcarbamoyl]-2-cyclohexyl-ethyl}-amide;
Morpholine-4-carboxylic acid [1-(3-cyano-1-cyclohexyl-pyrrolidin-3-ylcarbamoyl)-2-cyclohexyl-ethyl]-amide;
Morpholine-4-carboxylic acid {1-[3-cyano-1-(1-methyl-piperidine-4-yl)-pyrrolidin-3-ylcarbamoyl]-2-cyclohexyl-ethyl}-amide;
Morpholine-4-carboxylic acid [1-(3-cyano-1-ethyl-pyrrolidin-3-ylcarbamoyl)-2-cyclohexyl-ethyl]-amide;
Morpholine-4-carboxylic acid [1-(3-cyano-1-methyl-pyrrolidin-3-ylcarbamoyl)-2-cyclohexyl-ethyl]-amide;
Morpholine-4-carboxylic acid {1-[3-cyano-1-(3-methyl-benzyl)-pyrrolidin-3-ylcarbamoyl]-2-cyclohexyl-ethyl}-amide;
Morpholine-4-carboxylic acid {1-[3-cyano-1-(2-phenoxy-benzyl)-pyrrolidin-3-ylcarbamoyl]-2-cyclohexyl-ethyl}-amide;
Morpholine-4-carboxylic acid {1-[3-cyano-1-(2-methyl-pent-2-enyl)-pyrrolidin-3-ylcarbamoyl]-2-cyclohexyl-ethyl}-amide;
Morpholine-4-carboxylic acid {1-[3-cyano-1-(4-fluoro-benzyl)-pyrrolidin-3-ylcarbamoyl]-2-cyclohexyl-ethyl}-amide;
Morpholine-4-carboxylic acid {1-[3-cyano-1-(2,4,6-trimethyl-benzyl)-pyrrolidin-3-ylcarbamoyl]-2-cyclohexyl-ethyl}-amide;
Morpholine-4-carboxylic acid {1-[3-cyano-1-(1H-indol-3-ylmethyl)-pyrrolidin-3-ylcarbamoyl]-2-cyclohexyl-ethyl}-amide;
Morpholine-4-carboxylic acid [1-(3-cyano-1-cyclopropyl-pyrrolidin-3-ylcarbamoyl)-2-cyclohexyl-ethyl]-amide;
Morpholine-4-carboxylic acid {1-[3-cyano-1-(1-pyridin-3-ylmethyl)-pyrrolidin-3-ylcarbamoyl]-2-cyclohexyl-ethyl}-amide;
Pyrrolidine-1-carboxylic acid [1-(1-benzyl-3-cyano-pyrrolidin-3-ylcarbamoyl)-2-cyclohexyl-ethyl]-amide;
Morpholine-4-carboxylic acid [1-(1-benzyl-3-cyano-1-oxy-pyrrolidin-3-ylcarbamoyl)-2-cyclohexyl-ethyl]-amide;
Isoxazole-5-carboxylic acid [1-(1-benzyl-3-cyano-pyrrolidin-3-ylcarbamoyl)-3,3-dimethyl-butyl]-amide;
Morpholine-4-carboxylic acid [1-(3-cyano-1-cyclohexylmethyl-pyrrolidin-3-ylcarbamoyl)-3,3-dimethyl-butyl]-amide;
Morpholine-4-carboxylic acid [1-(3-cyano-1-isobutyl-pyrrolidin-3-ylcarbamoyl)-2-cyclohexyl-ethyl]-amide;
1H-Imidazole-4-carboxylic acid [1-(1-benzyl-3-cyano-pyrrolidin-3-ylcarbamoyl)-3,3-dimethyl-butyl]-amide;
Morpholine-4-carboxylic acid {1-[3-cyano-1-(5,5-dimethyl-3-oxo-cyclohex-1-enyl)-pyrrolidin-3-ylcarbamoyl]-2-cyclohexyl-ethyl}-amide;
Morpholine-4-carboxylic acid [1-(3-cyano-1-isopropyl-pyrrolidin-3-ylcarbamoyl)-3,3-dimethyl-butyl]-amide;
Morpholine-4-carboxylic acid [1-(3-cyano-1-isobutyl-pyrrolidin-3-ylcarbamoyl)-3,3-dimethyl-butyl]-amide;
Morpholine-4-carboxylic acid {1-[3-cyano-1-(1-ethyl-propyl)-pyrrolidin-3-ylcarbamoyl]-2-cyclohexyl-ethyl}-amide;
Morpholine-4-carboxylic acid {1-[3-cyano-1-(1-ethyl-propyl)-pyrrolidin-3-ylcarbamoyl]-3,3-dimethyl-butyl}-amide;
Morpholine-4-carboxylic acid [1-(3-cyano-1-phenethyl-pyrrolidin-3-ylcarbamoyl)-2-cyclohexyl-ethyl]-amide;
Morpholine-4-carboxylic acid [1-(3-cyano-1-cyclopropylmethyl-pyrrolidin-3-ylcarbamoyl)-2-cyclohexyl-ethyl]-amide;
Morpholine-4-carboxylic acid [1-(3-cyano-1-methyl-piperidin-3-ylcarbamoyl)-2-cyclohexyl-ethyl]-amide;
Morpholine-4-carboxylic acid [1-(1-benzyl-3-cyano-azetidin-3-ylcarbamoyl)-2-cyclohexyl-ethyl]-amide;
4-Cyano-4-{3-cyclohexyl-2-[(4-methyl-piperazine-1-carbonyl)-amino]-propionylamino}-piperidine-1-carboxylic acid ethyl ester;
Morpholine-4-carboxylic acid [1-(3-cyano-1-propyl-pyrrolidin-3-ylcarbamoyl)-3,3-dimethyl-butyl]-amide;
Morpholine-4-carboxylic acid [1-(3-cyano-1-propyl-pyrrolidin-3-ylcarbamoyl)-2-cyclohexyl-ethyl]-amide;
Morpholine-4-carboxylic acid {1-[3-cyano-1-(trans-4-methyl-cyclohexyl)-pyrrolidin-3-ylcarbamoyl]-2-cyclohexyl-ethyl}-amide;
Morpholine-4-carboxylic acid {1-[3-cyano-1-(cis-4-methyl-cyclohexyl)-pyrrolidin-3-ylcarbamoyl]-2-cyclohexyl-ethyl}-amide;
N-[4-Cyano-tetrahydro-pyran-4-ylcarbamoyl)-2-cyclohexyl-ethyl]-isonicotinamide;
Morpholine-4-carboxylic acid [1-(3-cyano-1-cyclopentyl-pyrrolidin-3-ylcarbamoyl)-3,3-dimethyl-butyl]-amide;
Morpholine-4-carboxylic acid [1-(3-cyano-1-isobutyl-piperidin-3-ylcarbamoyl)-2-cyclohexyl-ethyl]-amide;
Morpholine-4-carboxylic acid [1-(3-cyano-1-cyclopentyl-pyrrolidin-3-ylcarbamoyl)-2-cyclohexyl-ethyl]-amide;
Morpholine-4-carboxylic acid {1-[3-cyano-1-(cis-4-methyl-cyclohexyl)-pyrrolidin-3-ylcarbamoyl]-3,3-dimethyl-butyl}-amide;
Morpholine-4-carboxylic acid [1-(3-cyano-pyrrolidin-3-ylcarbamoyl)-2-cyclohexyl-ethyl]-amide;
Morpholine-4-carboxylic acid {1-[3-cyano-1-(trans-4-methyl-cyclohexyl)-pyrrolidin-3-ylcarbamoyl]-3,3-dimethyl-butyl}-amide;

Morpholine-4-carboxylic acid (1-{3-cyano-1-[1-(toluene-4-sulfonyl)-1H-indol-3-ylmethyl]-pyrrolidin-3-ylcarbamoyl}-2-cyclohexyl-ethyl)-amide;
Morpholine-4-carboxylic acid [1-(3-cyano-1-cyclohexyl-pyrrolidin-3-ylcarbamoyl)-2-(4-iodo-phenyl)-ethyl]-amide;
Morpholine-4-carboxylic acid [1-(3-cyano-1-cyclohexyl-pyrrolidin-3-ylcarbamoyl)-2-p-tolyl-ethyl]-amide;
Morpholine-4-carboxylic acid [(3-cyano-1-cyclohexyl-pyrrolidin-3-ylcarbamoyl)cyclohexyl-methyl]-amide;
Morpholine-4-carboxylic acid [1-(1-benzyl-3-cyano-pyrrolidin-3-ylcarbamoyl)-2-naphthalen-2-yl-ethyl]-amide;
Morpholine-4-carboxylic acid [1-(1-benzyl-3-cyano-pyrrolidin-3-ylcarbamoyl)-2-(4-chloro-phenyl)-ethyl]-amide;
Morpholine-4-carboxylic acid {1-[3-cyano-1-(2-methyl-2-phenyl-propyl)-pyrrolidin-3-ylcarbamoyl]-2-cyclohexyl-ethyl}-amide;
Morpholine-4-carboxylic acid {1-[3-cyano-1-(indan-2-ylmethyl)-pyrrolidin-3-ylcarbamoyl]-2-cyclohexyl-ethyl}-amide;
Morpholine-4-carboxylic acid {1-[3-cyano-1-(5-methyl-thiophen-2-ylmethyl)-pyrrolidin-3-ylcarbamoyl]-2-cyclohexyl-ethyl}-amide;
1-Benzyl-3-cyano-3-{3-cyclohexyl-2-[(morpholine-4-carbonyl)-amino]-propionylamino}-pyrrolidine-2-carboxylic acid methyl ester;
N-[1-(1-Benzyl-3-cyano-pyrrolidin-3-ylcarbamoyl)-2-cyclohexyl-ethyl]-isobutyramide;
[1-(1-Benzyl-3-cyano-pyrrolidin-3-ylcarbamoyl)-2-cyclohexyl-ethyl]-carbamic acid benzyl ester;
Morpholine-4-carboxylic acid [1-(1-benzyl-3-cyano-pyrrolidin-3-ylcarbamoyl)-3-methyl-but-3-enyl]-amide;
Morpholine-4-carboxylic acid {1-[3-cyano-1-(3-methoxy-benzyl)-pyrrolidin-3-ylcarbamoyl]-2-cyclohexyl-ethyl}-amide;
Morpholine-4-carboxylic acid {1-[3-cyano-1-(naphthalen-2-ylmethyl)-pyrrolidin-3-ylcarbamoyl]-2-cyclohexyl-ethyl}-amide;
Cyclohexanecarboxylic acid [1-(1-benzyl-3-cyano-pyrrolidin-3-ylcarbamoyl)-2-cyclohexyl-ethyl]-amide;
Morpholine-4-carboxylic acid [1-(3-cyano-1-cyclopentylmethyl-pyrrolidin-3-ylcarbamoyl)-2-cyclohexyl-ethyl]-amide;
Morpholine-4-carboxylic acid {1-[4-cyano-1-(1-methyl-piperidine-4-carbonyl)-piperidin-4-ylcarbamoyl]-2-cyclohexyl-ethyl}-amide;
Morpholine-4-carboxylic acid {1-[4-cyano-1-(pyridine-4-carbonyl)-piperidin-4-ylcarbamoyl]-2-cyclohexyl-ethyl}-amide;
Morpholine-4-carboxylic acid [1-(1-benzyl-3-cyano-2-hydroxymethyl-pyrrolidin-3-ylcarbamoyl)-3,3-dimethyl-butyl]-amide;
Morpholine-4-carboxylic acid [1-(3-cyano-1-cyclohexylmethyl-pyrrolidin-3-ylcarbamoyl)-3-methyl-butyl]-amide;
4-Chloro-N-[1-(4-cyano-1-propyl-piperidin-4-ylcarbamoyl)-3,3-dimethyl-butyl]-benzamide;
Pyrazine-2-carboxylic acid [1-(4-cyano-1-propyl-piperidin-4-ylcarbamoyl)-3,3-dimethyl-butyl]-amide;
4,4-dimethyl-2-(2-thiophen-2-yl-acetylamino)-pentanoic acid (4-cyano-1-propyl-piperidin-4-yl)-amide;
Morpholine-4-carboxylic acid [1-(1-benzyl-3-cyano-pyrrolidin-3-ylcarbamoyl)-3-methyl-butyl]-amide;
N-(4-Cyano-1-methyl-piperidin-4-yl)-3-cyclohexyl-2-[(morpholine-4-carbothioyl)amino]-propionamide;
Morpholine-4-carboxylic acid [1-(4-cyano-1-cyclohexyl-piperidin-4-ylcarbamoyl)-3,3-dimethyl-butyl]-amide;
Morpholine-4-carboxylic acid {1-[4-cyano-1-(tetrahydro-pyran-4-yl)-piperidin-4-ylcarbamoyl]-3,3-dimethyl-butyl}-amide;
Morpholine-4-carboxylic acid [2-(4-chloro-phenyl)-1-(4-cyano-1-propyl-piperidin-4-ylcarbamoyl)-ethyl]-amide;
Morpholine-4-carboxylic acid [1-(4-cyano-1-propyl-piperidin-4-ylcarbamoyl)-2-(3,4-dichloro-phenyl)-ethyl]-amide;
Morpholine-4-carboxylic acid [1-(4-cyano-1-propyl-piperidin-4-ylcarbamoyl)-2-naphthalen-2-yl-ethyl]-amide;
Morpholine-4-carboxylic acid [1-(4-cyano-1-propyl-piperidin-4-ylcarbamoyl)-3-methyl-butyl]-amide;
Morpholine-4-carboxylic acid [1-(4-cyano-1,2-dimethyl-piperidin-4-ylcarbamoyl)-3,3-dimethyl-butyl]-amide;
Naphthalene-2-carboxylic acid [1-(1-benzyl-3-cyano-pyrrolidin-3-ylcarbamoyl)-3-methyl-butyl]-amide;
and the pharmaceutically acceptable derivatives thereof.

The following are preferred compounds of the formulas (I) and (II) of the invention:
Morpholine-4-carboxylic acid [1-(4-cyano-1-methyl-piperidin-4-ylcarbamoyl)-2-cyclohexyl-ethyl]-amide;
4-Acetylamino-N-[1-(4-cyano-1-methyl-piperidin-4-ylcarbamoyl)-2-cyclohexyl-ethyl]-benzamide;
4-Acetylamino-N-[1-(4-cyano-1-methyl-piperidin-4-ylcarbamoyl)-3,3-dimethyl-butyl]-benzamide;
Morpholine-4-carboxylic acid [1-(4-cyano-1-methyl-piperidin-4-ylcarbamoyl)-3,3-dimethyl-butyl]-amide;
Morpholine-4-carboxylic acid [1-(1-benzyl-4-cyano-piperidin-4-ylcarbamoyl)-2-cyclohexyl-ethyl]-amide;
Morpholine-4-carboxylic acid [1-(4-cyano-piperidin-4-ylcarbamoyl)-2-cyclohexyl-ethyl]-amide hydrochloride;
Morpholine-4-carboxylic acid {1-[4-cyano-1-(1-methyl-ethyl)-piperidin-4-ylcarbamoyl]-2-cyclohexyl-ethyl}-amide;
Morpholine-4-carboxylic acid [1-(4-cyano-1-phenethyl-piperidin-4-ylcarbamoyl)-2-cyclohexyl-ethyl]-amide;
Morpholine-4-carboxylic acid {1-[3-cyano-1-benzyl-pyrrolidin-3-ylcarbamoyl]-2-cyclohexyl-ethyl}-amide;
Morpholine-4-carboxylic acid [1-(4-cyano-1-propyl-piperidin-4-ylcarbamoyl)-2-cyclohexyl-ethyl]-amide;
Morpholine-4-carboxylic acid [1-(4-cyano-1-isopropyl-piperidin-4-ylcarbamoyl)-3,3-dimethyl-butyl]-amide;
Morpholine-4-carboxylic acid [1-(1-phenethyl-4-cyano-piperidin-4-ylcarbamoyl)-3,3-dimethyl-butyl]-amide;
Morpholine-4-carboxylic acid [1-(1-n-propyl-4-cyano-piperidin-4-ylcarbamoyl)-3,3-dimethyl-butyl]-amide;
Morpholine-4-carboxylic acid [1-(1-benzyl-4-cyano-piperidin-4-ylcarbamoyl)-3,3-dimethyl-butyl]-amide;
4-Acetylamino-N-[1-(1-benzyl-4-cyano-piperidin-4-ylcarbamoyl)-2-cyclohexyl-ethyl]-benzamide;
4-Acetylamino-N-[1-(4-cyano-1-isopropyl-piperidin-4-ylcarbamoyl)-2-cyclohexyl-ethyl]-benzamide;
Morpholine-4-carboxylic acid [i-(1-benzyl-3-cyano-piperidin-3-ylcarbamoyl)-2-cyclohexyl-ethyl]-amide;
N-[1-(4-cyano-1-methyl-piperidin-4-ylcarbamoyl)-2-cyclohexyl-ethyl]-benzamide;
4-(Acetylamino-methyl)-N-[1-(4-cyano-1-methyl-piperidin-4-ylcarbamoyl)-2-cyclohexyl-ethyl]-benzamide;
N-[1-(4-cyano-1-methyl-piperidin-4-ylcarbamoyl)-2-cyclohexyl-ethyl]-isonicotinamide;
Pyrazine-2-carboxylic acid [1-(4-cyano-1-methyl-piperidin-4-ylcarbamoyl)-2-cyclohexyl-ethyl]-amide;
5-Chloro-thiophene-2-carboxylic acid [1-(4-cyano-1-methyl-piperidin-4-ylcarbamoyl)-2-cyclohexyl-ethyl]-amide;

4-Chloro-N-[1-(4-cyano-1-methyl-piperidin-4-ylcarbamoyl)-2-cyclohexyl-ethyl]-benzamide;
N-[1-(4-cyano-1-methyl-piperidin-4-ylcarbamoyl)-2-cyclohexyl-ethyl]-3-phenoxy-benzamide;
N-[1-(1-Benzyl-3-cyano-pyrrolidin-3-ylcarbamoyl)-2-cyclohexyl-ethyl-ethyl]-isonicotinamide;
Pyrazine-2-carboxylic acid [1-(1-benzyl-3-cyano-pyrrolidin-3-ylcarbamoyl)-2-cyclohexyl-ethyl]-amide;
Morpholine-4-carboxylic acid {1-[3-cyano-1-(cyclohexyl-methyl)-pyrrolidin-3-ylcarbamoyl]-2-cyclohexyl-ethyl}-amide;
Morpholine-4-carboxylic acid [1-(3-cyano-1-benzyl-pyrrolidin-3-ylcarbamoyl)-3,3-dimethyl-butyl]-amide;
N-[1-(1-Benzyl-3-cyano-pyrrolidin-3-ylcarbamoyl)-3,3-dimethyl-butyl]-benzamide;
Pyrazine-2-carboxylic acid [1-(1-benzyl-3-cyano-pyrrolidin-3-ylcarbamoyl)-3,3-dimethyl-butyl]-amide;
Morpholine-4-carboxylic acid {1-[3-cyano-1-(1-methyl-ethyl)-pyrrolidin-3-ylcarbamoyl]-2-cyclohexyl-ethyl}-amide;
N-[1-(1-benzyl-3-cyano-pyrrolidin-3-ylcarbamoyl)-3,3-dimethyl-butyl]-4-methanesulfonylamino-benzamide;
N-[1-(1-Benzyl-3-cyano-pyrrolidin-3-ylcarbamoyl)-2-cyclohexyl-ethyl]-4-methanesulfonylamino-benzamide;
N-[1-(4-cyano-1-methyl-piperidin-4-ylcarbamoyl)-3,3-dimethyl-butyl]-benzamide;
N-[1-(4-cyano-1-methyl-piperidin-4-ylcarbamoyl)-2-cyclohexyl-ethyl]-4-fluoro-benzamide;
N-[1-(4-cyano-1-methyl-piperidin-4-ylcarbamoyl)-3,3-dimethyl-butyl]-4-methanesulfonylamino-benzamide;
Morpholine-4-carboxylic acid [1-(3-cyano-1-cyclohexyl-pyrrolidin-3-ylcarbamoyl)-2-cyclohexyl-ethyl]-amide;
Morpholine-4-carboxylic acid [1-(3-cyano-1-ethyl-pyrrolidin-3-ylcarbamoyl)-2-cyclohexyl-ethyl]-amide;
Morpholine-4-carboxylic acid [1-(3-cyano-1-methyl-pyrrolidin-3-ylcarbamoyl)-2-cyclohexyl-ethyl]-amide;
Morpholine-4-carboxylic acid {1-[3-cyano-1-(3-methyl-benzyl)-pyrrolidin-3-ylcarbamoyl]-2-cyclohexyl-ethyl}-amide;
Morpholine-4-carboxylic acid {1-[3-cyano-1-(2-methyl-pent-2-enyl)-pyrrolidin-3-ylcarbamoyl]-2-cyclohexyl-ethyl}-amide;
Morpholine-4-carboxylic acid {1-[3-cyano-1-(1H-indol-3-ylmethyl)-pyrrolidin-3-ylcarbamoyl]-2-cyclohexyl-ethyl}-amide;
Pyrrolidine-1-carboxylic acid [1-(1-benzyl-3-cyano-pyrrolidin-3-ylcarbamoyl)-2-cyclohexyl-ethyl]-amide;
Morpholine-4-carboxylic acid [1-(3-cyano-1-cyclohexylmethyl-pyrrolidin-3-ylcarbamoyl)-3,3-dimethyl-butyl]-amide;
Morpholine-4-carboxylic acid [1-(3-cyano-1-isobutyl-pyrrolidin-3-ylcarbamoyl)-2-cyclohexyl-ethyl]-amide;
Morpholine-4-carboxylic acid [1-(3-cyano-1-isopropyl-pyrrolidin-3-ylcarbamoyl)-3,3-dimethyl-butyl]-amide;
Morpholine-4-carboxylic acid [1-(3-cyano-1-isobutyl-pyrrolidin-3-ylcarbamoyl)-3,3-dimethyl-butyl]-amide;
Morpholine-4-carboxylic acid {1-[3-cyano-1-(1-ethyl-propyl)-pyrrolidin-3-ylcarbamoyl]-2-cyclohexyl-ethyl}-amide;
Morpholine-4-carboxylic acid {1-[3-cyano-1-(1-ethyl-propyl)-pyrrolidin-3-ylcarbamoyl]-3,3-dimethyl-butyl}-amide;
Morpholine-4-carboxylic acid [1-(3-cyano-1-phenethyl-pyrrolidin-3-ylcarbamoyl)-2-cyclohexyl-ethyl]-amide;
Morpholine-4-carboxylic acid [1-(3-cyano-1-cyclopropylmethyl-pyrrolidin-3-ylcarbamoyl)-2-cyclohexyl-ethyl]-amide;
Morpholine-4-carboxylic acid [1-(3-cyano-1-methyl-piperidin-3-ylcarbamoyl)-2-cyclohexyl-ethyl]-amide;
Morpholine-4-carboxylic acid [1-(1-benzyl-3-cyano-azetidin-3-ylcarbamoyl)-2-cyclohexyl-ethyl]-amide;
Morpholine-4-carboxylic acid [1-(3-cyano-1-propyl-pyrrolidin-3-ylcarbamoyl)-3,3-dimethyl-butyl]-amide;
Morpholine-4-carboxylic acid [1-(3-cyano-1-propyl-pyrrolidin-3-ylcarbamoyl)-2-cyclohexyl-ethyl]-amide;
Morpholine-4-carboxylic acid {1-[3-cyano-1-(trans-4-methyl-cyclohexyl)-pyrrolidin-3-ylcarbamoyl]-2-cyclohexyl-ethyl}-amide;
Morpholine-4-carboxylic acid [1-(3-cyano-1-cyclopentyl-pyrrolidin-3-ylcarbamoyl)-3,3-dimethyl-butyl]-amide;
Morpholine-4-carboxylic acid [1-(3-cyano-1-isobutyl-piperidin-3-ylcarbamoyl)-2-cyclohexyl-ethyl]-amide;
Morpholine-4-carboxylic acid [1-(3-cyano-1-cyclopentyl-pyrrolidin-3-ylcarbamoyl)-2-cyclohexyl-ethyl]-amide;
Morpholine-4-carboxylic acid [1-(3-cyano-pyrrolidin-3-ylcarbamoyl)-2-cyclohexyl-ethyl]-amide;
Morpholine-4-carboxylic acid {1-[3-cyano-1-(trans-4-methyl-cyclohexyl)-pyrrolidin-3-ylcarbamoyl]-3,3-dimethyl-butyl}-amide;
Morpholine-4-carboxylic acid [1-(1-benzyl-3-cyano-pyrrolidin-3-ylcarbamoyl)-2-naphthalen-2-yl-ethyl]-amide;
Morpholine-4-carboxylic acid [1-(1-benzyl-3-cyano-pyrrolidin-3-ylcarbamoyl)-2-(4-chloro-phenyl)-ethyl]-amide;
Morpholine-4-carboxylic acid {1-[3-cyano-1-(5-methyl-thiophen-2-ylmethyl)-pyrrolidin-3-ylcarbamoyl]-2-cyclohexyl-ethyl}-amide;
Morpholine-4-carboxylic acid [1-(1-benzyl-3-cyano-pyrrolidin-3-ylcarbamoyl)-3-methyl-but-3-enyl]-amide;
Morpholine-4-carboxylic acid [1-(3-cyano-1-cyclopentylmethyl-pyrrolidin-3-ylcarbamoyl)-2-cyclohexyl-ethyl]-amide;
Morpholine-4-carboxylic acid [1-(3-cyano-1-cyclohexylmethyl-pyrrolidin-3-ylcarbamoyl)-3-methyl-butyl]-amide;
4-Chloro-N-[1-(4-cyano-1-propyl-piperidin-4-ylcarbamoyl)-3,3-dimethyl-butyl]-benzamide;
Pyrazine-2-carboxylic acid [1-(4-cyano-1-propyl-piperidin-4-ylcarbamoyl)-3,3-dimethyl-butyl]-amide;
4,4-dimethyl-2-(2-thiophen-2-yl-acetylamino)-pentanoic acid (4-cyano-1-propyl-piperidin-4-yl)-amide;
Morpholine-4-carboxylic acid [1-(1-benzyl-3-cyano-pyrrolidin-3-ylcarbamoyl)-3-methyl-butyl]-amide;
Morpholine-4-carboxylic acid [1-(4-cyano-1-cyclohexyl-piperidin-4-ylcarbamoyl)-3,3-dimethyl-butyl]-amide;
Morpholine-4-carboxylic acid [2-(4-chloro-phenyl)-1-(4-cyano-1-propyl-piperidin-4-ylcarbamoyl)-ethyl]-amide;
Morpholine-4-carboxylic acid [1-(4-cyano-1-propyl-piperidin-4-ylcarbamoyl)-2-(3,4-dichloro-phenyl)-ethyl]-amide;
Morpholine-4-carboxylic acid [1-(4-cyano-1-propyl-piperidin-4-ylcarbamoyl)-2-naphthalen-2-yl-ethyl]-amide;
Morpholine-4-carboxylic acid [1-(4-cyano-1-propyl-piperidin-4-ylcarbamoyl)-3-methyl-butyl]-amide;
Morpholine-4-carboxylic acid [1-(4-cyano-1,2-dimethyl-piperidin-4-ylcarbamoyl)-3,3-dimethyl-butyl]-amide;
and the pharmaceutically acceptable derivatives thereof.

The activity of particular compounds disclosed herein against cathepsin K may be determined without undue experimentation by one of ordinary skill in the art in view of the art, the guidance provided throughout this specification and by the screens described in the section entitled "Assessment of Biological Properties."

The following subgeneric aspect of the compounds of the formula (II) have Cathepsin K activity:

The compound according to the third embodiment above of formula (II) and wherein:

Het is piperidinyl, pyrrolidinyl, azetidinyl, azepanyl, oxepanyl, tetrahydropyranyl, oxetanyl or tetrahydrothiopyranyl each ring being optionally substituted with one or more $R_5$;

$R_1$ is a bond, C1–4 alkyl, C1–4 alkoxy, cyclopropyl, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is methyl, ethyl, propyl, i-propyl, cyclopropyl, cyclohexyl, phenyl, pyrrolidinyl, piperidinyl, morpholinyl, thiomorpholinyl, piperazinyl, thienyl, imidazolyl, methoxy, ethoxy, acetyl, acetoxy, phenoxy, naphthyloxy, benzyloxy, methoxycarbonyl, ethoxycarbonyl, phenoxycarbonyl, naphthyloxycarbonyl, benzoyloxy, carbamoyl wherein the nitrogen atom may be independently mono or di-substituted by methyl, ethyl, phenyl, naphthyl, pyrrolidinyl, piperidinyl, morpholinyl, thiomorpholinyl or piperazinyl, or $R_a$ is acetylamino, benzoylamino, methylthio wherein the sulfur atom may be oxidized to a sulfoxide or sulfone, ethylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl, phenyl, naphthyl, pyrrolidinyl, piperidinyl, morpholinyl, thiomorpholinyl or piperazinyl, or $R_a$ is methoxycarbonylamino, ethoxycarbonylamino, phenoxycarbonylamino, C1–2 alkylcarbamoyloxy, phenylcarbamoyloxy, naphthylcarbamoyloxy, C1–2 alkylsulfonylamino, phenylsulfonylamino, naphthylsulfonylamino, C1–2 alkylaminosulfonyl, phenylaminosulfonyl, naphthylaminosulfonyl, amino wherein the nitrogen atom may be independently mono or di-substituted by methyl, ethyl, phenyl, naphthyl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is methyl, ethyl, cyclopropyl, cyclohexyl, phenyl, methoxy, ethoxy, phenoxy, benzyloxy, fluoro, chloro, bromo, hydroxy, oxo, carboxy, cyano, nitro or carboxamide;

$R_2$ is hydrogen or methyl;

$R_3$ is a bond, methyl, ethyl, n-propyl, i-propyl, n-butyl, i-butyl, n-pentyl, propenyl, i-butenyl, cyclohexyl, benzyl or naphthylmethyl wherein $R_3$ is optionally substituted by one or more $R_c$;

$R_c$ is methyl, ethyl, cyclohexyl, cyclopentyl, phenyl, naphthyl, bicyclo[3.1.0]hexanyl, bicyclo[1.1.1] pentanyl, cubanyl, furanyl, tetrahydropyranyl, thienyl, oxazolyl, thiazolyl, imidazolyl, pyrimidinyl, methoxy, ethoxy, phenoxy, acetyl, benzoyl, methoxycarbonyl, phenoxycarbonyl, acetoxy, benzoyloxy, carbamoyl wherein the nitrogen atom may be independently mono or di-substituted by methyl or phenyl, or $R_c$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl or phenyl, or $R_c$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl or phenyl, or $R_c$ is chloro, fluoro, hydroxy, oxo, carboxy or cyano;

$R_2$ and $R_3$ together with the carbon they are attached optionally form a ring selected from cyclopentyl, cyclohexyl, cycloheptyl, tetrahydropyranyl, tetrahydrothiopyranyl, tetrahydrofuranyl, pyrrolidinyl, piperidinyl, piperazinyl, morpholinyl or tetrahydrothiophenyl;

$R_4$ is hydrogen;

$R_5$ is a bond, hydrogen, carbonyl, C1–5 alkyl, C1–5alkoxyC1–5alkyl, C1–5alkylaminoC1–5alkyl, C1–5alkylthioC1–5alkyl wherein the sulfur atom may be oxidized to a sulfoxide or sulfone, C1–5 alkoxy, phenoxy, naphthyloxy, cyclopropyl, cyclopentyl, cyclohexyl, phenyl, benzyl, heterocyclyl selected from pyrrolidinyl, piperidinyl, morpholinyl, tetrahydropyranyl, pyridinyl, and pyrimidinyl, heterocyclyloxy wherein the heterocyclyl moiety is selected from those herein described in this paragraph, acetyl, benzoyl, acetyloxy, benzyloxy, methoxycarbonyl, ethoxycarbonyl, benzyloxycarbonyl, benzoyloxy, carbamoyl wherein the nitrogen atom may be independently mono or di-substituted by methyl, ethyl or phenyl, or $R_5$ is acetylamino, benzoylamino, phenylthio wherein the sulfur atom may be oxidized to a sulfoxide or sulfone, ureido wherein either nitrogen atom may be independently substituted by methyl, ethyl or phenyl, or $R_5$ is methoxycarbonylamino, ethoxycarbonylamino, phenoxycarbonylamino, methylcarbamoyloxy, phenylcarbamoyloxy, phenylsulfonylamino, phenylaminosulfonyl, amino wherein the nitrogen atom may be independently mono or di-substituted by methyl, ethyl or phenyl, or $R_5$ is fluoro, chloro, hydroxy, oxo, carboxy or carboxamide, $R_5$ may be further optionally substituted by one or more $R_e$;

$R_e$ is methyl ethyl, methoxy, ethoxy, cyclopropyl, cyclopentyl, cyclohexyl, phenyl, naphthyl, indanyl, piperidinyl, morpholinyl, indolyl, thienyl, pyridinyl, methoxy, ethoxy, acetyl, benzoyl, acetyloxy, phenoxy, benzyloxy, methoxycarbonyl, ethoxycarbonyl, carbamoyl wherein the nitrogen atom may be independently mono or di-substituted by methyl, ethyl or phenyl, or $R_e$ is acetylamino, benzoylamino, methylthio wherein the sulfur atom may be oxidized to a sulfoxide or sulfone, phenylthio methylthio wherein the sulfur atom may be oxidized to a sulfoxide or sulfone, ureido wherein either nitrogen atom may be independently substituted by methyl, ethyl or phenyl, or $R_e$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_e$ is fluoro, chloro, hydroxy, oxo, carboxy or carboxamide, $R_e$ may be further optionally substituted by one or more $R_f$;

$R_f$ is methyl, phenyl, tolylsulfonyl, phenoxy, benzyloxy, fluoro, chloro or oxo.

Another embodiment of the compounds of the formula (II) having Cathepsin K activity are those described immediately above and wherein:

$R_1$ is a bond, methyl, ethyl, n-propyl, i-propyl, methoxy, ethoxy, benzyloxy, cyclopropyl, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is methyl, cyclopropyl, phenyl, halogen, hydroxy, oxo, carboxy, cyano, nitro or carboxamide;

$R_3$ is a bond, methyl, ethyl, n-propyl, i-propyl, n-butyl, i-butyl, n-pentyl, propenyl, i-butenyl, benzyl or naphthylmethyl wherein $R_3$ is optionally substituted by one or more $R_c$;

$R_c$ is methyl, ethyl, cyclohexyl, cyclopentyl, phenyl, furanyl, tetrahydropyranyl, thienyl, oxazolyl, thiazolyl, methoxy, phenoxy, acetyl, benzoyl, methoxycarbonyl, carbamoyl wherein the nitrogen atom may be independently mono or di-substituted by methyl or phenyl, or $R_c$ is acetylamino, benzoylamino, methylthio, methoxycarbonylamino, methylcarbamoyloxy, methylsulfonylamino, methylaminosulfonyl, amino wherein the nitrogen atom may be independently mono or di-substituted by methyl, or $R_c$ is fluoro or oxo;

$R_2$ and $R_3$ together with the carbon they are attached optionally form a ring selected from cyclopentyl, cyclohexyl, cycloheptyl, tetrahydropyranyl, tetrahydrothiopyranyl, tetrahydrofuranyl, pyrrolidinyl or piperidinyl;

$R_5$ is methyl, ethyl, n-propyl, n-butyl, n-pentyl, 2-pentyl, 3-pentyl, phenethyl, phenpropyl, 2,2-dimethylpropyl, t-butyl, i-propyl, i-butyl, cyclopropyl, cyclopentyl, cyclohexyl, cyclopropylmethyl, cyclopentylmethyl, cyclohexylmethyl, phenyl, benzyl, 2-methylbenzyl, 3-methylbenzyl, 4-methylbenzyl, 2,6-dimethylbenzyl, 2,5-dimethylbenzyl, 2,4-dimethylbenzyl, 2,3-dimethylbenzyl, 3,4-dimethylbenzyl, 3,5-dimethylbenzyl, 2,4,6-trimethylbenzyl, 2-methoxybenzyl, 3-methoxybenzyl, 4-methoxybenzyl, 2-phenoxybenzyl, 3-phenoxybenzyl, 4-phenoxybenzyl, 2-benzyloxybenzyl, 3-benzyloxybenzyl, 4-benzyloxybenzyl, 2-fluorobenzyl, 3-fluorobenzyl, 4-fluorobenzyl, 2,6-difluorobenzyl, 2,5-difluorobenzyl, 2,4-difluorobenzyl, 2,3-difluorobenzyl, 3,4-difluorobenzyl, 3,5-difluorobenzyl, 2,4,6-triflurobenzyl, 2-trifluoromethylbenzyl, 3-trifluoromethylbenzyl, 4-trifluoromethylbenzyl, naphthylmethyl, indanylmethyl, pyridinylmethyl, indolylmethyl, thienylmethyl, 5-methylthienylmethyl, piperidinyl, piperidinylcarbonyl, pyridinylcarbonyl, tetrahydropyranyl, pyrimidinyl, acetyl, benzoyl, ethoxycarbonyl, benzyloxycarbonyl, t-butoxycarbonyl, methylcarbamoyl, phenylcarbamoyl, benzylcarbamoyl, methylsulfonylamino, phenylsulfonylamino, methylamino, dimethylamino, fluoro, oxo or carboxy.

Yet another embodiment of the compounds of the formula (II) having Cathepsin K activity are those described immediately above and wherein:

$R_1$ is methoxy, benzyloxy, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is methyl, phenyl, fluoro, chloro, hydroxy, oxo, carboxy or carboxamide;

$R_3$ is a bond, methyl, ethyl, n-propyl, i-propyl, n-butyl, i-butyl, n-pentyl, propenyl, i-butenyl or benzyl wherein $R_3$ is optionally substituted by one or more $R_c$;

$R_c$ is methyl, ethyl, cyclohexyl, cyclopentyl, phenyl, furanyl, tetrahydropyranyl, thienyl, oxazolyl, thiazolyl, methoxy, phenoxy, acetyl, benzoyl, methoxycarbonyl, acetylamino, methylthio, methylsulfonylamino or fluoro;

$R_2$ and $R_3$ together with the carbon they are attached optionally form a ring selected from cyclopentyl, cyclohexyl, cycloheptyl, tetrahydropyranyl, tetrahydrothiopyranyl or tetrahydrofuranyl;

$R_5$ is methyl, ethyl, n-propyl, n-butyl, phenethyl, phenpropyl, t-butyl, i-propyl, i-butyl, cyclopropyl, cyclohexyl, cyclopropylmethyl, cyclohexylmethyl, phenyl, benzyl, 2-methoxybenzyl, 3-methoxybenzyl, 4-methoxybenzyl 4-fluorobenzyl, 3,5-difluorobenzyl, 4-trifluoromethylbenzyl, naphthylmethyl, pyridinylmethyl, indolylmethyl, thienylmethyl, acetyl, benzoyl, ethoxycarbonyl, benzyloxycarbonyl, t-butoxycarbonyl, phenylcarbamoyl, phenylsulfonylamino or fluoro.

Yet still another embodiment of the compounds of the formula (II) having Cathepsin K activity are those described immediately above and wherein:

Het is pyrrolidinyl, piperidinyl or tetrahydropyranyl;

$R_1$ is benzyloxy, phenoxy, naphthyloxy, phenyl, naphthyl, pyrrolidinyl, piperidinyl, morpholinyl, thiomorpholinyl, piperazinyl, pyridinyl, indolyl, quinolinyl, benzofuranyl, benzthienyl, benzimidazolyl, benzthiazolyl, benzoxazolyl or phenylamino;

$R_3$ is n-propyl, i-butyl, propenyl, i-butenyl or 2,2-dimethylpropyl;

$R_2$ and $R_3$ together with the carbon they are attached optionally form a ring selected from cyclopentyl, cyclohexyl, or cycloheptyl;

$R_5$ is methyl, ethyl, n-propyl, phenethyl, t-butyl, i-propyl, i-butyl, cyclohexyl, cyclohexylmethyl, benzyl, 4-fluorobenzyl, naphthylmethyl, acetyl, benzoyl or benzyloxycarbonyl.

Representative compounds possessing CAT K activity are the following:

[1-(1-Benzyl-4-cyano-piperidin-4-ylcarbarnoyl)-3-methyl-butyl]-carbamic acid benzyl ester;

[1-(1-Benzyl-3-cyano-pyrrolidin-3-ylcarbamoyl)-cyclohexyl]-carbamic acid t-butyl ester;

[1-(4-Cyano-1-methyl-piperidin-4-ylcarbamoyl)-3-methyl-butyl]-carbamic acid benzyl ester;

[1-(1-Benzyl-3-cyano-pyrrolidin-3-ylcarbamoyl)-cyclohexyl]-carbamic acid benzyl ester;

Naphthalene-2-carboxylic acid [1-(1-benzyl-3-cyano-pyrrolidin-3-ylcarbamoyl)-3-methyl-butyl]-amide;

Morpholine-4-carboxylic acid [1-(4-cyano-1-propyl-piperidin-4-ylcarbamoyl)-3-methyl-butyl]-amide;

Naphthalene-2-carboxylic acid [1-(3-cyano-1-cyclohexylmethyl-pyrrolidin-3-ylcarbamoyl)-3-methyl-butyl]-amide;

[1-(1-Benzyl-3-cyano-pyrrolidin-3-ylcarbamoyl)-3-methyl-butyl]-carbamic acid benzyl ester;
Morpholine-4-carboxylic acid [i-(1-benzyl-3-cyano-pyrrolidin-3-ylcarbamoyl)-3-methyl-butyl]-amide;
[1-(3-Cyano-1-cyclohexylmethyl-pyrrolidin-3-ylcarbamoyl)-3-methyl-butyl]-carbamic acid benzyl ester;
Morpholine-4-carboxylic acid [1-(3-cyano-1-cyclohexylmethyl-pyrrolidin-3-ylcarbamoyl)-3-methyl-butyl]-amide;
Morpholine-4-carboxylic acid [1-(1-benzyl-3-cyano-pyrrolidin-3-ylcarbamoyl)-3-methyl-but-3-enyl]-amide.

In a third broad generic aspect of the invention, there are provided novel compounds of the formulas (Ia) and (Ib):

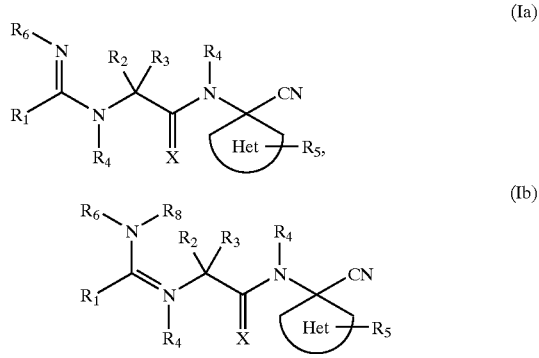

wherein:
Het is azepanyl, piperidinyl, pyrrolidinyl, azetidinyl, oxepanyl, tetrahydropyranyl, tetrahydrothiopyranyl, tetrahydrofuranyl, oxetanyl, azocanyl, oxocanyl, 1,3-diazocanyl, 1,4-diazocanyl, 1,5-diazocanyl, 1,3-dioxocanyl, 1,4-dioxocanyl, 1,5-dioxocanyl, 1,3-oxazocanyl, 1,4-oxazocanyl, 1,5-oxazocanyl, 1,3-diazepanyl, 1,4-diazepanyl, 1,3-dioxepanyl, 1,4-dioxepanyl, 1,3-oxazepanyl, 1,4-oxazepanyl, 1,2-thiazocanyl-1,1-dioxide, 1,2,8-thiadiazocanyl-1,1-dioxide, 1,2-thiazepanyl-1,1-dioxide, 1,2,7-thiadiazepanyl-1,1-dioxide, tetrahydrothiophenyl, hexahydropyrimidinyl, hexahydropyridazinyl, piperazinyl, 1,4,5,6-tetrahydropyrimidinyl, pyrazolidinyl, dihydro-oxazolyl, dihydrothiazolyl, dihydroimidazolyl, isoxazolinyl, oxazolidinyl, 1,2-thiazinanyl-1,1-dioxide, 1,2,6-thiadiazinanyl-1,1-dioxide, isothiazolidinyl-1,1-dioxide, imidazolidinyl-2,4-dione, imidazolidinyl, morpholinyl, dioxanyl, tetrahydropyridinyl, thiomorpholinyl, thiazolidinyl, dihydropyranyl, dithianyl, decahydro-quinolinyl, decahydro-isoquinolinyl, 1,2,3,4-tetrahydro-quinolinyl, indolinyl, octahydro-quinolizinyl, dihydro-indolizinyl, octahydro-indolizinyl, octahydro-indolyl, decahydroquinazolinyl, decahydroquinoxalinyl, 1,2,3,4-tetrahydroquinazolinyl or 1,2,3,4-tetrahydroquinoxalinyl;
A C6–10 bridged bicyclo wherein one or more carbon atoms are optionally replaced by a heteroatom chosen from N, O and S;
each being optionally substituted with one or more $R_5$;
$R_1$ is a bond, hydrogen, C1–10 alkyl, C1–10 alkoxy, aryloxy, C3–8 cycloalkyl, C3–8 cycloalkyloxy, aryl, benzyl, tetrahydronaphthyl, indenyl, indanyl, C1–10alkylsulfonylC1–10alkyl, C3–8cycloalkylsulfonylC1–10alkyl, arylsulfonylC1–10alkyl, heterocyclyl selected from azepanyl, azocanyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzisoxazolyl, quinolinyl, tetrahydroquinolinyl, isoquinolinyl, tetrahydroisoquinolinyl, quinazolinyl, tetrahydroquinazolinyl, benzoxazolyl and quinoxalinyl, heterocyclyloxy wherein the heterocyclyl moiety is selected from those herein described in this paragraph, hydroxy or amino; wherein $R_1$ is optionally substituted by one or more $R_a$;

$R_a$ is a bond, C1–10 alkyl, C3–8 cycloalkyl, aryl, tetrahydronaphthyl, indenyl, indanyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, benzisoxazolyl, quinolinyl, isoquinolinyl, quinazolinyl, quinoxalinyl, C1–10 alkoxy, C1–10alkanoyl, C1–10alkanoyloxy, aryloxy, benzyloxy, C1–10 alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofurannyl, benzothienyl, benzimidazolyl, benzthiazolyl, quinolinyl, isoquinolinyl, quinazolinyl or quinoxalinyl, or $R_a$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is halogen, hydroxy, oxo, carboxy, cyano, nitro, carboxamide, amidino or guanidino, $R_a$ may be further optionally substituted by one or more $R_b$; with the proviso that $R_1$ and $R_a$ simultaneously cannot be a bond;

$R_b$ is a C1–6 saturated or unsaturated branched or unbranched carbon chain optionally partially or fully halogenated wherein one or more carbon atoms are optionally replaced by O, N, S(O), S(O)$_2$ or S and wherein said chain is optionally independently substituted with 1–2 oxo groups, —NH$_2$, or one or more C1–4 alkyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl;

or R$_b$ is C3–6 cycloalkyl, aryl, aryloxy, benzyloxy, halogen, hydroxy, oxo, carboxy, cyano, nitro, mono-C1–5alkylamino, di-C1–5alkylamino, carboxamide, amidino or guanidino;

R$_2$ is hydrogen or C1–3 alkyl;

R$_3$ is a bond, hydrogen, C1–10 alkyl, C2–10alkylene, C3–8 cycloalkyl, arylC1–5alkyl or aryl wherein R$_3$ is optionally substituted by one or more R$_c$;

R$_c$ is C1–10 alkyl, C3–8 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo [1.1.1]pentanyl, cubanyl, 1,2,3,4-tetrahydronaphthyl, decahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, dihydrobenzofuranyl, octohydrobenzofuranyl, benzofuranyl, benzothienyl, benzimidazolyl, benzthiazolyl, tetrahydroquinolinyl, quinolinyl, tetrahydroisoquinolinyl, isoquinolinyl, quinazolinyl, quinoxalinyl, C1–10 alkoxy, aryloxy, C1–10 alkanoyl, aroyl, C1–10 alkoxycarbonyl, aryloxycarbonyl, C1–10 alkanoyloxy, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or R$_c$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofiranyl, benzothienyl, benzimidazolyl, benzthiazolyl, quinolinyl, isoquinolinyl, quinazolinyl or quinoxalinyl, or R$_c$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or R$_c$ is halogen, hydroxy, oxo, carboxy, cyano, nitro, amidino or guanidino, R$_c$ may be further optionally substituted by one or more R$_d$;

R$_d$ is C1–5 alkyl, C3–6 cycloalkyl, aryl, arylC1–5alkyl, C1–5 alkoxy, aryloxy, arylC1–5alkoxy, aroyl, amino, halogen, hydroxy, oxo, carboxy, cyano, nitro, amidino or guanidino;

R$_2$ and R$_3$ together with the carbon they are attached optionally form a nonaromatic 5–7 membered cycloalkyl or heterocyclic ring;

each R$_4$ is independently hydrogen, hydroxy or C1–3 alkyl;

R$_5$ is a bond, hydrogen, carbonyl, C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C1–10 alkoxy, aryloxy, C3–8 cycloalkyl, aryl, benzyl, tetrahydronaphthyl, indenyl, indanyl, C3–7cycloalkylsulfonylC1–5alkyl, arylsulfonylC1–5alkyl, heterocyclyl selected from pyrrolidinyl, piperidinyl, morpholinyl, thiomorpholinyl, piperazinyl, indolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridizinyl, tetrazolyl, triazolyl, pyrazolyl, indolyl, benzofuranyl, benzothienyl, benzimidazolyl, benzthiazolyl, quinolinyl, tetrahydroquinolinyl, isoquinolinyl, tetrahydroisoquinolinyl, quinazolinyl, tetrahydroquinazolinyl, benzoxazolyl and quinoxalinyl, heterocyclyloxy wherein the heterocyclyl moiety is selected from those herein described in this paragraph, C1–10alkanoyl, aroyl, C1–10alkanoyloxy, benzyloxy, C1–10alkoxycarbonyl, arylC1–5alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or R$_5$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or R$_5$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or R$_5$ is halogen, hydroxy, oxy, oxo, carboxy, cyano, nitro, carboxamide, amidino or guanidino, R$_5$ may be further optionally substituted by one or more R$_e$;

R_e is C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C1–10 alkoxy, C3–8 cycloalkyl, aryl, tetrahydronaphthyl, indenyl, indanyl, pyrrolidinyl, piperidinyl, morpholinyl, thiomorpholinyl, piperazinyl, indolinyl, thiopyranyl, tetrahydrothiopyranyl, pyranyl, tetrahydropyranyl, tetrahydrofuranyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, benzisoxazolyl, quinolinyl, isoquinolinyl, quinazolinyl, quinoxalinyl, C1–10alkanoyl, aroyl, C1–10alkanoyloxy, aryloxy, benzyloxy, C1–10 alkoxycarbonyl, arylC1–3alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is halogen, hydroxy, oxo, carboxy, cyano, nitro, carboxamide, amidino or guanidino, $R_e$ may be further optionally substituted by one or more $R_f$;

$R_f$ is C1–5 alkyl, C3–6 cycloalkyl, tolylsulfonyl, C1–5 alkoxy, aryl, aryloxy, benzyloxy, halogen, hydroxy, oxo, carboxy, cyano, nitro, carboxamide, amidino or guanidino;

$R_6$ is hydrogen, hydroxy, nitrile or a C1–6 saturated or unsaturated branched or unbranched carbon chain optionally partially or fully halogenated wherein one or more C atoms are optionally replaced by O, NH, S(O), S(O)$_2$ or S and wherein said chain is optionally independently substituted with 1–2 oxo groups, —NH$_2$, one or more C$_{1-4}$ alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl;

wherein $R_1$ and $R_6$ in the formulas (Ia) or (Ib) optionally form a 4 to 8 membered mono- or 7–12 membered polycyclo heteroring system, each aromatic or nonaromatic, wherein each heteroring is optionally substituted by one or more $R_7$;

each $R_7$ and $R_8$ are independently:
C1–5 alkyl chain optionally interrupted by one or two N, O or S(O)$_m$ and optionally substituted by 1–2 oxo, amino, hydroxy, halogen, C1–4alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl, aryl, aryloxy, aroyl, furanyl, thienyl, pyrrolyl, imidazolyl, pyridinyl, pyrimidinyl, C1–5 alkanoyl, C1–5 alkoxycarbonyl, aryloxycarbonyl, benzyloxycarbonyl, C1–5 alkanoylamino, aroylamino, C1–5 alkylthio, arylthio C1–5 alkylsulfonylamino, arylsulfonylamino, C1–5 alkylaminosulfonyl, arylaminosulfonyl, C3–6 cycloalkyl and benzyloxy each of the aforementioned are optionally halogenated,
halogen, hydroxy, oxo, carboxy, nitrile, nitro or NH$_2$C(O)—;
m is 0, 1 or 2;
X is =O, =S or =N—$R_6$ wherein $R_6$ is as defined above, and
pharmaceutically acceptable derivatives thereof.

In another embodiment of the invention, there are provided novel compounds of the formula (Ia) and formula (Ib) as described immediately above, and wherein:

Het is piperidinyl, pyrrolidinyl, tetrahydropyranyl, tetrahydrothiopyranyl, azetidinyl, azepanyl, oxepanyl, tetrahydrofuranyl, oxetanyl, hexahydropyrimidinyl, hexahydropryidazinyl, piperazinyl, 1,4,5,6-tetrahydropyrimidinyl, octahydro-indolizinyl, octahydro-quinolizinyl, decahydro-quinolinyl, 1,2,3,4-tetrahydro-quinolinyl, dihydro-oxazolyl, 1,2-thiazinanyl-1,1-dioxide, 1,2,6-thiadiazinanyl-1,1-dioxide, isothiazolidinyl-1,1-dioxide, imidazolidinyl, pyrazolidinyl or a bridged bicyclo chosen from aza-bicyclo[3.2.1]octane, aza-bicyclo[2.2.1]heptane, aza-bicyclo[2.2.2]octane, aza-bicyclo[3.2.2]nonane, aza-bicyclo[2.1.1]hexane, aza-bicyclo[3.1.1]heptane, aza-bicyclo[3.3.2]decane and 2-oxa or 2-thia-5-aza-bicyclo[2.2.1]heptane; each ring being substituted with one or more $R_5$;

$R_1$ is a bond, hydrogen, C1–7 alkyl, C1–7 alkoxy, C3–7 cycloalkyl, aryloxy, phenyl, benzyl, naphthyl, tetrahydronaphthyl, C1–7alkylsulfonylC1–7alkyl, C3–7cycloalkylsulfonylC1–7alkyl, arylsulfonylC1–7alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, thiazolyl, imidazolyl, pyridinyl, isoxazolyl, pyrimidinyl, pyrazinyl, pyridazinyl, indolyl, quinolinyl, benzofuranyl, benzthienyl, benzimidazolyl, benzthiazolyl, benzoisoxazolyl, benzoxazolyl or amino; wherein $R_1$ is optionally substituted by one or more $R_a$;

$R_a$ is a bond C1–7 alkyl, C3–6 cycloalkyl, phenyl, naphthyl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl, quinoxalinyl, C1–7 alkoxy, C1–7alkanoyl, C1–7alkanoyloxy, aryloxy, benzyloxy, C1–7 alkoxycarbonyl, aryloxycarbonyl, aroyloxy, carbamoyl wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–7 alkanoylamino, aroylamino, C1–7 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–7 alkoxycarbonylamino, aryloxycarbonylamino, C1–7 alkylcarbamoyloxy, arylcarbamoyloxy, C1–7 alkylsulfonylamino, arylsulfonylamino, C1–7 alkylaminosulfonyl, arylaminosulfonyl, amino wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is halogen, hydroxy, oxo, carboxy, cyano, nitro, carboxamide, amidino or guanidino, $R_a$ may be further optionally substituted by one or more $R_b$;

$R_b$ is C1–5 alkyl, C3–6 cycloalkyl, aryl, C1–5 alkoxy, aryloxy, benzyloxy, halogen, hydroxy, oxo, carboxy, cyano, nitro, carboxamide, amidino or guanidino;

$R_2$ is hydrogen or methyl or ethyl;

$R_3$ is a bond, hydrogen, C1–5 alkyl, C2–5alkylene, C3–7 cycloalkyl, arylC1–3alkyl or wherein $R_3$ is optionally substituted by one or more $R_c$;

$R_c$ is C1–5 alkyl, C3–7 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, C1–5 alkoxy, aryloxy, C1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–4 alkyl, C1–5 alkoxy, aryloxy, arylC1–5alkoxy, aroyl, halogen, hydroxy, oxo or cyano;

$R_4$ is hydrogen or methyl;

$R_5$ is a bond, hydrogen, carbonyl, C1–8 alkyl, C1–8alkoxyC1–8alkyl, C1–8alkylaminoC1–8alkyl, C1–8alkylthioC1–8alkyl wherein the sulfur atom may be oxidized to a sulfoxide or sulfone, C1–8 alkoxy, aryloxy, C3–7 cycloalkyl, aryl, benzyl, tetrahydronaphthyl, indanyl, heterocyclyl selected from pyrrolidinyl, piperidinyl, morpholinyl, thiomorpholinyl, piperazinyl, indolinyl, pyranyl, tetrahydropyranyl, thiopyranyl, tetrahydrothiopyranyl, furanyl, tetrahydrofuranyl, thienyl, oxazolyl, thiazolyl, imidazolyl, pyridinyl, pyrimidinyl, pyrazinyl, tetrazolyl, triazolyl, pyrazolyl, indolyl, benzofuranyl, benzothienyl, benzimidazolyl, benzthiazolyl, quinolinyl, isoquinolinyl, quinazolinyl, benzoxazolyl and quinoxalinyl, heterocyclyloxy wherein the heterocyclyl moiety is selected from those herein described in this paragraph, C1–7alkanoyl, aroyl, C1–7alkanoyloxy, benzyloxy, C1–7 alkoxycarbonyl, arylC1–4alkoxycarbonyl, aryloxycarbonyl, aroyloxy, carbamoyl wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is C1–7 alkanoylamino, aroylamino, C1–7 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is C1–7 alkoxycarbonylamino, aryloxycarbonylamino, C1–7 alkylcarbamoyloxy, arylcarbamoyloxy, C1–7 alkylsulfonylamino, arylsulfonylamino, C1–7 alkylaminosulfonyl, arylaminosulfonyl, amino wherein the nitrogen atom may be independently mono or di-substituted by C1–7 alkyl, aryl, pyrrolidinyl, piperidinyl, morpholinyl, thiomorpholinyl, piperazinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is halogen, hydroxy, oxy, oxo, carboxy, cyano, nitro or carboxamide, $R_5$ may be further optionally substituted by one or more $R_e$;

$R_e$ is C1–7 alkyl, C1–7alkoxyC1–7alkyl, C1–7alkylaminoC1–7alkyl, C1–7alkylthioC1–7alkyl wherein the sulfur atom may be oxidized to a sulfoxide or sulfone, C1–7 alkoxy, C3–7 cycloalkyl, aryl, tetrahydronaphthyl, indanyl, pyrrolidinyl, piperidinyl, morpholinyl, thiomorpholinyl, piperazinyl, thiopyranyl, tetrahydrothiopyranyl, tetrahydropyranyl, tetrahydrofurannyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl, quinoxalinyl, C1–5 alkanoyl, aroyl, C1–5alkanoyloxy, aryloxy, benzyloxy, C1–5 alkoxycarbonyl, aryloxycarbonyl, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is halogen, hydroxy, oxo, carboxy, cyano, nitro, carboxamide, amidino or guanidino, $R_e$ may be further optionally substituted by one or more $R_f$;

$R_f$ is methyl, ethyl, t-butyl, tolylsulfonyl, C1–3 alkoxy, cyclopropyl, cyclohexyl, phenyl, naphthyl, phenoxy, benzyloxy, fluoro, chloro, bromo, hydroxy, oxo, carboxy, cyano, nitro or carboxamide;

$R_6$ is hydrogen, hydroxy, nitrile or a C1–6 saturated or unsaturated branched or unbranched carbon chain optionally partially or fully halogenated wherein one or more C atoms are optionally replaced by O, NH, S(O), S(O)$_2$ or S and wherein said chain is optionally independently substituted with 1–2 oxo groups, —NH$_2$, one or more C1–4 alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofurannyl, benzothienyl, benzimidazolyl, benzthiazolyl, quinolinyl, isoquinolinyl, quinazolinyl, benzoxazolyl or quinoxalinyl;

$R_1$ and $R_6$ of the formula (Ia) or formula (Ib) form a monocyclic 5, 6 or 7 membered aromatic or nonaromatic heterocyclic ring optionally substituted by $R_7$;

or a bicyclic ring having one 5, 6 or 7 membered aromatic or nonaromatic heterocyclic ring fused to a second 5–7 membered aromatic or nonaromatic heterocyclic or carbocyclic ring wherein each ring is optionally independently substituted by one or more $R_7$;

$R_7$ and $R_8$ are independently C1–5 alkyl, C3–6 cycloalkyl, aryl, C1–5 alkoxy, aryloxy, benzyloxy each of the aforementioned are optionally halogenated or $R_x$ is halogen, hydroxy, oxo, carboxy, nitrile, nitro or NH$_2$C(O)—;

m is 0, 1 or 2 and

X is O or S.

In yet another embodiment of the invention, there are provided novel compounds of the formulas (Ia) and (Ib) as described immediately above, and wherein:

Het is piperidinyl, pyrrolidinyl, azetidinyl, azepanyl, oxepanyl, tetrahydropyranyl, tetrahydrothiopyranyl, tetrahydrofuranyl, oxetanyl, octahydro-indolizinyl, octahydro-quinolizinyl or aza-bicyclo[3.2.1]octanyl, each ring being optionally substituted with one or more $R_5$;

$R_1$ is a bond, C1–5 alkyl, C1–5 alkoxy, C3–6 cycloalkyl, aryloxy, phenyl, benzyl, naphthyl, C1–3alkylsulfonylC1–3alkyl, C3–6cycloalkylsulfonylC1–3alkyl, arylsulfonylC1–3alkyl, pyrrolidinyl, piperidinyl, morpholinyl, thiomorpholinyl, piperazinyl, furanyl, thienyl, oxazolyl, thiazolyl, imidazolyl, pyridinyl, isoxazolyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is a bond, C1–3 alkyl, cyclopropyl, cyclopentyl, cyclohexyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl, benzthiazolyl, benzoxazolyl, C1–3 alkoxy, C1–3alkanoyl, C1–3 alkanoyloxy, aryloxy, benzyloxy, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl, piperazinyl, thienyl, oxazolyl, thiazolyl, imidazolyl, pyridinyl, pyrimidinyl, benzimidazolyl or benzthiazolyl, or $R_a$ is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or $R_a$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl, aryl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is C1–3 alkyl, C3–6 cycloalkyl, aryl, C1–3 alkoxy, aryloxy, benzyloxy, halogen, hydroxy, oxo, carboxy, cyano, nitro, carboxamide, amidino or guanidino;

$R_2$ is hydrogen or methyl;

$R_3$ is a bond, hydrogen, C1–5 alkyl, C2–5alkylene, C4–6 cycloalkyl or arylC1–2alkyl wherein $R_3$ is optionally substituted by one or more $R_c$;

$R_c$ is C1–4 alkyl, C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, pyrrolidinyl, piperidinyl, morpholinyl, thiomorpholinyl, indolinyl, furanyl, tetrahydrofuranyl, pyranyl, tetrahydropyranyl, thienyl, pyrrolyl, oxazolyl, thiazolyl, imidazolyl, pyrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, C1–4 alkoxy, phenoxy, naphthyloxy, C1–3 alkanoyl, benzoyl, C1–3 alkoxycarbonyl, phenoxycarbonyl, C1–3 alkanoyloxy, benzoyloxy, carbamoyl wherein the nitrogen atom may be independently mono or di-substituted by C1–5 alkyl or aryl, or $R_c$ is C1–3 alkanoylamino, benzoylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–5 alkyl or aryl, or $R_c$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–5 alkyl or aryl, or $R_c$ is halogen, hydroxy, oxo, carboxy, cyano, nitro, amidino or guanidino, $R_c$ may be further optionally substituted by one or more $R_d$;

$R_d$ is C1–3 alkyl, C3–6 cycloalkyl, phenyl, benzyl, C1–3 alkoxy, phenoxy, phenylC1–3alkyl, benzoyl, halogen, hydroxy, oxo or cyano;

$R_4$ is hydrogen;

$R_5$ is a bond, hydrogen, carbonyl, C1–6 alkyl, C1–6alkoxyC1–6alkyl, C1–6alkylaminoC1–6alkyl, C1–6alkylthioC1–6alkyl wherein the sulfur atom may be oxidized to a sulfoxide or sulfone, C1–6 alkoxy, phenoxy, naphthyloxy, C3–6 cycloalkyl, phenyl, naphthyl, benzyl, indanyl, heterocyclyl selected from pyrrolidinyl, piperidinyl, morpholinyl, thiomorpholinyl, piperazinyl, tetrahydropyranyl, tetrahydrothiopyranyl, furanyl, tetrahydrofuranyl, thienyl, oxazolyl, thiazolyl, imidazolyl, pyridinyl, pyrimidinyl, pyrazolyl, benzofuranyl, benzothienyl, benzimidazolyl, benzthiazolyl, quinolinyl, isoquinolinyl, and benzoxazolyl, heterocyclyloxy wherein the heterocyclyl moiety is selected from those herein described in this paragraph, C1–3alkanoyl, benzoyl, naphthoyl, C1–4alkanoyloxy, benzyloxy, C1–4 alkoxycarbonyl, arylC1–2alkoxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–4 alkanoylamino, aroylamino, C1–4 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, phenyl, naphthyl, pyrrolidinyl, piperidinyl, morpholinyl, piperazinyl, oxazolyl, thiazolyl, imidazolyl, pyridinyl, pyrimidinyl, pyrazinyl, indolyl, benzofuranyl, benzothienyl, benzimidazolyl or benzthiazolyl, or $R_5$ is C1–4 alkoxycarbonylamino, phenoxycarbonylamino, C1–4 alkylcarbamoyloxy, phenylcarbamoyloxy, C1–4 alkylsulfonylamino, phenylsulfonylamino, C1–3 alkylaminosulfonyl, phenylaminosulfonyl, amino wherein the nitrogen atom may be independently mono or di-substituted by C1–4 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzthiazolyl, or $R_5$ is halogen, hydroxy, oxo, carboxy, cyano, nitro or carboxamide, $R_5$ may be further optionally substituted by one or more $R_e$;

$R_e$ is C1–4 alkyl, C1–4 alkoxy, C3–7 cycloalkyl, phenyl, naphthyl, indanyl, pyrrolidinyl, piperidinyl, morpholinyl, thiomorpholinyl, piperazinyl, tetrahydrothiopyranyl, tetrahydropyranyl, tetrahydrofuranyl, thienyl, oxazolyl, thiazolyl, imidazolyl, pyridinyl, pyrimidinyl, pyrazinyl, indolyl, benzimidazolyl, benzthiazolyl, benzoxazolyl, quinolinyl, isoquinolinyl, quinazolinyl, quinoxalinyl, C1–4 alkanoyl, aroyl, C1–4alkanoyloxy, phenoxy, naphthyloxy, benzyloxy, C1–4 alkoxycarbonyl, phenoxycarbonyl, benzoyloxy, carbamoyl wherein the nitrogen atom may be independently mono or di-substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl, or benzthiazolyl, or $R_e$ is C1–4 alkanoylamino, benzoylamino, C1–4 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzthiazolyl, or $R_e$ is C1–4 alkoxycarbonylamino, phenoxycarbonylamino, C1–4 alkylcarbamoyloxy, phenylcarbamoyloxy, C1–4 alkylsulfonylamino, phenylsulfonylamino, C1–4 alkylaminosulfonyl, phenylaminosulfonyl, amino wherein the nitrogen atom may be independently mono or di-substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzthiazolyl, or $R_e$ is halogen, hydroxy, oxo, carboxy, cyano, nitro or carboxamide, $R_e$ may be further optionally substituted by one or more $R_f$;

$R_f$ is methyl, ethyl, t-butyl, tolylsulfonyl, methoxy, cyclopropyl, phenyl, phenoxy, benzyloxy, fluoro, chloro, bromo, hydroxy, oxo, carboxy or carboxamide.

$R_1$ and $R_6$ of the formula (Ia) or Formula (Ib) optionally form a monocyclic 5 or 6 membered aromatic or nonaromatic heterocyclic ring optionally substituted by $R_7$;

or a bicyclic ring having one 5, 6 or 7 membered aromatic or nonaromatic heterocyclic ring fused to a second 5–6 membered aromatic or nonaromatic heterocyclic or carbocyclic ring wherein each ring is optionally independently substituted by one or more $R_7$;

$R_7$ and $R_8$ are independently C1–4 alkyl, C5–6 cycloalkyl, C1–4 alkoxy, halogen, hydroxy, oxo, carboxy, nitrile, nitro or $NH_2C(O)$—;

and

X is O.

In yet still another embodiment of the invention, there are provided novel compounds of the formulas (Ia) and (Ib) as described immediately above, and wherein:

Het is piperidinyl, pyrrolidinyl, azetidinyl, azepanyl, oxepanyl, tetrahydropyranyl, oxetanyl or tetrahydrothiopyranyl each ring being optionally substituted with one or more $R_5$;

$R_1$ is a bond, C1–5 alkyl, C1–5 alkoxy, C3–6 cycloalkyl, aryloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofurannyl, benzthienyl, benzimidazolyl, benzthiazolyl, benzoxazolyl or amino; wherein $R_1$ is optionally substituted by one or more $R_a$;

$R_a$ is a bond, C1–3 alkyl, cyclopropyl, cyclohexyl, phenyl, pyrrolidinyl, piperidinyl, morpholinyl, thiomorpholinyl, piperazinyl, thienyl, imidazolyl, C1–3 alkoxy, C1–3alkanoyl, C1–3alkanoyloxy, aryloxy, benzyloxy, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl or piperazinyl, or $R_a$ is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or $R_a$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl, aryl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is methyl, ethyl, n-propyl, i-propyl, cyclopropyl, cyclopentyl, cyclohexyl, phenyl, methoxy, ethoxy, n-propoxy, i-propoxy, phenoxy, benzyloxy, fluoro, chloro, bromo, iodo, hydroxy, oxo, carboxy, cyano, nitro or carboxamide;

$R_2$ is hydrogen;

$R_3$ is a bond, C1–3 alkyl, C2–4alkylene, C5–6 cycloalkyl, benzyl or naphthylmethyl wherein $R_3$ is optionally substituted by one or more $R_c$;

$R_c$ is C1–3 alkyl, C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, furanyl, tetrahydropyranyl, thienyl, oxazolyl, thiazolyl, imidazolyl, pyrimidinyl, indolyl, benzofuranyl, benzothienyl, benzthiazolyl, C1–3 alkoxy, phenoxy, naphthyloxy, C1–2 alkanoyl, benzoyl, C1–2 alkoxycarbonyl, phenoxycarbonyl, C1–2alkanoyloxy, benzoyloxy, carbamoyl wherein the nitrogen atom may be independently mono or di-substituted by C1–3 alkyl or aryl, or $R_c$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl or aryl, or $R_c$ is C1–2 alkoxycarbonylamino, phenoxycarbonylamino, C1–2 alkylcarbamoyloxy, arylcarbamoyloxy, C1–2 alkylsulfonylamino, phenylsulfonylamino, C1–2alkylaminosulfonyl, phenylaminosulfonyl, amino wherein the nitrogen atom may be independently mono or di-substituted by C1–3 alkyl or phenyl, or $R_c$ is halogen, hydroxy, oxo, carboxy or cyano, $R_c$ may be further optionally substituted by one or more $R_d$;

$R_d$ is methyl, cyclopropyl, cyclohexyl, phenyl, benzyl, methoxy, phenoxy, benzyloxy, benzoyl, fluoro, chloro, oxo or cyano;

$R_5$ is a bond, hydrogen, carbonyl, C1–5 alkyl, C1–5alkoxyC1–5alkyl, C1–5alkylamino C1–5alkyl, C1–5alkylthioC1–5alkyl wherein the sulfur atom may be oxidized to a sulfoxide or sulfone, C1–5 alkoxy, phenoxy, C3–6 cycloalkyl, phenyl, naphthyl, benzyl, indanyl, heterocyclyl selected from pyrrolidinyl, piperidinyl, morpholinyl, thiomorpholinyl, piperazinyl, tetrahydropyranyl, oxazolyl, thiazolyl, imidazolyl, pyridinyl, pyrimidinyl, benzimidazolyl and benzthiazolyl, heterocyclyloxy wherein the heterocyclyl moiety is selected from those herein described in this paragraph, C1–3alkanoyl, benzoyl, naphthoyl, C1–3alkanoyloxy, benzyloxy, C1–3 alkoxycarbonyl, benzyloxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–3 alkanoylamino, aroylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzofurannyl, benzothienyl, benzimidazolyl or benzthiazolyl, or $R_5$ is C1–3 alkoxycarbonylamino, phenoxycarbonylamino, C1–3 alkylcarbamoyloxy, phenylcarbamoyloxy, C1–3 alkylsulfonylamino, phenylsulfonylamino, C1–3 alkylaminosulfonyl, phenylaminosulfonyl, amino wherein the nitrogen atom may be independently mono or di-substituted by C1–3 alkyl, phenyl, pyrrolidinyl, piperidinyl, morpholinyl, thiomorpholinyl, piperazinyl, oxazolyl, thiazolyl, imidazolyl, pyridinyl, pyrimidinyl, benzimidazolyl or benzthiazolyl, or $R_5$ is halogen, hydroxy, oxo, carboxy, cyano or carboxamide, $R_5$ may be further optionally substituted by one or more $R_e$;

$R_e$ is C1–3 alkyl, C1–3 alkoxy, C3–7 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzthiazolyl, benzoxazolyl, C1–3 alkanoyl, aroyl, C1–3 alkanoyloxy, phenoxy, benzyloxy, C1–3 alkoxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is C1–3 alkanoylamino, benzoylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is C1–3 alkoxycarbonylamino, phenoxycarbonylamino, C1–3 alkylcarbamoyloxy, phenylcarbamoyloxy, C1–3 alkylsulfonylamino, phenylsulfonylamino, C1–3 alkylaminosulfonyl, phenylaminosulfonyl, amino wherein the nitrogen atom may be independently mono or di-substituted by C1–3 alkyl, phenyl, naphthyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is halogen, hydroxy, oxo, carboxy, cyano or carboxamide, $R_e$ may be further optionally substituted by one or more $R_f$; and $R_f$ is methyl, phenyl, tolylsulfonyl, methoxy, phenoxy, benzyloxy, fluoro, chloro, bromo, hydroxy, oxo, carboxy or carboxamide;

$R_1$ and $R_6$ of the formula (Ia) or Formula (Ib) form a bicyclic ring having one 5 or 6 membered aromatic or nonaromatic heterocyclic ring fused to a second 5–6 membered heteroaryl, heterocycle or phenyl ring; wherein each ring is optionally independently substituted by one or two $R_7$.

In yet a further embodiment of the invention, there are provided novel compounds of the formulas (Ia) and (Ib) as described immediately above, and wherein:

Het is piperidinyl, pyrrolidinyl, azetidinyl, azepanyl or tetrahydropyranyl each ring being substituted with one or more $R_5$;

$R_1$ is a bond, methyl, ethyl, i-propyl, methoxy, ethoxy, cyclopropyl, cyclopentyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein $R_1$ is optionally substituted by one or more $R_a$;

$R_a$ is a bond, methyl, ethyl, cyclopropyl, phenyl, pyrrolidinyl, piperidinyl, morpholinyl, thiomorpholinyl, piperazinyl, thienyl, imidazolyl, methoxy, acetyl, acetoxy, phenoxy, benzyloxy, methoxycarbonyl, phenoxycarbonyl, benzoyloxy, carbamoyl wherein the nitrogen atom may be independently mono or di-substituted by methyl, ethyl or phenyl, or $R_a$ is acetylamino, benzoylamino, methylthio, phenylthio wherein the sulfur atom may be oxidized to a sulfoxide or sulfone, ureido wherein either nitrogen atom may be independently substituted by methyl, ethyl or phenyl, or $R_a$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl or phenyl, or $R_a$ is fluoro, chloro, bromo, iodo, hydroxy, oxo, carboxy, cyano, nitro or carboxamide, $R_a$ may be further optionally substituted by one or more $R_b$;

$R_b$ is methyl, cyclopropyl, phenyl, methoxy, phenoxy, benzyloxy, fluoro, chloro, hydroxy, oxo, carboxy or carboxamide;

$R_3$ is a bond, C1–3 alkyl, C2–4alkylene, C5–6 cycloalkyl, benzyl or naphthylmethyl wherein $R_3$ is optionally substituted by one or more $R_c$;

$R_c$ is methyl, ethyl, n-propyl, i-propyl, C5–6 cycloalkyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, thienyl, oxazolyl, thiazolyl, indolyl, benzofuranyl, benzothienyl, benzthiazolyl, methoxy, ethoxy, phenoxy, acetyl, benzoyl, methoxycarbonyl, phenoxycarbonyl, acetoxy, benzoyloxy, carbamoyl wherein the nitrogen atom may be independently mono or di-substituted by methyl, ethyl or aryl, or $R_c$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or aryl, or $R_c$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_c$ is fluoro, chloro or oxo, $R_c$ may be further optionally substituted by one or more $R_d$;

$R_d$ is methyl, cyclopropyl, phenyl, methoxy, fluoro, chloro or oxo;

$R_5$ is a bond, hydrogen, carbonyl, C1–4 alkyl, C1–4alkoxyC1–4alkyl, C1–4alkylaminoC1–4alkyl, C1–4alkylthioC1–4alkyl wherein the sulfur atom may be oxidized to a sulfoxide or sulfone, C1–4 alkoxy,phenoxy, cyclopropyl, cyclopentyl, cyclohexyl, phenyl, naphthyl, benzyl, indanyl, heterocyclyl selected from pyrrolidinyl, piperidinyl, morpholinyl, piperazinyl, tetrahydropyranyl, oxazolyl, thiazolyl, imidazolyl, pyridinyl, pyrimidinyl, benzimidazolyl and benzthiazolyl, heterocyclyloxy wherein the heterocyclyl moiety is selected from those herein described in this paragraph, C1–2alkanoyl, benzoyl, naphthoyl, C1–2alkanoyloxy, benzyloxy, C1–2 alkoxycarbonyl, benzyloxycarbonyl, phenoxycarbonyl, benzoyloxy, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_5$ is C1–2 alkoxycarbonylamino, phenoxycarbonylamino, C1–2 alkylcarbamoyloxy, phenylcarbamoyloxy, C1–2 alkylsulfonylamino, phenylsulfonylamino, C1–2 alkylaminosulfonyl, phenylaminosulfonyl, amino wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_5$ is fluoro, chloro, bromo, hydroxy, oxo, carboxy or carboxamide, $R_5$ may be further optionally substituted by one or more $R_e$;

$R_e$ is C1–3 alkyl, C1–2 alkoxy, C3–6 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzthiazolyl, benzoxazolyl, C1–2 alkanoyl, aroyl, C1–2 alkanoyloxy, phenoxy, benzyloxy, C1–2 alkoxycarbonyl, phenoxycarbonyl, benzoyloxy, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is C1–2 alkoxycarbonylamino, phenoxycarbonylamino, C1–2 alkylcarbamoyloxy, phenylcarbamoyloxy, C1–2 alkylsulfonylamino, phenylsulfonylamino, C1–2 alkylaminosulfonyl, phenylaminosulfonyl, amino wherein the nitrogen atom may be independently mono or di-substituted by C1–2 alkyl, phenyl, naphthyl, pyrrolidinyl, piperidinyl, morpholinyl, piperazinyl, oxazolyl, thiazolyl, imidazolyl, pyridinyl or pyrimidinyl, or $R_e$ is fluoro, chloro, bromo, hydroxy, oxo, carboxy or carboxamide, $R_e$ may be further optionally substituted by one or more $R_f$;

$R_f$ is methyl, phenyl, tolylsulfonyl, methoxy, phenoxy, benzyloxy, fluoro, chloro, hydroxy, oxo, carboxy or carboxamide and $R_1$ and $R_6$ of the formula (Ia) or Formula (Ib) form a bicyclic ring having one 5–6 membered aromatic or nonaromatic heterocyclic ring fused to a phenyl ring; wherein each ring is optionally independently substituted by one or two $R_7$.

In yet still a further embodiment of the invention, there are provided novel compounds of the formula (Ia) or formula (Ib) as described immediately above, and wherein:

Het is piperidin-4-yl, piperidin-3-yl, pyrrolidin-3-yl, azetidin-3-yl, azepan-3-yl, azepan-4-yl or tetrahydropyran-4-yl, each ring being optionally substituted with one or more $R_5$;

$R_1$ is a bond, methyl, ethyl, i-propyl, methoxy, cyclopropyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein $R_1$ is optionally substituted by one or more $R_a$;

$R_a$ is methyl, phenyl, thienyl, methoxy, acetyl, acetoxy, phenoxy, benzyloxy, methoxycarbonyl, benzoyloxy, carbamoyl wherein the nitrogen atom may be independently mono or di-substituted by methyl or phenyl, or $R_a$ is acetylamino, methylthio, phenylthio wherein the sulfur atom may be oxidized to a sulfoxide or sulfone, ureido wherein either nitrogen atom may be independently substituted by methyl or phenyl, or $R_a$ is methoxycarbonylamino, methylcarbamoyloxy, phenylcarbamoyloxy, methylsulfonylamino, phenylsulfonylamino, amino wherein the nitrogen atom may be independently mono or di-substituted by methyl or phenyl, or $R_a$ is fluoro, chloro, hydroxy, oxo, carboxy, cyano or carboxamide;

$R_3$ is a bond, methyl, ethyl, n-propyl, propenyl, butenyl, i-butenyl, cyclohexyl, benzyl or naphthylmethyl wherein $R_3$ is optionally substituted by one or more $R_c$;

$R_c$ is methyl, ethyl, n-propyl, i-propyl, cyclohexyl, cyclopentyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, methoxy, phenoxy, acetyl, benzoyl, methoxycarbonyl, phenoxycarbonyl, acetoxy, benzoyloxy, methylthio wherein the sulfur atom may be oxidized to a sulfoxide or sulfone, phenylthio wherein the sulfur atom may be oxidized to a sulfoxide or sulfone, fluoro, chloro or oxo;

$R_5$ is a bond, hydrogen, carbonyl, C1–4 alkyl, C1–2alkoxyC1–2alkyl, C1–2alkylaminoC1–2alkyl, C1–2alkylthioC1–2alkyl wherein the sulfur atom may be oxidized to a sulfoxide or sulfone, C1–2 alkoxy, phenoxy, cyclopropyl, cyclopentyl, cyclohexyl, phenyl, benzyl, heterocyclyl selected from pyrrolidinyl, piperidinyl, morpholinyl, tetrahydropyranyl, pyridinyl, and pyrimidinyl, heterocyclyloxy wherein the heterocyclyl moiety is selected from those herein described in this paragraph, acetyl, benzoyl, acetyloxy, benzyloxy, methoxycarbonyl, ethoxycarbonyl, benzyloxycarbonyl, benzoyloxy, carbamoyl wherein the nitrogen atom may be independently mono or di-substituted by methyl, ethyl or phenyl, or $R_5$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or phenyl, or $R_5$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_5$ is fluoro, chloro, hydroxy, oxo, carboxy or carboxamide, $R_5$ may be further optionally substituted by one or more $R_e$;

$R_e$ is methyl, methoxy, ethoxy, cyclopropyl, cyclopentyl, cyclohexyl, phenyl, naphthyl, indanyl, piperidinyl, morpholinyl, indolyl, thienyl, pyridinyl, acetyl, benzoyl, acetyloxy, phenoxy, benzyloxy, methoxycarbonyl, ethoxycarbonyl, carbamoyl wherein the nitrogen atom may be independently mono or di-substituted by methyl, ethyl or phenyl, or $R_e$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or phenyl, or $R_e$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_e$ is fluoro, chloro, hydroxy, oxo, carboxy or carboxamide, $R_e$ may be further optionally substituted by one or more $R_f$; and $R_f$ is methyl, phenyl, tolylsulfonyl, phenoxy, benzyloxy, fluoro, chloro or oxo;

$R_1$ and $R_6$ of the formula (Ia) or Formula (Ib) form the bicyclic ring

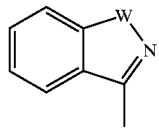

wherein W is —S(O)$_n$—, —O—C(O)— or —N—C(O)—, n is 0, 1 or 2 and wherein each ring is optionally independently substituted by one or two $R_7$.

In a further embodiment of the invention, there are provided novel compounds of the formulas (Ia) and (Ib) as described immediately above, and wherein:

Het is piperidin-4-yl, piperidin-3-yl, pyrrolidin-3-yl, azetidin-3-yl or tetrahydropyran-4-yl, each ring being substituted with one or more $R_5$;

$R_1$ is i-propyl, benzyloxy, cyclohexyl, phenyl, 4-(acetylamino)-phenyl, 4-(methanesulfonylamino)-phenyl, 4-methoxyphenyl, 3-phenoxyphenyl, 4-chlorophenyl, 4-fluorophenyl, 2-fluorophenyl, 2-fluoro-4-chlorophenyl, naphthyl, thienylmethyl, piperidinyl, morpholinyl, pyrrolidinyl, piperazinyl, furanyl, thienyl, 5-chlorothienyl, pyridin-4-yl, pyrazinyl, methylamino, ethylamino, dimethylamino or diethylamino;

$R_3$ is ethyl, n-propyl, propenyl, butenyl, i-butenyl, benzyl or naphthylmethyl wherein $R_3$ is optionally substituted by one or more $R_c$;

$R_c$ is methyl, cyclohexyl, cyclopentyl, indanyl, 1,2,3,4-tetrahydronaphthyl, methoxy, methylthio wherein the sulfur atom may be oxidized to a sulfoxide or sulfone, fluoro or chloro;

$R_5$ is a bond, carbonyl, methyl, ethyl, n-propyl, n-butyl, t-butyl, i-propyl, i-butyl, cyclopropyl, cyclopentyl, cyclohexyl, phenyl, benzyl, piperidinyl, tetrahydropyranyl, pyrimidinyl, acetyl, benzoyl, ethoxycarbonyl, benzyloxycarbonyl, methylsulfonylamino, phenylsulfonylamino, methylamino, dimethylamino, fluoro, oxo or carboxy, $R_5$ may be further optionally substituted by one or more $R_e$;

$R_e$ is methyl, cyclopropyl, cyclopentyl, cyclohexyl, phenyl, naphthyl, indanyl, thienyl, 5-methylthienyl, methoxy, phenoxy, benzyloxy, piperidinyl, pyridinyl, indolyl, 1-(tolyl-sulfonyl)-indolyl, carbamoyl wherein the nitrogen atom may be independently mono or di-substituted by methyl, phenyl or benzyl, or $R_e$ is hydroxy, fluoro, chloro, oxo, dimethylamino or trifluoromethyl; and n is 2.

In another embodiment of the invention, there are provided novel compounds of the formulas (Ia) and (Ib) as described for the broadest generic aspect above and wherein:

$R_1$ and $R_6$ remain acyclic,

Het is piperidinyl, pyrrolidinyl, azetidinyl, azepanyl, oxepanyl, tetrahydropyranyl, oxetanyl or tetrahydrothiopyranyl each ring being optionally substituted with one or more $R_5$;

$R_1$ is a bond, C1–5 alkyl, C1–5 alkoxy, C3–6 cycloalkyl, aryloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is a bond, C1–3 alkyl, cyclopropyl, cyclohexyl, phenyl, pyrrolidinyl, piperidinyl, morpholinyl, thiomorpholinyl, piperazinyl, thienyl, imidazolyl, C1–3 alkoxy, C1–3alkanoyl, C1–3alkanoyloxy, aryloxy, benzyloxy, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl or piperazinyl, or $R_a$ is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or $R_a$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl, aryl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is methyl, ethyl, n-propyl, i-propyl, cyclopropyl, cyclopentyl, cyclohexyl, phenyl, methoxy, ethoxy, n-propoxy, i-propoxy, phenoxy, benzyloxy, fluoro, chloro, bromo, iodo, hydroxy, oxo, carboxy, cyano, nitro or carboxamide;

$R_2$ is hydrogen;

$R_3$ is a bond, C1–3 alkyl, C2–4alkylene, C5–6 cycloalkyl, benzyl or naphthylmethyl wherein $R_3$ is optionally substituted by one or more $R_c$;

$R_c$ is C1–3 alkyl, C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, furanyl, tetrahydropyranyl, thienyl, oxazolyl, thiazolyl, imidazolyl, pyrimidinyl, indolyl, benzofuranyl, benzothienyl, benzthiazolyl, C1–3 alkoxy, phenoxy, naphthyloxy, C1–2 alkanoyl, benzoyl, C1–2 alkoxycarbonyl, phenoxycarbonyl, C1–2alkanoyloxy, benzoyloxy, carbamoyl wherein the nitrogen atom may be independently mono or di-substituted by C1–3 alkyl or aryl, or $R_c$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl or aryl, or $R_c$ is C1–2 alkoxycarbonylamino, phenoxycarbonylamino, C1–2 alkylcarbamoyloxy, arylcarbamoyloxy, C1–2 alkylsulfonylamino, phenylsulfonylamino, C1–2alkylaminosulfonyl, phenylaminosulfonyl, amino wherein the nitrogen atom may be independently mono or di-substituted by C1–3 alkyl or phenyl, or $R_c$ is halogen, hydroxy, oxo, carboxy or cyano, $R_c$ may be further optionally substituted by one or more $R_d$;

$R_d$ is methyl, cyclopropyl, cyclohexyl, phenyl, benzyl, methoxy, phenoxy, benzyloxy, benzoyl, fluoro, chloro, oxo or cyano;

$R_4$ is hydrogen;

$R_5$ is a bond, hydrogen, carbonyl, C1–5 alkyl, C1–5alkoxyC1–5alkyl, C1–5alkylaminoC1–5alkyl, C1–5alkylthioC1–5alkyl wherein the sulfur atom may be oxidized to a sulfoxide or sulfone, C1–5 alkoxy, phenoxy, C3–6 cycloalkyl, phenyl, naphthyl, benzyl, indanyl, heterocyclyl selected from pyrrolidinyl, piperidinyl, morpholinyl, thiomorpholinyl, piperazinyl, tetrahydropyranyl, oxazolyl, thiazolyl, imidazolyl, pyridinyl, pyrimidinyl, benzimidazolyl and benzthiazolyl, heterocyclyloxy wherein the heterocyclyl moiety is selected from those herein described in this paragraph, C1–3alkanoyl, benzoyl, naphthoyl, C1–3alkanoyloxy, benzyloxy, C1–3 alkoxycarbonyl, benzyloxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–3 alkanoylamino, aroylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzofuranyl, benzothienyl, benzimidazolyl or benzthiazolyl, or $R_5$ is C1–3 alkoxycarbonylamino, phenoxycarbonylamino, C1–3 alkylcarbamoyloxy, phenylcarbamoyloxy, C1–3 alkylsulfonylamino, phenylsulfonylamino, C1–3 alkylaminosulfonyl, phenylaminosulfonyl, amino wherein the nitrogen atom may be independently mono or di-substituted by C1–3 alkyl, phenyl, pyrrolidinyl, piperidinyl, morpholinyl, thiomorpholinyl, piperazinyl, oxazolyl, thiazolyl, imidazolyl, pyridinyl, pyrimidinyl, benzimidazolyl or benzthiazolyl, or $R_5$ is halogen, hydroxy, oxo, carboxy, cyano or carboxamide, $R_5$ may be further optionally substituted by one or more $R_e$;

$R_e$ is C1–3 alkyl, C1–3 alkoxy, C3–7 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzthiazolyl, benzoxazolyl, C1–3 alkanoyl, aroyl, C1–3 alkanoyloxy, phenoxy, benzyloxy, C1–3 alkoxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is C1–3 alkanoylamino, benzoylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is C1–3 alkoxycarbonylamino, phenoxycarbonylamino, C1–3 alkylcarbamoyloxy, phenylcarbamoyloxy, C1–3 alkylsulfonylamino, phenylsulfonylamino, C1–3 alkylaminosulfonyl, phenylaminosulfonyl, amino wherein the nitrogen atom may be independently mono or di-substituted by C1–3 alkyl, phenyl, naphthyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is halogen, hydroxy, oxo, carboxy, cyano or carboxamide, $R_e$ may be further optionally substituted by one or more $R_f$;

$R_f$ is methyl, phenyl, tolylsulfonyl, methoxy, phenoxy, benzyloxy, fluoro, chloro, bromo, hydroxy, oxo, carboxy or carboxamide;

$R_6$ is hydroxy, nitrile or a C1–5 saturated or unsaturated branched or unbranched carbon chain optionally partially or fully halogenated wherein one or more C atoms are optionally replaced by O, NH, or $S(O)_2$ and wherein said chain is optionally independently substituted with 1–2 oxo groups, —$NH_2$, one or more C1–4 alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl; and X is O.

In another embodiment of the invention, there are provided novel compounds of the formula (Ia) and (Ib) as described immediately above, and wherein:

$R_1$ is a bond, methyl, ethyl, i-propyl, methoxy, ethoxy, cyclopropyl, cyclopentyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein $R_1$ is optionally substituted by one or more $R_a$;

$R_a$ is a bond, methyl, ethyl, cyclopropyl, phenyl, pyrrolidinyl, piperidinyl, morpholinyl, thiomorpholinyl, piperazinyl, thienyl, imidazolyl, methoxy, acetyl, acetoxy, phenoxy, benzyloxy, methoxycarbonyl, phenoxycarbonyl, benzoyloxy, carbamoyl wherein the nitrogen atom may be independently mono or di-substituted by methyl, ethyl or phenyl, or $R_a$ is acetylamino, benzoylamino, methylthio, phenylthio wherein the sulfur atom may be oxidized to a sulfoxide or sulfone, ureido wherein either nitrogen atom may be independently substituted by methyl, ethyl or phenyl, or $R_a$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl or phenyl, or $R_a$ is fluoro, chloro, bromo, iodo, hydroxy, oxo, carboxy, cyano, nitro or carboxamide, $R_a$ may be further optionally substituted by one or more $R_b$;

$R_b$ is methyl, cyclopropyl, phenyl, methoxy, phenoxy, benzyloxy, fluoro, chloro, hydroxy, oxo, carboxy or carboxamide;

$R_3$ is a bond, C1–3 alkyl, C2–4 alkylene, C5–6 cycloalkyl, benzyl or naphthylmethyl wherein $R_3$ is optionally substituted by one or more $R_c$;

$R_c$ is methyl, ethyl, n-propyl, i-propyl, C5–6 cycloalkyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, thienyl, oxazolyl, thiazolyl, indolyl, benzofuranyl, benzothienyl, benzthiazolyl, methoxy, ethoxy, phenoxy, acetyl, benzoyl, methoxycarbonyl, phenoxycarbonyl, acetoxy, benzoyloxy, carbamoyl wherein the nitrogen atom may be independently mono or di-substituted by methyl, ethyl or aryl, or $R_c$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or aryl, or $R_c$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_c$ is fluoro, chloro or oxo, $R_c$ may be further optionally substituted by one or more $R_d$;

$R_d$ is methyl, cyclopropyl, phenyl, methoxy, fluoro, chloro or oxo;

$R_5$ is a bond, hydrogen, carbonyl, C1–4 alkyl, C1–4alkoxyC1–4alkyl, C1–4alkylaminoC1–4alkyl, C1–4alkylthioC1–4alkyl wherein the sulfur atom may be oxidized to a sulfoxide or sulfone, C1–4 alkoxy,phenoxy, cyclopropyl, cyclopentyl, cyclohexyl, phenyl, naphthyl, benzyl, indanyl, heterocyclyl selected from pyrrolidinyl, piperidinyl, morpholinyl, piperazinyl, tetrahydropyranyl, oxazolyl, thiazolyl, imidazolyl, pyridinyl, pyrimidinyl, benzimidazolyl and benzthiazolyl, heterocyclyloxy wherein the heterocyclyl moiety is selected from those herein described in this paragraph, C1–2alkanoyl, benzoyl, naphthoyl, C1–2alkanoyloxy, benzyloxy, C1–2 alkoxycarbonyl, benzyloxycarbonyl, phenoxycarbonyl, benzoyloxy, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_5$ is C1–2 alkoxycarbonylamino, phenoxycarbonylamino, C1–2 alkylcarbamoyloxy, phenylcarbamoyloxy, C1–2 alkylsulfonylamino, phenylsulfonylamino, C1–2 alkylaminosulfonyl, phenylaminosulfonyl, amino wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_5$ is fluoro, chloro, bromo, hydroxy, oxo, carboxy or carboxamide, $R_5$ may be further optionally substituted by one or more $R_e$;

$R_e$ is C1–3 alkyl, C1–2 alkoxy, C3–6 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzthiazolyl, benzoxazolyl, C1–2 alkanoyl, aroyl, C1–2alkanoyloxy, phenoxy, benzyloxy, C1–2 alkoxycarbonyl, phenoxycarbonyl, benzoyloxy, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is C1–2 alkoxycarbonylamino, phenoxycarbonylamino, C1–2 alkylcarbamoyloxy, phenylcarbamoyloxy, C1–2 alkylsulfonylamino, phenylsulfonylamino, C1–2 alkylaminosulfonyl, phenylaminosulfonyl, amino wherein the nitrogen atom may be independently mono or di-substituted by C1–2 alkyl, phenyl, naphthyl, pyrrolidinyl, piperidinyl, morpholinyl, piperazinyl, oxazolyl, thiazolyl, imidazolyl, pyridinyl or pyrimidinyl, or $R_e$ is fluoro, chloro, bromo, hydroxy, oxo, carboxy or carboxamide, $R_e$ may be further optionally substituted by one or more $R_f$;

$R_f$ is methyl, phenyl, tolylsulfonyl, methoxy, phenoxy, benzyloxy, fluoro, chloro, hydroxy, oxo, carboxy or carboxamide and $R_6$ is nitrile or a C1–5 saturated or unsaturated branched or unbranched carbon chain optionally partially or fully halogenated wherein one or more C atoms are optionally replaced by O, NH, or $S(O)_2$ and wherein said chain is optionally independently substituted with oxo, $-NH_2$, piperidinyl, morpholinyl, thiomorpholinyl, piperazinyl, pyridinyl, pyrimidinyl or pyrazinyl.

In yet another embodiment of the invention, there are provided novel compounds of the formula (Ia) or formula (Ib) as described immediately above, and wherein:

Het is piperidin-4-yl, piperidin-3-yl, pyrrolidin-3-yl, azetidin-3-yl, azepan-3-yl, azepan-4-yl or tetrahydropyran-4-yl, each ring being optionally substituted with one or more $R_5$;

$R_1$ is a bond, methyl, ethyl, i-propyl, methoxy, cyclopropyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein $R_1$ is optionally substituted by one or more $R_a$;

$R_a$ is methyl, phenyl, thienyl, methoxy, acetyl, acetoxy, phenoxy, benzyloxy, methoxycarbonyl, benzoyloxy, carbamoyl wherein the nitrogen atom may be independently mono or di-substituted by methyl or phenyl, or $R_a$ is acetylamino, methylthio, phenylthio wherein the sulfur atom may be oxidized to a sulfoxide or sulfone, ureido wherein either nitrogen atom may be independently substituted by methyl or phenyl, or $R_a$ is methoxycarbonylamino, methylcarbamoyloxy, phenylcarbamoyloxy, methylsulfonylamino, phenylsulfonylamino, amino wherein the nitrogen atom may be independently mono or di-substituted by methyl or phenyl, or $R_a$ is fluoro, chloro, hydroxy, oxo, carboxy, cyano or carboxamide;

$R_3$ is a bond, methyl, ethyl, n-propyl, propenyl, butenyl, i-butenyl, cyclohexyl, benzyl or naphthylmethyl wherein $R_3$ is optionally substituted by one or more $R_c$;

$R_c$ is methyl, ethyl, n-propyl, i-propyl, cyclohexyl, cyclopentyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, methoxy, phenoxy, acetyl, benzoyl, methoxycarbonyl, phenoxycarbonyl, acetoxy, benzoyloxy, methylthio wherein the sulfur atom may be oxidized to a sulfoxide or sulfone, phenylthio wherein the sulfur atom may be oxidized to a sulfoxide or sulfone, fluoro, chloro or oxo; and wherein the configuration at the stereocenter defined by $R_2$ and $R_3$ when they are different and the carbon they are attached to is defined as L; and $R_5$ is a bond, hydrogen, carbonyl, C1–4 alkyl, C1–2alkoxyC1–2alkyl, C1–2alkylaminoC1–2alkyl, C1–2alkylthioC1–2alkyl wherein the sulfur atom may be oxidized to a sulfoxide or sulfone, C1–2 alkoxy, phenoxy, cyclopropyl, cyclopentyl, cyclohexyl, phenyl, benzyl, heterocyclyl selected from pyrrolidinyl, piperidinyl, morpholinyl, tetrahydropyranyl, pyridinyl, and pyrimidinyl, heterocyclyloxy wherein the heterocyclyl moiety is selected from those herein described in this paragraph, acetyl, benzoyl, acetyloxy, benzyloxy, methoxycarbonyl, ethoxycarbonyl, benzyloxycarbonyl, benzoyloxy, carbamoyl wherein the nitrogen atom may be independently mono or di-substituted by methyl, ethyl or phenyl, or $R_5$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or phenyl, or $R_5$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_5$ is fluoro, chloro, hydroxy, oxo, carboxy or carboxamide, $R_5$ may be further optionally substituted by one or more $R_e$;

$R_e$ is methyl, methoxy, ethoxy, cyclopropyl, cyclopentyl, cyclohexyl, phenyl, naphthyl, indanyl, piperidinyl, morpholinyl, indolyl, thienyl, pyridinyl, acetyl, benzoyl, acetyloxy, phenoxy, benzyloxy, methoxycarbonyl, ethoxycarbonyl, carbamoyl wherein the nitrogen atom may be independently mono or di-substituted by methyl, ethyl or phenyl, or $R_e$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or phenyl, or $R_e$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_e$ is fluoro, chloro, hydroxy, oxo, carboxy or carboxamide, $R_e$ may be further optionally substituted by one or more $R_f$;

$R_f$ is methyl, phenyl, tolylsulfonyl, phenoxy, benzyloxy, fluoro, chloro or oxo;

$R_6$ is nitrile or a C1–5 saturated or unsaturated branched or unbranched carbon chain optionally partially or fully halogenated wherein one or more C atoms are optionally replaced by O, NH, or $S(O)_2$ and wherein said chain is optionally independently substituted with oxo, $—NH_2$, morpholinyl or piperazinyl.

In yet still another embodiment of the invention, there are provided novel compounds of the formulas (Ia) and (Ib) as described immediately above, and wherein:

Het is piperidin-4-yl, piperidin-3-yl, pyrrolidin-3-yl, azetidin-3-yl or tetrahydropyran-4-yl, each ring being substituted with one or more $R_5$;

$R_1$ is i-propyl, benzyloxy, cyclohexyl, phenyl, 4-(acetylamino)-phenyl, 4-(methanesulfonylamino)-phenyl, 4-methoxyphenyl, 3-phenoxyphenyl, 4-chlorophenyl, 4-fluorophenyl, 2-fluorophenyl, 2-fluoro-4-chlorophenyl, naphthyl, thienylmethyl, piperidinyl, morpholinyl, pyrrolidinyl, piperazinyl, furanyl, thienyl, 5-chlorothienyl, pyridin-4-yl, pyrazinyl, methylamino, ethylamino, dimethylamino or diethylamino;

$R_3$ is ethyl, n-propyl, propenyl, butenyl, i-butenyl, benzyl or naphthylmethyl wherein $R_3$ is optionally substituted by one or more $R_c$;

$R_c$ is methyl, cyclohexyl, cyclopentyl, indanyl, 1,2,3,4-tetrahydronaphthyl, methoxy, methylthio wherein the sulfur atom may be oxidized to a sulfoxide or sulfone, fluoro or chloro;

$R_5$ is a bond, carbonyl, methyl, ethyl, n-propyl, n-butyl, t-butyl, i-propyl, i-butyl, cyclopropyl, cyclopentyl, cyclohexyl, phenyl, benzyl, piperidinyl, tetrahydropyranyl, pyrimidinyl, acetyl, benzoyl, ethoxycarbonyl, benzyloxycarbonyl, methylsulfonylamino, phenylsulfonylamino, methylamino, dimethylamino, fluoro, oxo or carboxy, $R_5$ may be further optionally substituted by one or more $R_e$;

$R_e$ is methyl, cyclopropyl, cyclopentyl, cyclohexyl, phenyl, naphthyl, indanyl, thienyl, 5-methylthienyl, methoxy, phenoxy, benzyloxy, piperidinyl, pyridinyl, indolyl, 1-(tolyl-sulfonyl)-indolyl, carbamoyl wherein the nitrogen atom may be independently mono or di-substituted by methyl, phenyl or benzyl, or $R_e$ is hydroxy, fluoro, chloro, oxo, dimethylamino or trifluoromethyl; and $R_6$ is acetyl, C1–3alkylaminocarbonyl or C1–3alkoxycarbonyl.

In yet a further embodiment of the invention, there are provided novel compounds of the formulas (Ia) and (Ib) as described immediately above, and wherein:

Het is piperidin-4-yl or pyrrolidin-3-yl;

$R_1$ is morpholin-4-yl, p-fluorophenyl or p-methoxyphenyl;

$R_5$ is methyl, propyl, n-pentyl or cyclohexyl and $R_6$ is acetyl, ethylaminocarbonyl or ethoxycarbonyl.

The activity of particular compounds disclosed herein against cathepsin K may be determined without undue experimentation by one of ordinary skill in the art in view of the art, the guidance provided throughout this specification and by the screens described in the section entitled "Assessment of Biological Properties."

The following subgeneric aspect of the compounds of the formulas (Ia) and (Ib) is postulated to possess Cathepsin K activity:

The broadest embodiment of the formula (Ia) and (Ib) as described hereinabove and wherein Het is piperidinyl, pyrrolidinyl, azetidinyl, azepanyl, oxepanyl, tetrahydropyranyl, oxetanyl or tetrahydrothiopyranyl each ring being optionally substituted with one or more $R_5$;

$R_1$ is a bond, C1–4 alkyl, C1–4 alkoxy, cyclopropyl, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is methyl, ethyl, propyl, i-propyl, cyclopropyl, cyclohexyl, phenyl, pyrrolidinyl, piperidinyl, morpholinyl, thiomorpholinyl, piperazinyl, thienyl, imidazolyl, methoxy, ethoxy, acetyl, acetoxy, phenoxy, naphthyloxy, benzyloxy, methoxycarbonyl, ethoxycarbonyl, phenoxycarbonyl, naphthyloxycarbonyl, benzoyloxy, carbamoyl wherein the nitrogen atom may be independently mono or di-substituted by methyl, ethyl, phenyl, naphthyl, pyrrolidinyl, piperidinyl, morpholinyl, thiomorpholinyl or piperazinyl, or $R_a$ is acetylamino, benzoylamino, methylthio wherein the sulfur atom may be oxidized to a sulfoxide or sulfone, ethylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl, phenyl, naphthyl, pyrrolidinyl, piperidinyl, morpholinyl, thiomorpholinyl or piperazinyl, or $R_a$ is methoxycarbonylamino, ethoxycarbonylamino, phenoxycarbonylamino, C1–2 alkylcarbamoyloxy, phenylcarbamoyloxy, naphthylcarbamoyloxy, C1–2 alkylsulfonylamino, phenylsulfonylamino, naphthylsulfonylamino, C1–2 alkylaminosulfonyl, phenylaminosulfonyl, naphthylaminosulfonyl, amino wherein the nitrogen atom may be independently mono or di-substituted by methyl, ethyl, phenyl, naphthyl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is methyl, ethyl, cyclopropyl, cyclohexyl, phenyl, methoxy, ethoxy, phenoxy, benzyloxy, fluoro, chloro, bromo, hydroxy, oxo, carboxy, cyano, nitro or carboxamide;

$R_2$ is hydrogen or methyl;

$R_3$ is a bond, methyl, ethyl, n-propyl, i-propyl, n-butyl, i-butyl, n-pentyl, propenyl, i-butenyl, cyclohexyl, benzyl or naphthylmethyl wherein $R_3$ is optionally substituted by one or more $R_c$;

$R_c$ is methyl, ethyl, cyclohexyl, cyclopentyl, phenyl, naphthyl, bicyclo[3.1.0]hexanyl, bicyclo[1.1.1] pentanyl, cubanyl, furanyl, tetrahydropyranyl, thienyl, oxazolyl, thiazolyl, imidazolyl, pyrimidinyl, methoxy, ethoxy, phenoxy, acetyl, benzoyl, methoxycarbonyl, phenoxycarbonyl, acetoxy, benzoyloxy, carbamoyl wherein the nitrogen atom may be independently mono or di-substituted by methyl or phenyl, or $R_c$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl or phenyl, or $R_c$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl or phenyl, or $R_c$ is chloro, fluoro, hydroxy, oxo, carboxy or cyano;

$R_2$ and $R_3$ together with the carbon they are attached optionally form a ring selected from cyclopentyl, cyclohexyl, cycloheptyl, tetrahydropyranyl, tetrahydrothiopyranyl, tetrahydrofuranyl, pyrrolidinyl, piperidinyl, piperazinyl, morpholinyl or tetrahydrothiophenyl;

$R_4$ is hydrogen;

$R_5$ is a bond, hydrogen, carbonyl, C1–5 alkyl, C1–5alkoxyC1–5alkyl, C1–5alkylaminoC1–5alkyl, C1–5alkylthioC1–5alkyl wherein the sulfur atom may be oxidized to a sulfoxide or sulfone, C1–5 alkoxy, phenoxy, naphthyloxy, cyclopropyl, cyclopentyl, cyclohexyl, phenyl, benzyl, heterocyclyl selected from pyrrolidinyl, piperidinyl, morpholinyl, tetrahydropyranyl, pyridinyl, and pyrimidinyl, heterocyclyloxy wherein the heterocyclyl moiety is selected from those herein described in this paragraph, acetyl, benzoyl, acetyloxy, benzyloxy, methoxycarbonyl, ethoxycarbonyl, benzyloxycarbonyl, benzoyloxy, carbamoyl wherein the nitrogen atom may be independently mono or di-substituted by methyl, ethyl or phenyl, or $R_5$ is acetylamino, benzoylamino, phenylthio wherein the sulfur atom may be oxidized to a sulfoxide or sulfone, ureido wherein either nitrogen atom may be independently substituted by methyl, ethyl or phenyl, or $R_5$ is methoxycarbonylamino, ethoxycarbonylamino, phenoxycarbonylamino, methylcarbamoyloxy, phenylcarbamoyloxy, phenylsulfonylamino, phenylaminosulfonyl, amino wherein the nitrogen atom may be independently mono or di-substituted by methyl, ethyl or phenyl, or $R_5$ is fluoro, chloro, hydroxy, oxo, carboxy or carboxamide, $R_5$ may be further optionally substituted by one or more $R_e$;

$R_e$ is methyl ethyl, methoxy, ethoxy, cyclopropyl, cyclopentyl, cyclohexyl, phenyl, naphthyl, indanyl, piperidinyl, morpholinyl, indolyl, thienyl, pyridinyl, methoxy, ethoxy, acetyl, benzoyl, acetyloxy, phenoxy, benzyloxy, methoxycarbonyl, ethoxycarbonyl, carbamoyl wherein the nitrogen atom may be independently mono or di-substituted by methyl, ethyl or phenyl, or $R_e$ is acetylamino, benzoylamino, methylthio wherein the sulfur atom may be oxidized to a sulfoxide or sulfone, phenylthio methylthio wherein the sulfur atom may be oxidized to a sulfoxide or sulfone, ureido wherein either nitrogen atom may be independently substituted by methyl, ethyl or phenyl, or $R_e$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_e$ is fluoro, chloro, hydroxy, oxo, carboxy or carboxamide, $R_e$ may be further optionally substituted by one or more $R_f$;

$R_f$ is methyl, phenyl, tolylsulfonyl, phenoxy, benzyloxy, fluoro, chloro or oxo.

Preferred cathepsin K inhibitors are those as described immediately above and wherein:

$R_1$ is a bond, methyl, ethyl, n-propyl, i-propyl, methoxy, ethoxy, benzyloxy, cyclopropyl, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is methyl, cyclopropyl, phenyl, halogen, hydroxy, oxo, carboxy, cyano, nitro or carboxamide;

$R_3$ is a bond, methyl, ethyl, n-propyl, i-propyl, n-butyl, i-butyl, n-pentyl, propenyl, i-butenyl, benzyl or naphthylmethyl wherein $R_3$ is optionally substituted by one or more $R_c$;

$R_c$ is methyl, ethyl, cyclohexyl, cyclopentyl, phenyl, furanyl, tetrahydropyranyl, thienyl, oxazolyl, thiazolyl, methoxy, phenoxy, acetyl, benzoyl, methoxycarbonyl, carbamoyl wherein the nitrogen atom may be independently mono or di-substituted by methyl or phenyl, or $R_c$ is acetylamino, benzoylamino, methylthio, methoxycarbonylamino, methylcarbamoyloxy, methylsulfonylamino, methylaminosulfonyl, amino wherein the nitrogen atom may be independently mono or di-substituted by methyl, or $R_c$ is fluoro or oxo;

$R_2$ and $R_3$ together with the carbon they are attached optionally form a ring selected from cyclopentyl, cyclohexyl, cycloheptyl, tetrahydropyranyl, tetrahydrothiopyranyl, tetrahydrofuranyl, pyrrolidinyl or piperidinyl;

$R_5$ is methyl, ethyl, n-propyl, n-butyl, n-pentyl, 2-pentyl, 3-pentyl, phenethyl, phenpropyl, 2,2-dimethylpropyl, t-butyl, i-propyl, i-butyl, cyclopropyl, cyclopentyl, cyclohexyl, cyclopropylmethyl, cyclopentylmethyl, cyclohexylmethyl, phenyl, benzyl, 2-methylbenzyl, 3-methylbenzyl, 4-methylbenzyl, 2,6-dimethylbenzyl, 2,5-dimethylbenzyl, 2,4-dimethylbenzyl, 2,3-dimethylbenzyl, 3,4-dimethylbenzyl, 3,5-dimethylbenzyl, 2,4,6-trimethylbenzyl, 2-methoxybenzyl, 3-methoxybenzyl, 4-methoxybenzyl, 2-phenoxybenzyl, 3-phenoxybenzyl, 4-phenoxybenzyl, 2-benzyloxybenzyl, 3-benzyloxybenzyl, 4-benzyloxybenzyl, 2-fluorobenzyl, 3-fluorobenzyl, 4-fluorobenzyl, 2,6-difluorobenzyl, 2,5-difluorobenzyl, 2,4-difluorobenzyl, 2,3-difluorobenzyl, 3,4-difluorobenzyl, 3,5-difluorobenzyl, 2,4,6-triflurobenzyl, 2-trifluoromethylbenzyl, 3-trifluoromethylbenzyl, 4-trifluoromethylbenzyl, naphthylmethyl, indanylmethyl, pyridinylmethyl, indolylmethyl, thienylmethyl, 5-methylthienylmethyl, piperidinyl, piperidinylcarbonyl, pyridinylcarbonyl, tetrahydropyranyl, pyrimidinyl, acetyl, benzoyl, ethoxycarbonyl, benzyloxycarbonyl, t-butoxycarbonyl, methylcarbamoyl, phenylcarbamoyl, benzylcarbamoyl, methylsulfonylamino, phenylsulfonylamino, methylamino, dimethylamino, fluoro, oxo or carboxy.

Most preferred cathepsin K inhibitors are those as described immediately above and wherein:

$R_1$ is methoxy, benzyloxy, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is methyl, phenyl, fluoro, chloro, hydroxy, oxo, carboxy or carboxamide;

$R_3$ is a bond, methyl, ethyl, n-propyl, i-propyl, n-butyl, i-butyl, n-pentyl, propenyl, i-butenyl or benzyl wherein $R_3$ is optionally substituted by one or more $R_c$;

$R_c$ is methyl, ethyl, cyclohexyl, cyclopentyl, phenyl, furanyl, tetrahydropyranyl, thienyl, oxazolyl, thiazolyl, methoxy, phenoxy, acetyl, benzoyl, methoxycarbonyl, acetylamino, methylthio, methylsulfonylamino or fluoro;

$R_2$ and $R_3$ together with the carbon they are attached optionally form a ring selected from cyclopentyl, cyclohexyl, cycloheptyl, tetrahydropyranyl, tetrahydrothiopyranyl or tetrahydrofuranyl;

$R_5$ is methyl, ethyl, n-propyl, n-butyl, phenethyl, phenpropyl, t-butyl, i-propyl, i-butyl, cyclopropyl, cyclohexyl, cyclopropylmethyl, cyclohexylmethyl, phenyl, benzyl, 2-methoxybenzyl, 3-methoxybenzyl, 4-methoxybenzyl 4-fluorobenzyl, 3,5-difluorobenzyl, 4-trifluoromethylbenzyl, naphthylmethyl, pyridinylmethyl, indolylmethyl, thienylmethyl, acetyl, benzoyl, ethoxycarbonyl, benzyloxycarbonyl, t-butoxycarbonyl, phenylcarbamoyl, phenylsulfonylamino or fluoro.

Most preferred cathepsin K inhibitors are those as described immediately above and wherein:

Het is pyrrolidinyl, piperidinyl or tetrahydropyranyl;

$R_1$ is benzyloxy, phenoxy, naphthyloxy, phenyl, naphthyl, pyrrolidinyl, piperidinyl, morpholinyl, thiomorpholinyl, piperazinyl, pyridinyl, indolyl, quinolinyl, benzofuranyl, benzthienyl, benzimidazolyl, benzthiazolyl, benzoxazolyl or phenylamino;

$R_3$ is n-propyl, i-butyl, propenyl, i-butenyl or 2,2-dimethylpropyl;

$R_2$ and $R_3$ together with the carbon they are attached optionally form a ring selected from cyclopentyl, cyclohexyl, or cycloheptyl;

$R_5$ is methyl, ethyl, n-propyl, phenethyl, t-butyl, i-propyl, i-butyl, cyclohexyl, cyclohexylmethyl, benzyl, 4-fluorobenzyl, naphthylmethyl, acetyl, benzoyl or benzyloxycarbonyl.

The following are representative compounds of the invention which possess desirable inhibition activity of Cathepsin S in a cell based assay as described in Riese, R. J. et al., Immunity, 1996, 4, 357–366, incorporated herein by reference.

'2-[(Acetylimino-phenyl-methyl)-amino]-N-[3-cyano-1-(1-ethyl-propyl)-pyrrolidin-3-yl]-3-cyclohexyl-propionamide;

'({1-[3-Cyano-1-(1-ethyl-propyl)-pyrrolidin-3-ylcarbamoyl]-2-cyclohexyl-ethylamino}-morpholin-4-yl-methylene)-carbamic acid ethyl ester;

'2-(N-Cyano-benzimidoyl-amino)-N-(4-cyano-1-methyl-piperidine-4-yl)-3-cyclohexyl-propionamide;

'N-(4-Cyano-1-methyl-piperidin-4-yl)-3-cyclohexyl-2-[(ethylcarbamoylimino-phenyl-methyl)-amino]-propionamide;

'N-[4-Cyano-1-methyl-piperidin-4-yl)-3-cyclohexyl-2 -(1,1-dioxo-1H-$\lambda^6$-benzo[d]isothiazol-3-ylamino)-propionamide;

'N-[3-Cyano-1-(1-ethyl-propyl)-pyrrolidin-3-yl]-3-cyclohexyl-2 -(1,1-dioxo-1H-$\lambda^6$-benzo[d]isothiazol-3-ylamino)-propionamide;

N-(3-Cyano-1-cyclohexyl-pyrrolidin-3-yl)-3-cyclohexyl-2-(1,1-dioxo-1H-$\lambda^6$-benzo[d]isothiazol-3-ylamino)-propionamide;

N-(4-Cyano-1-propyl-piperidin-4-yl)-3-cyclohexyl-2-(1,1-dioxo-1H-$\lambda^6$-benzo[d]isothiazol-3-ylamino)-propionamide;

'2-(1,1-Dioxo-1H-$\lambda^6$-benzo[d]isothiazol-3-ylamino)-4,4-dimethyl-pentanoic acid (4-cyano-1-propyl-piperidin-4-yl)-amide and the pharmaceutically acceptable derivatives thereof.

Another embodiment of the invention provides for the following compounds which have demonstrated potent inhibition of Cathepsin S in a cell based assay at concentrations of 50 nM or less.

{[1-(4-Cyano-1-propyl-piperidin-4-ylcarbamoyl)-3,3-dimethyl-butylimino]-morpholin-4-yl-methyl}-carbamic acid ethyl ester;

N-(4-Cyano-methyl-piperidin-4-yl)-3-cyclohexyl-2-(3-oxo-3H-isoindol-1-ylamino)-propionamide;

4,4-Dimethyl-2-(3-oxo-3H-isoindol-1-ylamino)-pentanoicacid-(4-cyano-1-propyl-piperidin-4-yl)-amide;

N-(4-cyano-1-methyl-piperidin-4-yl)-3-cyclohexyl-2-(2-oxo-2H-benzo[e][1,3]oxazin4-ylamino)-propionamide;

{[1-(4-cyano-1-methyl-piperidin-4-ylcarbamoyl)-2-cyclohexyl-ethylamino]-piperidin-1-yl-methyl}-carbamic acid ethyl ester;

'2-[(Acetylimino-phenyl-methyl)-amino]-N-(4-cyano-1-methyl-piperidin-4-yl)-3-cyclohexyl-propionamide;

'{[1-(4-Cyano-1-methyl-piperidin-4-ylcarbamoyl)-2-cyclohexyl-ethylamino]-morpholin-4-yl-methylen}-carbamic acid ethyl ester;

2-[(Acetylimino-phenyl-methyl)-amino]-N-[3-cyano-1-(1-ethyl-propyl)-pyrrolidin-3-yl]-3-cyclohexyl-propionamide;

'({1-[3-Cyano-1-(1-ethyl-propyl)-pyrrolidin-3-ylcarbamoyl]-2-cyclohexyl-ethylamino}-morpholin-4-yl-methylene)-carbamic acid ethyl ester;

'N-(4-Cyano-1-methyl-piperidin-4-yl)-3-cyclohexyl-2-[(ethylcarbamoylimino-phenyl-methyl)-amino]-propionamide;

'N-[4-Cyano-1-methyl-piperidin-4-yl)-3-cyclohexyl-2 -(1,1-dioxo-1H-$\lambda^6$-benzo[d]isothiazol-3-ylamino)-propionamide;

'N-[3-Cyano-1-(1-ethyl-propyl)-pyrrolidin-3-yl]-3-cyclohexyl-2-(1,1-dioxo-1H-$\lambda^6$-benzo[d]isothiazol-3-ylamino)-propionamide;

N-(3-Cyano-1-cyclohexyl-pyrrolidin-3-yl)-3-cyclohexyl-2-(1,1-dioxo-1H-$\lambda^6$-benzo[d]isothiazol-3-ylamino)-propionamide;

N-(4-Cyano-1-propyl-piperidin-4-yl)-3-cyclohexyl-2-(1,1-dioxo-1H-$\lambda^6$-benzo[d]isothiazol-3-ylamino)-propionamide and '2-(1,1-Dioxo-1H-$\lambda^6$-benzo[d]isothiazol-3-ylamino)-4,4-dimethyl-pentanoic acid (4-cyano-1-propyl-piperidin-4-yl)-amide.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration unless otherwise specified, or a combination of configurations.

Some of the compounds of formulas (I), (II), (Ia) and (Ib) can exist in more than one tautomeric form. The invention includes all such tautomers.

It shall be understood by one of ordinary skill in the art that all compounds of the invention are those which are chemically stable.

The invention includes pharmaceutically acceptable derivatives of compounds of formula (I), (II), (Ia) and (Ib). A "pharmaceutically acceptable derivative" refers to any pharmaceutically acceptable acid, salt or ester of a compound of this invention, or any other compound which, upon administration to a patient, is capable of providing (directly or indirectly) a compound of this invention, a pharmacologically active metabolite or pharmacologically active residue thereof.

In addition, the compounds of this invention include prodrugs of compounds of the formulas (I), (II), (Ia) and (Ib). Prodrugs include those compounds that, upon simple transformation, are modified to produce the compounds of the invention. Simple chemical transformations include hydrolysis, oxidation and reduction which occur enzymatically, metabolically or otherwise. Specifically, when a prodrug of this invention is administered to a patient, the prodrug may be transformed into a compound of formula (I), (II), (Ia) and (Ib), thereby imparting the desired pharmacological effect.

In order that the invention herein described may be more fully understood, the following detailed description is set forth. As used herein, the following abbreviations are used:
BOC or t-BOC is tertiary-butoxycarbonyl;
t-Bu is tertiary-butyl;
DMF is dimethylformamide;
EtOAc is ethyl acetate;
THF is tetrahydrofuran;
Ar is argon;
EDC is 1-(3-dimethylaminopropyl)-3-ethylcarbodimide hydrochloride and
HOBT is 1-hydroxybenzotriazole.

Also, as used herein, each of the following terms, used alone or in conjunction with other terms, are defined as follows (except where noted to the contrary):

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. Examples of "alkyl" include alkyl groups which are straight chain alkyl groups containing from one to eight carbon atoms and branched alkyl groups containing from three to eight carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O). Each alkyl or alkyl analog described herein shall be understood to be optionally partially or fully halogenated.

The term "cycloalkyl" refers to the cyclic analog of an alkyl group, as defined above. Examples of cycloalkyl groups are saturated or unsaturated nonaromatic cycloalkyl groups containing from three to eight carbon atoms, and other examples include cycloalkyl groups having three to six carbon atoms. Each cycloalkyl described herein shall be understood to be optionally partially or fully halogenated.

The term "aryl" refers to phenyl and naphthyl.

The term "halo" refers to a halogen radical selected from fluoro, chloro, bromo or iodo. Representative halo groups of the invention are fluoro, chloro and bromo.

The term "heteroaryl" refers to a stable 5–8 membered (but preferably, 5 or 6 membered) monocyclic or 7–12 membered polycyclic, preferably bicyclic aromatic heterocycle radical. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl, The term "heterocycle" refers to a stable 4–8 membered (but preferably, 5 or 6 membered) monocyclic or 7–12 membered polycyclic, preferably bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heterocycle" include radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidin-2-ylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione.

The terms "heterocycle", "heteroaryl" or "aryl", when associated with another moiety, unless otherwise specified shall have the same meaning as given above. For example, "aroyl" refers to phenyl or naphthyl linked to a carbonyl group (C=O).

Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

The term heterocycle as it pertains to "Het" shall to be understood to mean a stable non-aromatic spiroheterocycle, 4–8 membered (but preferably, 5 or 6 membered) monocyclic, 7–12 membered polycyclic, preferably bicyclic heterocycle radical which may be either saturated or unsaturated or a C6–C10 bridged bicyclo wherein one or more carbon atoms are optionally replaced by a heteroatom. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "Het" include the following heterocycles: azepanyl, piperidinyl, pyrrolidinyl, azetidinyl, oxepanyl, tetrahydropyranyl, tetrahydrothiopyranyl, tetrahydrofuranyl, oxetanyl, azocanyl, oxocanyl, 1,3-diazocanyl, 1,4-diazocanyl, 1,5-diazocanyl, 1,3-dioxocanyl, 1,4-dioxocanyl, 1,5-dioxocanyl, 1,3-oxazocanyl, 1,4-oxazocanyl, 1,5-oxazocanyl, 1,3-diazepanyl, 1,4-diazepanyl, 1,3-dioxepanyl, 1,4-dioxepanyl, 1,3-oxazepanyl, 1,4-oxazepanyl, 1,2-thiazocanyl-1,1-dioxide, 1,2,8-thiadiazocanyl-1,1-dioxide, 1,2-thiazepanyl-1,1-dioxide, 1,2,7-thiadiazepanyl-1,1-dioxide, tetrahydrothiophenyl, hexahydropyrimidinyl, hexahydropyridazinyl, piperazinyl, 1,4,5,6-tetrahydropyrimidinyl, pyrazolidinyl, dihydro-oxazolyl, dihydrothiazolyl, dihydroimidazolyl, isoxazolinyl, oxazolidinyl, 1,2-thiazinanyl-1,1-dioxide, 1,2,6-thiadiazinanyl-1,1-dioxide, isothiazolidinyl-1,1-dioxide, imidazolidinyl-2,4-dione, imidazolidinyl, morpholinyl, dioxanyl, tetrahydropyridinyl, thiomorpholinyl, thiazolidinyl, dihydropyranyl, dithianyl, decahydroquinolinyl, decahydro-isoquinolinyl, 1,2,3,4-tetrahydroquinolinyl, indolinyl, octahydro-quinolizinyl, dihydroindolizinyl, octahydro-indolizinyl, octahydro-indolyl, decahydroquinazolinyl, decahydroquinoxalinyl, 1,2,3,4-tetrahydroquinazolinyl or 1,2,3,4-tetrahydroquinoxalinyl, aza-bicyclo[3.2.1]octane, aza-bicyclo[2.2.1]heptane, aza-bicyclo[2.2.2]octane, aza-bicyclo[3.2.2]nonane, aza-bicyclo[2.1.1]hexane, aza-bicyclo[3.1.1]heptane, aza-bicyclo[3.3.2]decane and 2-oxa or 2-thia-5-aza-bicyclo[2.2.1]heptan eeach heterocyclic ring being substituted with one or more $R_5$. The substituent $R_5$ is defined above.

As used herein above and throughout this application, "nitrogen" and "sulfur" include any oxidized form of nitrogen and sulfur and the quaternized form of any basic nitrogen.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds. Starting materials used in the scheme below are either commercially available or easily prepared from commercially available materials by those skilled in the art.

General Synthetic Methods

The invention also provides processes of making the present novel compounds. Compounds of the invention may be prepared by methods described below. Standard peptide coupling, protection and deprotection reactions (see for example M. Bodanszky, 1984, The Practice of Peptide Synthesis, Springer-Verlag) are employed in these syntheses and are incorporated herein by reference in their entirety.

Compounds of the Formulas (I) and (II)

Compounds of the invention having formulas (I) and (II) may be prepared by Method A as illustrated in Scheme I.

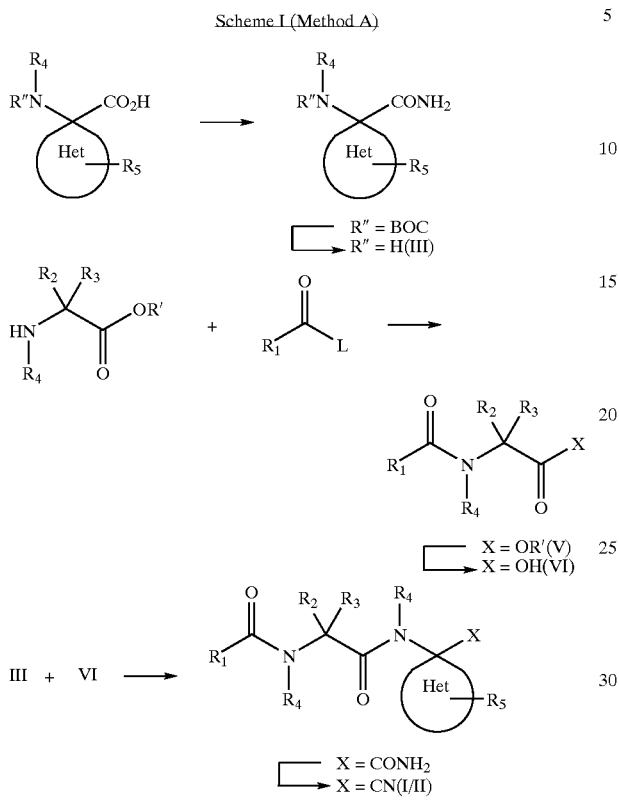

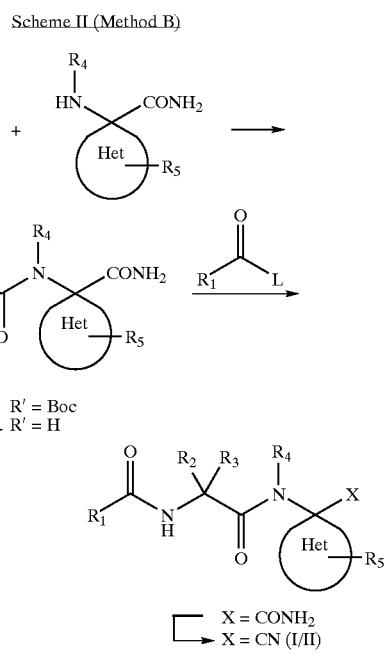

According to Method A a suitably protected amino acid bearing "Het" is allowed to react with ammonia under standard coupling conditions. An example of a suitable protecting group is the t-butoxycarbonyl (BOC) group. An example of standard coupling conditions would be combining the starting materials in the presence of a coupling reagent such as 1-(3-dimethylaminopropyl)-3-ethylcarbodiimide (EDC) with 1-hydroxybenzotriazole (HOBT), in a suitable solvent such as DMF or methylene chloride. A base such as N-methylmorpholine may be added. This is followed by deprotection to give amino acid amide III. An amino acid ester (IV) bearing $R_2$, $R_3$ and optionally $R_4$ other than H is then reacted with an activated acid [$R_1$C(O)L] such as acid chloride (L=Cl) in the presence of a suitable base such as N,N-diisopropylethylamine to provide V. Alternately, one may use the carboxylic acid [$R_1$C(O)L, L=OH] and activate using standard peptide coupling conditions, such as EDC and HOBT as described above. If $R_4$ is H in V, one may optionally react V with an alkyl halide in the presence of a suitable base such as sodium hydride, in a suitable solvent such as DMF or THF to provide V in which $R_4$ is alkyl Conversion to the carboxylic acid provides VI. Standard peptide coupling of III and VI, followed by dehydration of the amide provides the desired nitrile I or II. An example of suitable dehydration conditions is cyanuric chloride in DMF.

In a variation (Method B) illustrated in Scheme II, an amino acid amide bearing "Het" is coupled with an amine-protected amino acid bearing $R_2$ and $R_3$. A suitable protecting group and coupling conditions would be as described above. Deprotection is then followed by reaction with $R_1$C(O)L (as described in Method A). Conversion of the amide to the nitrile as above provides I or II.

Compounds of the invention having formula (I) and (II) may also be prepared by Method C as illustrated in Scheme III.

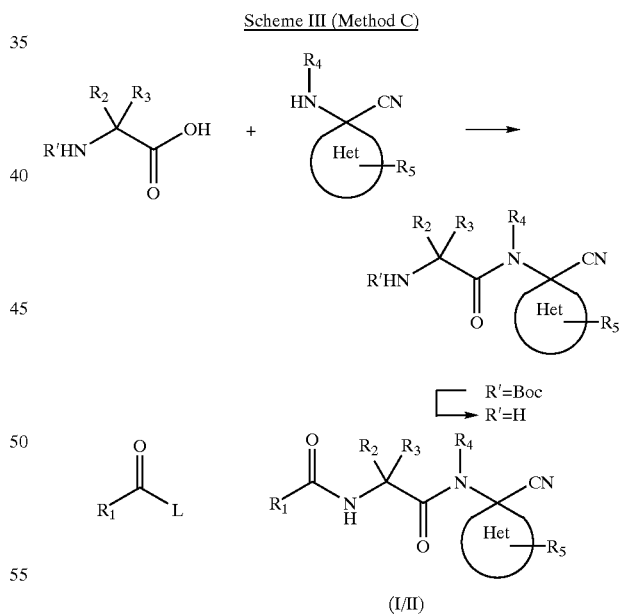

In this variation (Method C) an amino nitrile bearing "Het" is coupled with an amine protected amino acid bearing $R_2$ and $R_3$. A suitable protecting group and coupling conditions are described above. Deprotection is then followed by reaction with $R_1$C(O)L as described above to furnish the nitrile (I/II).

Compounds of the invention having formulas (I) and (II) may also be prepared by as outlined below in Scheme IV (Method D).

Scheme IV (Method D)

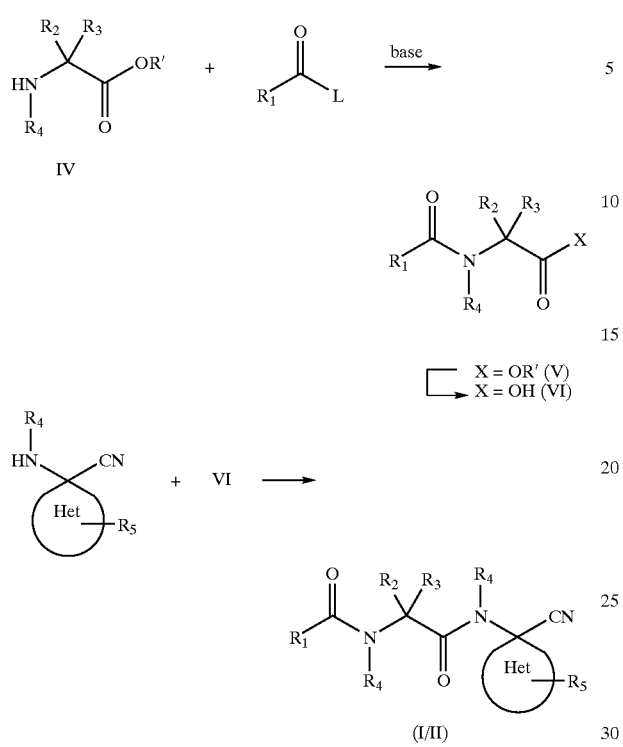

In a further variation (Method D) illustrated in Scheme IV, an amino acid ester (IV) bearing $R_2$, $R_3$ and optionally $R_4$ other than H is reacted with $R_1C(O)L$ as described in Method A. Conversion to the carboxylic acid provides VI. Standard peptide coupling of an amino nitrile bearing "Het" with VI yields the desired nitrile (I/II).

The intermediate aminonitrile used in Methods C, and D above may be prepared as outlined in Scheme V

Scheme V

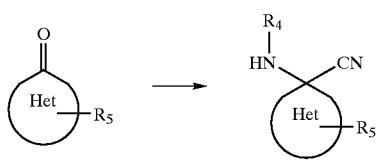

In this method, a ketone bearing "Het" is reacted with an a primary amine or an ammonium salt, such as ammonium chloride, and a cyanide salt, such as potassium cyanide or sodium cyanide, in a suitable solvent, such as water or a solution of ammonia in methanol, at about room temperature to reflux temperature.

In each of the methods described above, required starting materials are either commercially available or easily prepared by those skilled in the art, for example see:

Leung, M.-k.; Lai, J.-L.; Lau, K.-H.-; Yu, H.-h.; Hsiao, J.-J. *J. Org. Chem.* 1996, 61, 4175–4179.

Mee, J. D. *J. Org. Chem.* 1975, 40, 2135–2136.

Micovic, I. V.; Roglic, G. M.; Ivanovic, M. D.; Dosen-Micovic, L.; Kiricojevic, V. D.;

Popovic, J. B. *J. Chem. Soc, Perkin Trans.* 1, 1996, 2041–2050.

Tornus, I.; Schaumann, E. *Tetrahedron* 1996, 52, 725–732.

Jadhav, P. K.; Woerner, F. J. *Tetrahedron Letters* 1995, 36, 6383–6386.

Kochhar, K. S.; et al. *Tetrahedron Letters* 1984, 25, 1871–1874.

Fordon, K. J.; Crane, C. G.; Burrows, C. J. *Tetrahedron Letters* 1994, 35, 6215–6216. These references are incorporated herein by reference in their entirety, Compounds of the Formulas (Ia) and (Ib)

The invention also provides processes of making the present novel compounds of formula (Ia) and (Ib). Compounds of the invention may be prepared by methods described below.

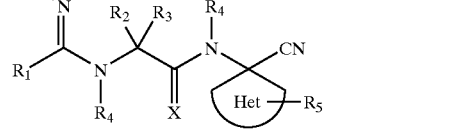

(Ia)

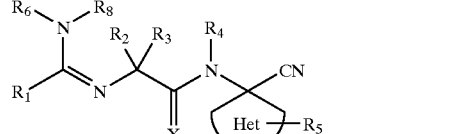

(Ib)

A key intermediate in the preparation of compounds of formula (Ia) and (Ib) is the dipeptide nitrile intermediate (VII).

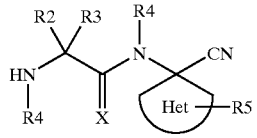

(VII)

The synthesis of intermediates of formula (VII) is described in U.S. provisional patent application No. 60/153,738 and outlined below in Schemes VI and VII.

Scheme VI

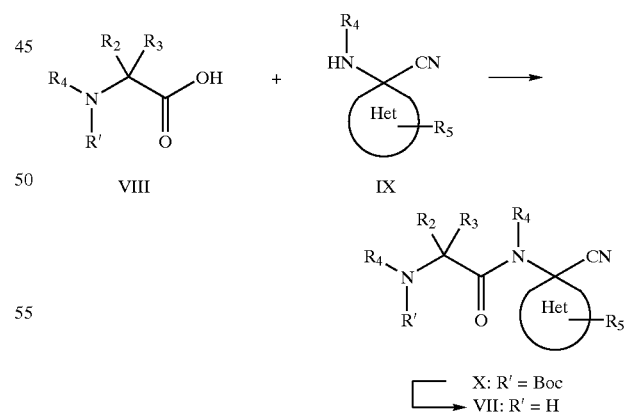

As illustrated in Scheme VI, an amino acid bearing a suitable protecting group R' (VIII), is reacted with an amino nitrile (IX) under suitable coupling conditions. An example of a suitable protecting group is the t-butoxycarbonyl (BOC) group. An example of standard coupling conditions would be combining the starting materials in the presence of a coupling reagent such as 1-(3-dimethylaminopropyl)-3- ethylcarbodiimide (EDC) with 1-hydroxybenzotriazole (HOBT), in a suitable solvent such as DMF or methylene chloride. A base such as N-methylmorpholine may be added. This is followed by deprotection to give amino acid nitrile VII.

The intermediate aminonitrile (IX) used in Scheme VI above may be prepared as outlined in Scheme VII.

Scheme VII

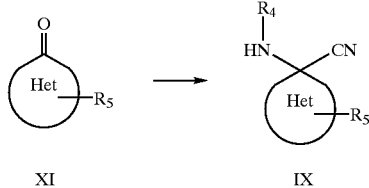

XI    IX

In this method, a ketone bearing "Het" (XI) is reacted with an a primary amine or an ammonium salt, such as ammonium chloride, and a cyanide salt, such as potassium cyanide or sodium cyanide, in a suitable solvent, such as water or a solution of ammonia in methanol, at about room temperature to reflux temperature.

Compounds having formula (Ia/Ib) may be prepared by Methods E–H, as illustrated in Schemes VIII–IX.

Scheme VII (Method E)

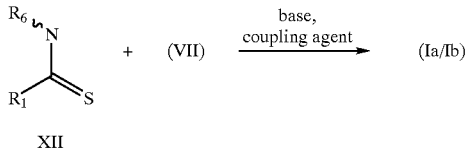

XII

According to Method E, a dipeptide nitrile intermediate (VII), or a basic salt thereof, is allowed to react with (XII) in the presence of a suitable coupling agent to provide the desired product (Ia/Ib). Suitable reaction conditions are known to those skilled in the art and some examples of suitable coupling agents include 2-chloro-1-methylpyridinium iodide (Yong, Y.F. et al., J. Org. Chem. 1997, 62, 1540), phosgene or triphosgene (Barton, D.H. et al., J. Chem. Soc. Perkin Trans. I, 1982, 2085), alkyl halides (Brand, E. and Brand, F. C., Org. Synth., 1955, 3, 440) carbodiimides (Poss, M. A. et al., Tetrahedron Lett., 1992, 40, 5933) and mercury salts (Su, W., Synthetic Comm., 1996, 26, 407 and Wiggall, K. J. and Richardson, S. K. J., Heterocyclic Chem., 1995, 32, 867).

Compounds having formulas (Ia) and (Ib) may also be prepared by Method B as illustrated in Scheme IV, where R is an alkyl or aryl group.

Scheme VIII (Method F)

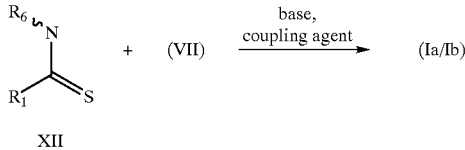

XII

According to Method F a dipeptide nitrile intermediate (VII), or a basic salt thereof, is allowed to react with XII, with or without an added base such as triethylamine, to provide the desired product (Ia/Ib). Suitable reaction conditions are known to those skilled in the art and examples of such amine additions may be found in the chemical literature, for example Haake, M. and Schummelfeder, B., Synthesis, 1991, 9, 753; Dauwe, C. and Buddrus, J., Synthesis 1995, 2, 171; Ried, W. and Piechaczek, D., Justus Liebigs Ann. Chem. 1966, 97, 696 and Dean, W. D. and Papadopoulos, E. P., J. Heterocyclic Chem., 1982, 19, 1117.

The intermediate XII is either commercially available or can be synthesized by methods known to those skilled in the art and described in the literature, for example Francesconi, I. et. al., J. Med. Chem. 1999, 42, 2260; Kurzer, F., Lawson, A.,Org. Synth. 1963, 645, and Gutman, A. D. US 3984410, 1976.

In a similar reaction, intermediate X IV having a halogen or other suitable leaving group (X) may be used in place of intermediate XIII, as illustrated in Method G, Scheme IX.:

Scheme IX (Method G)

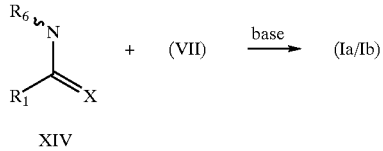

XIV

According to Method G, a dipeptide nitrile intermediate, or a basic salt thereof, is allowed to react with intermediate XIV, with or without an added base such as triethylamine, to provide the desired product (Ia/Ib). Procedures for accomplishing this reaction are known to those skilled in the art and described in the chemical literature (for example, Dunn, A. D. , Org. Prep. Proceed. Int., 1998, 30, 709; Lindstroem, S. et al., Heterocycles, 1994, 38, 529; Katritzky, A. R. and Saczewski, F., Synthesis, 1990, 561; Hontz, A. C. and Wagner, E. C., Org Synth., 1963, IV, 383; Stephen, E. and Stephen, H., J. Chem. Soc., 1957, 490).

Compounds having formula (Ia/Ib) in which $R_1$ is an amine may also be prepared by Method H as illustrated in Scheme X.

Scheme X (Method H)

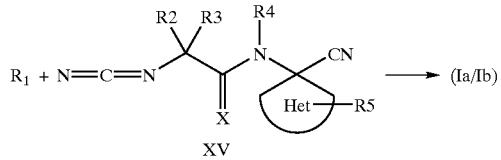

XV

According to Method H, a carbodiimide (XV) derivative of (VII) is allowed to react with an amine ($R_1$) to provide the desired guanidine (Ia/Ib) product. The conversion of amines to carbodiimides is known to those in the art and described in the literature (for example, Pri-Bar, I. and Schwartz, J., J. Chem. Soc. Chem. Commun., 1997, 347; Hirao, T. and Saegusa, T., J. Org. Chem., 1975, 40, 298). The reaction of carbodiimides with amine nucleophiles is also described in the literature (for example, Yoshiizumi, K. et al., Chem. Pharm. Bull., 1997, 45, 2005; Thomas, E. W. et al., J. Med. Chem., 1989, 32, 228; Lawson, A. and Tinkler, R. B., J. Chem. Soc. C, 1971, 1429.

In a modification of Method H, one may start with the thiourea XVI (formed by reaction of the corresponding amine with an isothiocyanate $R_6N{=}C{=}S$) and then form the corresponding carbodiimide (XV) in situ by reaction with a suitable desulfurizing agent, such as $HgCl_2$, in a suitable solvent such as DMF or acetonitrile.

XVI

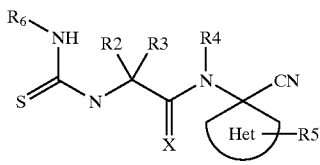

Compounds of formula (Ib), where $R_1$ is an amine may be prepared using a general procedure described by M. Haake and B. Schummfelder (Synthesis, 1991, 753). According to this procedure (Method I, Scheme XI), intermediate XVII bearing two suitable leaving groups Z, such as phenoxy groups, is reacted sequentially with amines $R_1$ and $R_6R_8NH$ in a suitable solvent such as methanol or isopropanol to provide the desired product. Reaction of the first amine may be carried out at about room temperature and reaction of the second amine is preferentially carried out with heating at the reflux temperature of the solvent. If XIII is allowed to react with a bifunctional nucleophile intermediate XVIII, where Y is a nucleophilic heteroatom such as N, O or S, one may obtain the product of formula (Ib) where $R_1$ and $R_6$ form a heterocyclic ring. Intermediate XVII may be prepared by reaction of VII ($R_4$=H) with dichlorodiphenoxymethane, which in turn, may be prepared by heating diphenyl carbonate with $PCl_5$ (R. L. Webb and C. S. Labow, J. Het. Chem., 1982, 1205).

Scheme XI (Method I)

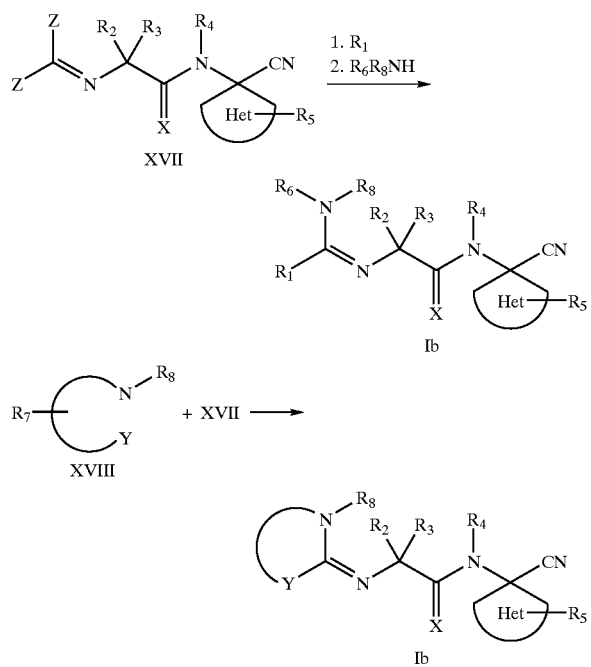

In order that this invention be more fully understood, the following examples are set forth. These examples are for the purpose of illustrating embodiments of this invention, and are not to be construed as limiting the scope of the invention in any way.

The examples which follow are illustrative and, as recognized by one skilled in the art, particular reagents or conditions could be modified as needed for individual compounds. Starting materials used in the scheme below are either commercially available or easily prepared from commercially available materials by those skilled in the art.

SYNTHETIC EXAMPLES

Example 1

Morpholine-4-carboxylic acid [1-(4-cyano-1-methyl-piperidin-4-ylcarbamoyl)-2-cyclohexyl-ethyl]-amide (a) 4-Amino-4-cyano-1-methylpiperidine A solution of ammonium chloride (1.89 g, 35.37 mmol) and potassium cyanide (2.30 g, 35.37 mmol) was prepared in 50 mL of water. 1-Methyl-4-piperidone (1.0 g, 8.84 mmol) was added to the solution and stirred for 2 days. The solution was brought to pH 11 with solid sodium carbonate and the reaction solution was extracted 3×100 mL of EtOAc. The organic layer was dried over anhydrous $Na_2SO_4$, decanted and concentrated to an orange oil (857 mg). $^1H$ NMR showed that the oil was a 2:1:1 mixture of the desired aminonitrile, cyanohydrin and starting ketone. The crude mixture was used in the next step without further purification.

(b) N-(4-morpholinecarbonyl)-L-cyclohexyl alanine methyl ester

Methyl L-β-cyclohexylalanine hydrochloride (1.45 g, 6.54 nunol) was dissolved in 20 mL of DMF and 10 mL of Hunig's base was added to give a clear colorless solution. 4-Morpholinecarbonyl chloride (1.17 g, 7.85 mmol) was added and the resulting reaction was stirred at ambient temperature for 6 h. The reaction mix was concentrated in vacuo and the residue was taken up in 200 mL of $CH_2Cl_2$ and washed with 1×100 mL of EtOAc and 2×100 mL of brine. The organic layer was dried over $Na_2SO_4$, decanted, and concentrated to a semi-solid (1.86 g) which was used in the next step without further purification.

(c) N-(4-morpholinecarbonyl)-L-cyclohexyl alanine

N-(4-Morpholinecarbonyl)-L-cyclohexyl alanine methyl ester (1.86 g, 6.23 mmol) was dissolved in 50 mL of MeOH to which was added 50 mL THF and 50 mL of water. LiOH monohydrate (2.61 g, 62.3 mmol) was added to the reaction solution and the reaction was monitored at 5 min and every 20 min thereafter using 5% MeOH in $CH_2Cl_2$. The starting material was consumed at 2 h and the reaction was washed with 150 mL of diethyl ether with the organic layer being discarded. The aqueous layer was brought to pH 1 with concentrated HCl and the product was extracted with 2×100 mL of EtOAc. The combined organic layers were dried over $Na_2SO_4$, decanted and concentrated to white solid foam (1.63 g): $^1H$ NMR ($CDCl_3$) δ8.90–7.90 (br, 1H), 5.05–4.99 (m, 1H), 4.55–4.39 (m, 1H), 3.71–3.62 (m, 4H), 3.50–3.36 (m, 4H), 1.90–0.83 (m, 13H).

(d) Morpholine-4-carboxylic acid [1-(4-cyano-1-methyl-piperidin-4-ylcarbamoyl)-2-cyclohexyl-ethyl]-amide N-(4-Morpholinecarbonyl)-L-cyclohexyl alanine (350 mg, 1.23 mmol) was dissolved in 15 mL of DMF. EDC (235 mg, 1.23 mmol) and HOBT (166 mg, 1.23 mmol) were added and the resulting mixture was stirred at ambient temperature for 20 min during which time the solids went into solution. 4-Amino-4-cyano-1-methylpiperidine (310 mg of the 2:1:1 mixture of aminonitrile:cyanohydrin:ketone, ≅1.1 mmol aminonitrile) was dissolved in 5 mL of DMF, N-methylmorpholine was added to this solution (497 mgs, 4.92 mmol), and the resultant solution added to the solution of the activated ester. The resulting mixture was stirred at ambient temperature for 16 h. The volatiles were removed in vacuo and the resulting residue was dissolved in 200 mL of EtOAc and washed sequentially with 2×200 mL saturated sodium bicarbonate and 1×100 mL brine. The organic layer was dried over anhydrous $Na_2SO_4$, decanted, and concentrated to a thick oil. The oil was purified by column chromatagraphy on SiO₂ using as eluent 100% CH₂Cl₂ to 12% MeOH in CH₂Cl₂ to give the desired product as a white powder (225 mg): ¹H NMR (CDCl₃) δ7.55 (s, 1H), 5.13–5.08 (m, 1H), 4.40–4.20 (m, 1H), 3.77–3.62 (m, 4H), 3.51–3.33 (m, 4H), 2.88–2.55 (m, 2H), 2.53–2.39 (m, 2H), 2.30 (s, 3H), 2.10–0.83 (m, 17H).

Following the above procedures the following compounds can be synthesised;

Morpholine-4-carboxylic acid [1-(4-cyano-1-methyl-piperidin-4-ylcarbamoyl)-2-naphthalen-2-yl-ethyl]-amide Morpholine-4-carboxylic acid [2-(3-chloro-phenyl)-1-(4-cyano-1-methyl-piperidin-4-ylcarbamoyl)-ethyl]-amide Morpholine-4-carboxylic acid [1-(4-cyano-1-methyl-piperidin-4-ylcarbamoyl)-2-(3,4-dichloro-phenyl)-ethyl]-amide Morpholine-4-carboxylic acid [2-(4-chloro-phenyl)-1-(4-cyano-1-methyl-piperidin-4-ylcarbamoyl)-ethyl]-amide Morpholine-4-carboxylic acid [1-(4-cyano-1-methyl-piperidin-4-ylcarbamoyl)-pentyl]-amide Morpholine-4-carboxylic acid [1-(4-cyano-1-methyl-piperidin-4-ylcarbamoyl)-3-methyl-butyl]-amide Morpholine-4-carboxylic acid [1-(4-cyano-1-phenyl-2,6-dioxo-piperidin-4-ylcarbamoyl)-2-cyclohexyl-ethyl]-amide Morpholine-4-carboxylic acid [1-(4-cyano-1-phenyl-2,6-dioxo-piperidin-4-ylcarbamoyl)-3,3-dimethyl-butyl]-amide Morpholine-4-carboxylic acid [1-(4-cyano-2-oxo-piperidin-4-ylcarbamoyl)-2-cyclohexyl-ethyl]-amide Morpholine-4-carboxylic acid [1-(4-cyano-2-oxo-piperidin-4-ylcarbamoyl)-3,3-dimethyl-butyl]-amide Morpholine-4-carboxylic acid [1-(4-cyano-1-methyl-2-oxo-piperidin-4-ylcarbamoyl)-2-cyclohexyl-ethyl]-amide Morpholine-4-carboxylic acid [1-(4-cyano-1-methyl-2-oxo-piperidin-4-ylcarbamoyl)-3,3-dimethyl-butyl]-amide Morpholine-4-carboxylic acid [1-(5-cyano-1,1-dioxo-1$\lambda^6$-[1,2]thiazinan-5-ylcarbamoyl)-2-cyclohexyl-ethyl]-amide Morpholine-4-carboxylic acid [1-(5-cyano-1,1-dioxo-1$\lambda^6$-[1,2]thiazinan-5-ylcarbamoyl)-3,3-dimethyl-butyl]-amide Morpholine-4-carboxylic acid [1-(5-cyano-2-methyl-1,1-dioxo-1$\lambda^6$-[1,2]thiazinan-5-ylcarbamoyl)-2-cyclohexyl-ethyl]-amide Morpholine-4-carboxylic acid [1-(5-cyano-2-methyl-1,1-dioxo-1$\lambda^6$-[1,2]thiazinan-5-ylcarbamoyl)-3,3-dimethyl-butyl]-amide Morpholine-4-carboxylic acid [1-(5-cyano-2-oxo-hexahydro-pyrimidin-5-ylcarbamoyl)-3,3-dimethyl-butyl]-amide Morpholine-4-carboxylic acid [1-(5-cyano-1,3-dimethyl-2-oxo-hexahydro-pyrimidin-5-ylcarbamoyl)-2-cyclohexyl-ethyl]-amide Morpholine-4-carboxylic acid [1-(4-cyano-1,1-dioxo-1$\lambda^6$-[1,2,6]thiadiazinan-4-ylcarbamoyl)-2-cyclohexyl-ethyl]-amide Morpholine-4-carboxylic acid [1-(4-cyano-2,6-dimethyl-1,1-dioxo-1$\lambda^6$-[1,2,6]thiadiazinan-4-ylcarbamoyl)-2-cyclohexyl-ethyl]-amide Morpholine-4-carboxylic acid [1-(3-cyano-5-oxo-pyrrolidin-3-ylcarbamoyl)-2-cyclohexyl-ethyl]-amide Morpholine-4-carboxylic acid [1-(3-cyano-1-methyl-5-oxo-pyrrolidin-3-ylcarbamoyl)-2-cyclohexyl-ethyl]-amide Morpholine-4-carboxylic acid [1-(3-cyano-5-oxo-pyrrolidin-3-ylcarbamoyl)-3,3-dimethyl-butyl]-amide Morpholine-4-carboxylic acid [1-(3-cyano-1-methyl-5-oxo-pyrrolidin-3-ylcarbamoyl)-3,3-dimethyl-butyl]-amide Example 2

Morpholine-4-carboxylic acid [1-(4-cyano-tetrahydro-pyran-4-ylcarbamoyl)-2-cyclohexyl-ethyl]-amide.

(a) 4-Amino-4-cyano-tetrahydropyran

A solution of ammonium chloride (2.12 g, 39.57 mmol) and potassium cyanide (2.58 g, 39.57 mmol) was prepared in 50 mL of water. Tetrahydropyran-4-one (1.0 g, 9.89 mmol) was added to the solution and stirring was continued for 2 days. The solution was brought to pH 11 with solid sodium carbonate and the reaction solution was extracted 3×100 mL of EtOAc. The organic layer was dried over anhydrous Na₂SO₄, decanted, and concentrated to an clear oil (1.02 g). ¹H NMR showed that the oil was a 7 to 1 mixture of the desired aminonitrile and cyanohydrin. The crude mixture was used in the next step without further purification.

(b) Morpholine-4-carboxylic acid [1-(4-cyano-tetrahydro-pyran-4-ylcarbamoyl)-2-cyclohexyl-ethyl]-amide N-(4-morpholinecarbonyl)-L-cyclohexyl alanine (350 mg, 1.23 mmol) was dissolved in 15 mL of DMF. EDC (235 mg, 1.23 mmol) and HOBT (166 mg, 1.23 mmol) were added and the resulting mixture was stirred at ambient temperature for 20 min during which time the solids went into solution. 4-Amino-4-cyano-tetrahydropyran (161 mg of the 7:1 mixture of aminonitrile, ≅1.1 mmol aminonitrile) was dissolved in 5 mL of DMF, N-methylmorpholine was added to this solution (497 mgs, 4.92 mmol), and the resultatnt solution added to the solution of the active ester. The resulting mixture was stirred at ambient temperature for 16 h. The volatiles were removed in vacuo and the resulting residue was vigorously stirred for 30 min with 100 mL of a 1 to 1 mixture of water and saturated sodium bicarbonate to give a fluffy white solid that was collected by filtration. The solid was washed with 3×50 mL of water and dried to give the desired product (210 mg): ¹H NMR (CDCl₃) δ7.80 (s, 1H), 5.25–5.15 (m, 1H), 4.41–20 (m, 1H), 3.97–3.62 (m, 8H), 3.50–3.41 (m, 4H), 2.50–2.37 (m 1H), 2.35–2.20 (m, 1H), 2.05–1.88 (m, 2H), 1.79–0.75 (m, 13H).

Example 3

4-Cyano-4-{3-cyclohexyl-2-[(morpholine-4-carbonyl)-amino]-propionylamino}-piperidine-1-carboxylic acid ethyl ester (a) 4-Amino-4-cyano-piperidine-1-carboxylic acid ethyl ester A solution of ammonium chloride (31 g, 584 mmol) and potassium cyanide (7.61 g, 116.8 mmol) was prepared in 250 mL of water. 1-(Ethoxycarbonyl)-4-piperidone (10 g, 58.4 mmol) was added to the solution followed by 50 mL of MeOH and stirring was continued for 3 days. The solution was brought to pH 11 with solid sodium carbonate (20 g) and the reaction solution was extracted with 3×250 mL of EtOAc. The organic layers were combined, dried over Na₂SO₄, decanted and concentrated to an thick oil. The oil was triturated with 500 mL of hexane and the resulting solid was collected by filtration (8.3 g). ¹H NMR showed that the product was better than 95% pure.

(b) 4-Cyano-4-{3-cyclohexyl-2-[(morpholine-4-carbonyl)-amino]-propionylamino}-piperidine-1-carboxylic acid ethyl ester N-(4-morpholinecarbonyl)-L-cyclohexyl alanine (555 mg, 1.95 mmol) was dissolved in 15 mL of DMF. EDC (373 mg, 1.95 mmol) and HOBt (264 mg, 1.95 mmol) were added and the resulting mixture was stirred at ambient temperature for 20 min during which time the solids went into solution.

4-Amino-4-cyano-piperidine-1-carboxylic acid ethyl ester (350 mg, 1.77 mmol) was dissolved in 5 mL of DMF and added to the solution of the active ester followed by addition of 2 mL of N-methylmorpholine. The resulting mixture was stirred at ambient temperature for 16 h. The volatiles were removed in vacuo and the resulting residue was dissolved in 200 mL of EtOAc and washed sequentially with 2×200 mL saturated sodium bicarbonate, 1×100 mL brine. The organic layer was dried over $Na_2SO_4$, decanted, and concentrated to a white solid. The solid was purified by column chromatagraphy on $SiO_2$ using as eluent 100% $CH_2Cl_2$ to 5% MeOH in $CH_2Cl_2$ to give the title compound as a white powder (511 mg): m.p. 140–143° C.

Example 4

Morpholine-4-carboxylic acid [1-(4-cyano-1-phenethyl-piperidin-4-ylcarbamoyl)-2-cyclohexyl-ethyl]-amide (a) 4-Amino-4-cyano-1-phenethylpiperidine was prepared according to the procedure from Example 1, step a, starting with 1-phenylethyl-4-piperidone.
(b) The title compound was prepared starting from N-(4-Morpholinecarbonyl)-L-cyclohexyl alanine and 4-amino-4-cyano-1-phenethylpiperidine according to the procedure from Example 2, step b, except that the compound was purified by HPLC using a 20×250 mm $C_{18}$ reverse phase column with the method being 30% acetonitrile in water to 100% acetonitrile. MS, m/z 496=M+1.

Example 5

Morpholine-4-carboxylic acid [1-(1-benzyl-4-cyano-piperidin-4-ylcarbamoyl)-2-cyclohexyl-ethyl]-amide (a) 4-Amino-4-cyano-1-benzylpiperidine was prepared according to the procedure from Example 1, step a, starting with 1-benzyl-4-piperidone
(b) The title compound was prepared starting from N-(4-Morpholinecarbonyl)-L-cyclohexyl alanine and 4-amino-4-cyano-1-benzylpiperidine according to the procedure from Example 2, step b, except that the compound was purified by HPLC using a 20×250 mm $C_{18}$ reverse phase column with the method being 30% acetonitrile in water to 100% acetonitrile. MS, m/z 482=M+1.

Example 6

Morpholine-4-carboxylic acid [1-(4-cyano-1-propyl-piperidin-4-ylcarbamoyl)-2-cyclohexyl-ethyl]-amide (a) 4-Amino-4-cyano-1-propylpiperidine was prepared according to the procedure from Example 1, step a, starting with 1-propyl-4-piperidone.
(b) The title compound was prepared starting from N-(4-Morpholinecarbonyl)-L-cyclohexyl alanine and 4-amino-4-cyano-1-propylpiperidine according to the procedure from Example 2, step b, except that the compound was purified by HPLC using a 20×250 mm $C_{18}$ reverse phase column with the method being 30% acetonitrile in water to 100% acetonitrile. MS, m/z 434=M+1.

Example 7

4-Cyano-4-{3-cyclohexyl-2-[(morpholine-4-carbonyl)-amino]-propionylamino}-piperidine-1-carboxylic acid benzyl ester (a) A solution of sodium cyanide (1052 mg, 21.5 mmol), ammonium chloride (1265 mg, 23.65 mmol), and benzyl 4-oxo-1-piperidine-carboxylate (5.0 gm, 21.5 mmol), was prepared in 5 M ammonia in methanol (8.6 mL, 43 mmol). The solution was brought to reflux for 4 h and then allowed to cool to room temperature. The solution was then filtered and washed with methanol (100 mL) and the filtrate was concentrated in vacuo. The resulting oil was taken up in MTBE (250 mL) and filtered again. The filter cake was washed with MTBE (100 mL) and the filtrate was concentrated in vacuo to yield 4-amino-4-cyano-piperidine-1-carboxylic acid benzyl ester as a clear oil (3.5 g) which was used without further purification.
(b) The title compound was prepared starting from N-(4-Morpholinecarbonyl)-L-cyclohexyl alanine and 4-amino-4-cyano-piperidine-1-carboxylic acid benzyl ester according to the procedure from Example 2, step b, except that the compound was purified by HPLC using a 20×250 mm $C_{18}$ reverse phase column with the method being 30% acetonitrile in water to 100% acetonitrile. MS, m/z 526=M+1.

Example 8

Morpholine-4-carboxylic acid [1-(4-cyano-tetrahydro-thiopyran-4-ylcarbamoyl)-2-cyclohexyl-ethyl]-amide (a) 4-Amino-tetrahydro-thiopyran-4-carbonitrile was prepared according to the procedure from Example 7, step a, starting from tetrahydrothiopyran-4-one.
(b) The title compound was prepared starting from N-(4-Morpholinecarbonyl)-L-cyclohexyl alanine and 4-amino-4-cyano-tetrahydrothiopyrane according to the procedure from Example 2, step b, except that the compound was purified by reverse phase HPLC using a 20×250 mm $C_{18}$ reverse phase column with the method being 30% acetonitrile in water to 100% acetonitrile. MS, m/z 409=M+1.

Example 9

Morpholine-4-carboxylic acid [1-(4-cyano-1-pyrimidin-2-yl-piperidin-4-ylcarbamoyl)-2-cyclohexyl-ethyl]-amide (a) 4-Amino-4-cyano-1-pyrimidin-2-yl-piperidine was prepared according to the procedure from Example 7, step a, starting with 1-(pyrimidin-2-yl)-4-piperidone with the exception that a 2 M ammonia in methanol solution replaced the 5 M ammonia in methanol solution.
(b) The title compound was prepared starting from N-(4-Morpholinecarbonyl)-L-cyclohexyl alanine and 4-amino-4-cyano-1-pyrimidin-2-yl-piperidine according to the procedure from Example 2, step b, except that the compound was purified by HPLC using a 20×250 mm $C_{18}$ reverse phase column with the method being 30% acetonitrile in water to 100% acetonitrile. MS, m/z 469=M+1.

Example 10

Morpholine-4-carboxylic acid [1-(4-cyano-2,6-diphenyl-piperidin-4-ylcarbamoyl)-2-cyclohexyl-ethyl]-amide (a) 4-Amino-4-cyano-2,6-diphenyl-piperidine was prepared according to the procedure from Example 9, step a, starting from 2,6-diphenyl-4-piperidone.
(b) The title compound was prepared starting from N-(4-Morpholinecarbonyl)-L-cyclohexyl alanine and 4-amino-4-cyano-2,6-diphenyl-piperidine according to the procedure from Example 2, step b, except that the compound was purified by HPLC using a 20×250 mm $C_{18}$ reverse phase column with the method being 30% acetonitrile in water to 100% acetonitrile. MS, m/z 544=M+1.

Example 11

Morpholine-4-carboxylic acid [1-(4-cyano-2,6-diphenyl-piperidin-4-ylcarbamoyl -3,3-dimethyl-butyl]-amide (a) 2-Amino-4,4-dimethyl-pentanoic acid methyl ester 2-Amino-4,4-dimethyl-pentanoic acid (1.00 g, 6.84 mmol) was suspended in 50 mL of methanol and cooled in an ice bath. Thionyl chloride (1.82 g, 15.0 mmol) was added dropwise, at which time all the acid went into solution. The reaction was then removed from the ice bath and heated to reflux for 3.5 h. The reaction mixture was concentrated in vacuo and the resulting solid (1.10 g) was used in the next step without further purification. MS, m/z 159.9=M+1

(b) 4,4-Dimethyl-2-[(morpholine-4-carbonyl)-amino]-pentanoic acid methyl ester

2-Amino-4,4-dimethyl-pentanoic acid methyl ester (5.35 g, 27.4 mmol) was dissolved in 100 mL of dichloromethane. Hunig's base (7.07 g, 54.7 mmol) and 4-morpholinecarbonyl chloride (4.08 g, 27.4 mmol) were added and the reaction was stirred at ambient temperature 16 h. The reaction mixture was concentrated in vacuo and taken up in 150 mL EtOAc. A white precipitate formed and was filtered and washed with EtOAc. EtOAc solutions were combined and washed with 3×50 mL 1 N HCl (aq), 3×50 mL saturated $NaHCO_3$ (aq), and 1×50 mL brine. The organic layer was dried over $Na_2SO_4$, decanted, and concentrated to a white solid (6.33 g). MS, m/z 273=M+1

(c) N-(4-morpholinecarbonyl)-L-neopentyl glycine 4,4-Dimethyl-2-[(morpholine-4-carbonyl)-amino]-pentanoic acid methyl ester (6.33 g, 23.2 mmol) was dissolved in 100 mL of THF and 50 mL of methanol. The solution was cooled on an ice bath and lithium hydroxide monohydrate (5.80 g, 116 mmol) was added as a suspension in 50 mL of water. The reaction was stirred at ambient temperature for 1 h. Additional water was added to the reaction (25 mL) and the mixture was extracted with diethyl ether 2×75 mL. The organic layer was discarded. The aqueous layer was acidified to pH 2 with 20% HCl (aq) and the product was extracted with 3×75 mL EtOAc. The EtOAc layer was washed with 1×50 mL brine and dried over $Na_2SO_4$, decanted, and concentrated in vacuo to a white solid (5.85 g). MS, m/z 259=M+1

(d) Morpholine-4-carboxylic acid [1-(4-cyano-2,6-diphenyl-piperidin-4-ylcarbamoyl)-3,3-dimethyl-butyl]-amide N-(4-morpholinecarbonyl)-L-neopentyl glycine (214 mg, 0.83 mmol) was dissolved in 25 mL of dichloromethane. EDC (175 mg, 0.91 mmol), HOBT (123 mg, 0.91 mmol), 4-amino-4-cyano-2,6-diphenylpiperidine (Example 10) (278 mg, 0.91 mmol), and N-methylmorpholine (420 mg, 4.2 mmol) were added to the solution. The reaction was stirred at ambient temperature for 16 h. The reaction was concentrated in vacuo and the resulting residue was dissolved in 150 mL of EtOAc. The EtOAc layer was washed with 2×50 mL saturated $NaHCO_3$, 1×50 mL brine, then dried over $Na_2SO_4$, decanted, and concentrated to an oil. Product was recrystallized from EtOAc/ hexanes to yield a white solid (42 mg). MS, m/z 518=M+1

Example 12

Morpholine-4-carboxylic acid [1-(1-acetyl-4-cyano-piperidin4-ylcarbamoyl)-2-cyclohexyl-ethyl]-amide (a) 4-Amino-4-cyano-1-acetylpiperidine was prepared according to the procedure from Example 9, step a, starting with 1-acetyl-4-piperidone.

(b) The title compound was prepared starting from N-(4-morpholinecarbonyl)-L-cyclohexyl alanine and 4-amino-4-cyano-1-acetylpiperidine according to the procedure from Example 2, step b, except that the compound was purified by HPLC using a 20×250 mm $C_{18}$ reverse phase column with the method being 30% acetonitrile in water to 100% acetonitrile. MS, m/z 433=M+1.

Example 13

Morpholine-4-carboxylic acid [1-(4-cyano-tetrahydro-pyran-4-ylcarbamoyl)-3,3-dimethyl-butyl]-amide (a) 4-Amino-4-cyano-tetrahydropyran was prepared according to the procedure from Example 1, step a, starting from tetrahydropyran-4-one.

(b) The title compound was prepared starting from N-(4-morpholinecarbonyl)-L-neopentyl glycine (Example 11, step c) and 4-amino-4-cyano-tetrahydropyrane according to the procedure from Example 2, step b, except that the compound was purified by HPLC using a 20×250 mm $C_{18}$ reverse phase column with the method being 30% acetonitrile in water to 100% acetonitrile. MS, m/z 367=M+1.

Example 14

Morpholine-4-carboxylic acid [1-(4-cyano-tetrahydro-thiopyran-4-ylcarbamoyl)-3,3-dimethyl-butyl]-amide The title compound was prepared starting from N-(4-Morpholinecarbonyl)-L-neopentyl glycine (Example 11, step c) and 4-amino-4-cyano-tetrahydrothiopyran (Example 8) according to the procedure from Example 1, step d, except that the compound was purified by HPLC using a 20×250 mm $C_{18}$ reverse phase column with the method being 30% acetonitrile in water to 100% acetonitrile. MS, m/z 383=M+1.

Example 15

Morpholine-4-carboxylic acid [1-(1-benzyl-4-cyano-piperidin-4-ylcarbamoyl)-3,3-dimethyl-butyl]-amide The title compound was prepared starting from N-(4-Morpholinecarbonyl)-L-neopentyl glycine (Example 11, step c) and 4-amino-4-cyano-1-benzylpiperidine (Example 5, step a) according to the procedure from Example 1, step d, except that the compound was purified by HPLC using a 20×250 mm $C_{18}$ reverse phase column with the method being 30% acetonitrile in water to 100% acetonitrile. MS, m/z 456=M+1.

Example 16

Morpholine-4-carboxylic acid [1-(1-isopropyl-4-cyano-piperidin-4-ylcarbamoyl)-3,3-dimethyl-butyl]-amide (a) 4-Amino-4-cyano-1-isopropylpiperidine was prepared according to the procedure from Example 1, step a, starting from 1-i-propyl-4-piperidone.

(b) The title compound was prepared starting from N-(4-morpholinecarbonyl)-L-neopentyl glycine (Example 11, step c) and 4-amino-4-cyano-1-isopropylpiperidine according to the procedure from Example 1, step d, except that the compound was purified by HPLC using a 20×250 mm $C_{18}$ reverse phase column with the method being 30% acetonitrile in water to 100% acetonitrile. MS, m/z 456=M+1.

Example 17

Morpholine-4-carboxylic acid [1-(1-phenethyl-4-cyano-piperidin-4-ylcarbamoyl -3,3-dimethyl-butyl]-amide The title compound was prepared starting from N-(4-morpholinecarbonyl)-L-neopentyl glycine (Example 11, step c) and 4-amino-4-cyano-1-phenethylpiperidine (Example 4) according to the procedure from Example 1, step d, except that the compound was purified by HPLC using a 20×250 mm $C_{18}$ reverse phase column with the method being 30% acetonitrile in water to 100% acetonitrile. MS, m/z 470=M+1.

Example 18

Morpholine-4-carboxylic acid [1-(1-n-propyl-4-cyano-piperidin-4-ylcarbamoyl)-3,3-dimethyl-butyl]-amide The title compound was prepared starting from N-(4-morpholinecarbonyl)-L-neopentyl glycine (Example 11, step c) and 4-amino-4-cyano-1-n-propylpiperidine (Example 6) according to the procedure from Example 1, step d, except that the compound was purified by HPLC using a 20×250 mm $C_{18}$ reverse phase column with the method being 30% acetonitrile in water to 100% acetonitrile. MS, m/z 408=M+1.

Example 19

4-Cyano-4-{3,3-dimethyl-2-[(morpholine-4-carbonyl-amino]-pentanoylamino}-piperidine-1-carboxylic acid benzyl ester The title compound was prepared starting from N-(4-morpholinecarbonyl)-L-neopentyl glycine (Example 11, step c) and 4-amino-4-cyano-piperidine-1-carboxylic acid benzyl ester (Example 7, step a) according to the procedure from Example 1, step d, except that the compound was purified by HPLC using a 20×250 mm $C_{18}$ reverse phase column with the method being 30% acetonitrile in water to 100% acetonitrile. MS, m/z 500=M+1.

Example 20

Morpholine-4-carboxylic acid [1-(1-acetyl-4-cyano-piperidin-4-ylcarbamoyl)-3,3-dimethyl-butyl]-amide (a) 1-Acetyl-4-amino-piperidin-4-carbonitrile 1-Acetyl-4-amino-piperidin-4-carbonitrile was prepared from N-acetyl-4-piperidone according to the procedure from Example 9, step a.
(b) The title compound was prepared starting from 1-Acetyl-4-amino-piperidine-4-carbonitrile and N-(4-morpholinecarbonyl)-L-neopentyl glycine (Example 11, step c) according to the procedure from Example 11, step d and purified by reverse phase HPLC (43 mg). MS, m/z 408=M+1.

Example 21

Morpholine-4-carboxylic acid [1-(1-benzoyl-4-cyano-piperidin-4-ylcarbamoyl)-3,3-dimethyl-butyl]-amide (a) 4-Amino-1-benzoyl-piperidine-4-carbonitrile was prepared from N-benzoyl-4-piperidone according to the procedure from Example 9, step a. MS, m/z 168=M+1

(b) The title compound was prepared starting from 4-amino-1-benzoyl-piperidine-4-carbonitrile and N-(4-morpholinecarbonyl)-L-neopentyl glycine (Example 11, step c) according to the procedure from Example 11, step d and purified by reverse phase HPLC (66 mg). MS, m/z 470=M+1

Example 22

4-Cyano-4-{4,4-dimethyl-2-1(morpholine-4-carbonyl)-amino]-pentanoylamino}-piperidine-1-carboxylic acid ethyl ester (a) 4-Amino-4-cyano-piperidine-1-carboxylic acid ethyl ester was prepared according to the procedure from Example 1, step a, from 4-oxopiperidine-1-carboxylic acid ethyl ester.
(b) The title compound was prepared starting from 4-Amino-4-cyano-piperidine-1-carboxylic acid ethyl ester and N-(4-morpholinecarbonyl)-L-neopentyl glycine (Example 11, step c) according to the procedure from Example 11, step d and purified by reverse phase HPLC (67 mg). MS, m/z 438=M+1

Example 23

Morpholine-4-carboxylic acid {1-[4-cyano-1-(2-dimethylamino-acetyl)-piperidin-4-ylcarbamoyl]-2-cyclohexyl-ethyl}-amide The title compound was prepared from N.N-dimethylaminoglycine and morpholine-4-carboxylic acid [1-(4-cyano-piperidin-4-ylcarbamoyl)-2-cyclohexyl-ethyl]-amide hydrochloride using the coupling method described in Example 1-part (d). The product was purified by reverse phase preparative HPLC to give the title compound as an off-white solid; MS, m/z 477=M+1.

Example 24

4-Acetylamino-N-[1-(4-cyano-tetrahydro-pyran-4-ylcarbamoyl)-2-cyclohexyl-ethyl]-benzamide
(a) t-Butoxycarboxylic acid [1-(4-cyano-tetrahydro-pyran-4-ylcarbamoyl)-2-cyclohexyl-ethyl]-amide.
  t-Butoxycarboxylic acid [1-(4-cyano-tetrahydro-pyran-4-ylcarbamoyl)-2-cyclohexyl-ethyl]-amide was prepared from N-Boc-L-cyclohexylalanine and 4-amino-4-cyano-tetrahydropyran by the method of Example 2-part (b). The product was used in the next step without further purification.
(b) [1-(4-cyano-tetrahydro-pyran-4-ylcarbamoyl)-2-cyclohexyl-ethyl]-amine hydrochloride
  t-Butoxycarboxylic acid [1-(4-cyano-tetrahydro-pyran-4-ylcarbamoyl)-2-cyclohexyl-ethyl]-amide (1000 mg, 2.62 mmol) was dissolved in 15 mL of 4 M HCl in dioxane. The solution was stirred at ambient temperature for 1 hr. The volatiles were removed in vacuo and the resulting paste was triturated with 25 mL of diethyl ether to give a fine white solid that was collected by filtration and dried in vacuo. The product was used without further purification. benzamide.
(c) 4-Acetylamino-N-[1-(4-cyan-tetrahydro-pyran-4-ylcarbamoyl)-2-cyclohexyl-ethyl]-benzamide
  4-Acetamidobenzoic acid (353 mg, 1.98 mmol), EDC (378 mg, 1.98 mmol), and HOBT (268 mg, 1.98 mmol) were combined in 15 mL of DMF and stirred for 20 min. Solid [1-(4-cyano-tetrahydro-pyran-4-ylcarbamoyl)-2-cyclohexyl-ethyl]-amine hydrochloride (625 mg, 1.98 mmol) was added. The reaction was stirred for 16 hours. The volatiles were removed with a pump and the resulting residue was triturated, with rapid stirring, with 250 mL of saturated aqueous sodium bicarbonate. The resulting solid was collected by filtration and washed with 250 mL of water. The solid was dried in vacuo to give the title compound (250 mg); MS, m/z 441=M+1.

Following the above procedures the following compounds can be synthesised;

4-Chloro-N-[1-(4-cyano-1-methyl-piperidin-4-ylcarbamoyl)-2-cyclohexyl-ethyl]-benzamide
N-[1-(4-Cyano-1-methyl-piperidin-4-ylcarbamoyl)-2-cyclohexyl-ethyl]-4-methoxy-benzamide
N-[1-(4-Cyano-1-methyl-piperidin-4-ylcarbamoyl)-2-cyclohexyl-ethyl]-isonicotinamide
Pyrazine-2-carboxylic acid [1-(4-Cyano-1-methyl-piperidin-4-ylcarbamoyl)-2-cyclohexyl-ethyl]-amide
N-[1-(4-Cyano-1-methyl-piperidin-4-ylcarbamoyl)-2-cyclohexyl-ethyl]-3-phenoxy-benzamide
Furan-2-carboxylic acid [1-(4-cyano-1-methyl-piperidin-4-ylcarbamoyl)-2-cyclohexyl-ethyl]-amide
Thiophene-2-carboxylic acid [1-(4-cyano-1-methyl-piperidin-4-ylcarbamoyl)-2-cyclohexyl-ethyl]-amide
5-Chloro-thiophene-2-carboxylic acid [1-(4-cyano-1-methyl-piperidin-4-ylcarbamoyl)-2-cyclohexyl-ethyl]-amide
N-(4-Cyano-1-methyl-piperidin-4-yl)-3-cyclohexyl-2-(2-thiophen-2-yl-acetylamino)-propionamide.

Example 25

Morpholine-4-carboxylic acid [1-(4-cyano-1-methyl-piperidin-4-ylcarbamoyl)-3,3-dimethyl-butyl]-amide (a) t-Butoxycarboxylic acid [1-(4-cyano-1-methyl-piperidin-4-ylcarbamoyl)-3,3-dimethyl-butyl]-amide t-Butoxycarboxylic acid [1-(4-cyano-1-methyl-piperidin-4-ylcarbamoyl)-3,3-dimethyl-butyl]-amide was prepared from N-Boc-L-neopentylglycine and 4-amino-4-cyano-1-methyl-piperidine by a method analogous to that of Example 2-part (b). The product was used without further purification.

(b) [1-(4-cyano-1-methyl-piperidin-4-ylcarbamoyl)-3,3-dimethyl-butyl]-amine dihydrochloride

[1-(4-Cyano-1-methyl-piperidin-4-ylcarbamoyl)-3,3-dimethyl-butyl]-amine dihydrochloride was prepared by a method analogous to that of Example 24-part (b). The product was used without further purification.

(c) Morpholine-4-carboxylic Acid [1-(4-cyano-1-methyl-piperidin-4-ylcarbamoyl)-3,3-dimethyl-butyl]-amide

[1-(4-cyano-1-methyl-piperidin-4-ylcarbamoyl)-3,3-dimethyl-butyl]-amine dihydrochloride (350 mg, 1.03 mmol) was mixed in 10 mL of DMF to which was added 1 mL of N-methyl morpholine followed by addition of 4-morpholine carbonyl chloride (180 mg, 1.20 mmol) as a solution in 5 mL of DMF. The reaction was stirred for 16 hours at which time the volatiles were removed in vacuo. The residue was redissolved in 150 mL of EtOAc and washed sequentially with 50 mL of saturated aqueous bicarbonate and 50 mL of brine. The organic layer was dried over sodium sulfate, decanted and concentrated. The product was purified by flash chromatography on silica gel using 100% methylene chloride to 12% methanol in methylene chloride as eluent to give the title compound as a thick oil (85 mg); MS, m/z 380=M+1.

Following the above procedures the following compounds can be synthesised;

4-Chloro-N-[1-(4-cyano-1-methyl-piperidin-4-ylcarbamoyl)-3,3-dimethyl-butyl]-benzamide
N-[1-(4-cyano-1-methyl-piperidin-4-ylcarbamoyl)-3,3-dimethyl-butyl]-4-methoxy-benzamide
N-[1-(4-cyano-1-methyl-piperidin-4-ylcarbamoyl)-3,3-dimethyl-butyl]-isonicotinamide
Pyrazine-2-carboxylic acid [1-(4-cyano-1-methyl-piperidin-4-ylcarbamoyl)-3,3-dimethyl-butyl]-amide
Furan-2-carboxylic acid [1-(4-cyano-1-methyl-piperidin-4-ylcarbamoyl)-3,3-dimethyl-butyl]-amide
Thiophene-2-carboxylic acid [1-(4-cyano-1-methyl-piperidin-4-ylcarbamoyl)-3,3-dimethyl-butyl]-amide
4,4-Dimethyl-2-(2-thiophen-2-yl-acetylamino)-pentanoic acid (4-cyano-1-methyl-piperidin-4-yl)-amide
N-[1-(4-Cyano-1-methyl-piperidin-4-ylcarbamoyl)-3,3-dimethyl-butyl]-3-phenoxy-benzamide
5-Chloro-thiophene-2-carboxylic acid [1-(4-cyano-1-methyl-piperidin-4-ylcarbamoyl)-3,3-dimethyl-butyl]-amide.

Example 26

4-Acetylamino-N-1-(4-cyano-1-methyl-piperidin-4-ylcarbamoyl)-2-cyclohexyl-ethyl]-benzamide The title compound was prepared by a method analogous to that of Example 24; MS, m/z 454=M+1.

Example 27

4-Acetlamino-N-[1-(4-cyano-1-methyl-piperidin-4-ylcarbamoyl)-3,3-dimethyl-butyl]-benzamide The title compound was prepared by a method analogous to that of Example 24; MS, m/z 428=M+1.

Example 28

4-Cyano-4-{3-cyclohexyl-2-[(morpholine-4-carbonyl)-amino]-propionylamino}-piperidine-1-carboxylic acid t-butyl ester (a) 4-Amino-4-cyano-piperidine-1-carboxylic acid t-butyl ester 4-Amino-4-cyano-piperidine-1-carboxylic acid t-butyl ester was prepared by a method analogous to that of Example 3-part (a). The product was used without further purification.

(b) 4-Cyano-4-{3-cyclohexyl-2-[(morpholine-4-carbonyl)-amino]-propionylamino}-piperidine-1-carboxylic acid t-butyl ester 4-Cyano-4-{3-cyclohexyl-2-[(morpholine-4-carbonyl)-amino]-propionylamino}-piperidine-1-carboxylic acid t-butyl ester was prepared by a method analogous to that of Example 3-part (b); MS, m/z 391, M-t-butoxycarbonyl).

Example 29

Morpholine-4-carboxylic acid [1-(4-cyano-piperidin-4-ylcarbamoyl)-2-cyclohexyl-ethyl]-amide hydrochloride 4-Cyano-4-{3-cyclohexyl-2-[(morpholine-4-carbonyl)-amino]-propionylamino}-piperidine-1-carboxylic acid t-butyl ester (1000 mg, 2.03 mmol) was dissolved in 20 mL of 4 M HCl in dioxane and stirred for 1 hour at which time the volatiles were remove in vacuo. The resulting residue was triturated with 100 mL of diethyl ether and the resulting solid was collected by filtration under inert atmosphere (the solid is very hygroscopic) and washed 2×50 mL of diethyl ether and dried in vacuo to yield the title compound as a bright white powder (802 mg); MS, m/z 392, M-35).

Example 30

Morpholine-4-carboxylic acid {1-[4-cyano-1-(1-methyl-ethyl)-piperidin-4-ylcarbamoyl]-2-cyclohexyl-ethyl}-amide (a) 4-Amino-4-cyano-1-(1-methyl-ethyl)-piperidine 4-Amino-4-cyano-1-(1-methyl-ethyl)-piperidine was prepared by a method analogous to that of Example 1-part (a). The product was used without further purification.

(b) Morpholine-4-carboxylic acid {1-[4-cyano-1-(1-methyl-ethyl)-piperidin-4-ylcarbamoyl]-2-cyclohexyl-ethyl}-amide Morpholine-4-carboxylic acid {1-[4-cyano-1-(1-methyl-ethyl)-piperidin-4-ylcarbamoyl]-2-cyclohexyl-ethyl}-amide was prepared by a method analogous to that of Example 1-part (d); MS, m/z 434=M+1.

Example 31

Morpholine-4-carboxylic acid {1-[3-cyano-1-benzyl-pyrrolidin-3-ylcarbamoyl]-2-cyclohexyl-ethyl}-amide (a) 3-Amino-3-cyano-1-benzylpyrrolidine 3-Amino-3-cyano-1-benzylpyrrolidine was prepared by a method analogous to that of Example 1-part (a) with the exception that no sodium carbonate was added to the reaction mixture. The product was extracted from the crude reaction with 3×100 ML of EtOAc and was used without purification.

(b) Morpholine-4-carboxylic acid {1-[3-cyano-1-benzyl-pyrrolidin-3-ylcarbamoyl]-2-cyclohexyl-ethyl}-amide. Separated diastereomers Diastereomeric morpholine-4-carboxylic acid {1-[3-cyano-1-benzyl-pyrrolidin-3-ylcarbamoyl]-2-cyclohexyl-ethyl}-amide was prepared by a method analogous to that of Example 1-part (d). The purification was done by reverse phase preparative HPLC (Hypersil HyPURITY™, C18 column, 250×21.2 5μ) to separate the two diastereomers; MS, m/z 468=M+1.

Example 32

Morpholine-4-carboxylic acid [1-(4-cyano-2,6-dimethyl-piperidin-4-ylcarbamoyl)-2-cyclohexyl-ethyl]-amide (a) Cis-2,6-dimethyl-4-piperidone Into a mixture of dimethyl acetonedicarboxylate (10 g, 57.4 mmol) and acetaldehyde (4.4 g, 100 mmol) maintained at −25° C. was bubbled ammonia until the solution was saturated (careful bubbling required due to exothermic dissolution of $NH_3$). The resulting solution was stored at 0° C. for 20 hours, by which time it was a white sludge. To this was added 25 mL of 3 N hydrochloric acid and the solution was heated on the steam-bath. Carbon dioxide began to evolve soon, but after 24 hours was still evolving very slowly. The solution was evaporated almost to dryness. To the tan heavy precipitate was added 25 mL of water and the solution was again evaporated. To the residue was added a solution of 10 g of sodium carbonate in 45 mL of water and 20 mL of chloroform. The layers were shaken and separated. The water layer was extracted six times with 20 mL protions of methylene chloride. The organic layers were dried over magnesium sulfate and concentrated to give the desired crude product which was used without further purification.

(b) 4-Amino-4-cyano-2,6-dimethyl-piperidine

To a mixture of ammonium chloride (0.58 g, 9.98 mmol), sodium cyanide (0.50 g, 11.0 mmol), ammonium hydroxide (2 mL) was added a solution of cis-2,6-dimethylpiperidone (1.27 g, 9.98 mmol) in 5 mL of methanol. The resulting mixture was refluxed for 4 hours. The reaction mixture was evaporated to dryness and the residue was taken up in 50 mLEtOAc, washed with saturated sodium bicarbonate 3×50 mL. The organic layer was evaporated to dryness and purified by flash chromatography on silica gel using 90 to 9 methylene chloride and methanol to give the desired product.

(c) Morpholine-4-carboxylic acid [1-(4-cyano-2,6-dimethyl-piperidin-4-ylcarbamoyl)-2-cyclohexyl-ethyl]-amide The title compound was prepared by the standard method of Example 1-part (d); MS, m/z 420=M+1.

Example 33

Morpholine-4-carboxylic acid [1-(4-cyano-1,3-dimethyl-piperidin-4-ylcarbamoyl)-2-cyclohexyl-ethyl]-amide (a) 1,3-Dimethyl-4-piperidone hydrochloride To a solution of methylamine (100 mL of 2.0 M solution in methanol) was added, over the course of 1 hour at 0° C., a solution of methyl methacrylate (30.2 g, 300 mmol) in 20 mL of methanol. The resulting solution was allowed to stand for three days, at which time the volatiles were removed on a rotovap and the residue was vacuum distilled to give the desired product as a clear oil, b.p. 48–49 C. at 8.5 mm. The oil was dissolved in 100 mL of methanol and methyl acrylate (14.8 g, 200 mmol) was added and the reaction was allowed to stand for 3 days. The volatiles were removed.

30 mL of Xylene was prepared over sodium (2.42 g) and refluxed for 2 hours and cooled to 60° C. To this mixture was added the diester and the reaction was refluxed until the sodium particles had disappeared. The resulting dark red liquid was cooled and poured into 150 mL of ice water. The phases were separated and the xylene extracted with 50 mL of concentrated hydrochloric acid and, after washing with 50 mL of isopropyl ether, the aqueous layer was cooled, basified with potassium carbonate and extracted eight times with 75 mL portions of ethyl ether. The combined ethereal extracts were dried over potassium carbonate and treated with excess dry ethereal hydrogen chloride; the resulting salt was filtered and dried.

The salt was taken up in 60 mL of 6 N hydrochloric acid and heated on a water bath for three hours, at the end of which time the initially vigorous carbon dioxide evolution had become negligible. The resulting solution was evaporated to dryness and dried in vacuo, to yield 1,3-dimethyl-4-piperidone hydrochloride (5 g) which was used in the next step without further purification.

(b) 4-Amino-4-cyano-1,3-dimethylpiperidine

The title compound was prepared as described in the previous example for 4-amino-4-cyano-2,6-dimethylpiperidine. The crude product was used in the next step without further purification.

(c) Morpholine-4-carboxylic acid [1-(4-cyano-1,3-dimethyl-piperidin-4-ylcarbamoyl)-2-cyclohexyl-ethyl]-amide The title compound was prepared as in Example 1-part (d); MS, m/z 420=M+1.

Example 34

4-Cyano-4-{3-cyclohexyl-2-[({4-acetylamino}-phenyl-1-carbonyl)-amino]-propionylamino}-piperdine-1-carboxylic acid ethyl ester The title compound was prepared by a method analogous to that of Example 24; MS, m/z 512=M+1.

Example 35

4-Acetylamino-N-[1-(4-cyano-1-benzyl-piperidin-4-ylcarbamoyl)-2-cyclohexyl-ethyl]-benzamide The title compound was prepared by a method analogous to that of Example 24; MS, m/z 530=M+1.

Example 36

4-Acetylamino-N-{1-[4-cyano-1-(1-methyl-ethyl)-piperidin-4-ylcarbamoyl]-2-cyclohexyl-ethyl}-benzamide The title compound was prepared by the method of Example 24; MS, m/z 482 M+1.

Example 37

Morpholine-4-carboxylic acid {1-[3-cyano-1-benzyl-piperidin-3-ylcarbamoyl]-2-cyclohexyl-ethyl}-amide The title compound, separated into two diastereomers, was prepared by a method analogous to that of Example 3 1; MS, m/z 482 M+1.

Example 38

4-Cyano-4-{3-cyclohexyl-2-[({4-acetylamino}-phenyl-1-carbonyl)-amino]-propionylamino}-piperidine-1-carboxylic acid benzyl ester The title compound was prepared by a method analogous to that of Example 24; MS, m/z 574=M+1.

Example 39

N-[1-(4-cyano-1-methyl-piperidin-4-ylcarbamoyl)-2-cyclohexyl-ethyl]-benzamide

The title compound was prepared by a method analogous to that of Example 24; MS, m/z 397=M+1.

Example 40

4-Acetylamino-N-{1-[4-cyano-1-(2-phenyl-ethyl)-piperidin-4-ylcarbamoyl]-2-cyclohexyl-ethyl}-benzamide The title compound was prepared by a method analogous to that of Example 24; MS, m/z 544=M+1.

Example 41

4-(Acetylamino-methyl)-N-[1-(4-cyano-1-methyl-piperidin-4-ylcarbamoyl)-2-cyclohexyl-ethyl]-benzamide (a) 4-(Acetylamino-methyl)-benzoic acid Methyl-4-(acetylamino-methyl)-benzoate was prepared from acetic acid and methyl 4-(aminomethyl)benzoate using a method analogous to that of Example 1-part (d). The crude N-acyl ester was saponified using a method analogous to that of Example 1-part (c). The crude product was used without further purification.

(b) 4-(Acetylamino-methyl)-N-[1-(4-cyano-1-methyl-piperidin-4-ylcarbamoyl)-2-cyclohexyl-ethyl]-benzamide.

The title compound was prepared by a method analogous to that of Example 24-part (c); MS, m/z 468=M+1.

Example 42

Morpholine-4-carboxylic acid [1-(3-cyano-8-methyl-8-aza-bicyclo [3.2.1]oct-3-ylcarbamoyl)-2-cyclohexyl-ethyl]-amide (a) 3-Amino-3-cyano-8-methyl-8-aza-bicyclo[3.2.1]octane The aminonitrile was prepared from tropinone using a method analogous to that of Example 1-part (a).

(b) Morpholine-4-carboxylic acid [1-(3-cyano-8-methyl-8-aza-bicyclo [3.2.1]oct-3-ylcarbamoyl)-2-cyclohexyl-ethyl]-amide The title compound was prepared using a method analogous to that of Example 1-part (d); MS, m/z 432=M+1.

Example 43

Morpholine-4-carboxylic acid [1-(1-carbamimidoyl-4-cyano-piperidin-4-ylcarbamoyl)-2-cyclohexyl-ethyl]-amide p-toluenesulfonate (a) 1-Carbamimidoyl-1,2,3-benztriazolep-toluenesulfonate A mixture of benztriazole (11.9 g, 100 mmol), cyanamide (4.2 g, 100 mmol), and p-toluene sulfonic acid hydrate (19.2 g, 100 mmol) in dioxane was refluxed for 24 hours. The reaction mixture was allowed to cool to room temperature and was diluted with ether, stirred vigorously, then filtered. The filter cake was washed with ether and recrystallized from ethanol to give the desired product as a white solid.

(b) Morpholine-4-carboxylic acid [1-(1-carbamimidoyl-4-cyano-piperidin-4-ylcarbamoyl)-2-cyclohexyl-ethyl]-amide p-toluenesulfonate Morpholine-4-carboxylic acid [1-(4-cyano-piperidin-4-ylcarbamoyl)-2-cyclohexyl-ethyl]-amide hydrochloride (0.2 g, 0.47 mmol) was dissolved in 3 mL of DMF and 2 equiv of Hunig's base was added followed by 1-carbamimidoyl-1,2,3-benztriazole p-toluenesulfonate (0.16 g, 0.47 mmol). The reaction was stirred 24 hours at which time the solvent was removed in vacuo. The resulting paste was purified by preparative HPLC to give the title compound; MS, m/z 434, M+1-p-toluene sulfonate).

Example 44

4-Acetylamino-N-[1-(4-cyano-tetrahydro-pyran-4-ylcarbamoyl)-3,3-dimethyl-butyl]-benzamide 4-Amino-4-cyano-tetrahydropyran prepared according to the procedure from Example 1, step a, starting from tetrahydropyran-4-one.

The title compound was prepared from 4-amino-4-cyano-tetrahydropyran, L-neopenyyl glycine and 4-acetylaminobenzoic acid analogous to the procedure described in Example 24.

Example 45

Morpholine-4-carboxylic acid [1-(4-cyano-1-methanesulfonyl-piperidin-4-ylcarbamoyl)-2-cyclohexyl-ethyl]-amide The title compound is prepared by treatment of morpholine-4-carboxylic acid [1-(4-cyano-piperidin-4-ylcarbamoyl)-2-cyclohexyl-ethyl]-amide hydrochloride with methanesulfonyl chloride and a tertiary amine base such as N-methylmorpholine in a solvent such as methylene chloride.

Example 46

4-Acetylamino-piperidine-1-carboxylic acid [1-(4-cyano-1-methyl-piperidin-4-ylcarbamoyl)-2-cyclohexyl-ethyl]-amide The title compound is prepared by a method analogous to that of Example 24.

Example 47

Morpholine-4-carboxylic acid {1-[1-(2-chloro-benzyl)-3-cyano-pyrrolidin-3-ylcarbamoyl]-2-cyclohexyl-ethyl}-amide.

The title compound is prepared by a method analogous to that of Example 31.

Example 48

Morpholine-4-carboxylic acid [1-(1-benzylcarbamoyl-4-cyano-piperidin-4-ylcarbamoyl)-3,3-dimethyl-butyl]-amide The title compound is prepared from morpholine-4-carboxylic acid [1-(4-cyano-piperidin-4-ylcarbamoyl)-3,3-dimethyl-butyl]-amide hydrochloride and benzyl isocyanate in the presence of a tertiary amine base such as N-methylmorpholine in a solvent such as methylene chloride.

Example 49

Morpholine-4-carboxylic acid [1-(1-phenylcarbamoyl-4-cyano-piperidin-4-ylcarbamoyl)-3,3-dimethyl-butyl]-amide The title compound is prepared from morpholine-4-carboxylic acid [1-(4-cyano-piperidin-4-ylcarbamoyl)-3,3-dimethyl-butyl]-amide hydrochloride and phenyl isocyanate in the presence of a tertiary amine base such as N-methylmorpholine in a solvent such as methylene chloride.

Example 50

Morpholine-4-carboxylic acid {1-[4-cyano-1-(morpholine-4-carbonyl)-piperidin-4-ylcarbamoyl]-3,3-dimethyl-butyl]-amide The title compound is prepared from morpholine-4-carboxylic acid [1-(4-cyano-piperidin-4-ylcarbamoyl)-3,3-dimethyl-butyl]-amide hydrochloride and 4-morpholine carbonyl chloride in the presence of a tertiary amine base such as N-methylmorpholine in a solvent such as methylene chloride.

Example 51

Morpholine-4-carboxylic acid (1-{4-cyano-1-[(pyridin-3-ylmethyl)-carbamoyl]-piperidin-4-ylcarbamoyl}-3,3-dimethyl-butyl)-amide The title compound is prepared from morpholine-4-carboxylic acid [1-(4-cyano-piperidin-4-ylcarbamoyl)-3,3-dimethyl-butyl]-amide hydrochloride and 3-pyridyl-methyl isocyanate in the presence of a tertiary amine base such as N-methylmorpholine in a solvent such as methylene chloride.

Example 52

Morpholine-4-carboxylic acid {1-[4-cyano-1-(4-methyl-piperazine-1-carbonyl)-piperidin-4-ylcarbamoyl)-2-cyclohexyl-ethyl]-amide The title compound is prepared from morpholine-4-carboxylic acid [1-(4-cyano-piperidin-4-ylcarbamoyl)-2-cyclohexyl-ethyl]-amide hydrochloride and 4-methyl-piperzine carbonyl chloride in the presence of a tertiary amine base such as N-methylmorpholine in a solvent such as methylene chloride.

Example 53

4-(4-Cyano-4-{3-cyclohexyl-2-[(morpholine-4-carbonyl)-amino]-propionylamino}-piperidin-1-yl)-butyric acid The title compound is prepared from morpholine-4-carboxylic acid [1-(4-cyano-piperidin-4-ylcarbamoyl)-2-cyclohexyl-ethyl]-amide hydrochloride and 4-bromobutyric acid in the presence of a hindered tertiary amine base such as Hunig's base in a solvent such as methylene chloride.

Example 54

Morpholine-4-carboxylic acid [1-(4-cyano-1-cyclopropyl-piperidin-4-ylcarbamoyl)-2-cyclohexyl-ethyl]-amide The title compound may be prepared from morpholine-4-carboxylic acid [1-(4-cyano-piperidin-4-ylcarbamoyl)-2-cyclohexyl-ethyl]-amide hydrochloride and 1-ethoxy-1-trimethylsilyloxy-cyclopropane using a reducing agent such sodium cyanoborohydride in a solvent system such as acetic acid in methanol.

Example 55

Morpholine-4-carboxylic acid {1-[4-cyano-1-(2-dimethylamino-ethyl)-piperidin-4-ylcarbamoyl]-2-cyclohexyl-ethyl}-amide.

The title compound is prepared by the method of Example 33.

Example 56

Morpholine-4-carboxylic acid [1-(4-cyano-1-phenyl-piperidin-4-ylcarbamoyl)-2-cyclohexyl-ethyl]-amide.

The title compound is prepared by a method analogous to that of Example 58.

Example 57

Morpholine-4-carboxylic acid {1-[4-cyano-1-(1,1-dimethyl-ethyl)-piperidin-4-ylcarbamoyl]-2-cyclohexyl-ethyl}-amide The title compound can be prepared by a method analogous to that of the method of Example 59.

Example 58

Morpholine-4-carboxylic acid [1-(4-cyano-1-phenyl-piperidin-4-ylcarbamoyl)-3,3-dimethyl-butyl]-amide.

(a) N-Phenyl-4-piperidone

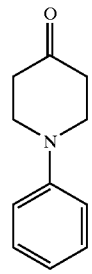

1,4-Dioxa-8-azaspiro[4.5]-decane (2.0 g, 14.0 mmol, 1.0 equiv), Pd$_2$(DBA)$_3$ (0.31 mmol, 0.024 equiv), BINAP (0.64 g, 1.0 mmol, 0.073 equiv), NaO-t-Bu (3.9 g, 41 mmol, 3.0 equiv) and bromobenzene (2.6 g, 17.7 mmol, 1.3 equiv) were combined under Ar in 50 mL of dry toluene. The resulting mixture was refluxed under Ar for 4 h. The reaction mix was cooled and poured into 250 mL of saturated sodium bicarbonate solution. The product was extracted with 3×100 mL CH$_2$Cl$_2$. The organic extracts were combined and concentrated. The product was purified by flash chromatography on SiO$_2$ using 50% hexanes in CH$_2$Cl$_2$ to pure CH$_2$Cl$_2$ to give the N-phenyl ketal (2.9 g). The purified ketal was dissolved in mixture of 50 mL 1,4-dioxane, 50 mL water, and 20 mL concentrated HCl. The mixture was refluxed for 3 h at which time mass spectrometry showed disappearance of the starting ketal. The cooled mixture was carefully poured into 600 mL of saturated sodium bicarbonate solution and the product extracted with 3×200 mL EtOAc. The combined organic extracts were combined and dried over Na$_2$SO$_4$, decanted and concentrated to a red oil (2.3 g) which was used without further purification; MS, m/z 176=M+1.
(b) 4-Amino-4-cyano-1-phenyl-piperidine

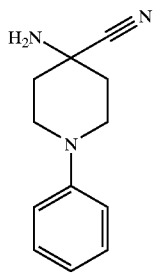

N-Phenyl-4-piperidone (2.3 g, 13 mmol, 1.0 equiv) was dissolved in 26 mL of 2 M NH$_3$ in MeOH and NaCN (0.76 g, 15 mmol, 1.2 equiv) and NH$_4$Cl (0.80 g, 15 mmol, 1.2 equiv) were added and the mixture was refluxed for 2 h at which time an additional 26 mL of 2 M NH$_3$/MeOH was added followed by another 2 h of reflux. The reaction mixture was cooled and filtered. The filtrate was concentrated. The crude product was purified by flash chromatography on SiO$_2$ eluting with 100% CH$_2$Cl$_2$ and 2% MeOH in CH$_2$Cl$_2$ to give the pure product (1.92 g) as a thick yellow oil which solidified on standing; MS, m/z 202=M+1.
(c) Morpholine-4-carboxylic acid [1-(4-cyano-1-phenyl-piperidin-4-ylcarbamoyl)-3,3-dimethyl-butyl]-amide.

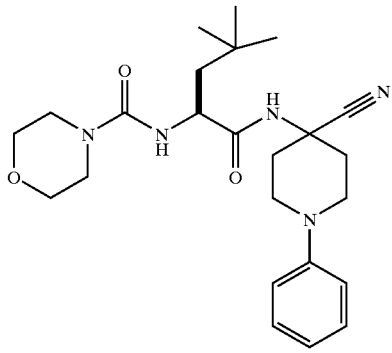

N-(4-morpholinecarbonyl)-L-neopenylglycine (0.2 g, 0.97 mmol, 1.0 equiv) and EDC (0.19 g, 0.97 mmol, 1.0 equiv) were combined in 10 mL of CH$_2$Cl$_2$ and stirred for 15 min at room temperature. A solution of 4-amino-4-cyano-1-phenyl-piperidine (0.20 g, 0.97 mmol, 1.0 equiv) in 5 mL of CH$_2$Cl$_2$ and N-methyl-morpholine (0.31 g, 3.1 mmol, 4.0 equiv) were added and stirring was continued for 16 h. The reaction was concentrated in vacuo and the residue was triturated with 100 mL saturated sodium bicarbonate solution with rapid stirring for 2 h. The resulting solid was collected by filtration and recrystallized from CH$_3$CN and water (2 to 1) to yield the title compound as an off-white solid (165 mg, 39%); MS, m/z 443=M+1.

Following the above procedures the following compounds can be synthesized:

Morpholine-4-carboxylic acid {1-[4-cyano-1-(2-methoxy-phenyl)-piperidin-4-ylcarbamoyl]-3,3-dimethyl-butyl}-amide Morpholine-4-carboxylic acid {1-[4-cyano-1-(3-methoxy-phenyl)-piperidin-4-ylcarbamoyl]-3,3-dimethyl-butyl}-amide Morpholine-4-carboxylic acid {1-[4-cyano-1-(4-methoxy-phenyl)-piperidin-4-ylcarbamoyl]-3,3-dimethyl-butyl}-amide Morpholine-4-carboxylic acid {1-[4-cyano-1-(2-methyl-phenyl)-piperidin-4-ylcarbamoyl]-3,3-dimethyl-butyl}-amide Morpholine-4-carboxylic acid {1-[4-cyano-1-(3-methyl-phenyl)-piperidin-4-ylcarbamoyl]-3,3-dimethyl-butyl}-amide Morpholine-4-carboxylic acid {1-[4-cyano-1-(4-methyl-phenyl)-piperidin-4-ylcarbamoyl]-3,3-dimethyl-butyl}-amide Morpholine-4-carboxylic acid {1-[4-cyano-1-(2-phenyl-phenyl)-piperidin-4-ylcarbamoyl]-3,3-dimethyl-butyl}-amide Morpholine-4-carboxylic acid {1-[4-cyano-1-(3-phenyl-phenyl)-piperidin-4-ylcarbamoyl]-3,3-dimethyl-butyl}-amide Morpholine-4-carboxylic acid {1-[4-cyano-1-(4-phenyl-phenyl)-piperidin-4-ylcarbamoyl]-3,3-dimethyl-butyl}-amide Morpholine-4-carboxylic acid {1-[4-cyano-1-(2-methoxy-phenyl)-piperidin-4-ylcarbamoyl]-2-cyclohexyl-ethyl}-amide Morpholine-4-carboxylic acid {1-[4-cyano-1-(3-methoxy-phenyl)-piperidin-4-ylcarbamoyl]-2-cyclohexyl-ethyl}-amide Morpholine-4-carboxylic acid {1-[4-cyano-1-(4-methoxy-phenyl)-piperidin-4-ylcarbamoyl]-2-cyclohexyl-ethyl}-amide Morpholine-4-carboxylic acid {1-[4-cyano-1-(2-methyl-phenyl)-piperidin-4-ylcarbamoyl]-2-cyclohexyl-ethyl}-amide Morpholine-4-carboxylic acid {1-[4-cyano-1-(3-methyl-phenyl)-piperidin-4-ylcarbamoyl]-2-cyclohexyl-ethyl}-amide Morpholine-4-carboxylic acid {1-[4-cyano-1-(4-methyl-phenyl)-piperidin-4-ylcarbamoyl]-2-cyclohexyl-ethyl}-amide Morpholine-4-carboxylic acid {1-[4-cyano-1-(2-phenyl-phenyl)-piperidin-4-ylcarbamoyl]-2-cyclohexyl-ethyl}-amide Morpholine-4-carboxylic acid {1-[4-cyano-1-(3-phenyl-phenyl)-piperidin-4-ylcarbamoyl]-2-cyclohexyl-ethyl}-amide Morpholine-4-carboxylic acid {1-[4-cyano-1-(4-phenyl-phenyl)-piperidin-4-ylcarbamoyl]-2-cyclohexyl-ethyl}-amide

Example 59

Morpholine-4-carboxylic acid [1-(1-tert-butyl-4-cyano-piperidin-4-ylcarbamoyl)-3,3-dimethyl-butyl]-amide (a) N-Methoxy-N-methyl-acrylamide

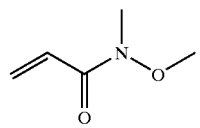

Acrolyl chloride (20 g, 221 mmol, 1.0 equiv) was dissolved n 500 mL of CH$_2$Cl$_2$ and cooled to 0° C. Solid N,O-dimethyl-hydroxylamine hydrochloride (21.5 g, 221 mmol, 1.0 equiv) was added all at once. Et$_3$N was added dropwise over a 2 h period to give a thick yellow mixture. The reaction was stirred for an additional hour during which time it was allowed to warm to room temperature. The mixture was poured into 1 L of water. Layers were separated and the organic layer was washed with 1×500 mL water, 1×500 mL brine and dried over Na$_2$SO$_4$. The solution was decanted and concentrated in vacuo to give the desired product as a yellow oil (23 g, 90%) which was used without further purification.

(b) 3-(t-Butyl-amino)-N-methoxy-N-methyl-propanamide

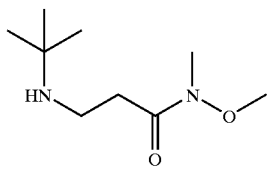

N-Methoxy-N-methyl-acrylamide (5 g, 43.4 mmol, 1.0 equiv) was dissolved in t-butylamine (3.36 g, 46 mmol, 1.06 equiv). The resulting solution was stirred at room temperature for 48 h. The excess primary amine was removed in vacuo and the crude product was purified by flash chromatography on silica using 100% CH$_2$Cl$_2$ to 2% MeOH in CH$_2$Cl$_2$ to give the desired product as a light yellow oil (5.7 g, 70%); MS, m/z 189=M+1.

(c) 1-t-Butyl-4-piperidone

3-(t-Butyl-amino)-N-methoxy-N-methyl-propanamide (5 g, 26.6 mmol, 1.0 equiv) was dissolved in dry THF (50 mL) under Ar. The solution was cooled to −78° C. and a 1 M solution of vinylmagnesium bromide (66.5 mL, 66.5 mmol, 2.5 equiv) was added dropwise over a 20 min period. The reaction was then stirred at −78° C. for 30 min and at 0° C. for 30 min at which time the reaction solution was transferred via a double-ended cannula into ice-cold saturated sodium bicarbonate solution under Ar. The mixture was stirred for 10 min and the crude product was extracted 2×150 mL EtOAc. The organic extracts were combined and concentrated in vacuo to a red oil. Purification was done by flash chromatography on silica using 100% CH$_2$Cl$_2$ through 4, 8, and 16% MeOH in CH$_2$Cl$_2$. The product was isolated as an orange oil (1.3 g, 32%); MS, m/z 156=M+1.

(d) 4-Amino-1-t-butyl-4-cyano-piperidine

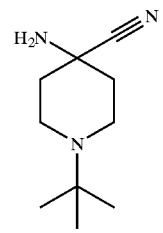

1-t-Butyl-4-piperidone (1.3 g, 8.4 mmol, 1.0 equiv), NaCN (0.61 g, 12.6 mmol, 1.5 equiv), and NH$_4$Cl (0.67 g, 12.6 mmol, 1.5 equiv) were combined in 34 mL of 2 M NH$_3$ in MeOH. The mixture was refluxed for 2 h at which time an additional 34 mL of 2 M NH$_3$ in MeOH was added followed by another 2 h at reflux. The mixture was cooled and filtered. The filtrate was concentrated in vacuo and the residue was triturated with CH$_2$Cl$_2$ and filtered again. The solution was concentrated to a thick red oil which was used without further purification; MS, m/z 182=M+1.

(e) Morpholine-4-carboxylic acid [1-(1-tert-butyl-4-cyano-piperidin-4-ylcarbamoyl)-3,3-dimethyl-butyl]-amide

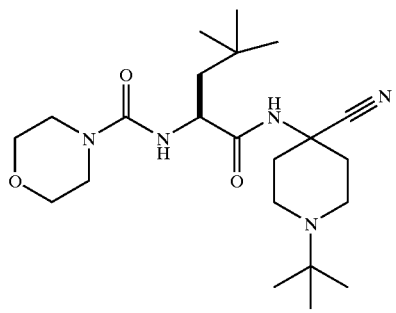

N-(4-morpholinecarbonyl)-L-neopenylglycine (0.070 g, 0.27 mmol, 1.0 equiv) and EDC (0.057 g, 0.30 mmol, 1.1 equiv) were combined in 10 mL of DMF and stirred for 15 min at room temperature. A solution of 4-amino-1-t-butyl-4-cyano-piperidine (0.054 g, 0.30 mmol, 1.1 equiv) in 5 mL of DMF and N-methyl-morpholine (0.11 g, 1.1 mmol, 4.0 equiv) were added and stirring was continued for 16 h. The reaction was diluted with 50 mL of saturated sodium bicarbonate solution and the product was extracted with 3×50 mL EtOAc. The organic extracts were combined and concentrated in vacuo. The product was purified by semi-prep reverse-phase HPLC using 20 to 60% CH$_3$CN in water over a 25 min gradient to yield the title compound as a white solid after concentration (25 mg, 22%); MS, m/z 422=M+1.

Example 60

Morpholine-4-carboxylic acid [1-(4-cyano-1,2-dimethyl-piperidin-4-ylcarbamoyl)-3,3-dimethyl-butyl]-amide (a) 3-(Benzyl-methyl-amino)-butyric acid methyl ester

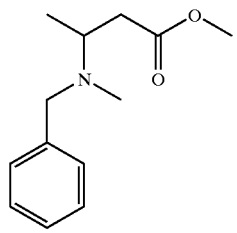

Benzyl-methyl-amine (20 g, 165 mmol, 1.0 equiv) was added neat to methyl crotonate (19.8 g, 198 mmol, 1.2 equiv). The resulting solution was stirred at room temperature for 72 h. The excess crotonic ester was removed in vacuo to yield the desired product (40.3 g,~100%) which was used without further purification; MS, m/z 222=M+1.

(b) 3-Methylamino-butyric acid methyl ester

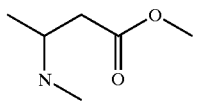

3-(Benzyl-methyl-amino)-butyric acid methyl ester (15 g, 67.8 mmol, 1.0 equiv) was placed in a Parr hydrogenation bottle and dissolved in 50 mL of MeOH. 20% Palladium hydroxide on carbon (0.5 g, 0.94 mmol, 0.014 equiv) was added and the mixture was shaken at 50 psi $H_2$ for 16 h. The reaction was judged as complete when the uptake of $H_2$ had stopped. The bottle was opened and 10 g of diatomaceous earth in 100 mL of MeOH was added. The mixture was filtered on a pad of diatomaceous earth which was then washed with 2×100 mL of MeOH. The filtrates were combined and concentrated in vacuo to yield the desired product as an oil that is somewhat volatile (7.6 g, 85%). The crude product was used without further purification; MS, m/z 132=M+1.

(c) 3-[(2-Methoxycarbonyl-ethyl)-methyl-amino]-butyric acid methyl ester

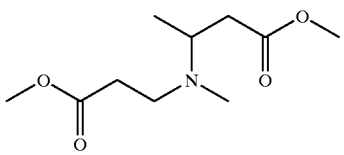

3-Methylamino-butyric acid methyl ester (7.6 g, 58 mmol, 1.0 equiv) was added neat to methyl acrylate (7.5 g, 87 mmol, 1.5 equiv). The resulting solution was refluxed for 16 h. The reaction was cooled and diluted with hexanes (200 mL) and an insoluble polymer separated out. The hexane solution was decanted and the polymer washed 2×100 mL hexanes with vigorous stirring. The combined hexane solutions were then concentrated in vacuo. The crude product was purified by flash chromatography on $SiO_2$ using pure $CH_2Cl_2$ as an eluent. The pure product was isolated as a clear colorless oil (7.3 g, 58%); MS, m/z 218=M+1.

(d) 1,2-Dimethyl-4-piperidone

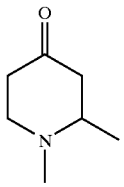

A 1 M solution of $TiCl_4$ in $CH_2Cl_2$ (23 mL, 23 mmol, 1.0 equiv) was added to a flask under Ar and cooled to −15° C. with a MeOH/ice water bath. 3-[(2-Methoxycarbonyl-ethyl)-methyl-amino]-butyric acid methyl ester (5 g, 23 mmol, 1.0 equiv) was added dropwise over a 25 min period as a solution in 75 mL of dry $CH_2Cl_2$ to give a dark red mixture that was difficult to stir with a magnetic stir bar. Stirring was continued an additional 1 h and then $Et_3N$ (5.1 g, 50.6 mmol, 2.2 equiv) was added dropwise over a 30 min period and then the reaction was stirred an additional 1.5 h at −15° C. The reaction mix was poured into 150 mL of brine and 150 mL of $CH_2Cl_2$ was added. After thorough mixing, the pH of the water was brought to 8–9 with $Et_3N$. The mix was filtered and the gel-like solid was washed 3×100 mL $CH_2Cl_2$. The filtrate layers were separated and the aqueous layer was washed 3×50 mL $CH_2Cl_2$. All of the organic layers were combined and concentrated to a thick red oil. The residue was taken up in 150 mL of concentrated HCl and the solution was refluxed 4 h. The cooled reaction solution was evaporated to dryness and the residue was dissolved in 200 mL of saturated sodium bicarbonate solution. The product ketone was extracted with 2×100 mL of EtOAc. The organic layers were combined and dried over $Na_2SO_4$. The product was purified by flash chromatography on $SiO_2$ using pure $CH_2Cl_2$ to 4% MeOH in $CH_2Cl_2$ as eluent. The product was isolated as an orange oil (1.23 g, 42%); MS, m/z 128=M+1.

(e) 4-Amino-4-cyano-1,2-dimethyl-piperidine

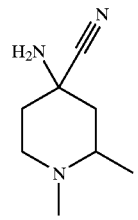

1,2-Dimethyl-4-piperidone (1.23 g, 9.67 mmol, 1.0 equiv) was dissolved in 39 mL of 2 M $NH_3$ in MeOH (8 equiv $NH_3$). To this solution was added NaCN (0.52 g, 10.6 mmol, 1.1 equiv) and $NH_4Cl$ (0.57 g, 10.6 mmol, 1.1 equiv). The resulting mixture was refluxed for 2 h at which time an additional 39 mL of 2 M $NH_3$ in MeOH was added followed by an additional 2 h of reflux. The reaction was cooled and filtered. The filtrate was concentrated and taken up in 100 mL of $CH_2Cl_2$ giving more salt precipitate which was removed by a second filtration. The filtrate was then concentrated to thick orange oil (1.32 g, 89%). $^1$H NMR showed a 3 to 1 mixture of diastereomers of unknown configuration. The crude product was used without further purification; MS, m/z 154=M+1.

(f) Morpholine-4-carboxylic acid [1-(4-cyano-1,2-dimethyl-piperidin-4-ylcarbamoyl)-3,3-dimethyl-butyl]-amide

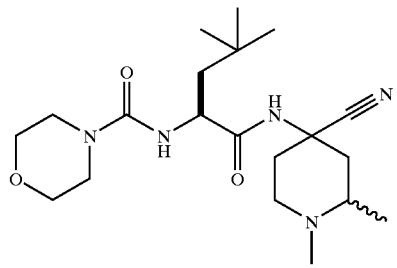

N-(4-morpholinecarbonyl)-L-neopenylglycine (0.20 g, 0.77 mmol, 1.0 equiv) and EDC (0.15 g, 0.77 mmol, 1.0 equiv) were combined in 10 mL of DMF and stirred for 15 min at room temperature. A solution of 4-amino-4-cyano-1,2-dimethyl-piperidine (0.11 g, 0.74 mmol, 0.95 equiv) in 5 mL of DMF and N-methyl-morpholine (0.31 g, 3.1 mmol, 4.0 equiv) were added and stirring was continued for 16 h. The reaction was diluted with 50 mL of saturated sodium bicarbonate solution and the product was extracted with 3×50 mL of EtOAc. The organic layers were combined and concentrated. The crude product was purified by semi-prep reverse-phase HPLC using 20% CH$_3$CN in water to 60% CH$_3$CN in water over a gradient of 16 min to give two peaks (diastereomers) eluting at 13.1 and 14.0 min (49 mg and 20 mg respectively); MS, m/z 394=M+1 for each peak.

Following the above procedures the following compounds can be synthesised:

Morpholine-4-carboxylic acid [1-(4-cyano-2-methyl-1-propyl-piperidin-4-ylcarbamoyl)-3,3-dimethyl-butyl]-amide Morpholine-4-carboxylic acid [1-(4-cyano-2-ethyl-1-propyl-piperidin-4-ylcarbamoyl)-3,3-dimethyl-butyl]-amide Morpholine-4-carboxylic acid [1-(4-cyano-1,2-dipropyl-piperidin-4-ylcarbamoyl)-3,3-dimethyl-butyl]-amide Morpholine-4-carboxylic acid [1-(2-butyl-4-cyano-1-propyl-piperidin-4-ylcarbamoyl)-3,3-dimethyl-butyl]-amide Morpholine-4-carboxylic acid [1-(2-benzyl-4-cyano-1-propyl-piperidin-4-ylcarbamoyl)-3,3-dimethyl-butyl]-amide Morpholine-4-carboxylic acid [1-(4-cyano-2-cyclohexyl-1-propyl-piperidin-4-ylcarbamoyl)-3,3-dimethyl-butyl]-amide Morpholine-4-carboxylic acid [1-(4-cyano-2-cyclohexylmethyl-1-propyl-piperidin-4-ylcarbamoyl)-3,3-dimethyl-butyl]-amide Morpholine-4-carboxylic acid [1-(4-cyano-2-methyl-1-propyl-piperidin-4-ylcarbamoyl)-2-cyclohexyl-ethyl]-amide Morpholine-4-carboxylic acid [1-(4-cyano-2-ethyl-1-propyl-piperidin-4-ylcarbamoyl)-2-cyclohexyl-ethyl]-amide Morpholine-4-carboxylic acid [1(4-cyano-1,2-dipropyl-piperidin-4-ylcarbamoyl)-2-cyclohexyl-ethyl]-amide Morpholine-4-carboxylic acid [1-(2-butyl-4-cyano-1-propyl-piperidin-4-ylarbamoyl)-2 cyclohexyl-ethyl]-amide Morpholine-4-carboxylic acid [1-(2-benzyl-4-cyano-1-propyl-piperidin-4-ylcarbamoyl)-2-cyclohexyl-ethyl]-amide Morpholine-4-carboxylic acid [1-(4-cyano-2-cyclohexyl-1-propyl-piperidin-4-ylcarbamoyl)-2-cyclohexyl-ethyl]-amide Morpholine-4-carboxylic acid [1-(4-cyano-2-cyclohexylmethyl-1-propyl-piperidin-4-ylcarbamoyl)-2-cyclohexyl-ethyl]-amide Example 61

Morpholine-4-carboxylic acid [1-(4-cyano-1-cyclohexyl-piperidin-4-ylcarbamoyl)-3,3-dimethyl-butyl]-amide (a) 4-Amino-4-cyano-piperidine-1-carboxylic acid t-butyl ester

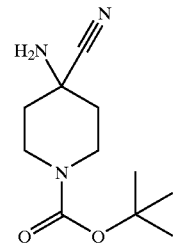

t-Butyl 4-oxo-1-piperidine-carboxylate (10 g, 50 mmol, 1.0 equiv) was dissolved 100 mL of 2 M NH$_3$ in MeOH. NaCN (2.7 g, 55 mmol, 1.1 equiv) and NH$_4$Cl (3 g, 55 mmol, 1.1 equiv) were added and the resulting mixture was refluxed for 2 h at which time an additional 100 mL of 2 M NH$_3$ in MeOH was added followed by another 2 h of reflux. The reaction mixture was cooled and filtered. The MeOH was removed in vacuo and the residue triturated with 100 mL of CH$_2$Cl$_2$ and filtered again. The filtrate was concentrated by about 75% and 200 mL of hexanes was added to give a tan precipitate that was collected by filtration to yield, after drying under vacuum, the desired product as cream-colored solid (10.1 g) which was used without further purification.

(b) 4-Cyano-4-{3,3-dimethyl-2-[(morpholine-4-carbonyl)-amino]-pentanoylamino}-piperidine-1-carboxylic acid t-butyl ester

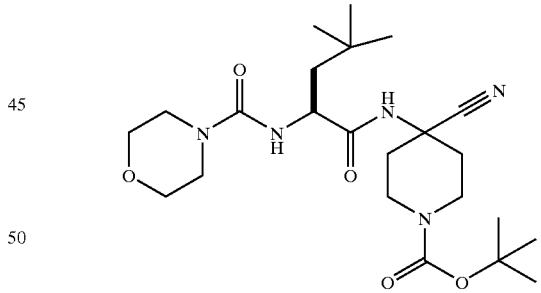

N-(4-morpholinecarbonyl)-L-neopenylglycine (1.00 g, 3.87 mmol, 1.00 equiv) and EDC (0.739 g, 3.87 mmol, 1.00 equiv) were mixed in 20 mL of CH$_2$Cl$_2$ and stirred for 15 min. A solution of 4-amino-4-cyano-piperidine-1-carboxylic acid t-butyl ester (0.872 g, 3.87 mmol, 1.00 equiv) in 10 mL CH$_2$Cl$_2$ and N-methyl-morpholine (1.56 g, 15.5 mmol, 4.0 equiv) were added and the resulting solution was stirred at room temperature for 16 h. The reaction was diluted with 100 mL CH$_2$Cl$_2$ and 100 mL saturated sodium bicarbonate solution. The layers were separated and the aqueous was washed 2×50 mL CH$_2$Cl$_2$. The organic extracts were combined and dried over Na$_2$SO$_4$. The solution was decanted and concentrated to a white solid. The solid was dissolved in 20 mL of CH$_3$CN and water (100 mL) was added to precipitate the product. The fluffy white solid was collected by filtration and dried under high vacuum to yield the desired compound as a white powder (1.51 g).

(c) Morpholine-4-carboxylic acid [1-(4-cyano-piperidin-4-ylcarbamoyl)-3,3-dimethyl-butyl]-amide hydrochloride

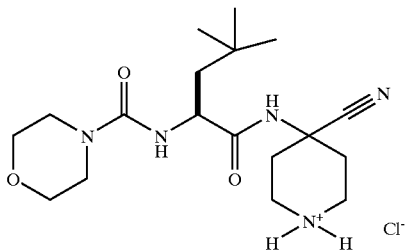

4-Cyano-4-{3,3-dimethyl-2-[(morpholine-4-carbonyl)-amino]-pentanoylamino}-piperidine-1-carboxylic acid t-butyl ester (1.51 g, 3.24 mmol, 1.0 equiv) was dissolved in 50 mL of dry Et$_2$O under Ar. 4 M HCl in 1,4-dioxane (16 mL, 20 equiv) was added and the mixture was stirred for 20 min. A white solid precipitated almost immediately upon addition of the acid. The mixture was filtered under Ar and the solid was washed 2×25 mL of dry Et$_2$O. The solid was dried under high vacuum to a bright white powder (1.25 g, 96%) which was used without further purification.

(d) Morpholine-4-carboxylic acid [1-(4-cyano-1-cyclohexyl-piperidin-4-ylcarbamoyl)-3,3-dimethyl-butyl]-amide

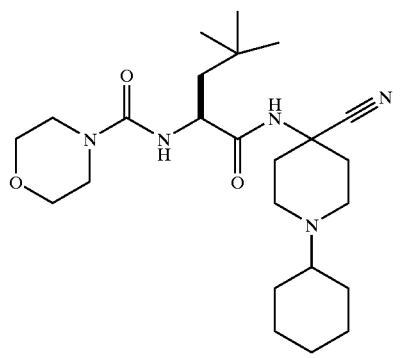

Morpholine-4-carboxylic acid [1-(4-cyano-piperidin-4-ylcarbamoyl)-3,3-dimethyl-butyl]-amide hydrochloride (0.050 g, 0.12 mmol, 1.0 equiv), cyclohexanone (0.015 g, 0.15 mmol, 1.2 equiv), and Na(OAc)$_3$BH (0.046 g, 0.22 mmol, 1.75 equiv) were mixed in 15 mL of 1% AcOH in THF. The reaction was stirred at room temperature for 16 h. The reaction was diluted with 25 mL of saturated sodium bicarbonate solution and the product was extracted 4×25 mL EtOAc. The organic extracts were combined and concentrated. The crude product was purified by semi-prep reverse-phase HPLC using 20 to 80% CH$_3$CN in water over a gradient of 25 min to yield the desired product, pure, as a white solid (0.012 g, 21%); MS, m/z 448=M+1.

Following the above procedures the following compound was synthesised:

Morpholine-4-carboxylic acid {1-[4-cyano-1-(tetrahydro-pyran-4-yl)-piperidin-4-ylcarbamoyl]-3,3-dimethyl-butyl}-amide; MS, m/z 450=M+1

Following the above procedures the following compounds can be synthesized;

Morpholine-4-carboxylic acid [1-(1-butyl-4-cyano-piperidin-4-ylcarbamoyl)-3,3-dimethyl-butyl]-amide Morpholine-4-carboxylic acid [1-(4-cyano-1-pentyl-piperidin-4-ylcarbamoyl)-3,3-dimethyl-butyl]-amide Morpholine-4-carboxylic acid [1-(4-cyano-1-hexyl-piperidin-4-ylcarbamoyl)-3,3-dimethyl-butyl]-amide Morpholine-4-carboxylic acid {1-[4-cyano-1-(1-ethyl-propyl)-piperidin-4-ylcarbamoyl]-3,3-dimethyl-butyl}-amide Morpholine-4-carboxylic acid {1-[4-cyano-1-(2-methyl-cyclohexyl)-piperidin-4-ylcarbamoyl]-3,3-dimethyl-butyl}-amide Morpholine-4-carboxylic acid {1-[4-cyano-1-(3-methyl-cyclohexyl)-piperidin-4-ylcarbamoyl]-3,3-dimethyl-butyl}-amide Morpholine-4-carboxylic acid {1-[4-cyano-1-(4-methyl-cyclohexyl)-piperidin-4-ylcarbamoyl]-3,3-dimethyl-butyl}-amide Morpholine-4-carboxylic acid {1-[4-cyano-1-(2-phenyl-cyclohexyl)-piperidin-4-ylcarbamoyl]-3,3-dimethyl-butyl}-amide Morpholine-4-carboxylic acid {1-[4-cyano-1-(3-phenyl-cyclohexyl)-piperidin-4-ylcarbamoyl]-3,3-dimethyl-butyl}-amide Morpholine-4-carboxylic acid {1-[4-cyano-1-(4-phenyl-cyclohexyl)-piperidin-4-ylcarbamoyl]-3,3-dimethyl-butyl}-amide Morpholine-4-carboxylic acid {1-[4-cyano-1-(cyclohexyl-methyl)-piperidin-4-ylcarbamoyl]-3,3-dimethyl-butyl}-amide Morpholine-4-carboxylic acid {1-[4-cyano-1-(cyclopropyl-methyl)-piperidin-4-ylcarbamoyl]-3,3-dimethyl-butyl}-amide Morpholine-4-carboxylic acid [1-(1-butyl-4-cyano-piperidin-4-ylcarbamoyl)-2-cyclohexyl-ethyl]-amide Morpholine-4-carboxylic acid [1-(4-cyano-1-pentyl-piperidin-4-ylcarbamoyl)-2-cyclohexyl-ethyl]-amide Morpholine-4-carboxylic acid [1-(4-cyano-1-hexyl-piperidin-4-ylcarbamoyl)-2-cyclohexyl-ethyl]-amide Morpholine-4-carboxylic acid {1-[4-cyano-1-(1-ethyl-propyl)-piperidin-4-ylcarbamoyl]-2-cyclohexyl-ethyl}-amide Morpholine-4-carboxylic acid {1-[4-cyano-1-(2-methyl-cyclohexyl)-piperidin-4-ylcarbamoyl]-2-cyclohexyl-ethyl}-amide Morpholine-4-carboxylic acid {1-[4-cyano-1-(3-methyl-cyclohexyl)-piperidin-4-ylcarbamoyl]-2-cyclohexyl-ethyl}-amide Morpholine-4-carboxylic acid {1-[4-cyano-1-(4-methyl-cyclohexyl)-piperidin-4-ylcarbamoyl]-2-cyclohexyl-ethyl}-amide Morpholine-4-carboxylic acid {1-[4-cyano-1-(2-phenyl-cyclohexyl)-piperidin-4-ylcarbamoyl]-2-cyclohexyl-ethyl}-amide Morpholine-4-carboxylic acid {1-[4-cyano-1-(3-phenyl-cyclohexyl)-piperidin-4-ylcarbamoyl]-2-cyclohexyl-ethyl}-amide Morpholine-4-carboxylic acid {1-[4-cyano-1-(cyclopropyl-methyl)-piperidin-4-ylcarbamoyl]-2-cyclohexyl-ethyl}-amide Morpholine-4-carboxylic acid {1-[4-cyano-1-(4-phenyl-cyclohexyl)-piperidin-4-ylcarbamoyl]-2-cyclohexyl-ethyl}-amide Morpholine-4-carboxylic acid {1-[4-cyano-1-(cyclohexyl-methyl)-piperidin-4-ylcarbamoyl]-2-cyclohexyl-ethyl}-amide

Example 62

Morpholine-4-carboxylic acid [1-(3-cyano-1-cyclopropylmethyl-pyrrolidin-3-ylcarbamoyl)-2-cyclohexyl-ethyl]-amide (a) 1-Cyclopropylmethyl-3-hydroxy-pyrrolidine

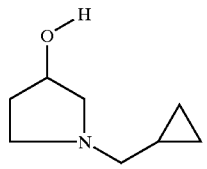

3-Hydroxy-pyrrolidine (5.65 g, 65 mmol, 1.0 equiv) was dissolved in 100 mL of 1% AcOH in THF and cooled to 0° C. Na(OAc)₃BH (24 g, 114 mmol, 1.75 equiv) and cyclopropylcarboxaldehyde (5.0 g, 71 mmol, 1.1 equiv) were added and the resulting mixture was stirred at 0° C. for 1 h and room temperature overnight (16 h). The reaction was diluted with 200 mL of 2 N NaOH, and the product was extracted 3×200 mL of CH₂Cl₂. The organic extracts were combined, dried over Na₂SO₄, decanted and concentrated to yield the desired product as a free-flowing oil (7.26 g, 79%) which was used without further purification; MS, m/z 142=M+1.

(b) 1-Cyclopropylmethyl-pyrrolidin-3-one

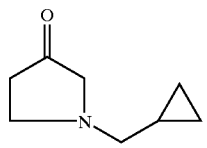

A solution of oxalyl chloride (13.1 g, 103 mmol, 2.0 equiv) was prepared in 200 mL of dry CH₂Cl₂ and cooled under Ar to −78° C. DMSO (16.1 g, 206 mmol, 4.0 equiv) was added as a solution in 20 mL of CH₂Cl₂ dropwise over a 30 min period giving vigorous gas formation. After addition, the mixture was stirred for an additional 15 min and then a solution of 1-cyclopropylmethyl-3-hydroxy-pyrrolidine (7.26 g, 52 mmol, 1.0 equiv) in 50 mL of CH₂Cl₂ was added dropwise over a 30 min period. After complete addition the reaction was stirred an additional a hour at −78° C. Et₃N (31 g, 309 mmol, 6.0 equiv) was added over a period of 10 min. The cold-bath was removed and the mixture was stirred while warming for 1 h. The mixture was diluted with 500 mL of water and 100 mL of CH₂Cl₂. After thorough mixing, the layers were separated and the organic layer was washed with 200 mL of water, dried over Na₂SO₄, decanted, and concentrated to a yellow oil (6.1 g, 85%) which was used without further purification.

(c) 3-Amino-3-cyano-1-cyclopropyl-pyrrolidine

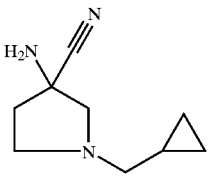

1-Cyclopropylmethyl-pyrrolidin-3-one (6.1 g, 44 mmol, 1.0 equiv), NaCN (2.4 g, 48 mmol, 1.1 equiv) and NH₄Cl (2.6 g, 48 mmol, 1.1 equiv) were mixed in 88 mL of 2 M NH3 in MeOH, and the resulting mixture was refluxed for 2 h at which time another 88 mL of 2 M NH₃ in MeOH was added followed by another 2 h at reflux. The reaction mixture was cooled, filtered, concentrated, and taken up in 100 mL of CH₂Cl₂. The mixture was filtered a second time and concentrated to a red oil (5.9 g) which was used without further purification.

(d) Morpholine-4-carboxylic acid [1-(3-cyano-1-cyclopropylmethyl-pyrrolidin-3-ylcarbamoyl)-2-cyclohexyl-ethyl]-amide

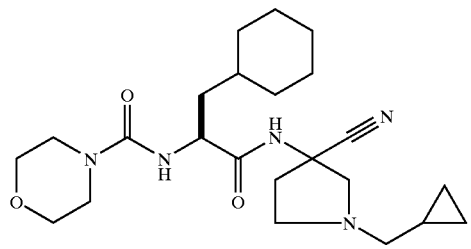

N-(4-morpholinecarbonyl)-L-cyclohexyl alanine (1.00 g, 3.52 mmol, 1.00 equiv) and EDC (1.01 g, 4.58 mmol, 1.30 equiv), and HoBt (0.72 g, 4.58 mmol, 1.30 equiv) were mixed 20 mL of DMF for 15 min followed by addition of 3-amino-3-cyano-1-cyclopropyl-pyrrolidine (0.86 g, 5.28 mmol, 1.5 equiv) and N-methyl-morpholine (1.42 g, 14.1 mmol, 4.0 equiv). The resulting solution was stirred at room temperature for 16 h. The reaction solution was diluted with 100 mL saturated sodium bicarbonate solution and the product was extracted with 2×100 mL EtOAc. The organic extracts were combined and concentrated. The crude product was purified by semi-prep reverse-phase HPLC using 40 to 90% CH₃CN in water over a gradient time of 30 min to give the desired product in two peaks (diastereomers) eluting at 9.5 min and 10.3 min respectively (128 mg and 98 mg, 15% total purified yield); MS, m/z 432=M+1 for both peaks.

Following the above procedures the following compounds were also prepared:

Morpholine-4-carboxylic acid {1-[3-cyano-1-(2-chloro-benzyl)-pyrrolidin-3-ylcarbamoyl]-2-cyclohexyl-ethyl}-amide; MS, m/z 502=M+1

Morpholine-4-carboxylic acid {1-[3-cyano-1-(cyclohexyl-methyl)-pyrrolidin-3-ylcarbamoyl]-2-cyclohexyl-ethyl}-amide; MS, m/z 474=M+1

Morpholine-4-carboxylic acid {1-[3-cyano-1-(1-methyl-ethyl)-pyrrolidin-3-ylcarbamoyl]-2-cyclohexyl-ethyl}-amide MS, m/z 420=M+1

Morpholine-4-carboxylic acid {1-[3-cyano-1-(3-benzyloxy-benzyl)-pyrrolidin-3-ylcarbamoyl]-2-cyclohexyl-ethyl}-amide; MS, m/z 574=M+1

Morpholine-4-carboxylic acid {1-[3-cyano-1-(2-benzyloxy-benzyl)-pyrrolidin-3-ylcarbamoyl]-2-cyclohexyl-ethyl}-amide; MS, m/z 574=M+1

Morpholine-4-carboxylic acid {1-[3-cyano-1-(3,5-difluoro-benzyl)-pyrrolidin-3-ylcarbamoyl]-2-cyclohexyl-ethyl}-amide; MS, m/z 504=M+1

Morpholine-4-carboxylic acid {1-[3-cyano-1-(2,6-difluoro-benzyl)-pyrrolidin-3-ylcarbamoyl]-2-cyclohexyl-ethyl}-amide; MS, m/z 504=M+1

Morpholine-4-carboxylic acid {1-[3-cyano-1-(3-trifluoromethyl-benzyl)-pyrrolidin-3-ylcarbamoyl]-2-cyclohexyl-ethyl}-amide; MS, m/z 536=M+1

Morpholine-4-carboxylic acid {1-[3-cyano-1 (3-phenoxy-benzyl)-pyrrolidin-3-ylcarbamoyl]-2-cyclohexyl-ethyl}-amide; MS, m/z 560=M+1

Morpholine-4-carboxylic acid [1-(3-cyano-1-cyclohexyl-pyrrolidin-3-ylcarbamoyl)-2-cyclohexyl-ethyl]-amide; MS, m/z 460=M+1

Morpholine-4-carboxylic acid {1-[3-cyano-1-(1-methyl-piperidine-4-yl)-pyrrolidin-3-ylcarbamoyl]-2-cyclohexyl-ethyl}-amide; MS, m/z 475=M+1
Morpholine-4-carboxylic acid {1-[3-cyano-1-(3-methyl-benzyl)-pyrrolidin-3-ylcarbamoyl]-2-cyclohexyl-ethyl}-amide; MS, m/z 482=M+1
Morpholine-4-carboxylic acid {1-[3-cyano-1-(2-phenoxy-benzyl)-pyrrolidin-3-ylcarbamoyl]-2-cyclohexyl-ethyl}-amide; MS, m/z 560=M+1
Morpholine-4-carboxylic acid {1-[3-cyano-1-(4-fluoro-benzyl)-pyrrolidin-3-ylcarbamoyl]-2-cyclohexyl-ethyl}-amide; MS, m/z 486=M+1
Morpholine-4-carboxylic acid {1-[3-cyano-1-(2,4,6-trimethyl-benzyl)-pyrrolidin-3-ylcarbamoyl]-2-cyclohexyl-ethyl}-amide; MS, m/z 510=M+1
Morpholine-4-carboxylic acid {1-[3-cyano-1-(1H-indol-3-ylmethyl)-pyrrolidin-3-ylcarbamoyl]-2-cyclohexyl-ethyl}-amide; MS, m/z 507=M+1
Morpholine-4-carboxylic acid [1-(3-cyano-1-cyclopropyl-pyrrolidin-3-ylcarbamoyl)-2-cyclohexyl-ethyl]-amide; MS, m/z 418=M+1
Morpholine-4-carboxylic acid {1-[3-cyano-1-(1-pyridin-3-ylmethyl)-pyrrolidin-3-ylcarbamoyl]-2-cyclohexyl-ethyl}-amide; MS, m/z 469=M+1
Morpholine-4-carboxylic acid [1-(3-cyano-1-cyclohexylmethyl-pyrrolidin-3-ylcarbamoyl)-3,3-dimethyl-butyl]-amide; MS, m/z 448=M+1
Morpholine-4-carboxylic acid [1-(1-benzyl-3-cyano-2-hydroxymethyl-pyrrolidin-3-ylcarbamoyl)-3,3-dimethyl-butyl]-amide; MS, m/z 472=M+1
Morpholine-4-carboxylic acid [1-(3-cyano-1-isobutyl-pyrrolidin-3-ylcarbamoyl)-2-cyclohexyl-ethyl]-amide; MS, m/z 434=M+1
Morpholine-4-carboxylic acid [1-(3-cyano-1-isopropyl-pyrrolidin-3-ylcarbamoyl)-3,3-dimethyl-butyl]-amide; MS, m/z 394=M+1
Morpholine-4-carboxylic acid [1-(3-cyano-1-isobutyl-pyrrolidin-3-ylcarbamoyl)-3,3-dimethyl-butyl]-amide; MS, m/z 408=M+1
Morpholine-4-carboxylic acid {1-[3-cyano-1-(1-ethyl-propyl)-pyrrolidin-3-ylcarbamoyl]-2-cyclohexyl-ethyl}-amide; MS, m/z 448=M+1
Morpholine-4-carboxylic acid {1-[3-cyano-1-(1-ethyl-propyl)-pyrrolidin-3-ylcarbamoyl]-3,3-dimethyl-butyl}-amide; MS, m/z 422=M+1
Morpholine-4-carboxylic acid [1-(3-cyano-1-phenethyl-pyrrolidin-3-ylcarbamoyl)-2-cyclohexyl-ethyl]-amide; MS, m/z 482=M+1
Morpholine-4-carboxylic acid [1-(3-cyano-1-methyl-piperidin-3-ylcarbamoyl)-2-cyclohexyl-ethyl]-amide; MS, m/z 406=M+1
Morpholine-4-carboxylic acid [1-(3-cyano-1-propyl-pyrrolidin-3-ylcarbamoyl)-3,3-dimethyl-butyl]-amide; MS, m/z 394=M+1
Morpholine-4-carboxylic acid [1-(3-cyano-1-propyl-pyrrolidin-3-ylcarbamoyl)-2-cyclohexyl-ethyl]-amide; MS, m/z 420=M+1
Morpholine-4-carboxylic acid {1-[3-cyano-1-(trans-4-methyl-cyclohexyl)-pyrrolidin-3-ylcarbamoyl]-2-cyclohexyl-ethyl}-amide; MS, m/z 474=M+1
Morpholine-4-carboxylic acid {1-[3-cyano-1-(cis-4-methyl-cyclohexyl)-pyrrolidin-3-ylcarbamoyl]-2-cyclohexyl-ethyl}-amide; MS, m/z 474=M+1
Morpholine-4-carboxylic acid [1-(3-cyano-1-cyclopentyl-pyrrolidin-3-ylcarbamoyl)-3,3-dimethyl-butyl]-amide; MS, m/z 420=M+1
Morpholine-4-carboxylic acid [1-(3-cyano-1-isobutyl-piperidin-3-ylcarbamoyl)-2-cyclohexyl-ethyl]-amide; MS, m/z 448=M+1
Morpholine-4-carboxylic acid [1-(3-cyano-1-cyclopentyl-pyrrolidin-3-ylcarbamoyl)-2-cyclohexyl-ethyl]-amide; MS, m/z 446=M+1
1-Benzyl-3-cyano-3-{3-cyclohexyl-2-[(morpholine-4-carbonyl)-amino]-propionylamino}-pyrrolidine-2-carboxylic acid methyl ester; MS, m/z 526=M+1
Morpholine-4-carboxylic acid {1-[3-cyano-1-(cis-4-methyl-cyclohexyl)-pyrrolidin-3-ylcarbamoyl]-3,3-dimethyl-butyl}-amide; MS, m/z 448=M+1
Morpholine-4-carboxylic acid {1-[3-cyano-1-(trans-4-methyl-cyclohexyl)-pyrrolidin-3-ylcarbamoyl]-3,3-dimethyl-butyl}-amide; MS, m/z 448=M+1
Morpholine-4-carboxylic acid [1-(3-cyano-1-cyclohexyl-pyrrolidin-3-ylcarbamoyl)-2-(4-iodo-phenyl)-ethyl]-amide; MS, m/z 580=M+1

Morpholine-4-carboxylic acid {1-[3-cyano-1-(3-methoxy-benzyl)-pyrrolidin-3-ylcarbamoyl]-2-cyclohexyl-ethyl}-amide; MS, m/z 498=M+1

Morpholine-4-carboxylic acid {1-[3-cyano-1-(naphthalen-2-ylmethyl)-pyrrolidin-3-ylcarbamoyl]-2-cyclohexyl-ethyl}-amide; MS, m/z 518=M+1
Morpholine-4-carboxylic acid [1-(3-cyano-1-cyclopentylmethyl-pyrrolidin-3-ylcarbamoyl)-2-cyclohexyl-ethyl]-amide; MS, m/z 460=M+1
Morpholine-4-carboxylic acid [1-(3-cyano-1-cyclohexylmethyl-pyrrolidin-3-ylcarbamoyl)-3-methyl-butyl]-amide; MS, m/z 434=M+1
[1-(3-Cyano-1-cyclohexylmethyl-pyrrolidin-3-ylcarbamoyl)-3-methyl-butyl]-carbamic acid benzyl ester; MS, m/z 455=M+1

Example 63

Morpholine-4-carboxylic acid (1-{3-cyano-1-[1-(toluene-4-sulfonyl)-1H-indol-3-ylmethyl]-pyrrolidin-3-ylcarbamoyl}-2-cyclohexyl-ethyl)-amide (a) 1-[1-(Toluene-4-sulfonyl)-1H-indol-3-ylmethyl]-3-hydroxy-pyrrolidine

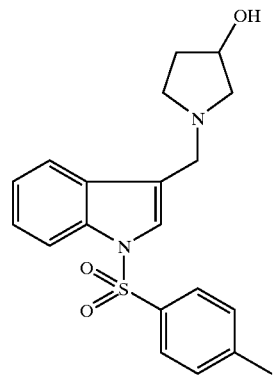

1-(Toluene-4-sulfonyl)-1H-indole-3-carboxaldehyde (prepared as described in Chatterjee, R. K.; Indian J. Chem Sect. B 1994, 33(1), 32–37) was reacted with 3-hydroxypyrrolidine as described for cyclopropylcarboxaldehyde in Example 60 part (a) to provide the desired product.

(b) Morpholine-4-carboxylic acid (1-{3-cyano-1-[1-(toluene-4-sulfonyl)-1H-indol-3-ylmethyl]-pyrrolidin-3-ylcarbamoyl}-2-cyclohexyl-ethyl)-amide

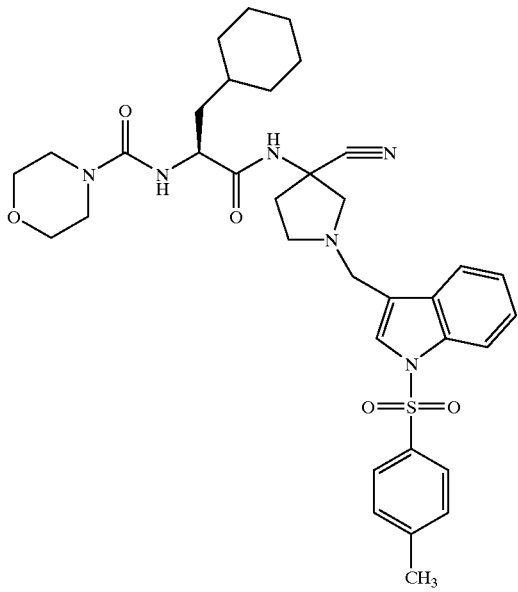

The title compound was prepared from the product of part (a) and N-(4-morpholinecarbonyl)-L-cyclohexyl alanine by the procedure described in Example 60; MS, m/z 661=M+1.

Example 64

Morpholine-4-carboxylic acid {1-[4-cyano-1-(1-methyl-piperidine-4-carbonyl)-piperidin-4-ylcarbamoyl]-2-cyclohexyl-ethyl}-amide

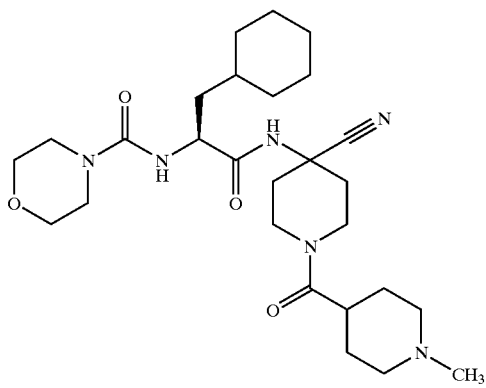

A solution of 1-methyl-piperidin-4-yl carboxylic acid (0.050 g, 0.30 mmol, 1.0 equiv) and EDC (0.057 g, 0.30 mmol, 1.0 equiv) was prepared in 15 mL of DMF. After 15 min morpholine-4-carboxylic acid [1-(4-cyano-piperidin-4-ylcarbamoyl)-2-cyclohexyl-ethyl]-amide hydrochloride (0.128 g, 0.30 mmol, 1.0 equiv) was added followed by N-methyl-morpholine (0.12 g, 1.2 mmol, 4.0 equiv) followed by stirring overnight (16 h). The reaction mixture was diluted with 100 mL of saturated sodium bicarbonate solution and the product was extracted with 2×50 mL of EtOAc. The combined organic extracts were concentrated. The crude product was purified by semi-prep reverse-phase HPLC using 20 to 80% CH$_3$CN in water over a gradient of 25 min to yield the desired product as a white solid (39 mg); MS, m/z 517=M+1.

Following the above procedure the following compound was also synthesized;
Morpholine-4-carboxylic acid {1-[4-cyano-1-(pyridine-4-carbonyl)-piperidin-4-ylcarbamoyl]-2-cyclohexyl-ethyl}-amide; MS, m/z 497=M+1

Example 65

N-[1-(4-Cyano-1-methyl-piperidin-4-ylcarbamoyl)-2-cyclohexyl-ethyl]-4-methanesulfonylamino-benzamide (a) 4-Methanesulfonylamino-benzoic acid

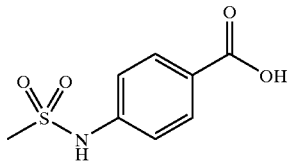

Ethyl 4-amino-benzoate (5 g, 30 mmol, 1.0 equiv) was mixed in 50 mL of CH$_2$Cl$_2$ with Et$_3$N (6.1 g, 60 mmol, 2.0 equiv). The solution was cooled to 0° C. and methanesulfonyl chloride (3.8 g, 33 mmol. 1.1 equiv) was added as a solution in 15 mL of CH$_2$Cl$_2$ dropwise over a 15 min period. The reaction was stirred for 4 h at which time it was diluted with 50 mL of water. Layers were separated and the organic layer was washed with 50 mL of saturated sodium bicarbonate solution and concentrated. The resulting ester was dissolved in 50 mL of MeOH and treated with 50 mL of 5 N NaOH for 4 h. The reaction solution was extracted with Et$_2$O and the aqueous layer was acidified to give a white precipitate that was collected by filtration. The solid was dried and used without further purification.

(b) N-[1-(4-Cyano-1-methyl-piperidin-4-ylcarbamoyl)-2-cyclohexyl-ethyl]-4-methanesulfonylamino-benzamide

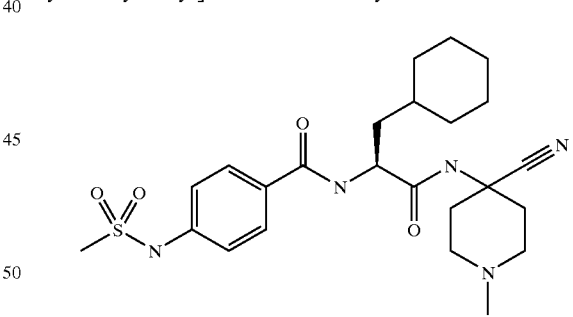

This compound was prepared from the product of part (a) using the procedure described in Example 24 to yield the desired product as a white solid; MS, m/z 490=M+1.

Following the above procedures the following compounds were also prepared:
N-[1-(1-benzyl-3-cyano-pyrrolidin-3-ylcarbamoyl)-3,3-dimethyl-butyl]-4-methanesulfonylamino-benzamide; MS, m/z 526=M+1
N-[1-(1-benzyl-3-cyano-pyrrolidin-3-ylcarbamoyl)-2-cyclohexyl-ethyl]-4-methanesulfonylamino-benzamide; MS, m/z 552=M+1
N-[1-(4-cyano-1-methyl-piperidin-4-ylcarbamoyl)-3,3-dimethyl-butyl]-4-methanesulfonylamino-benzamide; MS, m/z 464=M+1

Example 66

Morpholine-4-carboxylic acid [1-(1-benzyl-3-cyano-1-oxy-pyrrolidin-3-ylcarbamoyl)-2-cyclohexyl-ethyl]-amide (a) Morpholine-4-carboxylic acid [1-(1-benzyl-3-cyano-1-oxy-pyrrolidin-3-ylcarbamoyl)-2-cyclohexyl-ethyl]-amide

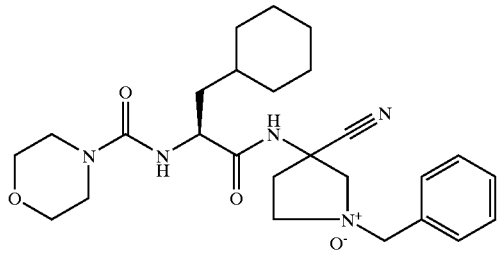

Morpholine-4-carboxylic acid [1-(1-benzyl-3-cyano-pyrrolidin-3-ylcarbamoyl)-2-cyclohexyl-ethyl]-amide (0.50 g, 1.1 mmol, 1.0 equiv) was dissolved in $CH_2Cl_2$ (25 mL) and cooled to −78° C. under Ar. Solid $K_2CO_3$ (0.22 g, 1.7 mmol, 1.5 equiv) was added followed by addition of solid m-CPBA (0.24 g, 1.1 mmol, 1.0 equiv). The resulting mixture was stirred at −78° C. for 2 h and, then, allowed to warm to room temperature. The reaction mixture was filtered and the solvent removed in vacuo. The residue was purified by flash chromatography on silica gel using 10–75% MeOH-EtOAc as a gradient eluent to give the desired product (0.32 g, 62%) as a white solid; MS, m/z 484=M+1.

Example 66

3-Cyano-3-{3-cyclohexyl-2-[(morpholine-4-carbonyl)-amino]-propionylamino}-pyrrolidine-1-carboxylic acid benzyl ester.

(a) 3-Hydroxy-pyrrolidine-1-carboxylic acid benzyl ester

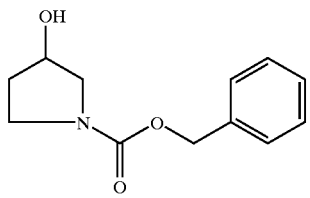

3-Hydroxy-pyrrolidine (10 g, 115 mmol, 1.0 equiv) was dissolved in 2 N NaOH (100 mL) and the mixture was cooled to 0° C. Benzylchloroformate (21 g, 126 mmol, 1.1 equiv) was added dropwise over a 45 min period. After addition, the reaction was stirred at room temperature for 4 h at which time the pH was adjusted to 7–8 using concentrated HCl. The product was extracted with 3×100 mL of $CH_2Cl_2$. The organic extracts were combined and dried over $Na_2SO_4$, decanted and concentrated in vacuo to yield the desired product as a light yellow oil (24.1 g, 95%) that was used without further purification.

(b) 3-Oxo-pyrrolidine-1-carboxylic acid benzyl ester

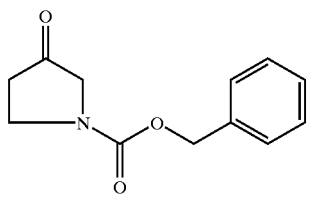

A solution of oxalyl chloride (12.6 g, 99 mmol, 2.0 equiv) was prepared in 250 mL of dry $CH_2Cl_2$ and cooled under Ar to −78° C. DMSO (15.5 g, 199 mmol, 4.0 equiv) was added dropwise over a 15 min period giving vigorous gas formation. After addition, the mixture was stirred for an additional 25 min and then a solution of 3-hydroxy-pyrrolidine-1-carboxylic acid benzyl ester (11 g, 50 mmol, 1.0 equiv) in 20 mL of $CH_2Cl_2$ was added dropwise over a 10 min period. After complete addition the reaction was stirred an additional a hour at −78° C. $Et_3N$ (55 mL, 398 mmol, 8.0 equiv) was added over a period of 10 min. The cold-bath was removed and the mixture was stirred while warming for 2 h. The mixture was diluted with 500 mL of water. After thorough mixing, the layers were separated and the aqueous layer was extracted 2×50 mL of $CH_2Cl_2$. The combined organic layers were washed with 200 mL of sodium bicarbonate solution and 200 mL of brine, dried over $Na_2SO_4$, decanted, and concentrated to a yellow oil. The product was purified by flash chromatography on silica gel using $CH_2Cl_2$ as eluent to yield the desired product as a colorless oil (8.5 g).

(c) 3-Amino-3-cyano-pyrrolidine-1-carboxylic acid benzyl ester

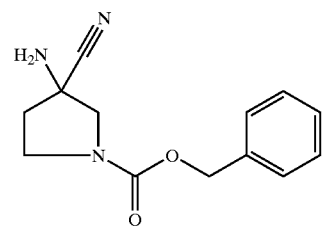

3-Amino-3-cyano-pyrrolidine-1-carboxylic acid benzyl ester was prepared from the ketone from part (b) using the procedure described in Example 1 part (a) to yield the desired product as a 2 to 1 to 1 mixture of amino-nitrile, cyanohydrin and starting ketone that was used without further purification.

(d) 3-Cyano-3-{3-cyclohexyl-2-[(morpholine-4-carbonyl)-amino]-propionylamino}-pyrrolidine-1-carboxylic acid benzyl ester

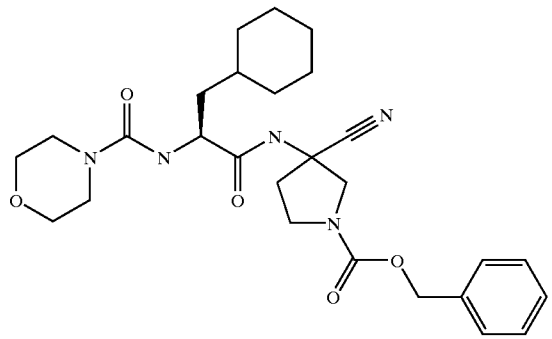

3-Cyano-3-{3-cyclohexyl-2-[(morpholine-4-carbonyl)-amino]-propionylamino}-pyrrolidine-1-carboxylic acid benzyl ester was prepared from the amine from part (c) using the procedure described in Example 1 part (a) to yield after purification on silica, the desired product as an off-white hard foam; MS, m/z 512=M+1.

Following the above procedures the following compound was also synthesized;

3-Cyano-3-{3-cyclohexyl-2-[(morpholine-4-carbonyl)-amino]-propionylamino}-pyrrolidine-1-carboxylic acid (2-propen-1-yl) ester; MS, m/z 462=M+1.

Example 68

Morpholine-4-carboxylic acid {1-[3-cyano-1-(5,5-dimethyl-3-oxo-cyclohex-1-enyl)-pyrrolidin-3-ylcarbamoyl]-2-cyclohexyl-ethyl}-amide

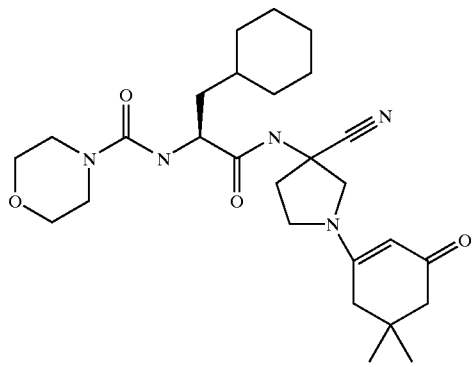

3-Cyano-3-{3-cyclohexyl-2-[(morpholine-4-carbonyl)-amino]-propionylamino}-pyrrolidine-1-carboxylic acid (2-propen-1-yl) ester (1.35 g, 2.93 mmol, 1.00 equiv) was dissolved in 35 mL of CH$_2$Cl$_2$ along with dimedone (3.30 g, 23.5 mmol, 8.03 equiv). Pd(PPh$_3$)$_4$ (0.25 g, 0.22 mmol, 0.07 equiv) was added and the suspension was stirred at room temperature for 3.5 h. The reaction mixture was concentrated and taken up into EtOAc (100 mL) and extracted with 1 N HCl (2×50 mL). Concentration of the organic phase and purification of the crude mixture by reverse-phase HPLC provide the product as two separate diastereomers; MS, m/z 500=M+1.

Example 69

4-Cyano-4-{3-cyclohexyl-2-[(piperidine-4-carbonyl)-amino]-propionylamino}-piperidine-1-carboxylic acid ethyl ester (a) 4-Cyano-4-{3-cyclohexyl-2-[(1-t-butoxycarbonyl-piperidine-4-carbonyl)-amino]-propionylamino}-piperidine-1-carboxylic acid ethyl ester

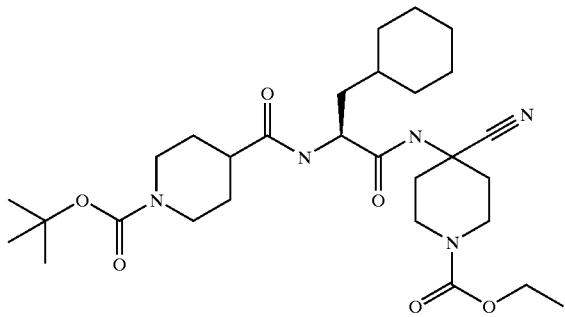

This intermediate was prepared from 1-t-butoxycarbonyl-piperidine carboxylic acid and 4-cyano-4-{[3-cyclohexyl-2-amino]-propionylamino}-piperidine carboxylic acid ethyl ester hydrochloride using the procedure described in Example 24.

(b) 4-Cyano-4-{3-cyclohexyl-2-[(piperidine-4-carbonyl)-amino]-propionylamino}-piperidine-1-carboxylic acid ethyl ester

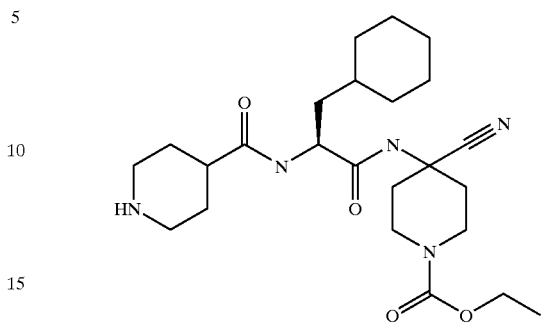

The ester from (a) was dissolved in 10 mL of 4 N HCl in 1,4-dioxane at 0° C. for 1 hour. The solution was concentrated in vacuo and the salt neutralized by sodium bicarbonate solution and the product extracted with CH$_2$Cl$_2$. After concentration of the organic extract, the crude product was purified by reverse-phase HPLC to yield the desired product; MS, m/z 462=M+1.

Following the above procedures the following compounds were also synthesized:

4-Cyano-4-{3-cyclohexyl-2-[(4-methyl-piperazine-1-carbonyl)-amino]-propionylamino}-piperidine-1-carboxylic acid ethyl ester; MS, m/z 477=M+1

4-Methyl-piperazine-1-carboxylic acid [1-(4-cyano-tetrahydro-pyran-4-ylcarbamoyl)-2-cyclohexyl-ethyl] amide; MS, m/z 406=M+1.

Example 70

Morpholine-4-carboxylic acid [1-(1-benzyl-3-cyano-azetidin-3-ylcarbamoyl)-2-cyclohexyl-ethyl]-amide (a) 3-Amino-1-benzyl-3-cyano-azetidine

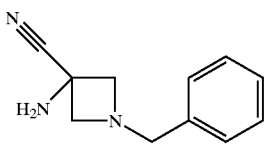

1-Benzyl-3-oxo-azetidine (1.6 g, 10 mmol, 1.0 equiv), prepared as described in the literature (Katritzky, A. R.; Cundy, D. J.; J. Heterocyclic Chem. 1994, 31 271–275), was dissolved in dry MeOH and the solution was cooled to −78° C. Gaseous ammonia was was bubbled through the solution for 30 mins at which time 3 angstrom molecular sieves were added and the mixture transferred to a pressure tube. The solution was heated for 30 min at 60° C. The mixture was cooled to −78° C., the tube opened and KCN (0.65 g, 10 mmol, 1.0 equiv) and NH$_4$Cl (0.27 g, 5 mmol, 0.5 equiv) were added and the tube was resealed and heated at 60° C. for 4 h. The reaction mixture was filtered and the filtrate was evaporated. The crude residue was purified by flash chromatography using 2% MeOH in CH$_2$Cl$_2$ to give the desired product (0.11 g, 6%) as a brown oil; MS, m/z 188=M+1.

(b) Morpholine-4-carboxylic acid [1-(1-benzyl-3-cyano-azetidin-3-ylcarbamoyl)-2-cyclohexyl-ethyl]-amide

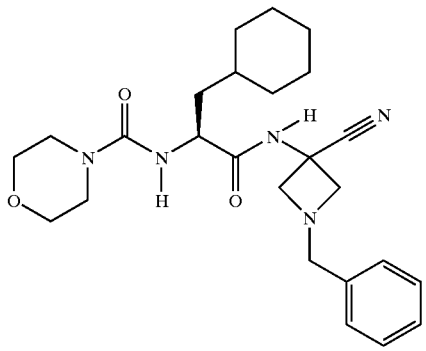

The title compound was prepared from 3-amino-1-benzyl-3-cyano-azetidine and N-(4-morpholinecarbonyl)-L-cyclohexyl alanine using to the procedure described in Example 1 step (d) to yield the desired product as a white solid; MS, m/z 454=M+1.

Example 71

Morpholine-4-carboxylic acid [1-(3-cyano-pyrrolidin-3-ylcarbamoyl)-2-cyclohexyl-ethyl]-amide

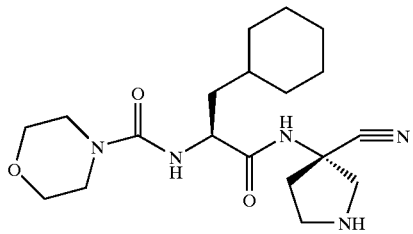

3-Cyano-3-{3-cyclohexyl-2-[(morpholine-4-carbonyl)-amino]-propionylamino}-pyrrolidine-1-carboxylic acid benzyl ester (0.1 g, 0.20 mmol, 1.0 equiv) was dissolved in 15 mL of absolute EtOH. 10% Pd on carbon (20 mg) was added and the mixture was stirred under 1 atm of $H_2$ until the starting material disappeared by TLC (5% MeOH in $CH_2Cl_2$. The crude mixture was filtered on diatomaceous earth and the filtrate was concentrated. The crude material was purified by reverse-phase HPLC to give two diastereomers; MS, m/z 378=M+1.

Example 72

Morpholine-4-carboxylic acid {1-[3-cyano-1-(2-methyl-2-phenyl-propyl)-pyrrolidin-3-ylcarbamoyl]-2-cyclohexyl-ethyl}-amide

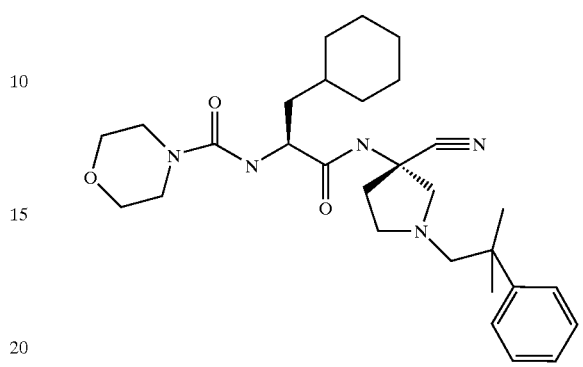

Reductive amination of morpholine-4-carboxylic acid [1-(3-cyano-pyrrolidin-3-ylcarbamoyl)-2-cyclohexyl-ethyl]-amide with 2,2-dimethyl-2-phenyl-acetaldehyde and Na(OAc)$_3$BH in 1% AcOH in THF provided the desired product; MS, 510=M+1.

Following the above procedure the following compounds were also synthesized;

Morpholine-4-carboxylic acid {1-[3-cyano-1-(indan-2-ylmethyl)-pyrrolidin-3-ylcarbamoyl]-2-cyclohexyl-ethyl}-amide; MS, m/z 508=M+1

Morpholine-4-carboxylic acid {1-[3-cyano-1-(5-methyl-thiophen-2-ylmethyl)-pyrrolidin-3-ylcarbamoyl]-2-cyclohexyl-ethyl}-amide; MS, m/z 488=M+1.

Example 72

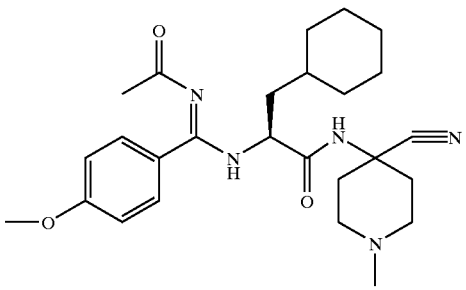

2-{[Acetylimino-(4-methoxy-phenyl)-methyl]-amino}-N-(4-cyano-1-methyl-piperidin-4-yl)-3-cyclohexyl-propionamide (Method E)

(a) N-(4-methoxy-thiobenzoyl)acetamide

A solution of acetyl chloride (4.69 g, 59.8 mmol) in acetone (20 mL) was added dropwise to a solution of 4-methoxythiobenzamide (5.00 g, 29.9 mmol) and pyridine (4.76 g, 60.1 mmol) in acetone (30 mL). The reaction mixture was heated to reflux for 30 min then poured onto ice water. The resulting precipitate was isolated via filtration and dried under vacuum overnight to provide a light yellow/orange solid (4.52 g, 72%). $^1$H NMR (400 MHz, CDCl$_3$) δ2.56 (s, 3H), 3.87 (s, 3H), 6.89 (dd, J=6.9, 2.0 Hz, 2H), (dd, J=6.9, 2.0 Hz, 2H).

(b) 2-{[Acetylimino-(4-methoxy-phenyl)-methyl]-amino}-N-(4-cyano-1-methyl-piperidin-4-yl)-3-cyclohexyl-propionamide 2-Chloro-N-methylpyridinium iodide (660 mg, 2.58 mmol), was added to a solution of N-(4-methoxy-thiobenzoyl)acetamide (420 mg, 2.01 mmol), 2-amino-N-(4-cyano-1-methyl-piperidin-4-yl)-3-cyclohexyl-propionamide bis hydrochloride salt (730 mg, 2.00 mmol), and N,N-diisopropylethylamine (1.05 mL, 6.02 mmol) in dichloromethane (8.0 mL). The reaction mixture was stirred at room temperature for 2 h, then diluted with dichloromethane (100 mL) and washed with 2×150 mL of saturated sodium bicarbonate. The organic phase was dried (MgSO$_4$) and concentrated. The resulting residue was chromatographed over 100 g of flash silica first using EtOAc, then dichloromethane/methanol 9:1 as the eluant to provide the desired product as an off white solid (377 mg, 40%). $^1$H NMR (400 MHz, DMSO-d6) δ0.70–0.90 (m, 2H), 1.00–1.30 (m, 4H), 1.35–1.65 (m, 8H), 1.72 (s, 3H), 1.85–2.20 (m, 6H), 2.48–2.60 (m, 1H), 3.78 (s, 3H), 4.20–4.35 (m, 1H), 6.95–6.99 (m, 2H), 7.33 (d, J=8.4 Hz, 1H), 7.72 (d, J=8.4 Hz, 1H). MS, m/z 468=M+1.

Example 73

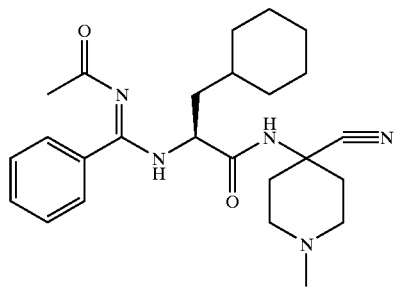

2-[(Acetylimino-phenyl-methyl)-amino]-N-(4-cyano-1-methyl-piperidin-4-yl)-3-cyclohexyl-propionamide (a) Thiobenzoyl acetamide was prepared according to the procedure from Example 1, step a, starting with thiobenzamide.
(b) The title compound was prepared starting from thiobenzoyl acetamide and 2-amino-N-(4-cyano-1-methyl-piperidin-4-yl)-3-cyclohexyl-propionamide bis hydrochloride salt according to the procedure from Example 72, step b. MS, m/z 438=M+1.

Example 74

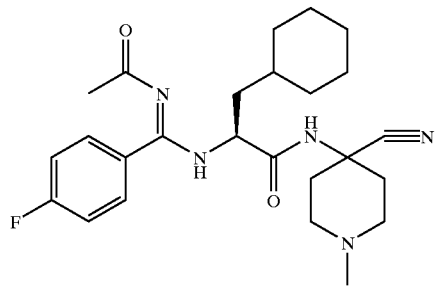

2-{[Acetylimino-(4-fluoro-phenyl)-methyl]-amino}-N-(4-cyano-1-methyl-piperidin-4-yl)-3-cyclohexyl-propionamide (a) N-(4-Fluoro-thiobenzoyl)acetamide was prepared according to the procedure from Example 72, step a, starting with 4-fluorothiobenzamide.
(b) The title compound was prepared starting from N-(4-fluoro-thiobenzoyl) acetamide and 2-amino-N-(4-cyano-1-methyl-piperidin-4-yl)-3-cyclohexyl-propionamide bis hydrochloride salt according to the procedure from Example 72, step b. MS, m/z 456=M+1.

Example 75

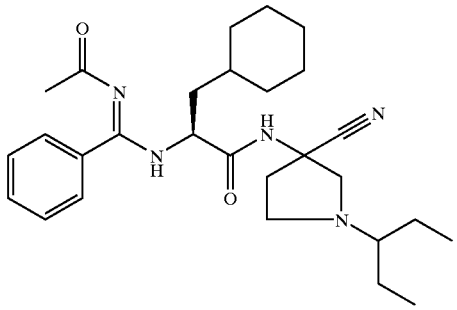

2-[(Acetylimino-phenyl-methyl)]-amino]-N-[3-cyano-1-(1-ethyl-propyl)-pyrrolidin-3-yl]-3-cyclohexyl-propionamide (a) The title compound was prepared starting from thiobenzoyl acetamide and 2-amino-N-[3-cyano-1-(1-ethyl-propyl)-pyrrolidin-3-yl]-3-cyclohexyl-propionamide bis hydrochloride salt according to the procedure from Example 72, step b, except that the compound was purified by HPLC using a 20×250 mm C18 reverse phase column with the method being 20% acetonitrile in water to 90% acetonitrile in water. MS, m/z 480=M+1.

Example 76

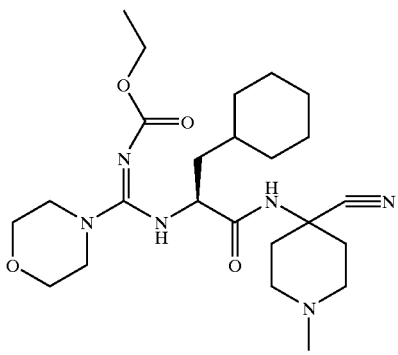

{[1-(4-Cyano-1-methyl-piperidin-4-ylcarbamoyl)-2-cyclohexyl-ethylamino]-morpholin-4-yl-methylen}-carbamic acid ethyl ester (Method E)

(a) (Morpholine-4-carbothioyl)-carbamic acid ethyl ester

Morpholine (7.5 mL, 86.0 mmol) was added dropwise to a solution of ethyl isothiocyanato formate (10.0 mL, 84.8 mmol) in tetrahydrofurann (200 mL). The reaction mixture was stirred at room temperature for 2.5 h, then concentrated and dried under vacuum to provide the desired product as a white solid (16.5 g, 89%). This material was used without further purification. $^1$H NMR (400 MHz, CDCl$_3$) δ1.28 (t, J=7.1 Hz, 3H), 3.61–3.97 (m, 8H), 4.16 (q, 7.1 Hz, 2H), 7.44 (br s, 1H).

(b) {[1-(4-Cyano-1-methyl-piperidin-4-ylcarbamoyl)-2-cyclohexyl-ethylamino]-morpholin-4-yl-methylen}-carbamic acid ethyl ester 2-Chloro-N-methylpyridinium iodide (680 mg, 2.66 mmol), was added to a solution of (Morpholine-4-carbothioyl)-carbamic acid ethyl ester (450 mg, 2.06 mmol), 2-amino-N-(4-cyano-1-methyl-piperidin-4-yl)-3-cyclohexyl-propionamide bis hydrochloride salt (745 mg, 2.04 mmol), and N,N-diisopropylethylamine (1.10 mL, 6.3 mmol) in dichloromethane (8.0 mL). The reaction was stirred at room temperature for 2.5 h then taken up in 10% citric acid solution and washed with EtOAc. The aqueous phase was then basified with saturated sodium carbonate and extracted with EtOAc. The organic extract was dried (MgSO$_4$) and concentrated to provide the desired product as a white solid (250 mg, 26%). This material was further purified by HPLC using a 20×250 mm C$_{18}$ reverse phase column with the method being 20% acetonitrile in water to 90% acetonitrile in water. MS, m/z 477=M+1.

Example 77

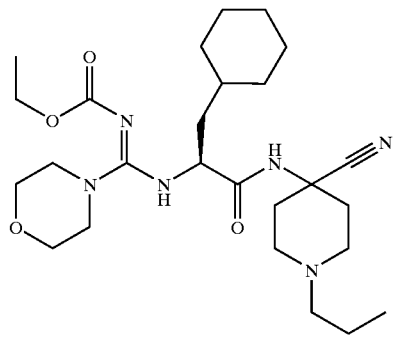

{[1-(4-Cyano-1-propyl-piperidin-4-ylcarbamoyl)-2-cyclohexyl-ethylimino]-morpholin-4-yl-methyl}-carbamic acid ethyl ester The title compound was prepared starting from (Morpholine-4-carbothioyl)-carbamic acid ethyl ester and 2-amino -N-(-4-cyano-1-propyl-piperidin-4-yl)-3-cyclohexylpropionamide bis hydrochloride salt according to the procedure from Example 76, step b, except that the compound was first purified by chromatography over silica gel using 9:1 methylene chloride: methanol as the eluant prior to reverse phase HPLC purification. MS, m/z 505=M+1.

Example 78

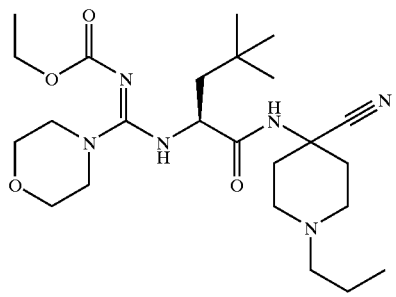

{[1-(4-Cyano-1-propyl-piperidin-4-ylcarbamoyl)-3,3-dimethyl-butylimino]-morpholin-4-yl-methyl}-carbamic acid ethyl ester The title compound was prepared starting from (Morpholine-4-carbothioyl)-carbamic acid ethyl ester and 2-amino -4,4-dimethyl-pentanoic acid (4-cyano-1-propyl-piperidin-4-yl)amide bis hydrochloride salt according to the procedure from Example 76. MS, m/z 460=M+1.

Example 79

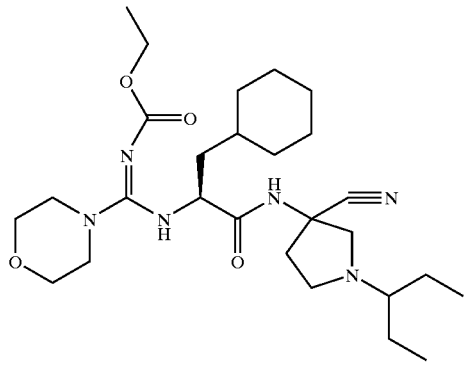

({1-[3-Cyano-1-(1-ethyl-propyl)-pyrrolidin-3-ylcarbamoyl]-2-cyclohexyl-ethylamino}-morpholin-4-yl-methylene)-carbamic acid ethyl ester The title compound was prepared starting from (Morpholine-4-carbothioyl)-carbamic acid ethyl ester and 2-amino-N-[3-cyano-1-(1-ethyl-propyl)-pyrrolidin-3-yl]-3-cyclohexyl-propionamide bis hydrochloride salt according to the procedure from Example 76, step b,. MS, m/z 519=M+1.

Example 80

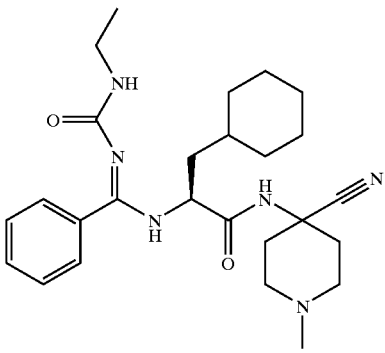

N-(4-Cyano-1-methyl-piperidin-4-yl)-3-cyclohexyl-2-[(ethylcarbamoylimino-phenyl-methyl)-amino]-propionamide (Method F)

(a) Benzimidic acid methyl ester

Benzimidic acid methyl ester hydrochloride (5 g, 29.1 mmol) was partitioned between saturated sodium carbonate solution (200 mL) and diethyl ether (100 mL). The organic layer was dried (MgSO$_4$) and concentrated to provide the desired product as a colorless liquid (3.20 g, 81%). This material was used without further purification. $^1$H NMR (400 MHz, CDCl$_3$) δ3.93 (s, 3H), 7.39–7.46 (m, 3H), 7.75 (d, J=1.1 Hz, 2H).

(b) 1-Ethyl-3-(methoxy-phenyl-methylene)-urea

A neat mixture of benzimidic acid methyl ester (750 mg, 5.56 mmol) and ethyl isocyanate (808 mg, 11.3 mmol) was stirred at 50° C. for 24 h. Excess isocyanate was removed under vacuum to provide the desired product as a colorless viscous oil (1.09 g, 95%). This material was used without further purification. $^1$H NMR (400 MHz, CDCl$_3$) δ1.07 (t, J=7.3 Hz, 3H), 3.25 (q, J=7.3 Hz, 2H), 3.87 (s, 3H), 4.97 (br s, 1H), 7.26–7.40 (m, 2H), 7.45 (d, J=7.4 Hz, 1H), 7.69–7.71 (m, 2H). MS, m/z 207=M+1.

(c) N-(4-Cyano-1-methyl-piperidin-4-yl)-3-cyclohexyl-2-[(ethylcarbamoylimino-phenyl-methyl)-amino]-propionamide A solution of 1-ethyl-3-(methoxy-phenyl-methylene)-urea (350 mg, 1.70 mmol), 2-amino-N-(4-cyano-1-methyl-piperidin-4-yl)-3-cyclohexyl-propionamide bis hydrochloride salt (512 mg, 1.40 mmol) and N,N-diisopropylethylamine (352 mg, 2.73 mmol) in dry methanol (5.0 mL) was stirred at room temperature for 60 h. The reaction mixture was concentrated and the resulting residue was chromatographed over 50 g of flash silica gel using dichloromethane to 5% methanol in dichloromethane as the eluant. This provided the desired product as a light yellow solid (280 mg, 43%) which was further purified by HPLC using a 20×250 mm C$_{18}$ reverse phase column with the method being 20% acetonitrile in water to 90% acetonitrile in water. MS, m/z 467=M+1.

Example 81

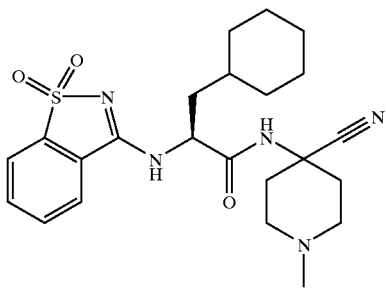

N-(4-Cyano-1-methyl-piperidin-4-yl)-3-cyclohexyl-2-(1,1-dioxo-1H-1λ$^6$-benzo[d]isothiazol-3-ylamino)-propionamide (Method G)

(a) A suspension of 3-chloro-benzo[d]isothiazole 1,1-dioxide (300 mg, 1.49 mmol) and 2-amino-N-(-4-cyano-1-methyl-piperidin-4-yl)-3-cyclohexylpropionamide bis hydrochloride salt (500 mg, 1.37 mmol) was prepared in 5.5 mL of acetonitrile. Triethylamine (575 µL, 4.10 mmol) was added and the reaction mixture was stirred at room temperature for 1 day. The suspension was filtered to remove triethylamine hydrochloride and the filtrate was concentrated. The resulting residue was chromatographed over 50 g of flash silica using dichloromethane/methanol 9:1 as the eluant to provide the desired product as a light yellow solid (310 mg, 49%). $^1$H NMR (400 MHz, CDCl$_3$) δ0.25–0.45 (m, 1H), 0.65–0.85 (m, 2H), 0.95–1.10 (m, 2H), 1.30–1.60 (m, 7H), 1.75–1.85 (m, 2H), 1.85–2.2 (m, 2H), 2.31 (s, 3H), 2.35–2.50 (m, 3H), 2.65–2.80 (m, 2H), 4.60–4.70 (m, 1H), 7.35–7.50 (m, 2H), 7.58 (t, J=7.3, 1H), 7.78 (d, J=7.77 Hz, 1H), 7.81 (br s, 1H), 8.91 (br s, 1H). MS, m/z 458=M+1.

Example 82

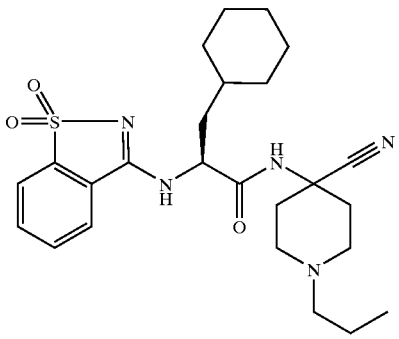

N-(4-Cyano-1-propyl-piperidin-4-yl)-3-cyclohexyl-2-(1,1-dioxo-1H-1λ$^6$-benzo[d]isothiazol-3-ylamino)-propionamide The title compound was prepared starting from 3-chloro-benzo[d]isothiazole 1,1-dioxide and 2-amino -N-(-4-cyano-1-propyl-piperidin-4-yl)-3-cyclohexylpropionamide bis hydrochloride salt according to the procedure from Example 81, except that the compound was further purified by HPLC using a 20×250 mm C$_{18}$ reverse phase column with the method being 20% acetonitrile in water to acetonitrile. MS, m/z 486=M+1.

Example 83

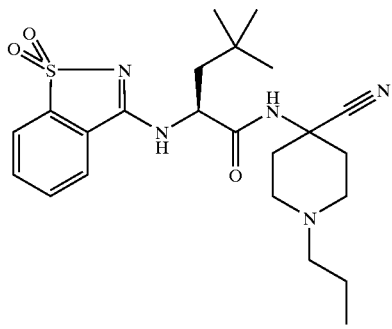

2-(1,1-dioxo-1H-1$\lambda^6$-benzo[d]isothiazol-3-ylamino)-4,4-dimethyl-pentanoic acid(4-cyano-1-propylpiperidin-4-yl)-amide The title compound was prepared starting from 3-chloro-benzo[d]isothiazole 1,1-dioxide and 2-amino -4,4-dimethyl-pentanoic acid (4-cyano-1-propyl-piperidin-4-yl)amide bis hydrochloride salt according to the procedure from Example 81, except that the compound was further purified by HPLC using a 20×250 mm $C_{18}$ reverse phase column with the method being 20% acetonitrile in water to acetonitrile. MS, m/z 460=M+1.

Example 84

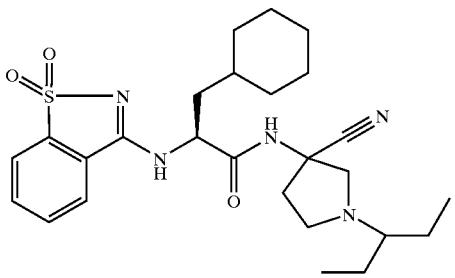

N-[3-Cyano-1-(1-ethyl-propyl)-pyrrolidin-3-yl]-3-cyclohexyl-2-(1,1-dioxo-1H-1$\lambda^6$-benzo[d]isothiazol-3-ylamino)-propionamide The title compound was prepared starting from 3-chloro benzo[d]isothiazole 1,1-dioxide and 2-amino-N-[3-cyano-1-(1-ethyl-propyl)-pyrrolidin-3-yl]-3-cyclohexyl-propionamide bis hydrochloride salt according to the procedure from Example 81, except that the compound was further purified by HPLC using a 20×250 mm $C_{18}$ reverse phase column with the method being 40% acetonitrile in water to acetonitrile. MS, m/z 500=M+1.

Example 85

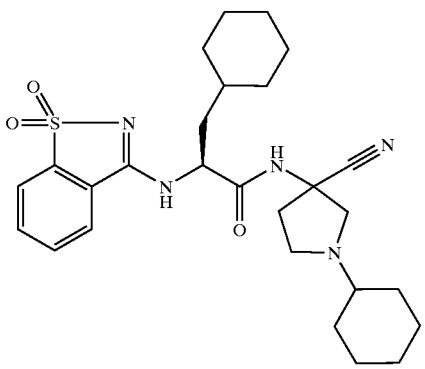

N-(3-Cyano-1-cyclohexyl-pyrrolidin-3-yl)-3-cyclohexyl-2-(1,1-dioxo-1H-1$\lambda^6$-benzo[d]isothiazol-3-ylamino)-propionamide The title compound was prepared starting from 3-chloro benzo[d]isothiazole 1,1-dioxide and 2-amino-N-(3-cyano-1-cyclohexyl-pyrrolidin-3-yl)-3-cyclohexyl-propionamide bis hydrochloride salt according to the procedure from Example 81, except that the compound was further purified by HPLC using a 20×250 mm $C_{18}$ reverse phase column with the method being 40% acetonitrile in water to acetonitrile. MS, m/z 512=M+1.

Example 86

N-(4-Cyano-methyl-piperidin-4-yl)-3-cyclohexyl-2-(3-oxo-3H-isoindol-1-ylamino)-propionamide The title compound was prepared starting from 3-imino-2,3-dihydro-isoindol-1-one and 2-amino-N-(4-cyano-1-methyl-piperidin-4-yl)-3-cyclohexyl-propionamide bis hydrochloride salt according to the procedure from Example 81, except that refluxing THF was used as the solvent. The compound was further purified by HPLC using a 20×250 mm $C_{18}$ reverse phase column with the method being 20% acetonitrile in water to acetonitrile. MS, m/z 422.5=M+1.

Example 87

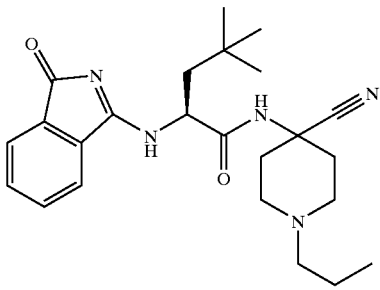

4,4-Dimethyl-2-(3-oxo-3H-isoindol-1-ylamino)-pentanoicacid-(4-cyano-1-propyl-piperidin-4-yl)-amide The title compound was prepared from 3-imino-2,3-dihydro-isoindol-1-one and 2-amino -4,4-dimethyl-pentanoic acid (4-cyano-1-propyl-piperidin-4-yl)amide bis hydrochloride salt according to the procedure from Example 86. MS, m/z 424.5=M+1.

Example 88

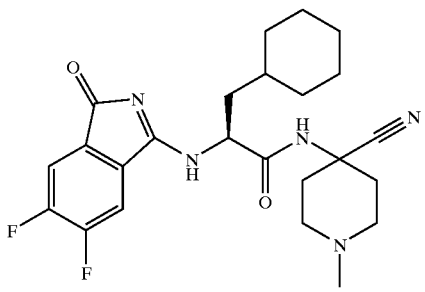

N-(4-cyano-1-methyl-piperidin-4-yl)-3-cyclohexyl-
2-(5,6-difluoro-3-oxo-3H-isoindol-1-ylamino)
propionamide (a) 2-Chloro-4,5-difluorobenzoic acid methyl ester 2-Chloro-4,5-difluorobenzoic acid (1.93 g, 10 mmol) was dissolved in 20 mL of acetone. Cesium carbonate (5.29 g, 15 mmol) was added followed by iodomethane (1.0 mL, 15 mmol). This reaction mixture was heated under reflux for 1 h and then cooled to room temperature. This suspension was then diluted with 40 mL of ethyl ether. The solid was removed by filtration and washed with ethyl ether. The filtrate was evaporated in vacuo to give the title compound in quantitative yield as a clear oil.

(b) 2-Cyano-4,5-difluorobenzoic acid methyl ester

The above oil (2.06 g, 10 mmol) was dissolved in 10 mL of N-methyl pyrrolidinone. Copper (I) cyanide (1.79 g, 20 mmol) was added. This mixture was heated at 195° C. under nitrogen for 1 h. After cooling to room temperature, this solution was diluted with 100 mL of water. The resulting solid was collected by filtration. This sold was then suspended in a rapidly stirred solution of potassium cyanide (0.5 g) in 30 mL of water for 1 h. EtOAc (30 mL) was added. The mixture was filtered through diatomaceous earth. The organic phase was separated and the aqueous phase was extracted with EtOAc (20 mL×2). The combined organic phase was washed with brine and dried over magnesium sulfate. The solvent was removed in vacuo. The residue was crystallized from ethyl ether and petroleum ether to give the title compound as a yellow solid (1.26 g, 64%).

(c) 5,6-Difluoro-2,3-dihydro-3-imino-1H-isoindol-1-one

The above solid (0.493 g, 2.5 mmol) was dissolved in 20 mL of MeOH. This solution was saturated with ammonia at 0° C. and then stirred in a pressure tube at room temperature for 3 days. The solid was collected by filtration and washed with ethyl ether to give the title compound as a yellow solid (0.363 g, 80%).

The title compound was prepared from 5,6-difluoro-2,3-dihydro-3-imino-1H-isoindol-1-one and 2-amino-N-(4-cyano-1-methyl-piperidin-4-yl)-3-cyclohexyl-propionamide bis hydrochloride salt according to the procedure from Example 86. MS, m/z 458.3=M+1.

Example 89

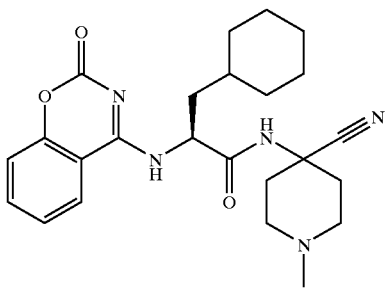

N-(4-cyano-1-methyl-piperidin-4-yl)-3-cyclohexyl-
2-(2-oxo-2H-benzo[e][1,3]oxazin-4-ylamino)-
propionamide The title compound was prepared starting from 4-chloro-benzo[e][1,3]oxazin-2-one (prepared from benzo [e][1,3] oxazin-2,4-dione and PCl₅ in refluxing toluene) and 2-amino-N-(4-cyano-1-methyl-piperidin-4-yl)-3-cyclohexyl-propionamide bis hydrochloride salt according to the procedure from Example 81. MS, m/z 438=M+1.

Example 90

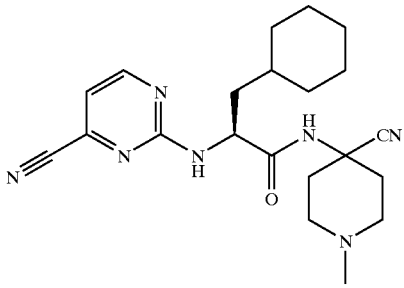

N-(4-cyano-1-methyl-piperidin-4-yl)-2-(4-cyano-
pyrimidin-2-ylamino)-3-cyclohexyl-propionamide
(Method G)

2-Chloro-4-pyrimidinecarbonitrile (0.3 mmol, Daves, G. D. Jr., O'Brien, D. E., Cheng, C. *C. J. Het. Chem,* 1964, 1, 130) and 2-amino-N-(4-cyano-1-methyl-piperidin-4-yl)-3-cyclohexyl-propionamide (0.7 mmol) were dissolved in acetonitrile (10 mL) containing N,N-diisopropylethylamine (0.6 mmol). The solution was heated to a gentle reflux for 17 h. The volatiles were evaporated and the residue was subjected to chromatography (silica gel, eluant=EtOAc then MeOH). The methanolic fraction was concentrated to a colorless solid which was rechromatographed (10% MeOH/EtOAc) to afford the title compound as a colorless solid (52%). The material was recrystallized from dichloromethane/petroleum ether.

Example 91

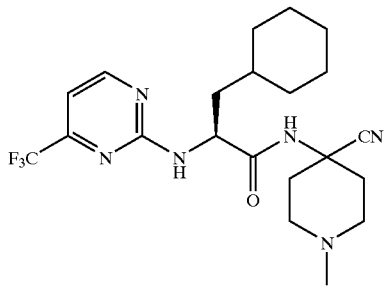

N-(4-cyano-1-methyl-piperidin-4-yl)-2-(4-trifluorometlhyl-pyrimidin-2-ylamino)-3-cyclohexyl-propionamide The title compound was prepared from 2-chloro-4-trifluoromethyl pyrimidine and 2-amino-N-(4-cyano-1-methyl-piperidin-4-yl)-3-cyclohexyl-propionamide according to the procedure from Example 90. MS, m/z 439.5=M+1.

Example 92

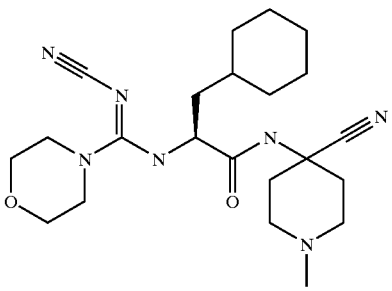

N-(4-cyano-1-methyl-piperidine-4-yl)-3-cyclohexyl-2[N-cyano-morpholine-4-carboximidoyl)-amino]-propionamide (Method H)

(a) 2-(N-Cyano-iminomethylene-amino)-N-(4-cyano-1-methyl-piperidine-4-yl)-3-cyclohexyl-propionamide A solution of diphenylcyanocarbonimidate (455 mg, 1.91 mmol), 2-amino-N-(4-cyano-1-methyl-piperidin-4-yl)-3-cyclohexyl-propionamide bis hydrochloride salt (680 mg, 1.86 mmol) and N,N-diisopropylethylamine (482 mg, 3.73 mmol) in isopropanol (5.0 mL) was stirred overnight at room temperature. The reaction mixture was then filtered to provide the desired carbodiimide as a white powder (140 mg, 22%). This material was used without further purification. $^1$H NMR (400 MHz, CDCl$_3$) δ0.80–1.00 (m, 2H), 1.05–1.20 (m, 1H), 1.20–1.40 (2H), 1.50–1.85 (m, 8H), 2.32 (s, 3H), 2.40–2.50 (m, 2H), 2.55–2.70 (m, 4H), 2.85–2.95 (m, 2H), 4.10–4.20 (m, 1H), 8.77 (br s, 1H). MS, m/z 343=M+1.

(b) 2-(N-Cyano-benzimidoyl-amino)-N-(4-cyano-1-methyl-piperidine-4-yl)-3-cyclohexyl-propionamide A suspension of 2-(N-Cyano-iminomethylene-amino)-N-(4-cyano-1-methyl-piperidine-4-yl)-3-cyclohexyl-propionamide (120 mg, 0.35 mmol) in tetrahydrofuran (1 mL) was treated with morpholine (4 mL, 45.9 mmol). The reaction mixture was stirred at room temperature for 3 days then concentrated to dryness. The residue was purified by HPLC using a 20×250 mm C$_{18}$ reverse phase column with the method being 20% acetonitrile in water to 90% acetonitrile in water. MS, m/z 430=M+1.

Example 93

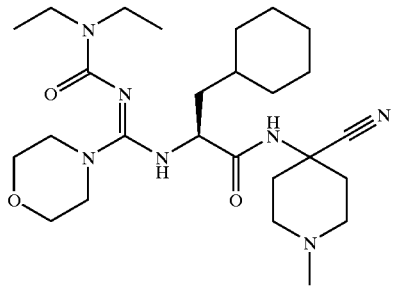

N-(4-Cyano-1-methyl-piperidin-4-yl)-3-cyclohexyl-2-{[(diethyl-carbamoylimino)-morpholin-4-yl-methyl]-amino}-propionamide (Method H)

(a) N,N-Diethyl carbamoyl thiocyanate

A suspension of sodium thiocyanate (3.30 g, 40.7 mmol) in dry acetonitrile (25 mL) at 80° C. was treated dropwise with a solution of N,N-diethyl carbamoyl chloride (5.0 g, 36.9 mmol) in dry acetonitrile (15 mL). The reaction mixture was stirred at 80° C. for 50 min, cooled to room temperature, then filtered through a fine glass frit. The resulting filtrate was used as a 0.9 M solution of N,N-diethyl carbamoyl thiocyanate in acetonitrile.

(b) N-(4-Cyano-1-methyl-piperidin-4-yl)-3-cyclohexyl-2-(3-diethylamino-carbonyl-thioureido)-propionamide A solution of 2-amino -N-(-4-cyano-1-propyl-piperidin-4-yl)-3-cyclohexylpropionamide bis hydrochloride salt (560 mg, 1.53 mmol) and triethylamine (500 μL, 3.59 mmol) in acetonitrile (4 mL) was treated with a solution of N,N-diethyl carbamoyl thiocyanate in acetonitrile (3.0 mL, 2.7 mmol). The reaction mixture was stirred overnight at room temperature and concentrated on a rotary evaporator. The resulting residue was chromatographed (ethyl acetate:hexanes 1:1 then ethyl acetate and finally methanol:methylene chloride 1:9 as the eluant) to provide the desired product as a light yellow solid (340 mg, 49%). MS, m/z 451.3=M+1.

The title compound was prepared by treating a solution of the resulting thiourea (340 mg, 0.75 mmol) and triethylamine (230 μL, 1.65 mmol) in dry acetonitrile (4 mL) with mercury (II) chloride (225 mg, 0.83 mmol) and morpholine (200 μL, 2.23 mmol). The reaction mixture was stirred at room temperature for 4 h then filtered through a 0.45 μm filter disc. The resulting filtrate was filtered through a column of silica (5% methanol/methylene chloride as the eluant) and the resulting crude product was further purified by HPLC using a 20×250 mm C$_{18}$ reverse phase column with the method being 20% acetonitrile in water to acetonitrile. MS, m/z 504.6=M+1.

The following examples were prepared by Method H in a parallel fashion:

Example 94

{[1-(4-cyano-1 methyl-piperidin-4-ylcarbamoyl)-2-cyclohexyl-ethylamino]-pyrrolidin-1-yl-methyl}-carbamic acid ethyl ester. MS, m/z 461=M+1.

Example 95

{[1-(4-cyano-1-methyl-piperidin-4-ylcarbamoyl)-2-cyclohexyl-ethylamino]-piperidin-1-yl-methyl}-carbamic acid ethyl ester. MS, m/z 477=M+1.

Example 96

{Azepan-1-yl-[1-(4-cyano-1-methyl-piperidin-4-ylcarbamoyl)-2-cyclohexyl-ethylamino]-methylene}-carbamic acid ethyl ester. MS, m/z 490=M+1.

Example 97

{Azocan-1-yl-[1-(4-cyano-1-methyl-piperidin-4-ylcarbamoyl)-2-cyclohexyl-ethylamino]-methylene}-carbamic acid ethyl ester. MS, m/z 504=M+1.

Example 98

1-{[1-(4-Cyano-1-methyl-piperidin-4-ylcarbamoyl)-2-cyclohexyl-ethylamino]-ethoxycarbonylimino-methyl}-piperidine-4-carboxylic acid ethyl ester. MS, m/z 548=M+1.

Example 99

1-{[1-(4-Cyano-1-methyl-piperidin-4-ylcarbamoyl)-2-cyclohexyl-ethylamino]-ethoxycarbonylimino-methyl}-piperidine-3-carboxylic acid ethyl ester. MS, m/z 548=M+1.

Example 100

[[1-(4-Cyano-1-methyl-piperidin-4-ylcarbamoyl)-2-cyclohexyl-ethylamino]-(4-pyrrolidin-1-yl-piperidin-1-yl)-methylene]-carbamic acid ethyl ester. MS, m/z 545=M+1.

Example 101

{[1,4']Bipiperidinyl-1'-yl-[1-(4-cyano-1-methyl-piperidin-4-ylcarbamoyl)-2-cyclohexyl-ethylamino]-methylene}-carbamic acid ethyl ester. MS, m/z 559=M+1.

Example 102

[[1-(4-Cyano-1-methyl-piperidin-4-ylcarbamoyl)-2-cyclohexyl-ethylamino]-(4-phenyl-piperazin-1-yl)-methylene]-carbamic acid ethyl ester. MS, m/z 553=M+1.

Example 103

[[1-(4-Cyano-1-methyl-piperidin-4-ylcarbamoyl)-2-cyclohexyl-ethylamino]-(4-ethyl-piperazin-1-yl)-methylene]-carbamic acid ethyl ester. MS, m/z 505=M+1.

Example 104

{(4-Acetyl-piperazin-1-yl)-[1-(4-cyano-1-methyl-piperidin-4-ylcarbamoyl)-2-cyclohexyl-ethylamino]-methylene}-carbamic acid ethyl ester. MS, m/z 519=M+1.

Example 105

4-{[1-(4-Cyano-1-methyl-piperidin-4-ylcarbamoyl)-2-cyclohexyl-ethylamino]-ethoxycarbonylimino-methyl}-piperazine-1-carboxylic acid ethyl ester. MS, m/z 549=M+1.

Example 106

[[1-(4-Cyano-1-methyl-piperidin-4-ylcarbamoyl)-2-cyclohexyl-ethylamino]-(3,3,5-trimethyl-6-aza-bicyclo[3.2.1]oct-6-yl)-methylene]-carbamic acid ethyl ester. MS, m/z 544=M+1.

The following examples may also be made by the methods described above:

2-[(Ethylcarbamoylimino-morpholin-4-yl-methyl)-amino]-4,4-dimethyl-pentanoic acid (4-cyano-1-propyl-piperidin-4-yl)-amide
2-[(Methanesulfonylimino-morpholin-4-yl-methyl)-amino]-4,4-dimethyl-pentanoic acid (4-cyano-1-propyl-piperidin-4-yl)-amide
2-[(Carbamoylimino-morpholin-4-yl-methyl)-amino]-4,4-dimethyl-pentanoic acid (4-cyano-1-propyl-piperidin-4-yl)-amide
2-[(Ethylcarbamoylimino-morpholin-4-yl-methyl)-amino]-4,4-dimethyl-pentanoic acid (4-cyano-1-methyl-piperidin-4-yl)-amide
2-[(Carbamoylimino-morpholin-4-yl-methyl)-amino]-4,4-dimethyl-pentanoic acid (4-cyano-1-methyl-piperidin-4-yl)-amide
2-[(Methanesulfonylimino-morpholin-4-yl-methyl)-amino]-4,4-dimethyl-pentanoic acid (4-cyano-1-methyl-piperidin-4-yl)-amide
{[1-(4-Cyano-1-methyl-piperidin-4-ylcarbamoyl)-3,3-dimethyl-butylamino]-morpholin-4-yl-methylene}-carbamic acid ethyl ester
{[1-(3-Cyano-1-cyclohexylmethyl-pyrrolidin-3-ylcarbamoyl)-3,3-dimethyl-butylamino]-morpholin-4-yl-methylene}-carbamic acid ethyl ester
2-[(Ethylcarbamoylimino-morpholin-4-yl-methyl)-amino]-4,4-dimethyl-pentanoic acid (3-cyano-1-cyclohexylmethyl-pyrrolidin-3-yl)-amide
2-[(Carbamoylimino-morpholin-4-yl-methyl)-amino]-4,4-dimethyl-pentanoic acid (3-cyano-1-cyclohexylmethyl-pyrrolidin-3-yl)-amide
2-[(Methanesulfonylimino-morpholin-4-yl-methyl)-amino]-4,4-dimethyl-pentanoic acid (3-cyano-1-cyclohexylmethyl-pyrrolidin-3-yl)-amide
2-[(Methanesulfonylimino-morpholin-4-yl-methyl)-amino]-4,4-dimethyl-pentanoic acid (3-cyano-1-cyclohexyl-pyrrolidin-3-yl)-amide
2-[(Ethylcarbamoylimino-morpholin-4-yl-methyl)-amino]-4,4-dimethyl-pentanoic acid (3-cyano-1-cyclohexyl-pyrrolidin-3-yl)-amide
2-[(Carbamoylimino-morpholin-4-yl-methyl)-amino]-4,4-dimethyl-pentanoic acid (3-cyano-1-cyclohexyl-pyrrolidin-3-yl)-amide
{[1-(3-Cyano-1-cyclohexyl-pyrrolidin-3-ylcarbamoyl)-3,3-dimethyl-butylamino]-morpholin-4-yl-methylene}-carbamic acid ethyl ester
({1-[3-Cyano-1-(4-methyl-cyclohexyl)-pyrrolidin-3-ylcarbamoyl]-3,3-dimethyl-butylamino}-morpholin-4-yl-methylene)-carbamic acid ethyl ester
2-[(Ethylcarbamoylimino-morpholin-4-yl-methyl)-amino]-4,4-dimethyl-pentanoic acid [3-cyano-1-(4-methyl-cyclohexyl)-pyrrolidin-3-yl]-amide
2-[(Carbamoylimino-morpholin-4-yl-methyl)-amino]-4,4-dimethyl-pentanoic acid [3-cyano-1-(4-methyl-cyclohexyl)-pyrrolidin-3-yl]-amide
2-[(Methanesulfonylimino-morpholin-4-yl-methyl)-amino]-4,4-dimethyl-pentanoic acid [3-cyano-1-(4-methyl-cyclohexyl)-pyrrolidin-3-yl]-amide
2-[(Methanesulfonylimino-morpholin-4-yl-methyl)-amino]-4,4-dimethyl-pentanoic acid [3-cyano-1-(1-ethyl-propyl)-pyrrolidin-3-yl]-amide
2-[(Carbamoylimino-morpholin-4-yl-methyl)-amino]-4,4-dimethyl-pentanoic acid [3-cyano-1-(1-ethyl-propyl)-pyrrolidin-3-yl]-amide
2-[(Ethylcarbamoylimino-morpholin-4-yl-methyl)-amino]-4,4-dimethyl-pentanoic acid [3-cyano-1-(1-ethyl-propyl)-pyrrolidin-3-yl]-amide
({1-[3-Cyano-1-(1-ethyl-propyl)-pyrrolidin-3-ylcarbamoyl]-3,3-dimethyl-butylamino}-morpholin-4-yl-methylene)-carbamic acid ethyl ester
({1-[3-Cyano-1-(1-H-indol-3-ylmethyl)-pyrrolidin-3-ylcarbamoyl]-3,3-dimethyl-butylamino}-morpholin-4-yl-methylene)-carbamic acid ethyl ester
2-[(Ethylcarbamoylimino-morpholin-4-yl-methyl)-amino]-4,4-dimethyl-pentanoic acid [3-cyano-1-(1-H-indol-3-ylmethyl)-pyrrolidin-3-yl]-amide
2-[(Methanesulfonylimino-morpholin-4-yl-methyl)-amino]-4,4-dimethyl-pentanoic acid [3-cyano-1-(1-H-indol-3-ylmethyl)-pyrrolidin-3-yl]-amide
2-[(Carbamoylimino-morpholin-4-yl-methyl)-amino]-4,4-dimethyl-pentanoic acid [3-cyano-1-(1-H-indol-3-ylmethyl)-pyrrolidin-3-yl]-amide 2-[(Carbamoylimino-morpholin-4-yl-methyl)-amino]-4,4-dimethyl-pentanoic acid (1-benzyl-3-cyano-pyrrolidin-3-yl)-amide
2-[(Ethylcarbamoylimino-morpholin-4-yl-methyl)-amino]-4,4-dimethyl-pentanoic acid (1-benzyl-3-cyano-pyrrolidin-3-yl)-amide
{[1-(1-Benzyl-3-cyano-pyrrolidin-3-ylcarbamoyl)-3,3-dimethyl-butylamino]-morpholin-4-yl-methylene}-carbamic acid ethyl ester
2-[(Methanesulfonylimino-morpholin-4-yl-methyl)-amino]-4,4-dimethyl-pentanoic acid (1-benzyl-3-cyano-pyrrolidin-3-yl)-amide
2-[(Methanesulfonylimino-morpholin-4-yl-methyl)-amino]-4,4-dimethyl-pentanoic acid (3-cyano-1-phenethyl-pyrrolidin-3-yl)-amide
{[1-(3-Cyano-1-phenethyl-pyrrolidin-3-ylcarbamoyl)-3,3-dimethyl-butylamino]-morpholin-4-yl-methylene}-carbamic acid ethyl ester
2-[(Ethylcarbamoylimino-morpholin-4-yl-methyl)-amino]-4,4-dimethyl-pentanoic acid (3-cyano-1-phenethyl-pyrrolidin-3-yl)-amide
2-[(Carbamoylimino-morpholin-4-yl-methyl)-amino]-4,4-dimethyl-pentanoic acid (3-cyano-1-phenethyl-pyrrolidin-3-yl)-amide
N-(4-Cyano-1-propyl-piperidin-4-yl)-3-cyclohexyl-2-[(ethylcarbamoylimino-morpholin-4-yl-methyl)-amino]-propionamide
N-(4-Cyano-1-propyl-piperidin-4-yl)-3-cyclohexyl-2-[(methanesulfonylimino-morpholin-4-yl-methyl)-amino]-propionamide
2-[(Carbamoylimino-morpholin-4-yl-methyl)-amino]-N-(4-cyano-1-propyl-piperidin-4-yl)-3-cyclohexyl-propionamide
N-(4-Cyano-1-methyl-piperidin-4-yl)-3-cyclohexyl-2-[(ethylcarbamoylimino-morpholin-4-yl-methyl)-amino]-propionamide
2-[(Carbamoylimino-morpholin-4-yl-methyl)-amino]-N-(4-cyano-1-methyl-piperidin-4-yl)-3-cyclohexyl-propionamide
N-(4-Cyano-1-methyl-piperidin-4-yl)-3-cyclohexyl-2-[(methanesulfonylimino-morpholin-4-yl-methyl)-amino]-propionamide
{[1-(3-Cyano-1-cyclohexylmethyl-pyrrolidin-3-ylcarbamoyl)-2-cyclohexyl-ethylamino]-morpholin-4-yl-methylene}-carbamic acid ethyl ester
N-(3-Cyano-1-cyclohexylmethyl-pyrrolidin-3-yl)-3-cyclohexyl-2-[(ethylcarbamoylimino-morpholin-4-yl-methyl)-amino]-propionamide
N-(3-Cyano-1-cyclohexylmethyl-pyrrolidin-3-yl)-3-cyclohexyl-2-[(methanesulfonylimino-morpholin-4-yl-methyl)-amino]-propionamide
2-[(Carbamoylimino-morpholin-4-yl-methyl)-amino]-N-(3-cyano-1-cyclohexylmethyl-pyrrolidin-3-yl)-3-cyclohexyl-propionamide
N-(3-Cyano-1-cyclohexyl-pyrrolidin-3-yl)-3-cyclohexyl-2-[(methanesulfonylimino-morpholin-4-yl-methyl)-amino]-propionamide
N-(3-Cyano-1-cyclohexyl-pyrrolidin-3-yl)-3-cyclohexyl-2-[(ethylcarbamoylimino-morpholin-4-yl-methyl)-amino]-propionamide
2-[(Carbamoylimino-morpholin-4-yl-methyl)-amino]-N-(3-cyano-1-cyclohexyl-pyrrolidin-3-yl)-3-cyclohexyl-propionamide
{[1-(3-Cyano-1-cyclohexyl-pyrrolidin-3-ylcarbamoyl)-2-cyclohexyl-ethylamino]-morpholin-4-yl-methylene}-carbamic acid ethyl ester
({1-[3-Cyano-1-(4-methyl-cyclohexyl)-pyrrolidin-3-ylcarbamoyl]-2-cyclohexyl-ethylamino}-morpholin-4-yl-methylene)-carbamic acid ethyl ester
N-[3-Cyano-1-(4-methyl-cyclohexyl)-pyrrolidin-3-yl]-3-cyclohexyl-2-[(ethylcarbamoylimino-morpholin-4-yl-methyl)-amino]-propionamide
2-[(Carbamoylimino-morpholin-4-yl-methyl)-amino]-N-[3-cyano-1-(4-methyl-cyclohexyl)-pyrrolidin-3-yl]-3-cyclohexyl-propionamide
N-[3-Cyano-1-(4-methyl-cyclohexyl)-pyrrolidin-3-yl]-3-cyclohexyl-2-[(methanesulfonylimino-morpholin-4-yl-methyl)-amino]-propionamide
N-[3-Cyano-1-(1-ethyl-propyl)-pyrrolidin-3-yl]-3-cyclohexyl-2-[(methanesulfonylimino-morpholin-4-yl-methyl)-amino]-propionamide
2-[(Carbamoylimino-morpholin-4-yl-methyl)-amino]-N-[3-cyano-1-(1-ethyl-propyl)-pyrrolidin-3-yl]-3-cyclohexyl-propionamide
N-[3-Cyano-1-(1-ethyl-propyl)-pyrrolidin-3-yl]-3-cyclohexyl-2-[(ethylcarbamoylimino-morpholin-4-yl-methyl)-amino]-propionamide
({1-[3-Cyano-1-(1H-indol-3-ylmethyl)-pyrrolidin-3-ylcarbamoyl]-2-cyclohexyl-ethylamino}-morpholin-4-yl-methylene)-carbamic acid ethyl ester
N-[3-Cyano-1-(-H-indol-3-ylmethyl)-pyrrolidin-3-yl]-3-cyclohexyl-2-[(ethylcarbamoylimino-morpholin-4-yl-methyl)-amino]-propionamide
N-[3-Cyano-1-(1-H-indol-3-ylmethyl)-pyrrolidin-3-yl]-3-cyclohexyl-2-[(methanesulfonylimino-morpholin-4-yl-methyl)-amino]-propionamide
2-[(Carbamoylimino-morpholin-4-yl-methyl)-amino]-N-[3-cyano-1-(1H-indol-3-ylmethyl)-pyrrolidin-3-yl]-3-cyclohexyl-propionamide
N-(1-Benzyl-3-cyano-pyrrolidin-3-yl)-2-[(carbamoylimino-morpholin-4-yl-methyl)-amino]-3-cyclohexyl-propionamide
N-(1-Benzyl-3-cyano-pyrrolidin-3-yl)-3-cyclohexyl-2-[(ethylcarbamoylimino-morpholin-4-yl-methyl)-amino]-propionamide
{[1-(1-Benzyl-3-cyano-pyrrolidin-3-ylcarbamoyl)-2-cyclohexyl-ethylamino]-morpholin-4-yl-methylene}-carbamic acid ethyl ester
N-(1-Benzyl-3-cyano-pyrrolidin-3-yl)-3-cyclohexyl-2-[(methanesulfonylimino-morpholin-4-yl-methyl)-amino]-propionamide
N-(3-Cyano-1-phenethyl-pyrrolidin-3-yl)-3-cyclohexyl-2-[(methanesulfonylimino-morpholin-4-yl-methyl)-amino]-propionamide
{[1-(3-Cyano-1-phenethyl-pyrrolidin-3-ylcarbamoyl)-2-cyclohexyl-ethylamino]-morpholin-4-yl-methylene}-carbamic acid ethyl ester
N-(3-Cyano-1-phenethyl-pyrrolidin-3-yl)-3-cyclohexyl-2-[(ethylcarbamoylimino-morpholin-4-yl-methyl)-amino]-propionamide
2-[(Carbamoylimino-morpholin-4-yl-methyl)-amino]-H-(3-cyano-1-phenethyl-pyrrolidin-3-yl)-3-cyclohexyl-propionamide
{[1-(4-Cyano-1-propyl-piperidin-4-ylcarbamoyl)-3-methyl-butylamino]-morpholin-4-yl-methylene}-carbamic acid ethyl ester
2-[(Ethylcarbamoylimino-morpholin-4-yl-methyl)-amino]-4-methyl-pentanoic acid (4-cyano-1-propyl-piperidin-4-yl)-amide
2-[(Methanesulfonylimino-morpholin-4-yl-methyl)-amino]-4-methyl-pentanoic acid (4-cyano-1-propyl-piperidin-4-yl)-amide
2-[(Carbamoylimino-morpholin-4-yl-methyl)-amino]-4-methyl-pentanoic acid (4-cyano-1-propyl-piperidin-4-yl)-amide
2-[(Ethylcarbamoylimino-morpholin-4-yl-methyl)-amino]-4-methyl-pentanoic acid (4-cyano-1-methyl-piperidin-4-yl)-amide 2-[(Carbamoylimino-morpholin-4-yl-methyl)-amino]-4-methyl-pentanoic acid (4-cyano-1-methyl-piperidin-4-yl)-amide 2-[(Methanesulfonylimino-morpholin-4-yl-methyl)-amino]-4-methyl-pentanoic acid (4-cyano-1-methyl-piperidin-4-yl)-amide {[1-(4-Cyano-1-methyl-piperidin-4-ylcarbamoyl)-3-methyl-butylamino]-morpholin-4-yl-methylene}-carbamic acid ethyl ester {[1-(3-Cyano-1-cyclohexylmethyl-pyrrolidin-3-ylcarbamoyl)-3-methyl-butylamino]-morpholin-4-yl-methylene}-carbamic acid ethyl ester 2-[(Ethylcarbamoylimino-morpholin-4-yl-methyl)-amino]-4-methyl-pentanoic acid (3-cyano-1-cyclohexylmethyl-pyrrolidin-3-yl)-amide 2-[(Methanesulfonylimino-morpholin-4-yl-methyl)-amino]-4-methyl-pentanoic acid (3-cyano-1-cyclohexylmethyl-pyrrolidin-3-yl)-amide 2-[(Carbamoylimino-morpholin-4-yl-methyl)-amino]-4-methyl-pentanoic acid (3-cyano-1-cyclohexylmethyl-pyrrolidin-3-yl)-amide 2-[(Methanesulfonylimino-morpholin-4-yl-methyl)-amino]-4-methyl-pentanoic acid (3-cyano-1-cyclohexyl-pyrrolidin-3-yl)-amide 2-[(Ethylcarbamoylimino-morpholin-4-yl-methyl)-amino]-4-methyl-pentanoic acid (3-cyano-1-cyclohexyl-pyrrolidin-3-yl)-amide 2-[(Carbamoylimino-morpholin-4-yl-methyl)-amino]-4-methyl-pentanoic acid (3-cyano-1-cyclohexyl-pyrrolidin-3-yl)-amide {[1-(3-Cyano-1-cyclohexyl-pyrrolidin-3-ylcarbamoyl)-3-methyl-butylamino]-morpholin-4-yl-methylene}-carbamic acid ethyl ester ({1-[3-Cyano-1-(4-methyl-cyclohexyl)-pyrrolidin-3-ylcarbamoyl]-3-methyl-butylamino}-morpholin-4-yl-methylene)-carbamic acid ethyl ester 2-[(Ethylcarbamoylimino-morpholin-4-yl-methyl)-amino]-4-methyl-pentanoic acid [3-cyano-1-(4-methyl-cyclohexyl)-pyrrolidin-3-yl]-amide 2-[(Carbamoylimino-morpholin-4-yl-methyl)-amino]-4-methyl-pentanoic acid [3-cyano-1-(4-methyl-cyclohexyl)-pyrrolidin-3-yl]-amide 2-[(Methanesulfonylimino-morpholin-4-yl-methyl)-amino]-4-methyl-pentanoic acid [3-cyano-1-(4-methyl-cyclohexyl)-pyrrolidin-3-yl]-amide 2-[(Methanesulfonylimino-morpholin-4-yl-methyl)-amino]-4-methyl-pentanoic acid [3-cyano-1-(1-ethyl-propyl)-pyrrolidin-3-yl]-amide 2-[(Carbamoylimino-morpholin-4-yl-methyl)-amino]-4-methyl-pentanoic acid [3-cyano-1-(1-ethyl-propyl)-pyrrolidin-3-yl]-amide 2-[(Ethylcarbamoylimino-morpholin-4-yl-methyl)-amino]-4-methyl-pentanoic acid [3-cyano-1-(1-ethyl-propyl)-pyrrolidin-3-yl]-amide ({1-[3-Cyano-1-(1-ethyl-propyl)-pyrrolidin-3-ylcarbamoyl]-3-methyl-butylamino}-morpholin-4-yl-methylene)-carbamic acid ethyl ester ({1-[3-Cyano-1-(1-H-indol-3-ylmethyl)-pyrrolidin-3-ylcarbamoyl]-3-methyl-butylamino}-morpholin-4-yl-methylene)-carbamic acid ethyl ester 2-[(Ethylcarbamoylimino-morpholin-4-yl-methyl)-amino]-4-methyl-pentanoic acid [3-cyano-1-(1-H-indol-3-ylmethyl)-pyrrolidin-3-yl]-amide 2-[(Methanesulfonylimino-morpholin-4-yl-methyl)-amino]-4-methyl-pentanoic acid [3-cyano-1-(1-H-indol-3-ylmethyl)-pyrrolidin-3-yl]-amide 2-[(Carbamoylimino-morpholin-4-yl-methyl)-amino]-4-methyl-pentanoic acid [3-cyano-1-(1-H-indol-3-ylmethyl)-pyrrolidin-3-yl]-amide 2-[(Carbamoylimino-morpholin-4-yl-methyl)-amino]-4-methyl-pentanoic acid (1-benzyl-3-cyano-pyrrolidin-3-yl)-amide 2-[(Ethylcarbamoylimino-morpholin-4-yl-methyl)-amino]-4-methyl-pentanoic acid (1-benzyl-3-cyano-pyrrolidin-3-yl)-amide 2-[(Carbamoylimino-morpholin-4-yl-methyl)-amino]-4-methyl-pentanoic acid (1-benzyl-3-cyano-pyrrolidin-3-yl)-amide 2-[(Methanesulfonylimino-morpholin-4-yl-methyl)-amino]-4-methyl-pentanoic acid (1-benzyl-3-cyano-pyrrolidin-3-yl)-amide 2-[(Methanesulfonylimino-morpholin-4-yl-methyl)-amino]-4-methyl-pentanoic acid (3-cyano-1-phenethyl-pyrrolidin-3-yl)-amide {[1-(3-Cyano-1-phenethyl-pyrrolidin-3-ylcarbamoyl)-3-methyl-butylamino]-morpholin-4-yl-methylene}-carbamic acid ethyl ester 2-[(Ethylcarbamoylimino-morpholin-4-yl-methyl)-amino]-4-methyl-pentanoic acid (3-cyano-1-phenethyl-pyrrolidin-3-yl)-amide 2-[(Carbamoylimino-morpholin-4-yl-methyl)-amino]-4-methyl-pentanoic acid (3-cyano-1-phenethyl-pyrrolidin-3-yl)-amide {[1-(4-Cyano-1-propyl-piperidin-4-ylcarbamoyl)-3,3-dimethyl-butylamino]-phenyl-methylene}-carbamic acid ethyl ester 2-[(Ethylcarbamoylimino-phenyl-methyl)-amino]-4,4-dimethyl-pentanoic acid (4-cyano-1-propyl-piperidin-4-yl)-amide 2-[(Methanesulfonylimino-phenyl-methyl)-amino]-4,4-dimethyl-pentanoic acid (4-cyano-1-propyl-piperidin-4-yl)-amide 2-[(Carbamoylimino-phenyl-methyl)-amino]-4,4-dimethyl-pentanoic acid (4-cyano-1-propyl-piperidin-4-yl)-amide {[1-(3-Cyano-1-cyclohexylmethyl-pyrrolidin-3-ylcarbamoyl)-3-methyl-butylamino]-piperazin-1-yl-methylene}-carbamic acid ethyl ester 2-[(Ethylcarbamoylimino-piperazin-1-yl-methyl)-amino]-4-methyl-pentanoic acid (3-cyano-1-cyclohexylmethyl-pyrrolidin-3-yl)-amide 2-[(Methanesulfonylimino-piperazin-1-yl-methyl)-amino]-4-methyl-pentanoic acid (3-cyano-1-cyclohexylmethyl-pyrrolidin-3-yl)-amide 2-[(Carbamoylimino-piperazin-1-yl-methyl)-amino]-4-methyl-pentanoic acid (3-cyano-1-cyclohexylmethyl-pyrrolidin-3-yl)-amide ({1-[3-Cyano-1-(4-methyl-cyclohexyl)-pyrrolidin-3-ylcarbamoyl]-2-cyclohexyl-ethylamino}-pyridin-4-yl-methylene)-carbamic acid ethyl ester N-[3-Cyano-1-(4-methyl-cyclohexyl)-pyrrolidin-3-yl]-3-cyclohexyl-2-[(ethylcarbamoylimino-pyridin-4-yl-methyl)-amino]-propionamide 2-[(Carbamoylimino-pyridin-4-yl-methyl)-amino]-N-[3-cyano-1-(4-methyl-cyclohexyl)-pyrrolidin-3-yl]-3-cyclohexyl-propionamide N-[3-Cyano-1-(4-methyl-cyclohexyl)-pyrrolidin-3-yl]-3-cyclohexyl-2-[(methanesulfonylimino-pyridin-4-yl-methyl)-amino]-propionamide N-(4-Cyano-1-methyl-piperidin-4-yl)-3-cyclohexyl-2-[(ethylcarbamoylimino-pyrazin-2-yl-methyl)-amino]-propionamide 2-[(Carbamoylimino-pyrazin-2-yl-methyl)-amino]-N-(4-cyano-1-methyl-piperidin-4-yl)-3-cyclohexyl-propionamide N-(4-Cyano-1-methyl-piperidin-4-yl)-3-cyclohexyl-2-[(methanesulfonylimino-pyrazin-2-yl-methyl)-amino]-propionamide {[1-(4-Cyano-1-methyl-piperidin-4-ylcarbamoyl)-2-cyclohexyl-ethylamino]-pyrazin-2-yl-methylene}-carbamic acid ethyl ester {[1-(1-Benzyl-3-cyano-pyrrolidin-3-ylcarbamoyl)-3-methyl-butylamino]-carbamoylimino-methyl}-carbamic acid benzyl ester {[1(1-Benzyl-3-cyano-pyrrolidin-3-ylcarbamoyl)-3-methyl-butylamino]-ethylcarbamoylimino-methyl}-carbamic acid benzyl ester {[1-(1-Benzyl-3-cyano-pyrrolidin-3-ylcarbamoyl)-3-methyl-butylamino]-methanesulfonylimino-methyl}-carbamic acid benzyl ester 2-(1,1-Dioxo-1H-1$\lambda^6$-benzo[d]isothiazol-3-ylamino)-4,4-dimethyl-pentanoic acid (4-cyano-1-methyl-piperidin-4-yl)-amide 2-(1,1-Dioxo-1H-1$\lambda^6$-benzo[d]isothiazol-3-ylamino)-4,4-dimethyl-pentanoic acid (3-cyano-1-cyclohexylmethyl-pyrrolidin-3-yl)-amide 2-(1,1-Dioxo-1H-1$\lambda^6$-benzo[d]isothiazol-3-ylamino)-4,4-dimethyl-pentanoic acid [3-cyano-1-(4-methyl-cyclohexyl)-pyrrolidin-3-yl]-amide 2-(1,1-Dioxo-1H-1$\lambda^6$-benzo[d]isothiazol-3-ylamino)-4,4-dimethyl-pentanoic acid [3-cyano-1-(1-ethyl-propyl)-pyrrolidin-3-yl]-amide 2-(1,1-Dioxo-1H-1$\lambda^6$-benzo[d]isothiazol-3-ylamino)-4,4-dimethyl-pentanoic acid [3-cyano-1-(1H-indol-3-ylmethyl)-pyrrolidin-3-yl]-amide 2-(1,1-Dioxo-1H-1$\lambda^6$-benzo[d]isothiazol-3-ylamino)-4,4-dimethyl-pentanoic acid (3-cyano-1-phenethyl-pyrrolidin-3-yl)-amide 2-(1,1-Dioxo-1H-1$\lambda^6$-benzo[d]isothiazol-3-ylamino)-4,4-dimethyl-pentanoic acid (1-benzyl-3-cyano-pyrrolidin-3-yl)-amide N-(3-Cyano-1-cyclohexylmethyl-pyrrolidin-3-yl)-3-cyclohexyl-2-(1,1-dioxo-1H-1$\lambda^6$-benzo-[d]isothiazol-3-ylamino)-propionamide N-[3-Cyano-1-(4-methyl-cyclohexyl)-pyrrolidin-3-yl]-3-cyclohexyl-2-(1,1-dioxo-1H-1$\lambda^6$-benzo[d]isothiazol-3-ylamino)-propionamide N-[3-Cyano-1-(1H-indol-3-ylmethyl)-pyrrolidin-3-yl]-3-cyclohexyl-2-(1,1-dioxo-1H-1$\lambda^6$-benzo[d]isothiazol-3-ylamino)-propionamide N-(3-Cyano-1-phenethyl-pyrrolidin-3-yl)-3-cyclohexyl-2-(1,1-dioxo-1H-1$\lambda^6$-benzo[d]isothiazol-3-ylamino)-propionamide N-(1-Benzyl-3-cyano-pyrrolidin-3-yl)-3-cyclohexyl-2-(1,1-dioxo-1H-1$\lambda^6$-benzo[d]isothiazol-3-ylamino)-propionamide 2-(1,1-Dioxo-1H-1$\lambda^6$-benzo[d]isothiazol-3-ylamino)-4-methyl-pentanoic acid (4-cyano-1-propyl-piperidin-4-yl)-amide 2-(1,1-Dioxo-1H-1$\lambda^6$-benzo[d]isothiazol-3-ylamino)-4-methyl-pentanoic acid (4-cyano-1-propyl-piperidin-4-yl)-amide 2-(1,1-Dioxo-1H-1$\lambda^6$-benzo[d]isothiazol-3-ylamino)-4-methyl-pentanoic acid (3-cyano-1-cyclohexylmethyl-pyrrolidin-3-yl)-amide 2-(1,1-Dioxo-1H-1$\lambda^6$-benzo[d]isothiazol-3-ylamino)-4-methyl-pentanoic acid (3-cyano-1-cyclohexyl-pyrrolidin-3-yl)-amide 2-(1,1-Dioxo-1H-1$\lambda^6$-benzo[d]isothiazol-3-ylamino)-4-methyl-pentanoic acid [3-cyano-1-(4-methyl-cyclohexyl)-pyrrolidin-3-yl]-amide 2-(1,1-Dioxo-1H-1$\lambda^6$-benzo[d]isothiazol-3-ylamino)-4-methyl-pentanoic acid [3-cyano-1-(1-ethyl-propyl)-pyrrolidin-3-yl]-amide 2-(1,1-Dioxo-1H-1$\lambda^6$-benzo[d]isothiazol-3-ylamino)-4-methyl-pentanoic acid [3-cyano-1-(1H-indol-3-ylmethyl)-pyrrolidin-3-yl]-amide 2-(1,1-Dioxo-1H-1$\lambda^6$-benzo[d]isothiazol-3-ylamino)-4-methyl-pentanoic acid (3-cyano-1-phenethyl-pyrrolidin-3-yl)-amide 2-(1,1-Dioxo-1H-1$^6$-benzo[d]isothiazol-3-ylamino)-4-methyl-pentanoic acid (1-benzyl-3-cyano-pyrrolidin-3-yl)-amide N-(4-Cyano-1-propyl-piperidin-4-yl)-3-cyclohexyl-2-(3-oxo-3H-isoindol-1-ylamino)-propionamide 4-Methyl-2-(3-oxo-3H-isoindol-1-ylamino)-pentanoic acid (4-cyano-1-propyl-piperidin-4-yl)-amide N-(4-Cyano-1-methyl-piperidin-4-yl)-3-cyclohexyl-2-(3,4-dihydro-1H-pyrano[4,3-c]pyridin-5-ylamino)-propionamide 2-(3,4-Dihydro-1H-pyrano[4,3-c]pyridin-5-ylamino)-4,4-dimethyl-pentanoic acid (4-cyano-1-methyl-piperidin-4-yl)-amide 2-(3,4-Dihydro-1H-pyrano[4,3-c]pyridin-5-ylamino)-4-methyl-pentanoic acid (4-cyano-1-methyl-piperidin-4-yl)-amide N-(3-Cyano-1-cyclohexylmethyl-pyrrolidin-3-yl)-3-cyclohexyl-2-(isoquinolin-1-ylamino)-propionamide 2-(Isoquinolin-1-ylamino)-4,4-dimethyl-pentanoic acid (3-cyano-1-cyclohexylmethyl-pyrrolidin-3-yl)-amide 2-(Isoquinolin-1-ylamino)-4-methyl-pentanoic acid (3-cyano-1-cyclohexylmethyl-pyrrolidin-3-yl)-amide 2-(Imidazo[1,5-a]pyridin-3-ylamino)-4-methyl-pentanoic acid (3-cyano-1-cyclohexyl-pyrrolidin-3-yl)-amide 2-(Imidazo[1,5-a]pyridin-3-ylamino)-4,4-dimethyl-pentanoic acid (3-cyano-1-cyclohexyl-pyrrolidin-3-yl)-amide N-(3-Cyano-1-cyclohexyl-pyrrolidin-3-yl)-3-cyclohexyl-2-(imidazo[1,5-a]pyridin-3-ylamino)-propionamide N-[3-Cyano-1-(4-methyl-cyclohexyl)-pyrrolidin-3-yl]-3-cyclohexyl-2-(8-oxo-8,9-dihydro-7H-purin-6-ylamino)-propionamide 4-Methyl-2-(8-oxo-8,9-dihydro-7H-purin-6-ylamino)-pentanoic acid [3-cyano-1-(4-methyl-cyclohexyl)-pyrrolidin-3-yl]-amide 4,4-Dimethyl-2-(8-oxo-8,9-dihydro-7H-purin-6-ylamino)-pentanoic acid [3-cyano-1-(4-methyl-cyclohexyl)-pyrrolidin-3-yl]-amide 2-{1-[3-Cyano-1-(1-ethyl-propyl)-pyrrolidin-3-ylcarbamoyl]-3,3-dimethyl-butylamino}-pyrimidine-4-carboxylic acid amide 2-{1-[3-Cyano-1-(1-ethyl-propyl)-pyrrolidin-3-ylcarbamoyl]-3-methyl-butylamino}-pyrimidine-4-carboxylic acid amide 2-{1-[3-Cyano-1-(1-ethyl-propyl)-pyrrolidin-3-ylcarbamoyl]-2-cyclohexyl-ethylamino}-pyrimidine-4-carboxylic acid amide 4-Methyl-2-(2-oxo-1,2-dihydro-quinazolin-4-ylamino)-pentanoic acid (3-cyano-1-cyclopentylmethyl-pyrrolidin-3-yl)-amide N-(3-Cyano-1-cyclopentylmethyl-pyrrolidin-3-yl)-3-cyclohexyl-2-(2-oxo-1,2-dihydro- quinazolin-4-ylamino)-propionamide 4,4-Dimethyl-2-(2-oxo-1,2-dihydro-quinazolin-4-ylamino)-pentanoic acid (3-cyano-1-cyclopentylmethyl-pyrrolidin-3-yl)-amide N-(4-Cyano-1-propyl-piperidin-4-yl)-3-cyclohexyl-2-(4-oxo-3,4-dihydro-phthalazin-1-ylamino)-propionamide 4-Methyl-2-(4-oxo-3,4-dihydro-phthalazin-1-ylamino)-pentanoic acid (4-cyano-1-propyl-piperidin-4-yl)-amide 4,4-Dimethyl-2-(4-oxo-3,4-dihydro-phthalazin-1-ylamino)-pentanoic acid (4-cyano-1-propyl-piperidin-4-yl)-amide 2-(1H-Indazol-3-ylamino)-4-methyl-pentanoic acid (4-cyano-1-methyl-piperidin-4-yl)-amide 2-(1H-Indazol-3-ylamino)-4,4-dimethyl-pentanoic acid (4-cyano-1-propyl-piperidin-4-yl)-amide
N-[4-Cyano-1-(2-hydroxy-ethyl)-piperidin-4-yl]-3-cyclohexyl-2-(1H-indazol-3-ylamino)-propionamide
4-Methyl-2-(2-oxo-2H-benzo[e][1,3]oxazin-4-ylamino)-pentanoic acid (4-cyano-1-methyl-piperidin-4-yl)-amide
4,4-Dimethyl-2-(2-oxo-2H-benzo[e][1,3]oxazin-4-ylamino)-pentanoic acid (4-cyano-1-propyl-piperidin-4-yl)-amide
N-[4-Cyano-1-(2-hydroxy-ethyl)-piperidin-4-yl]-3-cyclohexyl-2-(2-oxo-2H-benzo[e][1,3]oxazin-4-ylamino)-propionamide
2-(6-Hydroxy-1,1-dioxo-1H-1$\lambda^6$-benzo[d]isothiazol-3-ylamino)-4,4-dimethyl-pentanoic acid (4-cyano-1-propyl-piperidin-4-yl)-amide
Morpholine-4-carboxylic acid [1-(4-cyano-1-propyl-piperidin-4-ylcarbamoyl)-3,3-dimethyl-butylamino]-morpholin-4-yl-methyleneamide
4-Methyl-piperazine-1-carboxylic acid [1-(4-cyano-1-propyl-piperidin-4-ylcarbamoyl)-3,3-dimethyl-butylamino]-morpholin-4-yl-methyleneamide
4,4-Dimethyl-2-{[morpholin-4-yl-(2-morpholin-4-yl-ethylcarbamoylimino)-methyl]-amino}-pentanoic acid (4-cyano-1-propyl-piperidin-4-yl)-amide
N-(4-Cyano-1-methyl-piperidin-4-yl)-3-cyclohexyl-2-{[N-(5-methyl-oxazol-2-yl)-morpholine-4-carboximidoyl]-amino}-propionamide
N-(4-Cyano-1-methyl-piperidin-4-yl)-3-cyclohexyl-2-{[N-(1-methyl-1H-imidazol-2-yl)-morpholine-4-carboximidoyl]-amino}-propionamide
N-(4-Cyano-1-methyl-piperidin-4-yl)-3-cyclohexyl-2-{[N-(2-methyl-2H-[1,2,4]triazol-3-yl)-morpholine-4-carboximidoyl]-amino}-propionamide
[[1-(4-Cyano-1-methyl-piperidin-4-ylcarbamoyl)-2-cyclohexyl-ethylamino]-(2-oxa-5-aza-bicyclo[2.2.1]hept-5-yl)-methylene]-carbamic acid ethyl ester
[[1-(4-Cyano-1-methyl-piperidin-4-ylcarbamoyl)-2-cyclohexyl-ethylamino]-(2-methoxymethyl-morpholin-4-yl)-methylene]-carbamic acid ethyl ester
[[1-(4-Cyano-1-methyl-piperidin-4-ylcarbamoyl)-2-cyclohexyl-ethylamino]-(2,6-dimethyl-morpholin-4-yl)-methylene]-carbamic acid ethyl ester
N-(4-Cyano-1-methyl-piperidin-4-yl)-3-cyclohexyl-2-{[N-(4-methoxy-phenyl)-morpholine-4-carboximidoyl]-amino}-propionamide
4-({N-[1-(4-Cyano-1-methyl-piperidin-4-ylcarbamoyl)-2-cyclohexyl-ethyl]-morpholine-4-carboximidoyl}-amino)-benzamide
2-({N-[1-(4-Cyano-1-methyl-piperidin-4-ylcarbamoyl)-2-cyclohexyl-ethyl]-morpholine-4-carboximidoyl}-amino)-oxazole-5-carboxylic acid amide
2-({N-[1-(4-Cyano-1-methyl-piperidin-4-ylcarbamoyl)-2-cyclohexyl-ethyl]-morpholine-4-carboximidoyl}-amino)-oxazole-4-carboxylic acid amide
5-({N-[1-(4-Cyano-1-methyl-piperidin-4-ylcarbamoyl)-2-cyclohexyl-ethyl]-morpholine-4-carboximidoyl}-amino)-pyridine-2-carboxylic acid amide
2-({N-[1-(4-Cyano-1-methyl-piperidin-4-ylcarbamoyl)-2-cyclohexyl-ethyl]-morpholine-4-carboximidoyl}-amino)-3H-imidazole-4-carboxylic acid amide
2-[(N-Benzooxazol-2-yl-morpholine-4-carboximidoyl)-amino]-N-(4-cyano-1-methyl-piperidin-4-yl)-3-cyclohexyl-propionamide
N-(4-Cyano-1-methyl-piperidin-4-yl)-3-cyclohexyl-2-[(N-thiazol-2-yl-morpholine-4-carboximidoyl)-amino]-propionamide
N-(4-Cyano-1-methyl-piperidin-4-yl)-3-cyclohexyl-2-{[N-(5-phenyl-thiazol-2-yl)-morpholine-4-carboximidoyl]-amino}-propionamide
2-{[N-(5-Carbamoylmethyl-oxazol-2-yl)-morpholine-4-carboximidoyl]-amino}-N-(4-cyano-1-methyl-piperidin-4-yl)-3-cyclohexyl-propionamide
N-(4-Cyano-1-methyl-piperidin-4-yl)-3-cyclohexyl-2-{[N-(2-methyl-oxazol-5-yl)-morpholine-4-carboximidoyl]-amino}-propionamide
N-(4-Cyano-1-methyl-piperidin-4-yl)-3-cyclohexyl-2-(5,6-dihydro-8H-imidazo[5,1-c][1,4]oxazin-3-ylamino)-propionamide
N-(4-Cyano-1-methyl-piperidin-4-yl)-3-cyclohexyl-2-(5,6,8,8a-tetrahydro-1H-imidazo[5,1-c][1,4]oxazin-3-ylamino)-propionamide
[[1-(4-Cyano-1-methyl-piperidin-4-ylcarbamoyl)-2-cyclohexyl-ethylamino]-(2-methylcarbamoyl-morpholin-4-yl)-methylene]-carbamic acid ethyl ester
{[1-(4-Cyano-1-methyl-piperidin-4-ylcarbamoyl)-2-cyclohexyl-ethylamino]-[3-(1-methylcarbamoyl-2-phenyl-ethylcarbamoyl)-morpholin-4-yl]-methylene}-carbamic acid ethyl ester
N-(4-cyano-1-methyl-piperidin-4-yl)-3-cyclohexyl-2-(1H-indol-2-yl-amine)-propionamide
([1-(4-cyano-1-methyl-piperidin-4-yl-carbamoyl)-2-naphthalen-2-yl-ethylamino]-morpholin-4-yl-methylene)-carbamic acid ethyl ester
([1-(4-cyano-1-methyl-piperidin-4-yl-carbamoyl)-2-(6-dimethylaminomethy,naphthalen-2-yl-ethylamino]-morpholin-4-yl-methylene)-carbamic acid ethyl ester
2-(Benzooxazol-2-ylamino)-N-(4-cyano-1-methyl-piperidin-4-yl)-3-cyclohexyl-propionamide
2-(Benzooxazol-2-ylamino)-4,4-dimethyl-pentanoic acid (4-cyano-1-propyl-piperidin-4-yl)-amide
2-(Benzothiazol-2-ylamino)-N-(4-cyano-1-methyl-piperidin-4-yl)-3-cyclohexyl-propionamide
2-(Benzothiazol-2-ylamino)-4,4-dimethyl-pentanoic acid (4-cyano-1-propyl-piperidin-4-yl)-amide
2-(1H-Benzoimidazol-2-ylamino)-N-(4-cyano-1-methyl-piperidin-4-yl)-3-cyclohexyl-propionamide
2-(1H-Benzoimidazol-2-ylamino)-4,4-dimethyl-pentanoic acid (4-cyano-1-propyl-piperidin-4-yl)-amide
N-(4-Cyano-1-methyl-piperidin-4-yl)-3-cyclohexyl-2-(6-methanesulfonylamino-2H-indazol-3-ylamino)-propionamide
2-(6-Methanesulfonylamino-2H-indazol-3-ylamino)-4,4-dimethyl-pentanoic acid (4-cyano-1-propyl-piperidin-4-yl)-amide
2-(Benzo[d]isoxazol-3-ylamino)-N-(4-cyano-1-methyl-piperidin-4-yl)-3-cyclohexyl-propionamide
2-(Benzo[d]isoxazol-3-ylamino)-4,4-dimethyl-hexanoic acid (4-cyano-1-propyl-piperidin-4-yl)-amide
2-(Benzo[d]isothiazol-3-ylamino)-N-(4-cyano-1-methyl-piperidin-4-yl)-3-cyclohexyl-propionamide
2-(Benzo[d]isothiazol-3-ylamino)-4,4-dimethyl-pentanoic acid (4-cyano-1-propyl-piperidin-4-yl)-amide
N-(4-Cyano-1-methyl-piperidin-4-yl)-3-cyclohexyl-2-(7-methanesulfonylamino-imidazo[1,5-d]pyridin-3-ylamino)-propionamide
2-(7-Methanesulfonylamino-imidazo[1,5-a]pyridin-3-ylamino)-4,4-dimethyl-pentanoic acid (4-cyano-1-propyl-piperidin-4-yl)-amide
2-[1-(2-Carbamoyl-ethyl)-1H-imidazol-2-ylamino]-4,4-dimethyl-pentanoic acid (4-cyano-1-propyl-piperidin-4-yl)-amide
N-(4-Cyano-1-methyl-piperidin-4-yl)-3-cyclohexyl-2-(3-ureido-pyridin-2-ylamino)-propionamide
4,4-Dimethyl-2-(3-ureido-pyridin-2-ylamino)-pentanoic acid (4-cyano-1-propyl-piperidin-4-yl)-amide
2-[1-(2-Carbamoyl-ethyl)-1H-imidazol-2-ylamino]-N-(4-cyano-1-methyl-piperidin-4-yl)-3-cyclohexyl-propionamide 4,4-Dimethyl-2-(4-trifluoromethyl-pyrimidin-2-ylamino)-pentanoic acid (4-cyano-1-propyl-piperidin-4-yl)-amide {[1-(1-Benzyl-4-cyano-piperidin-4-ylcarbamoyl)-2-cyclohexyl-ethylimino]-morpholin-4-yl-methyl}-methyl-carbamic acid ethyl ester {[1-(4-Cyano-1-isopropyl-piperidin-4-ylcarbamoyl)-3-methyl-butylamino]-morpholin-4-yl-methylene}-carbamic acid benzyl ester {[1-(4-Cyano-1-ethyl-piperidin-4-ylcarbamoyl)-3,3-dimethyl-butylamino]-morpholin-4-yl-methylene}-carbamic acid cyclopentyl ester {[1-(4-Cyano-1-phenethyl-piperidin-4-ylcarbamoyl)-3,3-dimethyl-butylamino]-morpholin-4-yl-methylene}-carbamic acid 2-methoxy-ethyl ester {[1-(4-Cyano-1-cyclohexyl-piperidin-4-ylcarbamoyl)-3,3-dimethyl-butylamino]-phenyl-methylene}-carbamic acid ethyl ester

Methods of Therapeutic Use

The compounds of the invention are useful in inhibiting the activity of cathepsin S, K, F, L and B. In doing so, these compounds are useful in blocking disease processes mediated by these cysteine proteases.

Compounds of this invention effectively block degradation of the invariant chain to CLIP by cathepsin S, and thus inhibit antigen presentation and antigen-specific immune responses. Control of antigen specific immune responses is an attractive means for treating autoimmune diseases and other undesirable T-cell mediated immune responses. Thus, there is provided methods of treatment using the compounds of this invention for such conditions. These encompass autoimmune diseases and other diseases involving inappropriate antigen specific immune responses including, but not limited to, rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, glomerulonephritis, atopic dermatitis, insulin-dependent diabetes mellitus and asthma. The compounds of the invention can also be used to treat other disorders associated with extracellular proteolysis such as Alzheimer's disease and atherosclerosis. The compounds of the invention can also be used to treat other disorders associated with inappropriate autoimmune responses, T-cell mediated immune responses, or extracellular proteolysis mediated by cathepsin S, unrelated to those listed above or discussed in the Background of the Invention. Therefore, the invention also provides methods of modulating an autoimmune disease comprising administering to a patient in need of such treatment a pharmaceutically effect amount of a compound according to the invention.

Compounds of the invention also inhibit cathepsin K. In doing so, they may block inappropriate degradation of bone collagen and other bone matrix proteases. Thus, there is provided a method for treating diseases where these processes play a role such as osteoporosis. Inhibition of cathepsins F, L, and B are also within the scope of the inventiondue to similarity of the active sites in cysteine proteases as described above.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of the invention (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Assessment of Biological Properties
Expression and Purification of Recombinant Human Cathepsin S Cloning of human cathepsin S:

U937 RNA was subjected to reverse transcriptase/polymerase chain reaction with primer A (5'cacaatgaaacggctggtttg 3') and primer B (5'ctagatttctgggtaagaggg 3') designed to specifically amplify the cathepsin S cDNA. The resulting 900 bp DNA fragment was subcloned into pGEM-T (Promega) and sequenced to confirm its identity. This construct was used for all subsequent manipulations. This procedure is typical for cloning of known genes and is established in its field.

Human Pre-Pro-Cat S was removed from pGem-T vector (Promega, 2800 Woods Hollow Rd, Madison, Wis. 53711) by digestion with restriction enzyme SacII, followed by treatment with T4 DNA polymerase to generate a blunt end, and a second restriction enzyme digest with SalI. It was subcloned into pFastBac1 donor plasmid (GibcoBRL, 8717 Grovemont Cr., Gaithersburg, Md. 20884) which had been cut with restriction enzyme BamH1 and blunt-ended and then cut with restriction enzyme SalI. The ligation mixture was used to transform DH5a competent cells (GibcoBRL) and plated on LB plates containing 100 ug/ml ampicillin. Colonies were grown in overnight cultures of LB media containing 50 ug/ml Ampicillin, plasmid DNA isolated and correct insert confirmed by restriction enzyme digestion. Recombinant pFastBac donor plasmid was transformed into DH10Bac competent cells (GibcoBRL). Large white colonies were picked from LB plates containing 50 ug/ml kanamycin, 7 ug/ml gentamicin, 10 ug/ml tetracycline, 100 ug/ml Bluo-gal, and 40 ug/ml IPTG. DNA was isolated and used to transfect Sf9 insect cells using CellFECTIN reagent (GibcoBRL). Cells and supernatant were harvested after 72 hours. Viral supernatant was passaged twice and presence of Cat S confirmed by PCR of the supernatant.

SF9 cells were infected with recombinant baculovirus at a MOI of 5 for 48–72 hrs. Cell pellet was lysed and incubated in buffer at pH 4.5 at 37 for 2 hours to activate Cat S from pro-form to active mature form (Bromme, D & McGrath, M., *Protein Science*, 1996, 5:789–791.) Presence of Cat S was confirmed by SDS-PAGE and Western blot using rabbit anti-human proCat S.

Inhibition of Cathepsin S

Human recombinant cathepsin S expressed in Baculovirus is used at a final concentration of 10 nM in buffer. Buffer is 50 mM Na Acetate, pH 6.5, 2.5 mMEDTA, 2.5 mMTCEP. Enzyme is incubated with either compound or DMSO for 10 min at 37 C. Substrate 7-amino-4-methylcoumarin, CBZ-L-valyl-L-valyl-L-arginineamide (custom synthesis by Molecular Probes) is diluted to 20 uM in water (final concentration of 5 uM), added to assay and incubated for additional 10 minutes at 37 C. Compound activity is measured by diminished fluorescence compared to DMSO control when read at 360 nm excitation and 460 nm emission.

Examples listed above were evaluated for inhibition of cathepsin S in the above assay. All had $IC_{50}$ values of 100 micromolar or below.

Inhibition of Cathepsin K, F, L and B

Inhibition of these enzymes by particular compounds of the invention may be determined without undue experimentation by using art recognized methods as provided hereinbelow each of which is incorporated herein by reference:

Cathepsin B, and L assays are to be found in the following references:

1. Methods in Enzymology, Vol.244, Proteolytic Enzymes: Serine and Cysteine Peptidases, Alan J. Barrett, ed.

Cathepsin K assay is to be found in the following reference:

2. Bromme, D., Okamoto, K., Wang, B. B., and Biroc, S. (1996) *J. Biol. Chem.* 271, 2126–2132.

Cathepsin F assays are to be found in the following references:

3. Wang, B., Shi, G. P., Yao, P. M., Li, Z., Chapman, H. A., and Bromme, D. (1998) *J. Biol. Chem.* 273, 32000–32008.

4. Santamaria, I., Velasco, G., Pendas, A. M., Paz, A., and Lopez-Otin, C (1999) *J. Biol. Chem.* 274, 13800–13809.

Preferred compounds to be evaluated for inhibition of Cathepsin K, F, L and B in the above assays desirably have $IC_{50}$ values of 100 micromolar or below.

What is claimed is:

1. A compound of formula (II):

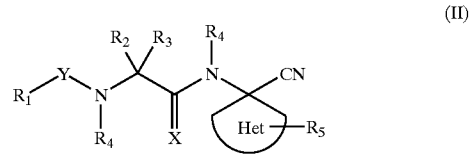

wherein:
Het is tetrahydropyranyl or tetrahydrothiopyranyl each being substituted or unsubstituted with one or more $R_5$;
Y is C(O);
$R_1$ is $R_a$;
$R_a$ is morpholinyl or thiomorpholinyl, $R_a$ may be further substituted or unsubstituted by one or more $R_b$;
$R_b$ is C1–6 saturated or unsaturated branched or unbranched carbon chain optionally partially or fully halogenated wherein one or more carbon atoms are optionally replaced by O, N, S(O), S(O)$_2$ or S and wherein said chain is optionally independently substituted with 1–2 oxo groups, —NH$_2$, or one or more C1–4 alkyl, pyrrolidinyl, piperdinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl;
or $R_b$ is C3–6 cycloalkyl, aryl, aryloxy, benzyloxy, halogen, hydroxy, oxo, carboxy, cyano, nitro, mono-C1–5alkylamino, di-C1–5alkylamino, carboxamide, amidino or guanidino;
$R_2$ is hydrogen or C1–3 alkyl;
$R_3$ is a bond, hydrogen, C1–10 alkyl, C2–10alkylene, C3–8 cycloalkyl, arylC1–5alkyl or aryl wherein $R_3$ is substituted or unsubstituted by one or more $R_c$;
$R_c$ is C1–10 alkyl, C3–8 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, decahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, dihydrobenzofuranyl, octohydrobenzofuranyl, benzofuranyl, benzothienyl, benzimidazolyl, benzthiazolyl, tetrahydroquinolinyl, quinolinyl, tetrahydroisoquinolinyl, isoquinolinyl, quinazolinyl, quinoxalinyl, C1–10 alkoxy, aryloxy, C1–10 alkanoyl, aroyl, C1–10 alkoxycarbonyl, aryloxycarbonyl, C1–10 alkanoyloxy, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further substituted or unsubstituted by one or more $R_d$;

$R_d$ is C1–5 alkyl, C3–6 cycloalkyl, aryl, arylC1–5alkyl, C1–5 alkoxy, aryloxy, arylC1–5alkoxy, aroyl, amino, halogen, hydroxy, oxo, carboxy, cyano, nitro, amidino or guanidino;

$R_2$ and $R_3$ together with the carbon they are attached optionally form a nonaromatic 5–7 membered cycloalkyl or heterocyclic ring;

$R_4$ is hydrogen, hydroxy or C1–3 alkyl;

$R_5$ is a bond, hydrogen, carbonyl, C1–10 alkyl, C1–10alkoxyC1–10alkyl, C1–10alkylaminoC1–10 alkyl, C1–10alkylthioC1–10alkyl wherein the sulfur atom may be oxidized to a sulfoxide or sulfone, C1–10 alkoxy, aryloxy, C3–8 cycloalkyl, aryl, benzyl, tetrahydronaphthyl, indenyl, indanyl, C3–7cycloalkylsulfonylC1–5alkyl, arylsulfonylC1–5alkyl, heterocyclyl selected from pyrrolidinyl, piperidinyl, morpholinyl, thiomorpholinyl, piperazinyl, indolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridizinyl, tetrazolyl, triazolyl, pyrazolyl, indolyl, benzofuranyl, benzothienyl, benzimidazolyl, benzthiazolyl, quinolinyl, tetrahydroquinolinyl, isoquinolinyl, tetrahydroisoquinolinyl, quinazolinyl, tetrahydroquinazolinyl, benzoxazolyl and quinoxalinyl, heterocyclyloxy wherein the heterocyclyl moiety is selected from those herein described in this paragraph, C1–10alkanoyl, aroyl, C1–10alkanoyloxy, benzyloxy, C1–10alkoxycarbonyl, arylC1–5alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is halogen, hydroxy, oxy, oxo, carboxy, cyano, nitro, carboxamide, amidino or guanidino, $R_5$ may be further substituted or unsubstituted by one or more $R_e$;

$R_e$ is C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C1–10 alkoxy, C3–8 cycloalkyl, aryl, tetrahydronaphthyl, indenyl, indanyl, pyrrolidinyl, piperidinyl, morpholinyl, thiomorpholinyl, piperazinyl, indolinyl, thiopyranyl, tetrahydrothiopyranyl, pyranyl, tetrahydropyranyl, tetrahydrofuranyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, benzisoxazolyl, quinolinyl, isoquinolinyl, quinazolinyl, quinoxalinyl, C1–10alkanoyl, aroyl, C1–10alkanoyloxy, aryloxy, benzyloxy, C1–10 alkoxycarbonyl, arylC1–3alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is halogen, hydroxy, oxo, carboxy, cyano, nitro, carboxamide, amidino or guanidino, $R_e$ may be further substituted or unsubstituted by one or more $R_f$;

$R_f$ is C1–5 alkyl, C3–6 cycloalkyl, tolylsulfonyl, C1–5 alkoxy, aryl, aryloxy, benzyloxy, halogen, hydroxy, oxo, carboxy, cyano, nitro, carboxamide, amidino or guanidino; and X is O or pharmaceutically acceptable acceptable salts, esters, tautomers, individual isomers and mixtures of isomers thereof.

2. The compound according to claim 1 wherein:

$R_b$ is C1–5 alkyl, C3–6 cycloalkyl, aryl, C1–5 alkoxy, aryloxy, benzyloxy, halogen, hydroxy, oxo, carboxy, cyano, nitro, carboxamide, amidino or guanidino;

$R_2$ is hydrogen or methyl or ethyl;

$R_3$ is a bond, hydrogen, C1–5 alkyl, C2–5alkylene, C3–7 cycloalkyl, arylC1–3alkyl or aryl wherein $R_3$ is substituted or unsubstituted by one or more $R_c$;

$R_c$ is C1–5 alkyl, C3–7 cycloalkyl, aryl, indanyl, indenyl, bicyclo[2.2.1]heptanyl, bicyclo[2.2.2] octanyl, bicyclo[4.1.0]heptanyl, bicyclo[3.1.0] hexanyl, bicyclo[1.1.1]pentanyl, cubanyl, 1,2,3,4-tetrahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, C1–5 alkoxy, aryloxy, C1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further substituted or unsubstituted by one or more $R_d$;

$R_d$ is C1–5 alkyl, C3–6 cycloalkyl, aryl, arylC1–4 alkyl, C1–5 alkoxy, aryloxy, arylC1–5alkoxy, aroyl, halogen, hydroxy, oxo or cyano;

$R_4$ is hydrogen or methyl;

$R_5$ is a bond, hydrogen, carbonyl, C1–5 alkyl, C1–8alkoxyC1–8alkyl, C1–8alkylaminoC1–8alkyl, C1–8alkylthioC1–8alkyl wherein the sulfur atom may be oxidized to a sulfoxide or sulfone, C1–8 alkoxy, aryloxy, C3–7 cycloalkyl, aryl, benzyl, tetrahydronaphthyl, indanyl, heterocyclyl selected from pyrrolidinyl, piperidinyl, morpholinyl, thiomorpholinyl, piperazinyl, indolinyl, pyranyl, tetrahydropyranyl, thiopyranyl, tetrahydrothiopyranyl, furanyl, tetrahydrofuranyl, thienyl, oxazolyl, thiazolyl, imidazolyl, pyridinyl, pyrimidinyl, pyrazinyl, tetrazolyl, triazolyl, pyrazolyl, indolyl, benzofuranyl, benzothienyl, benzimidazolyl, benzthiazolyl, quinolinyl, isoquinolinyl, quinazolinyl, benzoxazolyl and quinoxalinyl, heterocyclyloxy wherein the heterocyclyl moiety is selected from the heterocycyl moieties herein described in this paragraph, C1–7alkanoyl, aroyl, C1–7alkanoyloxy, benzyloxy, C1–7 alkoxycarbonyl, arylC1–4alkoxycarbonyl, aryloxycarbonyl, aroyloxy, carbamoyl wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is C1–7 alkanoylamino, aroylamino, C1–7 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is C1–7 alkoxycarbonylamino, aryloxycarbonylamino, C1–7 alkylcarbamoyloxy, arylcarbamoyloxy, C1–7 alkylsulfonylamino, arylsulfonylamino, C1–7 alkylaminosulfonyl, arylaminosulfonyl, amino wherein the nitrogen atom may be independently mono or di-substituted by C1–7 alkyl, aryl, pyrrolidinyl, piperidinyl, morpholinyl, thiomorpholinyl, piperazinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is halogen, hydroxy, oxy, oxo, carboxy, cyano, nitro or carboxamide, $R_5$ may be further substituted or unsubstituted by one or more $R_e$;

$R_e$ is C1–7 alkyl, C1–7alkoxyC1–7alkyl, C1–7alkylaminoC1–7alkyl, C1–7alkylthioC1–7alkyl wherein the sulfur atom may be oxidized to a sulfoxide or sulfone, C1–7 alkoxy, C3–7 cycloalkyl, aryl, tetrahydronaphthyl, indanyl, pyrrolidinyl, piperidinyl, morpholinyl, thiomorpholinyl, piperazinyl, thiopyranyl, tetrahydrothiopyranyl, tetrahydropyranyl, tetrahydrofuranyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl, quinoxalinyl, C1–5 alkanoyl, aroyl, C1–5alkanoyloxy, aryloxy, benzyloxy, C1–5 alkoxycarbonyl, aryloxycarbonyl, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is halogen, hydroxy, oxo, carboxy, cyano, nitro, carboxamide, amidino or guanidino, $R_e$ may be further substituted or unsubstituted by one or more $R_f$; and $R_f$ is methyl, ethyl, t-butyl, tolylsulfonyl, C1–3 alkoxy, cyclopropyl, cyclohexyl, phenyl, naphthyl, phenoxy, benzyloxy, fluoro, chloro, bromo, hydroxy, oxo, carboxy, cyano, nitro or carboxamide.

3. The compound according to claim 2 wherein:

$R_b$ is C1–3 alkyl, C3–6 cycloalkyl, aryl, C1–3 alkoxy, aryloxy, benzyloxy, halogen, hydroxy, oxo, carboxy, cyano, nitro, carboxamide, amidino or guanidino;

$R_2$ is hydrogen or methyl;

$R_3$ is a bond, hydrogen, C1–5 alkyl, C2–5alkylene, C4–6 cycloalkyl or arylC1–2alkyl wherein $R_3$ is substituted or unsubstituted by one or more $R_c$;

$R_c$ is C1–4 alkyl, C5–6 cyoloalkyl, phenyl, naphthyl, indanyl, bicyclo[2.2.1]heptanyl, bicyclo[2.2.2] octanyl, bicyclo[4.1.0]heptanyl, bicyclo[3.1.0] hexanyl, bicyclo[1.1.1]pentanyl, cubanyl, 1,2,3,4-tetrahydronaphthyl, pyrrolidinyl, piperidinyl, morpholinyl, thiomorpholinyl, indolinyl, furanyl, tetrahydrofuranyl, pyranyl, tetrahydropyranyl, thienyl, pyrrolyl, oxazolyl, thiazolyl, imidazolyl, pyrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, C1–4 alkoxy, phenoxy, naphthyloxy, C1–3 alkanoyl, benzoyl, C1–3 alkoxycarbonyl, phenoxycarbonyl, C1–3 alkanoyloxy, benzoyloxy, carbamoyl wherein the nitrogen atom may be independently mono or di-substituted by C1–5 alkyl or aryl, or $R_c$ is C1–3 alkanoylamino, benzoylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–5 alkyl or aryl, or $R_c$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–5 alkyl or aryl, or $R_c$ is halogen, hydroxy, oxo, carboxy, cyano, nitro, amidino or guanidino, $R_c$ may be further substituted or unsubstituted by one or more $R_d$;

$R_d$ is C1–3 alkyl, C3–6 cycloalkyl, phenyl, benzyl, C1–3 alkoxy, phenoxy, phenylC1–3alkoxy, benzoyl, halogen, hydroxy, oxo or cyano;

$R_4$ is hydrogen;

R5 is a bond, hydrogen, carbonyl, C1–6 alkyl, C1–6alkoxyC1–6alkyl, C1–6alkylaminoC1–6alkyl, C1–6alkylthioC1–6alkyl wherein the sulfur atom may be oxidized to a sulfoxide or sulfone, C1–6 alkoxy, phenoxy, naphthyloxy, C3–6 cycloalkyl, phenyl, naphthyl, benzyl, indanyl, heterocyclyl selected from pyrrolidinyl, piperidinyl, morpholinyl, thiomorpholinyl, piperazinyl, tetrahydropyranyl, tetrahydrothiopyranyl, furanyl, tetrahydrofuranyl, thienyl, oxazolyl, thiazolyl, imidazolyl, pyridinyl, pyrimidinyl, pyrazolyl, benzofuranyl, benzothienyl, benzimidazolyl, benzthiazolyl, quinolinyl, isoquinolinyl and benzoxazolyl, heterocyclyloxy wherein the heterocyclyl moiety is selected from the heterocycyl moieties herein described in this paragraph, C1–3alkanoyl, benzoyl, naphthoyl, C1–4alkanoyloxy, benzyloxy, C1–4 alkoxycarbonyl, arylC1–2alkoxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–4 alkanoylamino, aroylamino, C1–4 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, phenyl, naphthyl, pyrrolidinyl, piperidinyl, morpholinyl, piperazinyl, oxazolyl, thiazolyl, imidazolyl, pyridinyl, pyrimidinyl, pyrazinyl, indolyl, benzofuranyl, benzothienyl, benzimidazolyl or benzthiazolyl, or $R_5$ is C1–4 alkoxycarbonylamino, phenoxycarbonylamino, C1–4 alkylcarbamoyloxy, phenylcarbamoyloxy, C1–4 alkylsulfonylamino, phenylsulfonylamino, C1–3 alkylaminosulfonyl, phenylaminosulfonyl, amino wherein the nitrogen atom may be independently mono or di-substituted by C1–4 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, beuzimidazolyl or benzthiazolyl, or $R_5$ is halogen, hydroxy, oxo, carboxy, cyano, nitro or carboxaniide, $R_5$ may be further substituted or unsubstituted by one or more $R_e$;

$R_e$ is C1–4 alkyl, C1–4 alkoxy, C3–7 cycloalkyl, phenyl, naphthyl, indanyl, pyrrolidinyl, piperidinyl, morpholinyl, thiomorpholinyl, piperazinyl, tetrahydrothiopyranyl, tetrahydropyranyl, tetrahydrofuranyl, thienyl, oxazolyl, thiazolyl, imidazolyl, pyridinyl, pyrimidinyl, pyrazinyl, indolyl, benzimidazolyl, benzthiazolyl, benzoxazolyl, quinolinyl, isoquinolinyl, quinazolinyl, quinoxalinyl, C1–4 alkanoyl, aroyl, C1–4alkanoyloxy, phenoxy, naphthyloxy, benzyloxy, C1–4 alkoxycarbonyl, phenoxycarbonyl, benzoyloxy, carbamoyl wherein the nitrogen atom may be independently mono or di-substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl, or benzthiazolyl, or $R_e$ is C1–4 alkanoylamino, benzoylamino, C1–4 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzthiazolyl, or $R_e$ is C1–4 alkoxycarbonylamino, phenoxycarbonylamino, C1–4 alkylcarbamoyloxy, phenylcarbamoyloxy, C1–4 alkylsulfonylamino, phenylsulfonylamino, C1–4 alkylaminosulfonyl, phenylaminosulfonyl, amino wherein the nitrogen atom may be independently mono or di-substituted by C1–3 alkyl, phenyl, naphthyl, pyrrolidinyl, piperidinyl, morpholinyl, thiomorpholinyl, piperazinyl, fluranyl, thienyl, oxazolyl, thiazolyl, imidazolyl, pyridinyl, pyrimidinyl, benzimidazolyl or benzthiazolyl, or $R_e$ is halogen, hydroxy, oxo, carboxy, cyano, nitro or carboxamide, $R_e$ may be further substituted or unsubstituted by one or more $R_f$; and $R_f$ is methyl, ethyl, t-butyl, tolylsulfonyl, methoxy, cyclopropyl, phenyl, phenoxy, benzyloxy, fluoro, chloro, bromo, hydroxy, oxo, carboxy or carboxamide.

4. The compound according to claim 3 wherein:

$R_b$ is methyl, ethyl, n-propyl, i-propyl, cyclopropyl, cyclopentyl, cyclohexyl, phenyl, methoxy, ethoxy, n-propoxy, i-propoxy, phenoxy, benzyloxy, fluoro, chloro, bromo, iodo, hydroxy, oxo, carboxy, cyano, nitro or carboxamide;

$R_2$ is hydrogen;

$R_3$ is a bond, C1–3 alkyl, C2–4alkylene, C5–6 cycloalkyl, benzyl or naphthylmethyl wherein $R_3$ is substituted or unsubstituted by one or more $R_c$;

$R_c$ is C1–3 alkyl, C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4tetrahydronaphthyl, furanyl, tetrahydropyranyl, thienyl, oxazolyl, thiazolyl, imidazolyl, pyrimidinyl, indolyl, benzofuranyl, benzothienyl, benzthiazolyl, C1–3 alkoxy, phenoxy, naphthyloxy, C1–2 alkanoyl, benzoyl, C1–2 alkoxycarbonyl, phenoxycarbonyl, C1–2alkanoyloxy, benzoyloxy, carbarmoyl wherein the nitrogen atom may be independently mono or di-substituted by C1–3 alkyl or aryl, or $R_c$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl or aryl, or $R_c$ is C1–2 alkoxycarbonylamino, phenoxycarbonylamino, C1–2 alkylcarbamoyloxy, arylcarbamoyloxy, C1–2 alkylsulfonylamino, phenylsulfonylamino, C1–2alkylaminosulfonyl, phenylaminosulfonyl, amino wherein the nitrogen atom may be independently mono or di-substituted by C1–3 alkyl or phenyl, or $R_c$ is halogen, hydroxy, oxo, carboxy or cyano, $R_c$ may be further substituted or unsubstituted by one or more $R_d$;

$R_d$ is methyl, cyclopropyl, cyclohexyl, phenyl, benzyl, methoxy, phenoxy, benzyloxy, benzoyl, fluoro, chloro, oxo or cyano;

$R_5$ is a bond, hydrogen, carbonyl, C1–5 alkyl, C1–5alkoxyC1–5alkyl, C1–5alkylaminoC1–5alkyl, C1–5alkylthioC1–5alkyl wherein the sulfur atom may be oxidized to a sulfoxide or sulfone, C1–5 alkoxy, phenoxy, C3–6 cycloalkyl, phenyl, naphthyl, benzyl, indanyl, heterocyclyl selected from pyrrolidinyl, piperidinyl, morpholinyl, thiomorpholinyl, piperazinyl, tetrahydropyranyl, oxazolyl, thiazolyl, imidazolyl, pyridinyl, pyrimidinyl, benzimidazolyl and benzthiazolyl, heterocyclyloxy wherein the heterocyclyl moiety is selected from the heterocycyl moieties herein described in this paragraph, C1–3alkanoyl, benzoyl, naphthoyl, C1–3alkanoyloxy, benzyloxy, C1–3 alkoxycarbonyl, benzyloxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–3 alkanoylamino, aroylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzofuranyl, benzothienyl, benzimidazolyl or benzthiazolyl, or $R_5$ is C1–3 alkoxycarbonylamino, phenoxycarbonylamino, C1–3 alkylcarbamoyloxy, phenylcarbamoyloxy, C1–3 alkylsulfonylamino, phenylsulfonylamino, C1–3 alkylaminosulfonyl, phenylaminosulfonyl, amino wherein the nitrogen atom may be independently mono or di-substituted by C1–3 alkyl, phenyl, pyrrolidinyl, piperidinyl, morpholinyl, thiomorpholinyl, piperazinyl, oxazolyl, thiazolyl, imidazolyl, pyridinyl, pyrimidinyl, benzimidazolyl or benzthiazolyl, or $R_5$ is halogen, hydroxy, oxo, carboxy, cyano or carboxamide, $R_5$ may be further substituted or unsubstituted by one or more $R_e$;

$R_e$ is C1–3 alkyl, C1–3 alkoxy, C3–7 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzthiazolyl, benzoxazolyl, C1–3 alkanoyl, aroyl, C1–3alkanoyloxy, phenoxy, benzyloxy, C1–3 alkoxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is C1–3 alkanoylamino, benzoylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is C1–3 alkoxycarbonylamino, phenoxycarbonylamino, C1–3 alkylcarbamoyloxy, phenylcarbamoyloxy, C1–3 alkylsulfonylamino, phenylsulfonylamino, C1–3 alkylaminosulfonyl, phenylaminosulfonyl, amino wherein the nitrogen atom may be independently mono or di-substituted by C1–3 alkyl, phenyl, naphthyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is halogen, hydroxy, oxo, carboxy, cyano or carboxamide, $R_e$ may be further substituted or unsubstituted by one or more $R_f$; and $R_f$ is methyl, phenyl, tolylsulfonyl, methoxy, phenoxy, benzyloxy, fluoro, chloro, bromo, hydroxy, oxo, carboxy or carboxamide.

5. The compound according to claim 4 wherein:

Het is tetrahydropyranyl substituted or unsubstituted with one or more $R_5$;

$R_b$ is methyl, cyclopropyl, phenyl, methoxy, phenoxy, benzyloxy, fluoro, chloro, hydroxy, oxo, carboxy or carboxamide;

$R_3$ is a bond, C1–3 alkyl, C2–4 alkylene, C5–6 cycloalkyl, benzyl or naphthylmethyl wherein $R_3$ is substituted or unsubstituted by one or more $R_c$;

$R_c$ is methyl, ethyl, n-propyl, i-propyl, C5–6 cycloalkyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, thienyl, oxazolyl, thiazolyl, indolyl, benzofuranyl, benzothienyl, benzthiazolyl, methoxy, ethoxy, phenoxy, acetyl, benzoyl, methoxycarbonyl, phenoxycarbonyl, acetoxy, benzoyloxy, carbamoyl wherein the nitrogen atom may be independently mono or di-substituted by methyl, ethyl or aryl, or $R_c$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or aryl, or $R_c$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_c$ is fluoro, chloro or oxo, $R_c$ may be further substituted or unsubstituted by one or more $R_d$;

$R_d$ is methyl, cyclopropyl, phenyl, methoxy, fluoro, chloro or oxo;

$R_5$ is a bond, hydrogen, carbonyl, C1–4 alkyl, C1–4alkoxyC1–4alkyl, C1–4alkylaminoC1–4alkyl, C1–4alkylthioC1–4alkyl wherein the sulfur atom may be oxidized to a sulfoxide or sulfone, C1–4 alkoxy, phenoxy, cyclopropyl, cyclopentyl, cyclohexyl, phenyl, naphthyl, benzyl, indanyl, heterocyclyl selected from pyrrolidinyl, piperidinyl, morpholinyl, piperazinyl, tetrahydropyranyl, oxazolyl, thiazolyl, imidazolyl, pyridinyl, pyrimidinyl, benzimidazolyl and benzthiazolyl, heterocyclyloxy wherein the heterocyclyl moiety is selected from the heterocyclyl moieties herein described in this paragraph, C1–2alkanoyl, benzoyl, naphthoyl, C1–2alkanoyloxy, benzyloxy, C1–2 alkoxycarbonyl, benzyloxycarbonyl, phenoxycarbonyl, benzoyloxy, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_5$ is C1–2 alkoxycarbonylamino, phenoxycarbonylamino, C1–2 alkylcarbamoyloxy, phenylcarbamoyloxy, C1–2 alkylsulfonylamino, phenylsulfonylamino, C1–2 alkylaminosulfonyl, phenylaminosulfonyl, amino wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_5$ is fluoro, chloro, bromo, hydroxy, oxo, carboxy or carboxamide, $R_5$ may be further substituted or unsubstituted by one or more $R_e$;

$R_e$ is C1–3 alkyl, C1–2 alkoxy, C3–6 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzthiazolyl, benzoxazolyl, C1–2 alkanoyl, aroyl, C1–2alkanoyloxy, phenoxy, benzyloxy, C1–2 alkoxycarbonyl, phenoxycarbonyl, benzoyloxy, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is C1–2 alkoxycarbonylamino, phenoxycarbonylamino, C1–2 alkylcarbamoyloxy, phenylcarbamoyloxy, C1–2 alkylsulfonylamino, phenylsulfonylamino, C1–2 alkylaminosulfonyl, phenylaminosulfonyl, amino wherein the nitrogen atom may be independently mono or di-substituted by C1–2 alkyl, phenyl, naphthyl, pyrrolidinyl, piperidinyl, morpholinyl, piperazinyl, oxazolyl, thiazolyl, imidazolyl, pyridinyl or pyrimidinyl, or $R_e$ is fluoro, chloro, bromo, hydroxy, oxo, carboxy or carboxamide, $R_e$ may be further substituted or unsubstituted by one or more $R_f$; and $R_f$ is methyl, phenyl, tolylsulfonyl, methoxy, phenoxy, benzyloxy, fluoro, chloro, hydroxy, oxo, carboxy or carboxamide.

6. The compound according to claim 5 wherein:

Het is substituted or unsubstituted with one or more $R_5$;

$R_3$ is a bond, methyl, ethyl, n-propyl, propenyl, butenyl, i-butenyl, cyclohexyl, benzyl or naphthylmethyl wherein $R_3$ is substituted or unsubstituted by one or more $R_c$;

$R_c$ is methyl, ethyl, n-propyl, i-propyl, cyclohexyl, cyclopentyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, methoxy, phenoxy, acetyl, benzoyl, methoxycarbonyl, phenoxycarbonyl, acetoxy, benzoyloxy, methylthio wherein the sulfur atom may be oxidized to a sulfoxide or sulfone, phenylthio wherein the sulfur atom may be oxidized to a sulfoxide or sulfone, fluoro, chloro or oxo;

$R_5$ is a bond, hydrogen, carbonyl, C1–4 alkyl, C1–2alkoxyC1–alkyl, C1–alkylaminoC1–2alkyl, C1–2alkylthioC1–2alkyl wherein the sulfur atom may be oxidized to a sulfoxide or sulfone, C1–2 alkoxy, phenoxy, cyclopropyl, cyclopentyl, cyclohexyl, phenyl, benzyl, heterocyclyl selected from pyrrolidinyl, piperidinyl, morpholinyl, tetrahydropyranyl, pyridinyl, and pyrimidinyl, heterocyclyloxy wherein the heterocyclyl moiety is selected from the heterocycyl moieties herein described in this paragraph, acetyl, benzoyl, acetyloxy, benzyloxy, methoxycarbonyl, ethoxycarbonyl, benzyloxycarbonyl, benzoyloxy, carbamoyl wherein the nitrogen atom may be independently mono or di-substituted by methyl, ethyl or phenyl, or $R_5$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or phenyl, or $R_5$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_5$ is fluoro, chloro, hydroxy, oxo, carboxy or carboxamide, $R_5$ may be further substituted or unsubstituted by one or more $R_e$;

$R_e$ is methyl, methoxy, ethoxy, cyclopropyl, cyclopentyl, cyclohexyl, phenyl, naphthyl, indanyl, piperidinyl, morpholinyl, indolyl, thienyl, pyridinyl, acetyl, benzoyl, acetyloxy, phenoxy, benzyloxy, methoxycarbonyl, ethoxycarbonyl, carbamoyl wherein the nitrogen atom may be independently mono or di-substituted by methyl, ethyl or phenyl, or $R_e$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or phenyl, or $R_e$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_e$ is fluoro, chloro, hydroxy, oxo, carboxy or carboxamide, $R_e$ may be further substituted or unsubstituted by one or more $R_f$; and $R_f$ is methyl, phenyl, tolylsulfonyl, phenoxy, benzyloxy, fluoro, chloro or oxo.

7. The compound according to claim 6 wherein:

$R_3$ is ethyl, n-propyl, propenyl, butenyl, i-butenyl, benzyl or naphthylmethyl wherein $R_3$ is substituted or unsubstituted by one or more $R_c$;

$R_c$ is methyl, cyclohexyl, cyclopentyl, indanyl, 1,2,3,4-tetrahydronaphthyl, methoxy, methylthio wherein the sulfur atom may be oxidized to a sulfoxide or sulfone, fluoro or chloro;

$R_5$ is a bond, carbonyl, methyl, ethyl, n-propyl, n-butyl, t-butyl, i-propyl, i-butyl, cyclopropyl, cyclopentyl, cyclohexyl, phenyl, benzyl, piperidinyl, tetrahydropyranyl, pyrimidinyl, acetyl, benzoyl, ethoxycarbonyl, benzyloxycarbonyl, methylsulfonylamino, phenylsulfonylamino, methylamino, dimethylamino, fluoro, oxo or carboxy, $R_5$ may be further substituted or unsubstituted by one or more $R_e$;

$R_e$ is methyl, cyclopropyl, cyclopentyl, cyclohexyl, phenyl, naphthyl, indanyl, thienyl, 5-methylthienyl, methoxy, phenoxy, benzyloxy, piperidinyl, pyridinyl, indolyl, 1-(tolyl-sulfonyl)-indolyl, carbamoyl wherein the nitrogen atom may be independently mono or di-substituted by methyl, phenyl or benzyl, or $R_e$ is hydroxy, fluoro, chloro, oxo, dimethylamino or trifluoromethyl.

8. The compound according to claim 7 wherein:

$R_3$ is n-butyl, i-butyl, 2,2-dimethylpropyl, cyclohexylmethyl, propenyl, i-butenyl, 4-methoxybenzyl, 4-chlorobenzyl, 3,4-dichlorobenzyl, 3-chlorobenzyl, 2,4-dichlorobenzyl, 4-methylbenzyl, 3-methylbenzyl or naphth-2-ylmethyl; wherein the configuration at the asymmetric carbon atom defined by $R_2$ and $R_3$ when they are different is the L enantiomer; and $R_5$ is a bond, methyl, ethyl, n-propyl, n-butyl, n-pentyl, 2-pentyl, 3-pentyl, phenethyl, phenpropyl, 2,2-dimethylpropyl, t-butyl, i-propyl, i-butyl, cyclopropyl, cyclopentyl, cyclohexyl, cyclopropylmethyl, cyclopentylmethyl, cyclohexylmethyl, phenyl, benzyl, naphthylmethyl, indanylmethyl, pyridinylmethyl, indolylmethyl, thienylmethyl, 5-methylthienylmethyl, piperidinyl, piperidinylcarbonyl, pyridinylcarbonyl, tetrahydropyranyl, pyrimidinyl, acetyl, benzoyl, ethoxycarbonyl, benzyloxycarbonyl, t-butoxycarbonyl, methylcarbamoyl, phenylcarbamoyl, benzylcarbamoyl, methylsulfonylamino, phenylsulfonylamino, methylamino, dimethylamino, methylcyclohexyl, methylbenzyl, methoxybenzyl, phenoxybenzyl, benzyloxybenzyl, N-[(4-methylphenyl)-sulfonyl]-indolylmethyl, fluorobenzyl, difluorobenzyl, chlorobenzyl, N,N-dimethylaminoacetyl, trifluoromethylbenzyl, fluoro, oxo or carboxy.

9. The compound according to claim 3 wherein:

$R_b$ is methyl, ethyl, cyclopropyl, cyclohexyl, phenyl, methoxy, ethoxy, phenoxy, benzyloxy, fluoro, chloro, bromo, hydroxy, oxo, carboxy, cyano, nitro or carboxamide;

$R_2$ is hydrogen or methyl;

$R_3$ is a bond, methyl, ethyl, n-propyl, i-propyl, n-butyl, i-butyl, n-pentyl, propenyl, i-butenyl, cyclohexyl, benzyl or naphthylmethyl wherein $R_3$ is substituted or unsubstituted by one or more $R_c$;

$R_c$ is methyl, ethyl, cyclohexyl, cyclopentyl, phenyl, naphthyl, bicyclo[3.1.0]hexanyl, bicyclo[1.1.1]pentanyl, cubanyl, furanyl, tetrahydropyranyl, thienyl, oxazolyl, thiazolyl, imidazolyl, pyrimidinyl, methoxy, ethoxy, phenoxy, acetyl, benzoyl, methoxycarbonyl, phenoxycarbonyl, acetoxy, benzoyloxy, carbamoyl wherein the nitrogen atom may be independently mono or di-substituted by methyl or phenyl, or $R_c$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl or phenyl, or $R_c$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl or phenyl, or $R_c$ is chloro, fluoro, hydroxy, oxo, carboxy or cyano;

$R_2$ and $R_3$ together with the carbon they are attached optionally form a ring selected from cyclopentyl, cyclohexyl, cycloheptyl, tetrahydropyranyl, tetrahydrothiopyranyl, tetrahydrofuranyl, pyrrolidinyl, piperidinyl, piperazinyl, morpholinyl or tetrahydrothiophenyl;

$R_4$ is hydrogen;

$R_5$ is a bond, hydrogen, carbonyl, C1–5 alkyl, C1–5alkoxyC1–5alkyl, C1–5alkylaminoC1–5alkyl, C1–5alkylthioC1–5alkyl wherein the sulfur atom may be oxidized to a sulfoxide or sulfone, C1–5 alkoxy, phenoxy, naphthyloxy, cyclopropyl, cyclopentyl, cyclohexyl, phenyl, benzyl, heterocyclyl selected from pyrrolidinyl, piperidinyl, morpholinyl, tetrahydropyranyl, pyridinyl, and pyrimidinyl, heterocyclyloxy wherein the heterocyclyl moiety is selected from the heterocycyl moieties herein described in this paragraph, acetyl, benzoyl, acetyloxy, benzyloxy, methoxycarbonyl, ethoxycarbonyl, benzyloxycarbonyl, benzoyloxy, carbamoyl wherein the nitrogen atom may be independently mono or di-substituted by methyl, ethyl or phenyl, or $R_5$ is acetylamino, benzoylamino, phenylthio wherein the sulfur atom may be oxidized to a sulfoxide or sulfone, ureido wherein either nitrogen atom may be independently substituted by methyl, ethyl or phenyl, or $R_5$ is methoxycarbonylamino, ethoxycarbonylamino, phenoxycarbonylamino, mechylcarbamoyloxy, phenylcarbamoyloxy, phenylsulfonylamino, phenylaminosulfonyl, amino wherein the nitrogen atom may be independently mono or di-substituted by methyl, ethyl or phenyl, or $R_5$ is fluoro, chloro, hydroxy, oxo, carboxy or carboxamide, $R_5$ may be further substituted or unsubstituted by one or more $R_e$;

$R_e$ is methyl ethyl, methoxy, ethoxy, cyclopropyl, cyclopentyl, cyclohexyl, phenyl, naphthyl, indanyl, piperidinyl, morpholinyl, indolyl, thienyl, pyridinyl, methoxy, ethoxy, acetyl, benzoyl, acetyloxy, phenoxy, benzyloxy, methoxycarbonyl, ethoxycarbonyl, carbamoyl wherein the nitrogen atom may be independently mono or di-substituted by methyl, ethyl or phenyl, or $R_e$ is acetylamino, benzoylamino, methylthio wherein the sulfur atom may be oxidized to a sulfoxide or sulfone, phenylthio methylthio wherein the sulfur atom may be oxidized to a sulfoxide or sulfone, ureido wherein either nitrogen atom may be independently substituted by methyl, ethyl or phenyl, or $R_e$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_e$ is fluoro, chloro, hydroxy, oxo, carboxy or carboxamide, $R_e$ may be further substituted or unsubstituted by one or more $R_f$; and $R_f$ is methyl, phenyl, tolylsulfonyl, phenoxy, benzyloxy, fluoro, chloro or oxo.

10. The compound according to claim 9 wherein:
R₃ is a bond, methyl, ethyl, n-propyl, i-propyl, n-butyl, i-butyl, n-pentyl, propenyl, i-butenyl, benzyl or naphthylmethyl wherein R₃ is substituted or unsubstituted by one or more R_c;
R_c is methyl, ethyl, cyclohexyl, cyclopentyl, phenyl, furanyl, tetrahydropyranyl, thienyl, oxazolyl, thiazolyl, methoxy, phenoxy, acetyl, benzoyl, methoxycarbonyl, carbamoyl wherein the nitrogen atom may be independently mono or di-substituted by methyl or phenyl,
or R_c is acetylamino, benzoylamino, methylthio, methoxycarbonylamino, methylcarbamoyloxy, methylsulfonylamino, methylaminosulfonyl, amino wherein the nitrogen atom may be independently mono or di-substituted by methyl,
or R_c is fluoro or oxo;
R₂ and R₃ together with the carbon they are attached optionally form a ring selected from cyclopentyl, cyclohexyl, cycloheptyl, tetrahydropyranyl, tetrahydrothiopyranyl, tetrahydrofuranyl, pyrrolidinyl or piperidinyl;
R₅ is methyl, ethyl, n-propyl, n-butyl, n-pentyl, 2-pentyl, 3-pentyl, phenethyl, phenpropyl, 2,2-dimethylpropyl, t-butyl, i-propyl, i-butyl, cyclopropyl, cyclopentyl, cyclohexyl, cyclopropylmethyl, cyclopentylmethyl, cyclohexylmethyl, phenyl, benzyl, 2-methylbenzyl, 3-methylbenzyl, 4-methylbenzyl, 2,6-dimethylbenzyl, 2,5-dimethylbenzyl, 2,4-dimethylbenzyl, 2,3-dimethylbenzyl, 3,4-dimethylbenzyl, 3,5-dimethylbenzyl, 2,4,6-trimethylbenzyl, 2-methoxybenzyl, 3-methoxybenzyl, 4-methoxybenzyl, 2-phenoxybenzyl, 3-phenoxybenzyl, 4-phenoxybenzyl, 2-benzyloxybenzyl, 3-benzyloxybenzyl, 4-benzyloxybenzyl, 2-fluorobenzyl, 3-fluorobenzyl, 4-fluorobenzyl, 2,6-difluorobenzyl, 2,5-difluorobenzyl, 2,4-difluorobenzyl, 2,3-difluorobenzyl, 3,4-difluorobenzyl, 3,5-difluorobenzyl, 2,4,6-triflurobenzyl, 2-trifluoromethylbenzyl, 3-trifluoromethylbenzyl, 4-trifluoromethylbenzyl, naphthylmethyl, indanylmethyl, pyridinylmethyl, indolylmethyl, thienylmethyl, 5-methylthienylmethyl, piperidinyl, piperidinylcarbonyl, pyridinylcarbonyl, tetrahydropyranyl, pyrimidinyl, acetyl, benzoyl, ethoxycarbonyl, benzyloxycarbonyl, t-butoxycarbonyl, methylcarbamoyl, phenylcarbamoyl, benzylcarbamoyl, methylsulfonylamino, phenylsulfonylamino, methylamino, dimethylamino, fluoro, oxo or carboxy.

11. The compound according to claim 10 wherein:
R₃ is a bond, methyl, ethyl, n-propyl, i-propyl, n-butyl, i-butyl, n-pentyl, propenyl, i-butenyl or benzyl wherein R₃ is substituted or unsubstituted by one or more R_c;
R_c is methyl, ethyl, cyclohexyl, cyclopentyl, phenyl, furanyl, tetrahydropyranyl, thienyl, oxazolyl, thiazolyl, methoxy, phenoxy, acetyl, benzoyl, methoxycarbonyl, acetylamino, methylthio, methylsulfonylamino or fluoro;
R₂ and R₃ together with the carbon they are attached optionally form a ring selected from cyclopentyl, cyclohexyl, cycloheptyl, tetrahydropyranyl, tetrahydrothiopyranyl or tetrahydrofuranyl; and
R₅ is methyl, ethyl, n-propyl, n-butyl, phenethyl, phenpropyl, t-butyl, i-propyl, i-butyl, cyclopropyl, cyclohexyl, cyclopropylmethyl, cyclohexylmethyl, phenyl, benzyl, 2-methoxybenzyl, 3-methoxybenzyl, 4-methoxybenzyl 4-fluorobenzyl, 3,5-difluorobenzyl, 4-trifluoromethylbenzyl, naphthylmethyl, pyridinylmethyl, indolylmethyl, thienylmethyl, acetyl, benzoyl, ethoxycarbonyl, benzyloxycarbonyl, t-butoxycarbonyl, phenylcarbamoyl, phenylsulfonylamino or fluoro.

12. The compound according to claim 11 wherein:
Het is tetrahydropyranyl;
R₃ is n-propyl, i-butyl, propenyl, i-butenyl or 2,2-dimethylpropyl;
R₂ and R₃ together with the carbon they are attached optionally form a ring selected from cyclopentyl, cyclohexyl, or cycloheptyl;
R₅ is methyl, ethyl, n-propyl, phenethyl, t-butyl, i-propyl, i-butyl, cyclohexyl, cyclohexylmethyl, benzyl, 4-fluorobenzyl, naphthylmethyl, acetyl, benzoyl or benzyloxycarbonyl.

13. A compound selected from:
Morpholine-4-carboxylic acid [1-(4-cyano-tetrahydro-pyran-4-ylcarbamoyl)-2-cyclohexyl-ethyl]-amide;
Morpholine-4-carboxylic acid [1-(4-cyano-tetrahydro-pyran-4-ylcarbamoyl)-3,3-dimethyl-butyl]-amide;
Morpholine-4-carboxylic acid [1-(4-cyano-tetrahydro-thiopyran-4-ylcarbamoyl)-2-cyclohexyl-ethyl]-amide;
or the pharmaceutically acceptable acceptable salts, esters, tautomers, individual isomers and mixtures of isomers thereof.

14. A pharmaceutical composition comprising a pharmaceutically effective amount of a compound according to claims 1 or 9.

15. A method of treating an autoimmune disease, said method comprising administering to a patient in need of such treatment a pharmaceutically effective amount of a compound according to claim 1.

16. The method according to claim 15 wherein the autoimmune disease is rheumatoid arthritis, systemic lupus, erythematosus, Crohn's disease, ulcerative colitis, multiple sclerosis, Guillain-Barre syndrome, psoriasis, Grave's disease, myasthenia gravis, scleroderma, glomerulonephritis, atopic dermatitis or insulin-dependent diabetes mellitus.

17. A method of treating Alzheimer's disease comprising administering to a patient in need of such treatment a pharmaceutically effective amount of a compound according to claim 1.

18. A method of treating atherosclerosis comprising administering to a patient in need of such treatment a pharmaceutically effective amount of a compound according to claim 1.

19. A method of making a compound of the formula (II)

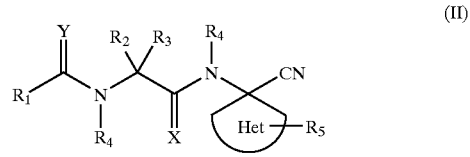

(II)

wherein Y, X, R₁, R₂, R₃, R₄, Het and R₅ are as defined in claim 1;
said method comprising:
a) reacting an amino acid ester (IV), wherein R' is a protecting group, under suitable reaction conditions with a $R_1C(O)L$ wherein L is a leaving group selected from Cl and OH:

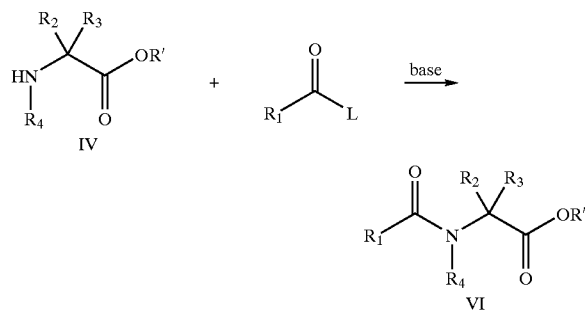

b) removing the protecting group R' from the compound produced in step a) to produce the corresponding carboxylic acid;

c) reacting the product of step b) under coupling conditions consisting of EDC and HOBT in a solvent selected from DMF and methylene chloride, with an amino nitrile bearing "Het-$R_5$" shown below to produce a compound of the formula (II):

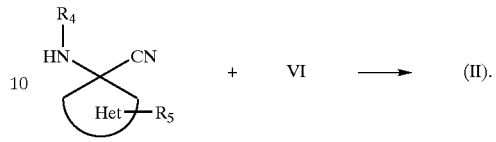

20. A method of treating osteoporosis comprising administering to a patient in need of such treatment a pharmaceutically effective amount of a compound according to claim 9.

* * * * *